US012528868B2

(12) United States Patent
Winau et al.

(10) Patent No.: US 12,528,868 B2
(45) **Date of Patent: *Jan. 20, 2026**

(54) CD1a ANTIBODIES AND USES THEREOF

(71) Applicants: Pfizer Inc., New York, NY (US); Children's Medical Center Corporation, Boston, MA (US)

(72) Inventors: Florian Winau, Boston, MA (US); Oleg V. Kovalenko, Arlington, MA (US); Chew Shun Chang, Quincy, MA (US); Di Wu, Lexington, MA (US); Nicholas Andrew Marze, Quincy, MA (US); Shian-Huey Chiang, Cary, NC (US)

(73) Assignees: Pfizer Inc., New York, NY (US); Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/354,934

(22) Filed: Jul. 19, 2023

(65) Prior Publication Data

US 2024/0076382 A1 Mar. 7, 2024

Related U.S. Application Data

(63) Continuation of application No. 17/450,283, filed on Oct. 7, 2021, now Pat. No. 11,746,154.

(60) Provisional application No. 63/090,055, filed on Oct. 9, 2020.

(51) Int. Cl.

| | |
|---|---|
| ***A61K 39/00*** | (2006.01) |
| ***A61K 39/395*** | (2006.01) |
| ***A61P 17/00*** | (2006.01) |
| ***C07K 16/28*** | (2006.01) |

(52) U.S. Cl.

CPC .......... *C07K 16/2833* (2013.01); *A61P 17/00* (2018.01); *A61K 2039/505* (2013.01); *C07K 2317/24* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 4,364,933 | A | 12/1982 | Kung et al. | |
| 5,624,821 | A | 4/1997 | Winter et al. | |
| 10,844,118 | B2 | 11/2020 | Winau et al. | |
| 11,746,154 | B2 * | 9/2023 | Winau | A61P 37/00 424/172.1 |

FOREIGN PATENT DOCUMENTS

| | | | |
|---|---|---|---|
| WO | 2005063819 | A2 | 7/2005 |
| WO | 2015042110 | A1 | 3/2015 |
| WO | 2020165350 | A1 | 8/2020 |

OTHER PUBLICATIONS

Chiricozzi et al. Targeting IL-4 for the Treatment of Atopic Dermatitis. Immunotargets Ther. Sep. 2020, 9:151-156. (Year: 2020).*

Angenieux et al., "Characterization of CD1 e, a Third Type of CD1 Molecule Expressed in Dendritic Cells" J Biol Chem, 2000, 275(48):37757-64.

Birkinshaw et al., "al3 T-cell receptor recognition of CD1 a presenting self-lipid antigens" Nature Immunol 2015, 16 (3):258-66.

De Jong et al., "CD1 a autoreactive T cells recognize natural skin oils that function as headless antigens" Nat Immunol 2014; 15(2) : 177-85.

Hunger et al., "Langerhans cells utilize CD1 a and langerin to efficiently present nonpeptide antigens to T cells" The Journal of Clinical Investigation 2004, 113(5), 701-708.

Igyarto et al., "Antigen Presentation by Langerhans Cells" Curr Opin Immunol 2013; 25(1) :115-9.

International Search Report and Written Opinion issued in Corresponding PCT Application No. PCT/US2021/071779, dated Jan. 21, 2022.

Kim et al. "CD1 a on Langerhans cells controls inflammatory skin disease" Nature Immulogy 2016, 17(10), 1159-1166.

Kobayashi et al., "GM-CSF-independent CD1 a expression in epidermal Langerhans cells: evidence from human CD1 A genome-transgenic mice" J. Invest. Dermatol. 2012, 132, 241-244.

Merad et al., "Origin, homeostasis and function of Langerhans cells and other langerin-expressing dendritic cells." Nat Rev Immunol2008; 8(12):935-47.

Milne et al., "CD1 c+ blood dendritic cells have Langerhans cell potential." Blood 2015, 125(3):4 70-3.

Olivier et al., "Plasticity of Migrating CD1 b+ and CD1 b- Lymph Dendritic Cells in the Promotion of Th1, Th2 and Th17 in Response to Salmonella and Helminth Secretions" PLoS One 2013, 8(11 ):e79537, 11 pages.

Sugita et al., "CD1 c molecules broadly survey the endocytic system." Proc Natl Acad Sci USA 2000, 97(15):8445-50.

Wollenberg et al., "Immunomorphological and ultrastructural characterization of Langerhans cells and a novel, inflammatory dendritic epidermal cell (IDEC) population in lesional skin of atopic eczema." J Invest Dermatol (1996) 106(3):446-53.

Rudikoff et al."Single amino acid substitution altering antigen-binding specificity." Proc Natl Acad Sci USA. Mar. 1982; 79(6): 1979-83. (Year: 1982).

Paul, Fundamental Immunology, 3rd Edition, 1993, pp. 292-295 (Year: 1993).

Brown et al. "Tolerance of single, but not multiple, amino acid replacements in antibody VH CDR 2: a means of minimizing B cell wastage from somatic hypermutation?" J. Immuno. May 1996, 3285-91. (Year: 1996).

(Continued)

*Primary Examiner* — Maher M Haddad

(74) *Attorney, Agent, or Firm* — Greenberg Traurig, LLP; Melissa Hunter-Ensor; Evelyn M. Kwon

(57) ABSTRACT

Antibodies, and antigen-binding fragments thereof, that specifically bind to Cluster of Differentiation 1a (CD1a) are provided. Embodiments include uses, and associated methods of using the antibodies, and antigen-binding fragments thereof.

19 Claims, 11 Drawing Sheets

Specification includes a Sequence Listing.

(56) References Cited

OTHER PUBLICATIONS

Klimka et al., Human anti-CD30 recombinant antibodies by guided phage antibody selection using cell planning. British Journal of Cancer (2000) 83: 252-260. (Year: 2000).
Beiboer et al., Guided selection of a pan carcinoma specific antibody reveals similar binding characteristics yet structural divergence between the original murine antibody and its human equivalent. J. Mol. Biol. 296: 833-849 (2000). (Year: 2000).
Vajdos et al., Comprehensive functional maps of the antigen-binding site of an anti-ErbB2 antibody obtained with shotgun scanning mutagensis. J. Mol. Biol. Jul. 5, 2002, 320(2): 415-28 (Year: 2002).
MacCallum et al. Antibody-antigen interactions: contact analysis and binding site topography. J. Mol. Biol., 262, 732-745, 1996. (Year: 1996).
Casset et al., "A peptide mimetic of an anti-CD4 monoclonal antibody by rational design." Biochemical and Biophysical Research Communications, 307: 198-205, 2003 (Year: 2003).
Edwards et al. The remarkable flexibility of the human antibody repertoire; isolation of over one thousand different antibodies to a single protein, BLyS. J Moi Biol. Nov. 14, 2003; 334(1): 103-18. (Year: 2003).
Lloyd et al., "Modeling the human immune response: performance of a 1011 human antibody repertoire against a broad panel of therapeutically relevant antigens." Protein Eng Des Sel. Mar. 2009; 22(3): 159-68. (Year: 2009).
Goel et al., "Plasticity within the antigen-combining site may manifest as molecular mimicry in the humoral immuneresponse." J Immunol. Dec. 15, 2004; 173(12): 7358-67. (Year: 2004).
Kanyavuz et al., "Breaking the law: unconventional strategies for antibody diversification." Nat19(6): 355-368. (Year: 2019).

* cited by examiner

| | Ab138 | Ab139 | Ab140 | Ab141 | Ab40 | Isotype Control |
|---|---|---|---|---|---|---|
| IC5O, nM | 1.94 | >100 | 2.23 | >100 | 1.51 | >100 |

CD1a ANTIBODIES AND USES THEREOF

CROSS-REFERENCE TO RELATED APPLICATIONS

This application is a continuation of U.S. application Ser. No. 17/450,283, filed Oct. 7, 2021, which claims the benefit of priority to U.S. Provisional Application Ser. No. 63/090,055, filed Oct. 9, 2020, which are hereby incorporated by reference in their entireties.

PARTIES TO A JOINT RESEARCH STATEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are CHILDREN'S MEDICAL CENTER CORPORATION and PFIZER INC.

SEQUENCE LISTING

The instant application contains a Sequence Listing which has been submitted in XML format and is hereby incorporated by reference in its entirety. Said XML copy, created on Oct. 23, 2023, is named "PFZRP0002 Sequence Listing.XML" and is 159,242 bytes in size.

FIELD OF THE INVENTION

The present invention is related to antibodies, and antigen-binding fragments thereof, that specifically bind Cluster of Differentiation 1a (CD1a), and compositions, methods and uses thereof, including use of antibodies of the disclosure to treat inflammatory diseases and conditions including treatment and prevention of atopic dermatitis (AD) and inflammatory bowel disease (IBD).

BACKGROUND

Atopic dermatitis (also known as AD) is the most common type of eczema affecting over 18 million people in the United States (US) alone (National Eczema Association). It is a chronic, relapsing inflammatory condition characterized by severe pruritus, dry skin and eczematous lesions. AD is associated with food allergy, asthma, and allergic rhinitis. Severe disease can be extremely debilitating due to major psychological problems including depression and anxiety disorders, significant sleep loss, and impaired quality of life.

The pathophysiology of AD is not completely understood but it is a multifactorial disease. Both genetic and environmental factors (e.g., low humidity, cold weather, etc.) are known to trigger or worsen AD. The disease involves a complex interplay between immunoglobulin E (IgE)-mediated hypersensitization, barrier dysfunction, alterations in cell mediated immune responses, and environmental factors. Loss of function mutations in filaggrin have been implicated in severe atopic dermatitis due to a potential increase in trans-epidermal water loss, pH alterations, and dehydration. The primary skin defect may be an immunological disturbance that causes IgE-mediated sensitization, with epithelial-barrier dysfunction that is the consequence of both genetic mutations and local inflammation.

Typical treatments for AD include topical lotions and moisturizers, corticosteroids, anti-histamines and antibiotics. However, long term, overuse of corticosteroids is associated with local and systemic adverse effects including striae, petechiae, telangiectasia, skin thinning, atrophy, and worsening acne (Charman C R, Morris A D, Williams H C. Topical corticosteroid phobia in patients with atopic eczema. *Br J Dermatol.* 2000; 142:931-6). Systemic adverse effects (primarily hypothalamic-pituitary-adrenal axis suppression, reduced linear growth in children, and bone density changes in adults) are the most worrisome side effects associated with corticosteroids. $H_1$-antihistamines, especially the sedating type, have been prescribed for a long time in AD in order to reduce pruritus, the crucial symptom with a major impact on health-related quality of life. However, no randomized trials comparing an oral $H_1$-antihistamine with placebo or control have been conducted. Moreover, most treatment options offer only temporary, incomplete, symptom relief, and many patients with moderate-to-severe AD become resistant to treatment. Thus, a significant need exists in the art for novel targeted therapies for the treatment and/or prevention of AD and, in particular, to address the underlying pathophysiology.

SUMMARY

The invention provides antibodies, and antigen-binding fragments thereof, that specifically bind to CD1a, as well as uses, and associated methods. Those skilled in the art will recognize or be able to ascertain using no more than routine experimentation, many equivalents to the specific embodiments of the invention described herein. Such equivalents are intended to be encompassed by the following embodiments (E).

E1. An isolated antibody, or antigen-binding fragment thereof, that specifically binds to Cluster of Differentiation 1a (CD1a; e.g., human, cynomolgus monkey, dog and/or rabbit CD1a).

E2. An isolated antibody, or antigen-binding fragment thereof, that binds an epitope on Cluster of Differentiation 1a (CD1a), wherein the epitope comprises Glu82 and/or His170, according to the numbering of SEQ ID NO: 1.

E3. The antibody, or antigen-binding fragment thereof, of E2, wherein the epitope further comprises Ile92 and/or Arg93, according to the numbering of SEQ ID NO: 1.

E4. The antibody, or antigen-binding fragment thereof, of any one of E1-E3, comprising a heavy chain complementarity determining region-three (CDR-H3), wherein the CDR-H3 comprises the amino acid sequence selected from the group consisting of SEQ ID NO: 17, 49, and 52.

E5. The antibody, or antigen-binding fragment thereof, of any one of E1-E3, comprising a heavy chain complementarity determining region-three (CDR-H3), wherein the CDR-H3 comprises the amino acid sequence of SEQ ID NO: 17 or 49.

E6. The antibody, or antigen-binding fragment thereof, of E5, comprising a heavy chain complementarity determining region-three (CDR-H3), wherein the CDR-H3 comprises the amino acid sequence of SEQ ID NO: 17.

E7. The antibody, or antigen-binding fragment thereof, of any one of E1-E6, wherein the antibody, or antigen-binding fragment thereof, comprises:

(i) a heavy chain complementarity determining region-one (CDR-H1) comprising the amino acid sequence selected from the group consisting of SEQ ID NO: 15, 30, 40, 62, and 66;

(ii) a CDR-H2 comprising the amino acid sequence selected from the group consisting of SEQ ID NO: 16, 31, 41, 48, 59, 63 and 76; and/or (iii) a CDR-H3 comprising the amino acid sequence selected from the group consisting of SEQ ID NO: 17, 49 and 52.

E8. The antibody, or antigen-binding fragment thereof, of any one of E1-E7, wherein the antibody, or antigen-binding fragment thereof, comprises a light chain complementarity determining region-one (CDR-L1) comprising the amino acid sequence of SEQ ID NO: 8, wherein one or two amino acids may be substituted by a different amino acid.

E9 The antibody, or antigen-binding fragment thereof, of E8, wherein the one or two amino acid substitutions is selected from the group consisting of (i) Ser at position 7 is substituted by Tyr, Leu, Arg, or Trp and (ii) Asn at position 8 is substituted by Phe, Glu, Ile, Lys, Leu, Met, Gln, Arg, Trp or Tyr.

E10. The antibody, or antigen-binding fragment thereof, of any one of E1-E9, wherein the antibody, or antigen-binding fragment thereof, comprises:

(i) a light chain complementarity determining region-one (CDR-L1) comprising the amino acid sequence selected from the group consisting of SEQ ID NO: 8 and 25, (ii) a CDR-L2 comprising the amino acid sequence selected from the group consisting of SEQ ID NO: 9, 26, 37, 44, and 71, and/or (iii) a CDR-L3 comprising the amino acid sequence selected from the group consisting of SEQ ID NO: 10, 27, 34, and 45.

E11. The antibody, or antigen binding fragment thereof, of any one of E1-E10, wherein the antibody, or antigen-binding fragment thereof, comprises:

(i) a CDR-H1 comprising the amino acid sequence selected from the group consisting of SEQ ID NO: 15, 30, 40, 62, and 66, (ii) a CDR-H2 comprising the amino acid sequence selected from the group consisting of SEQ ID NO: 16, 31, 41, 48, 59, 63 and 76, (iii) a CDR-H3 comprising the amino acid sequence selected from the group consisting of SEQ ID NO: 17, 49 ad 52, (iv) a CDR-L1 comprising the amino acid sequence selected from the group consisting of SEQ ID NO: 8 and 25, (v) a CDR-L2 comprising the amino acid sequence selected from the group consisting of SEQ ID NO: 9, 26, 37, 44, and 71, and/or (vi) a CDR-L3 comprising the amino acid sequence selected from the group consisting of SEQ ID NO: 10, 27, 34, and 45.

E12. The antibody, or antigen binding fragment thereof, of any one of E1-E11, wherein the antibody, or antigen-binding fragment thereof, comprises:

(i) a CDR-H1 comprising the amino acid sequence selected from the group consisting of SEQ ID NO: 15, 30 and 40, (ii) a CDR-H2 comprising the amino acid sequence selected from the group consisting of SEQ ID NO: 16, 41 and 63, (iii) a CDR-H3 comprising the amino acid sequence selected from the group consisting of SEQ ID NO: 17 and 49, (iv) a CDR-L1 comprising the amino acid sequence selected from the group consisting of SEQ ID NO: 8 and 25, (v) a CDR-L2 comprising the amino acid sequence selected from the group consisting of SEQ ID NO: 9, and 26, and/or (vi) a CDR-L3 comprising the amino acid sequence selected from the group consisting of SEQ ID NO: 10 and 27.

E13. The antibody, or antigen binding fragment thereof, of any one of E1-E12, wherein the antibody, or antigen-binding fragment thereof, comprises:

(i) a CDR-H1 comprising the amino acid sequence of SEQ ID NO: 15, (ii) a CDR-H2 comprising the amino acid sequence of SEQ ID NO: 16, (iii) a CDR-H3 comprising the amino acid sequence of SEQ ID NO: 17, (iv) a CDR-L1 comprising the amino acid sequence of SEQ ID NO: 8, (v) a CDR-L2 comprising the amino acid sequence of SEQ ID NO: 9, and (vi) a CDR-L3 comprising the amino acid sequence of SEQ ID NO: 10.

E14. The antibody, or antigen binding fragment thereof, of any one of E1-E52, wherein the antibody, or antigen-binding fragment thereof, comprises:

(i) a CDR-H1 comprising the amino acid sequence of SEQ ID NO: 30, (ii) a CDR-H2 comprising the amino acid sequence of SEQ ID NO: 41, (iii) a CDR-H3 comprising the amino acid sequence of SEQ ID NO: 17, (iv) a CDR-L1 comprising the amino acid sequence of SEQ ID NO: 25, (v) a CDR-L2 comprising the amino acid sequence of SEQ ID NO: 26, and (vi) a CDR-L3 comprising the amino acid sequence of SEQ ID NO: 27.

E15. The antibody, or antigen binding fragment thereof, of any one of E1-E12, wherein the antibody, or antigen-binding fragment thereof, comprises:

(i) a CDR-H1 comprising the amino acid sequence of SEQ ID NO: 40, (ii) a CDR-H2 comprising the amino acid sequence of SEQ ID NO: 63, (iii) a CDR-H3 comprising the amino acid sequence of SEQ ID NO: 49, (iv) a CDR-L1 comprising the amino acid sequence of SEQ ID NO: 25, (v) a CDR-L2 comprising the amino acid sequence of SEQ ID NO: 26, and (vi) a CDR-L3 comprising the amino acid sequence of SEQ ID NO: 27.

E16. The antibody, or antigen-binding fragment thereof, of any one of E1-E15, wherein the antibody, or antigen-binding fragment thereof, comprises a heavy chain variable region (VH) framework sequence derived from a human germline VH sequence selected from the group consisting of IGHV1-2*02, IGHV1-3*01, IGHV1-46*01, IGHV1-69*01, IGHV1-69*02, IGHV1-8*01, IGHV3-7*01, IGHV3-13*01, IGHV3-23*01, IGHV3-23*04, IGHV3-30*01, IGHV3-30*18, IGHV5-10-1*01, IGHV5-10-1*04, and IGHV5-51*01.

E17. The antibody, or antigen-binding fragment thereof, of E16, wherein the heavy chain variable region (VH) framework sequence is derived from a human germline VH sequence of IGHV3-7*01.

E18. The antibody, or antigen-binding fragment thereof, of any one of E1-E17, wherein the antibody, or antigen-binding fragment thereof, comprises a light chain variable region (VL) framework sequence derived from a human germline VL sequence selected from the group consisting of IGKV1-12*01, IGKV1-13*02, IGKV1-33*01, IGKV1-39*01, IGKV1-5*01, IGKV3-11*01, IGKV3-15*01, IGKV3-20*01, IGKV3D-20*02, and IGKV4-1*01.

E19. The antibody, or antigen-binding fragment thereof, of E18, wherein the light chain variable region (VL) framework sequence is derived from a human germline VL sequence of IGKV1-39*01.

E20. The antibody, or antigen binding fragment thereof, of any one of E1-E19 wherein the antibody, or antigen-binding fragment thereof, comprises:

(i) a heavy chain variable region (VH) comprising the amino acid sequence selected from the group consisting of SEQ ID NO: 22, 32, 42, 50, 53, 55, 57, 60, 64, 67, 69, 74 and 77; and (ii) a light chain variable region (VL) comprising the amino acid sequence selected from the group consisting of SEQ ID NO: 12, 28, 35, 38, 46, 72 and 79.

E21. The antibody, or antigen binding fragment thereof, of any one of E1-E20 wherein the antibody, or antigen-binding fragment thereof, comprises:

(i) a VH comprising an amino acid sequence at least 90%, at least 91%, at least 92%, at least 93%, at least 94%, at least 95%, at least 96%, at least 97%, at least 98%, at least 99%, or 100% identical to SEQ ID NO: 22, 32, 42, 50, 53, 55, 57, 60, 64, 67, 69, 74 or 77; and (ii) a VL comprising an amino acid sequence at least 90%, at least 91%, at least 92%, at least 93%, at least 94%, at least 95%, at least 96%, at least 97%, at least 98%, at least 99%, or 100% identical to SEQ ID NO: 12, 28, 35, 38, 46, 72 or 79.

E22. The antibody, or antigen binding fragment thereof, of any one of E1-E21, wherein the antibody, or antigen-binding fragment thereof, comprises:

(i) a VH comprising the amino acid sequence of SEQ ID NO: 22 and a VL comprising the amino acid sequence of SEQ ID NO: 12;

(ii) a VH comprising the amino acid sequence of SEQ ID NO: 55 and a VL comprising the amino acid sequence of SEQ ID NO: 28;

(iii) a VH comprising the amino acid sequence of SEQ ID NO: 74 and a VL comprising the amino acid sequence of SEQ ID NO: 28;

(iv) a VH comprising an amino acid sequence at least 90%, at least 91%, at least 92%, at least 93%, at least 94%, at least 95%, at least 96%, at least 97%, at least 98%, at least 99%, or 100% identical to SEQ ID NO: 22 and a VL comprising an amino acid sequence at least 90%, at least 91%, at least 92%, at least 93%, at least 94%, at least 95%, at least 96%, at least 97%, at least 98%, at least 99%, or 100% identical to SEQ ID NO: 12;

(v) a VH comprising an amino acid sequence at least 90%, at least 91%, at least 92%, at least 93%, at least 94%, at least 95%, at least 96%, at least 97%, at least 98%, at least 99%, or 100% identical to SEQ ID NO: 55 and a VL comprising an amino acid sequence at least 90%, at least 91%, at least 92%, at least 93%, at least 94%, at least 95%, at least 96%, at least 97%, at least 98%, at least 99%, or 100% identical to SEQ ID NO: 28; or (vi) a VH comprising an amino acid sequence at least 90%, at least 91%, at least 92%, at least 93%, at least 94%, at least 95%, at least 96%, at least 97%, at least 98%, at least 99%, or 100% identical to SEQ ID NO: 74 and a VL comprising an amino acid sequence at least 90%, at least 91%, at least 92%, at least 93%, at least 94%, at least 95%, at least 96%, at least 97%, at least 98%, at least 99%, or 100% identical to SEQ ID NO: 28.

E23. An antibody, or antigen binding fragment thereof, comprising:

(i) the CDR-H1, CDR-H2, and CDR-H3 sequences as set forth in SEQ ID NO: 22 and the CDR-L1, CDR-L2, and CDR-L3 sequences as set forth in SEQ ID NO: 12, (ii) the CDR-H1, CDR-H2, and CDR-H3 sequences as set forth in SEQ ID NO: 55 and the CDR-L1, CDR-L2, and CDR-L3 sequences as set forth in SEQ ID NO: 28, or (iii) the CDR-H1, CDR-H2, and CDR-H3 sequences as set forth in SEQ ID NO: 74 and the CDR-L1, CDR-L2, and CDR-L3 sequences as set forth in SEQ ID NO: 28.

E24. The antibody, or antigen-binding fragment thereof, of any one of E1-E23, wherein the antibody, or antigen-binding fragment thereof, comprises a human Vκ or $V_\lambda$ light chain constant domain.

E25. The antibody, or antigen-binding fragment thereof, of E24, wherein the antibody, or antigen-binding fragment thereof, comprises a human Vκ light chain constant domain.

E26. The antibody, or antigen-binding fragment thereof, of any one of E1-E25, wherein the antibody, or antigen-binding fragment thereof, comprises a heavy chain constant domain.

E27. The antibody, or antigen-binding fragment thereof, of E26, wherein the heavy chain constant domain comprises an IgA (for example $IgA_1$ or $IgA_2$), IgD, IgE, IgM, or IgG (for example $IgG_1$, $IgG_2$, $IgG_3$, or $IgG_4$).

E28. The antibody, or antigen-binding fragment thereof, of E27, wherein the heavy chain constant domain comprises an IgG.

E29. The antibody, or antigen-binding fragment thereof, of E28, wherein the IgG is selected from the group consisting of $IgG_1$, $IgG_2$, $IgG_3$, and $IgG_4$.

E30. The antibody, or antigen-binding fragment thereof, of E29, wherein the IgG is $IgG_1$.

E31. The antibody, or antigen-binding fragment thereof, of any one of E1-E30, wherein the antibody, or antigen-binding fragment thereof, comprises an Fc domain.

E32. The antibody, or antigen-binding fragment thereof, of E31, wherein the Fc domain comprises an IgG1 heavy chain $CH_2$ domain and an IgG heavy chain $CH_3$ domain.

E33. The antibody, or antigen binding fragment thereof, of any one of E1-E32, wherein the antibody, or antigen-binding fragment thereof, comprises:

(i) a heavy chain (HC) comprising the amino acid sequence selected from the group consisting of SEQ ID NO: 14, 29, 39, 47, 51, 54, 56, 58, 61, 65, 68, 73, and 75; and (ii) a light chain (LC) comprising the amino acid sequence selected from the group consisting of SEQ ID NO: 7, 24, 33, 36, 43, 70 and 78.

E34. The antibody, or antigen binding fragment thereof, of any one of E1-E33, wherein the antibody, or antigen-binding fragment thereof, comprises:

(i) a HC comprising an amino acid sequence at least 90%, at least 91%, at least 92%, at least 93%, at least 94%, at least 95%, at least 96%, at least 97%, at least 98%, at least 99%, or 100% identical to SEQ ID NO: 14, 29, 39, 47, 51, 54, 56, 58, 61, 65, 68, 73, and 75; and (ii) a LC comprising an amino acid sequence at least 90%, at least 91%, at least 92%, at least 93%, at least 94%, at least 95%, at least 96%, at least 97%, at least 98%, at least 99%, or 100% identical to SEQ ID NO: 7, 24, 33, 36, 43, 70 and 78.

E35. The antibody, or antigen binding fragment thereof, of any one of E1-E34, wherein the antibody, or antigen-binding fragment thereof, comprises:

(i) a HC comprising, or consisting of, the amino acid sequence of SEQ ID NO: 14 and a LC comprising, or consisting of, the amino acid sequence of SEQ ID NO: 7;

(ii) a HC comprising, or consisting of, the amino acid sequence of SEQ ID NO: 54 and a LC comprising, or consisting of, the amino acid sequence of SEQ ID NO: 24;

(iii) a HC comprising, or consisting of, the amino acid sequence of SEQ ID NO: 73 and a LC comprising, or consisting of, the amino acid sequence of SEQ ID NO: 24;

(iv) a HC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 14 and a LC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 7;

(v) a HC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 54 and a LC comprising, or consisting of, an amino acid sequence of SEQ ID NO: 24; or (vi) a HC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 73 and a LC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 24.

E36. An antibody, or antigen binding fragment thereof, comprising a HC comprising, or consisting of, the amino acid sequence of SEQ ID NO: 54 and a LC comprising, or consisting of, the amino acid sequence of SEQ ID NO: 24.

E37. An antibody, or antigen binding fragment thereof, comprising a HC comprising, or consisting of, the amino acid sequence of SEQ ID NO: 73 and a LC comprising, or consisting of, the amino acid sequence of SEQ ID NO: 24.

E38. The antibody, or antigen-binding fragment thereof, of any one of E1-E37, wherein the antibody, or antigen-binding fragment thereof, comprises the amino acid sequence encoded by the insert of the plasmid deposited at the ATCC and having ATCC Accession No. PTA-126810.

E39. The antibody, or antigen-binding fragment thereof, of any one of E1-E38, wherein the antibody, or antigen-binding fragment thereof, comprises the amino acid sequence encoded by the insert of the plasmid deposited at the ATCC and having ATCC Accession No. PTA-126811.

E40. An antibody, or antigen-binding fragment thereof, comprising the amino acid sequence encoded by the insert in the plasmid deposited at the ATCC and having ATCC Accession No. PTA-126810 and comprising the amino acid sequence encoded by the insert in the plasmid deposited at the ATCC and having ATCC Accession No. PTA-126811.

E41. The antibody, or antigen-binding fragment thereof, of any one of E1-E40, wherein the antibody, or antigen-binding fragment thereof, is an Fc fusion protein, a monobody, a maxibody, a bifunctional antibody, an scFab, an scFv, or a peptibody.

E42. The antibody, or antigen-binding fragment thereof, of any one of E2-E41, wherein the epitope further comprises at least one of the following amino acid residues: Glu78, Lys81, Thr85, Ile89, Arg93, Asp173, and Asn177, according to the numbering of SEQ ID NO: 1.

E43. The antibody, or antigen-binding fragment thereof, of E42, wherein the epitope comprises Glu78, Lys81, Glu82, Thr85, Ile89, Arg93, His170, Asp173, and Asn177, according to the numbering of SEQ ID NO: 1.

E44. The antibody, or antigen-binding fragment thereof, of any one of E2-E43, wherein (i) >80 Å$^2$ of accessible surface area (ASA) is buried by the interaction with CD1a, (ii) >90% of ASA in free state is buried by the interface and >30 Å$^2$ of ASA is buried by the interaction with CD1a, and/or (iii) at least one epitope amino acid residue interacts with the antibody, or antigen-binding fragment thereof, within 3.8 Å, via either a salt bridge or via a hydrogen bond, and at least 6 cross-interface non-hydrogen atom pairs lie within 3.8 Å.

E45. The antibody, or antigen-binding fragment thereof, of any one of E2-E44, wherein the epitope further comprises at least one of the following residues: Leu86, Asn146, Asn168, Ile174, His176, Asp181, and Arg185, according to the numbering of SEQ ID NO: 1.

E46. The antibody, or antigen-binding fragment thereof, of E45, wherein the epitope comprises the following residues: Glu78, Lys81, Leu86, Glu82, Thr85, Ile89, Arg93, Asn146, Asn168, His170, Asp173, Ile174, His176, Asn177, Asp181, and Arg185, according to the numbering of SEQ ID NO: 1.

E47. The antibody, or antigen-binding fragment thereof, of any one of E45-E46, wherein (i) >40 Å$^2$ of accessible surface area (ASA) is buried by the interaction with CD1a, (ii) >50% of ASA in free state is buried by the interaction with CD1a, (iii) at least one epitope amino acid residue interacts with the antibody, or antigen-binding fragment thereof, within 3.8 Å, and at least 4 cross-interface non-hydrogen atom pairs lie within 3.8 Å, (iv) at least one epitope amino acid residue interacts with the antibody, or antigen-binding fragment thereof, via a salt bridge, and/or (v) at least one epitope amino acid residue interacts with the antibody, or antigen-binding fragment thereof, via a hydrogen bond.

E48. The antibody, or antigen-binding fragment thereof, of any one of E2-E43, E45-E46, wherein the epitope further comprises at least one of the following residues: Glu79, Leu83, Glu84, Arg88, Ile92, Gln167, Gln169, Leu178, Ser180, and Thr182 according to the numbering of SEQ ID NO: 1.

E49. The antibody, or antigen-binding fragment thereof, of E48, wherein the epitope comprises the following residues: Glu78, Glu79, Lys81, Glu82, Leu83, Glu84, Thr85, Leu86, Arg88, Ile89, Ile92, Arg93, Asn146, Gln167, Asn168, Gln169, His170, Asp173, Ile174, His176, Asn177, Leu178, Ser180, Asp181, Thr182 and Arg185, according to the numbering of SEQ ID NO: 1.

E50. The antibody, or antigen-binding fragment thereof, of E49, wherein the epitope does not comprise Asn146 and/or Asn168 according to the numbering of SEQ ID NO: 1.

E51. The antibody, or antigen-binding fragment thereof, of any one of E48-E49, wherein (i) >20 Å$^2$ of accessible surface area (ASA) is buried by the interaction with CD1a, and which reciprocally buries >10 Å$^2$ of accessible surface area (ASA) of the CD1a epitope, (ii) at least one epitope amino acid residue interacts with the antibody, or antigen-binding fragment thereof, within 3.8 Å, (iii) at least one epitope amino acid residue interacts with the antibody, or antigen-binding fragment thereof, via a salt bridge, (iv) at least one epitope amino acid residue interacts with the antibody, or antigen-binding fragment thereof, via a water-mediated hydrogen bond and/or (v) at least one epitope amino acid residue interacts with the antibody, or antigen-binding fragment thereof, via a hydrogen bond.

E52. An antibody, or antigen-binding fragment thereof, that specifically binds to CD1a, wherein the antibody, or antigen-binding fragment thereof, is selected from the group consisting of: Ab138, Ab491, Ab492, Ab504, Ab514, Ab555, Ab556, Ab559, Ab560, Ab571, Ab572, Ab579, Ab585, Ab599, Ab609, Ab610, Ab616, Ab623, Ab624, Ab656, Ab657, Ab660, Ab673, Ab681, and Ab689 (e.g., as disclosed in Table 14).

E53. An isolated antibody, or antigen-binding fragment thereof, that competes for binding to CD1a with an antibody, or antigen-binding fragment thereof, of any one of E1-E52.

E54. An isolated antibody, or antigen-binding fragment thereof, that competes for binding to CD1a with an antibody, or antigen-binding fragment thereof, selected from the group consisting of: Ab138, Ab571, and Ab673.

E55. An isolated antibody, or antigen-binding fragment thereof, that competes for binding to CD1a with an antibody, or antigen-binding fragment thereof, of antibody Ab571.

E56. An isolated antibody, or antigen-binding fragment thereof, that specifically binds CD1a, wherein the antibody, or antigen-binding fragment thereof, binds substantially the same epitope as an antibody, or antigen-binding fragment thereof, of any one of E1-E52.

E57. An isolated antibody, or antigen-binding fragment thereof, that specifically binds CD1a, wherein the antibody, or antigen-binding fragment thereof, binds substantially the same epitope as an antibody, or antigen-binding fragment thereof, selected from the group consisting of: Ab138, Ab491, Ab492, Ab504, Ab514, Ab555, Ab556, Ab559, Ab560, Ab571, Ab572, Ab579, Ab585, Ab599, Ab609, Ab610, Ab616, Ab623, Ab624, Ab656, Ab657, Ab660, Ab673, Ab681, and Ab689 (e.g., as disclosed in Table 14).

E58. An isolated antibody, or antigen-binding fragment thereof, that specifically binds CD1a, wherein the antibody, or antigen-binding fragment thereof, binds substantially the same epitope as an antibody, or antigen-binding fragment thereof, selected from the group consisting of: Ab138, Ab571, and Ab673.

E59. An isolated antibody, or antigen-binding fragment thereof, that specifically binds CD1a, wherein the antibody, or antigen-binding fragment thereof, binds substantially the same epitope as an antibody Ab571.

E60. The antibody, or antigen-binding fragment thereof, of any one of E1-E59, wherein the antibody, or antigen binding fragment thereof, binds CD1a with a $K_D$ about or less than a value selected from the group consisting of about 500 nM, 400 nM, 300 nM, 200 nM, 175 nM, 150 nM, 125 nM, 100 nM, 90 nM, 80 nM, 70 nM, 60 nM, 50 nM, 40 nM, 30 nM, 20 nM, 10 nM, 5 nM, 4 nM, 3 nM, 2 nM, 1 nM, 900 pM, 800 pM, 700 pM, 600 pM, 500 pM, 400 pM, 300 pM, 200 pM, 180 pM, 160 pM, 140 pM, 120 pM, 100 pM, 80 pM, 60 pM, 40 pM, 20 pM and 10 pM.

E61. The antibody, or antigen-binding fragment thereof, of any one of E1-E60, wherein the antibody, or antigen binding fragment thereof, binds CD1a with a $K_D$ value of or less than 500 pM, 400 pM, 300 pM, 200 pM, 190 pM, 180 pM, 181 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM or 10 pM.

E62. The antibody, or antigen-binding fragment thereof, of any one of E1-E61, wherein the CD1a is a human CD1a, cyno CD1a, dog CD1a and/or rabbit CD1a.

E63. The antibody, or antigen-binding fragment thereof, of any one of E1-E62, wherein the antibody, or antigen binding fragment thereof, binds human CD1a with a $K_D$ value of about 250 pM to about 100 pM, about 200 pM to about 150 pM or about 190 pM to about 170 pM.

E64. The antibody, or antigen-binding fragment thereof, of E63, wherein the antibody, or antigen binding fragment thereof, binds human CD1a with a $K_D$ value of about 181.39+/−11.92 pM or about 0.17 nM.

E65. The antibody, or antigen-binding fragment thereof, of any one of E1-E64, wherein the antibody, or antigen binding fragment thereof, binds cynomolgus monkey CD1a with a $K_D$ value of about 100 pM to about 30 pM, about 80 pM to about 40 pM, or about 70 pM to about 50 pM.

E66. The antibody, or antigen-binding fragment thereof, of E65, wherein the antibody, or antigen binding fragment thereof, binds cynomolgus monkey CD1a with a $K_D$ value of about 60.35+/−11.04 pM.

E67. The antibody, or antigen-binding fragment thereof, of any one of E60-E66, wherein the antibody, or antigen binding fragment thereof, comprises a heavy chain complementarity determining region-three (CDR-H3) comprising the amino acid sequence selected from the group consisting of SEQ ID NO: 17, 49, and 52.

E68. The antibody, or antigen-binding fragment thereof, of any one of E60-E67, wherein the antibody, or antigen binding fragment thereof, comprises a heavy chain complementarity determining region-three (CDR-H3) comprising the amino acid sequence selected from the group consisting of SEQ ID NO: 17 and 49.

E69. The isolated antibody, or antigen-binding fragment thereof, of any one of E60-E68, wherein the $K_D$ value is measured by surface plasmon resonance (SPR), optionally using a Biacore T200 or a Biacore 8K instrument.

E70. The antibody, or antigen-binding fragment thereof, of any one of E60-E68, wherein the $K_D$ value is measured by bio-layer interferometry (BLI), optionally using a ForteBio Octet instrument.

E71. The antibody, or antigen-binding fragment thereof, of any one of E1-E70, wherein the antibody, or antigen-binding fragment thereof, does not induce anti-drug antibodies.

E72. The antibody, or antigen-binding fragment thereof, of any one of E1-E71, wherein the predicted immunogenic potential of the antibody, as indicated by the Tregitope (T-reg) adjusted score, is less than or equal to about −35.

E73. The antibody, or antigen-binding fragment thereof, of any one of E1-E71, wherein the predicted immunogenic potential of the antibody, as indicated by T-reg adjusted score, is less than or equal to about −52.

E74. The antibody, or antigen-binding fragment thereof, of any one of E1-E71, wherein the predicted immunogenic potential of the antibody, as indicated by T-reg adjusted score, is less than or equal to about −69.

E75. The antibody, or antigen-binding fragment thereof, of any one of E1-E72, wherein the predicted immunogenic potential of the antibody, as indicated by the T-reg adjusted score, is less than or equal to about −35 and there are 8 or less than 8 non-germline T cell epitopes.

E76. The antibody, or antigen-binding fragment thereof, of any one of E1-E73, wherein the predicted immunogenic potential of the antibody, as indicated by the T-reg adjusted score, is less than or equal to about −52 and there are 3 or less than 3 non-germline T cell epitopes.

E77. The antibody, or antigen-binding fragment thereof, of any one of E1-E74, wherein the predicted immunogenic potential of the antibody, as indicated by the Tregitope (T-reg) adjusted score, is less than or equal to about −69 and there is 1 or less than 1 non-germline T cell epitope.

E78. The antibody, or antigen-binding fragment thereof, of any one of E1-E77, wherein the antibody, or antigen-binding fragment thereof, is at low risk for polyreactivity, as measured by, for example an AC-SINS assay, a DNA binding assay and/or an insulin binding assay.

E79. The antibody, or antigen-binding fragment thereof, of any one of E1-E78, wherein the antibody, or antigen-binding fragment thereof, has weak or no binding to cyno or human CD1b, to cyno or human CD1c and/or to cyno, rat, mouse or human CD1d. “Weak” binding means a KD equal to or greater than 500 nM when measured by surface plasmon resonance or by biolayer interferometry.

E80. The antibody, or antigen-binding fragment thereof, of any one of E1-E79, wherein the antibody, or antigen-binding fragment thereof, inhibits CD1a-dependent Cluster of Differentiation 69 (CD69) expression with an $IC_{50}$ value of no more than about 50 nM, 40 nM, 20 nM, 10 nM, 5 nM, 4 nM, 3 nM, 2 nM, or 1 nM.

E81. The antibody, or antigen-binding fragment thereof, of any one of E1-E80, wherein the antibody, or antigen-binding fragment thereof, inhibits CD1a-dependent CD69 expression with an $IC_{50}$ value of no more than about 5 nM, 4 nM, 3 nM, 2 nM, 1.97 nM, 1.9 nM, 1.8 nM, 1.7 nM, 1.6 nM, 1.5 nM, 1.4 nM, 1.3 nM, 1.2 nM, 1.1 nM, 1 nM, 0.9 nM, 0.8 nM, 0.7 nM, 0.6 nM, 0.5 nM, 0.4 nM, 0.3 nM, 0.2 nM, or 0.1 nM.

E82. The antibody, or antigen-binding fragment thereof, of any one of E1-E81, wherein the antibody, or antigen-binding fragment thereof, inhibits CD1a-dependent CD69 expression with an $IC_{50}$ value of no more than about 2000 pM, 1970 pM, 1500 pM, 1110 pM, 1000 pM, 500 pM, 400 pM, 300 pM, 200 pM, 100 pM, 90 pM, 80 pM, 70 pM, 60 pM, 50 pM, 40 pm, 30 pM, 20 pM, 10 pM, 9 pM, 8 pM, 7 pM, 6 pM, 5 pM, 4 pM, 3 pM, 2 pM, or 1 pM.

E83. The antibody, or antigen-binding fragment thereof, of any one of E1-E82, wherein the antibody, or antigen-binding fragment thereof, inhibits CD1a-dependent CD69 expression with an $IC_{50}$ value of about 1.11 nM or 0.894 nM.

E84. The antibody, or antigen-binding fragment thereof, of any one of E1-E82, wherein the antibody, or antigen-binding fragment thereof, inhibits CD1a-dependent CD69 expression with an $IC_{50}$ value of about 1.97 nM.

E85. The antibody, or antigen-binding fragment thereof, of any one of E1-E82, wherein the antibody, or antigen-binding fragment thereof, inhibits CD1a-dependent CD69 expression with an $IC_{50}$ value of about 0.3 nM.

E86. The antibody, or antigen-binding fragment thereof, of any one of E1-E85, wherein the antibody, or antigen-binding fragment thereof, inhibits CD1a-dependent interleukin-2 (IL-2) production with an $IC_{50}$ value of no more than 5 nM, 4 nM, 3 nM, 2 nM, 1.9 nM, 1.8 nM, 1.7 nM, 1.6 nM, 1.5 nM, 1.4 nM, 1.3 nM, 1.2 nM, 1.1 nM, 1 nM, 0.9 nM, 0.8 nM, 0.7 nM, 0.6 nM, 0.5 nM, 0.4 nM, 0.3 nM, 0.22 nM, 0.2 nM, 0.18 nM, or 0.1 nM.

E87. The antibody, or antigen-binding fragment thereof, of any one of E1-E86, wherein the antibody, or antigen-binding fragment thereof, inhibits CD1a-dependent IL-2 production with an $IC_{50}$ value of no more than about 500 pM, 400 pM, 300 pM, 220 pM, 200 pM, 100 pM, 90 pM, 80 pM, 70 pM, 60 pM, 50 pM, 40 pm, 30 pM, 20 pM, 10 pM, 9 pM, 8 pM, 7 pM, 6 pM, 5 pM, 4 pM, 3 pM, 2 pM, or 1 pM.

E88. The antibody, or antigen-binding fragment thereof, of any one of E1-E87, wherein the antibody, or antigen-binding fragment thereof, inhibits CD1a-dependent IL-2 production with an $IC_{50}$ value of about 0.268 nM or 0.18 nM.

E89. The antibody, or antigen-binding fragment thereof, of any one of E80-E88, wherein the $IC_{50}$ values are determined using CD1a-restricted T cell receptor BK6-expressing Jurkat 76 (J76) cells.

E90. The antibody, or antigen-binding fragment thereof, of any one of E1-E89, wherein the antibody, or antigen-binding fragment thereof, reduces dermatitis score in patients with atopic dermatitis by at least 5%, 10%, 20%, 30%, 40%, 50%, 60%, 70%, 80%, 90%, 95%, 98%, or 100% as compared to the dermatitis score in untreated patients.

E91. The antibody, or antigen-binding fragment thereof, of E90, wherein the antibody, or antigen-binding fragment thereof, reduces dermatitis score in patients with atopic dermatitis by 70%, 75%, 80%, 85%, 90%, 95%, 98%, or 100% as compared to the dermatitis score in untreated patients.

E92. The antibody, or antigen-binding fragment thereof, of any one of E1-E91, wherein the antibody, or antigen-binding fragment thereof, reduces dermatitis score in a human CD1a transgenic house dust mite (HDM) induced dermatitis mouse model by at least 5%, 10%, 20%, 30%, 40%, 50%, 60%, 70%, 80%, 90%, 95%, 98%, or 100% as compared to the dermatitis score in untreated or isotype treated controls.

E93. The antibody, or antigen-binding fragment thereof, of E92, wherein the antibody, or antigen-binding fragment thereof, reduces dermatitis score in a human CD1a transgenic house dust mite (HDM) induced dermatitis mouse model by at least 70%, 75%, 80%, 85%, 90%, 95%, 98%, or 100% as compared to the dermatitis score in untreated or isotype treated controls.

E94. The antibody, or antigen-binding fragment thereof, of any one of E1-E93, wherein the antibody, or antigen-binding fragment thereof, reduces serum IgE levels in a human CD1a transgenic house dust mite (HDM) induced dermatitis mouse model by at least 5%, 10%, 20%, 30%, 40%, 50%, 60%, 70%, 80%, 90%, 95%, 98%, or 100% as compared to the serum IgE levels in untreated or isotype treated controls.

E95. The antibody, or antigen-binding fragment thereof, of E94, wherein the antibody, or antigen-binding fragment thereof, reduces serum IgE levels in a human CD1a transgenic house dust mite (HDM) induced dermatitis mouse model by at least 70%, 75%, 80%, 85%, 90%, 95%, 98%, or 100% as compared to the serum IgE levels in untreated or isotype treated controls.

E96. The antibody, or antigen-binding fragment thereof, of any one of E1-E95, wherein the antibody, or antigen-binding fragment thereof, reduces HDM-specific IgE antibody titer in a human CD1a transgenic house dust mite HDM induced dermatitis mouse model by at least 5%, 10%, 20%, 30%, 40%, 50%, 60%, 70%, 80%, 90%, 95%, 98%, or 100% as compared to the serum IgE levels in untreated or isotype treated controls.

E97. The antibody, or antigen-binding fragment thereof, of E96, wherein the antibody, or antigen-binding fragment thereof, reduces HDM-specific IgE antibody titer in a human CD1a transgenic HDM induced dermatitis mouse model by at least 70%, 75%, 80%, 85%, 90%, 95%, 98%, or 100% as compared to the HDM-specific IgE antibody titer in untreated or isotype treated controls.

E98. The antibody, or antigen-binding fragment thereof, of any one of E1-E97, wherein the antibody, or antigen-binding fragment thereof, reduces expression levels of atopic dermatitis-associated genes in a human CD1a transgenic house dust mite (HDM) induced dermatitis mouse model by at least 5%, 10%, 20%, 30%, 40%, 50%, 60%, 70%, 80%, 90%, 95%, 98%, or 100% as compared to the expression levels of atopic dermatitis-associated genes in untreated or isotype treated controls.

E99. The antibody, or antigen-binding fragment thereof, of E98, wherein the antibody, or antigen-binding fragment thereof, reduces expression levels of atopic dermatitis-associated genes in a human CD1a transgenic house dust mite (HDM) induced dermatitis mouse model by at least 70%, 75%, 80%, 85%, 90%, 95%, 98%, or 100% as compared to the expression levels of atopic dermatitis-associated genes in untreated or isotype treated controls.

E100. The antibody, or antigen-binding fragment thereof, of any one of E98-E99, wherein the atopic dermatitis-associated genes comprise Thymic Stromal Lymphopoietin (TSLP), filaggrin (FLG), interleukin-33 (IL-33), C—C motif chemokine ligand 26 (CCL-26), IL-23p40, C—X—C chemokine ligand 1 (CXCL-1) and CCL-20.

E101. An isolated nucleic acid molecule comprising a nucleic acid sequence encoding the antibody, or antigen binding fragment thereof, of any one of E1-E100.

E102. An isolated nucleic acid molecule comprising at least one nucleic acid sequence encoding the antibody, or antigen binding fragment thereof, of any one of E1-E101.

E103. An isolated nucleic acid molecule encoding an antibody, or antigen-binding fragment thereof, that specifically binds human CD1a, wherein said nucleic acid molecule comprises one or more nucleic acid sequences selected from the group consisting of:

(i) the nucleic acid sequence of SEQ ID NO: 80,
(ii) the nucleic acid sequence of SEQ ID NO: 81,
(iii) the nucleic acid sequence of SEQ ID NO: 82,
(iv) the nucleic acid sequence of SEQ ID NO: 83,
(v) the nucleic acid sequence of SEQ ID NO: 84,
(vi) the nucleic acid sequence of SEQ ID NO: 85,
(vii) the nucleic acid sequence of the insert of the vector deposited as Ab571-VH under ATCC Accession No. PTA-126810, and the nucleic acid sequence of the insert of the vector deposited as Ab571-VL under ATCC Accession No. PTA-126811.

E104. An isolated nucleic acid molecule comprising, or consisting of, the nucleic acid sequence of SEQ ID NO: 80, the nucleic acid sequence of SEQ ID NO: 81, or both.

E105. An isolated nucleic acid molecule comprising, or consisting of, the nucleic acid sequence of SEQ ID NO: 82, the nucleic acid sequence of SEQ ID NO: 83, or both.

E106. An isolated nucleic acid molecule encoding an antibody, or an antigen-binding fragment thereof, that specifically binds human CD1a, wherein said nucleic acid molecule comprises the nucleic acid sequence of the insert of the plasmid deposited with the ATCC and having the Accession No. PTA-126810.

E107. An isolated nucleic acid molecule encoding an antibody, or an antigen-binding fragment thereof, that specifically binds human CD1a, wherein said nucleic acid molecule comprises the nucleic acid sequence of the insert of the plasmid deposited with the ATCC and having the Accession No. PTA-126811.

E108. An isolated nucleic acid molecule encoding an antibody, or an antigen-binding fragment thereof, that specifically binds human CD1a, wherein said nucleic acid comprises the nucleic acid sequence of the insert of the plasmid deposited with the ATCC and having the Accession No. PTA-126810 and the nucleic acid sequence of the insert of the plasmid deposited with the ATCC and having the Accession No. PTA-126811.

E109. An isolated nucleic acid molecule comprising the nucleic acid sequence of the insert of the plasmid deposited with the ATCC and having the Accession No. PTA-126810.

E110. An isolated nucleic acid molecule comprising the nucleic acid sequence of the insert of the plasmid deposited with the ATCC and having the Accession No. PTA-126811.

E111. An isolated nucleic acid molecule comprising the nucleic acid sequence of the insert of the plasmid deposited with the ATCC and having the Accession No. PTA-126810, and the nucleic acid sequence of the insert of the plasmid deposited with the ATCC and having the Accession No. PTA-126811.

E112. An isolated nucleic acid molecule encoding the VH of an antibody, or antigen-binding fragment thereof, that specifically binds human CD1a, comprising a nucleic acid at least 90%, 91%, 92%, 93%, 94%, 95%, 96%, 97%, 98% or 99% identical to a nucleic acid sequence of SEQ ID NO: 80 or SEQ ID NO: 84.

E113. An isolated nucleic acid molecule encoding the VL of an antibody, or antigen-binding fragment thereof, that specifically binds human CD1a, comprising a nucleic acid at least 90%, 91%, 92%, 93%, 94%, 95%, 96%, 97%, 98% or 99% identical to a nucleic acid sequence of SEQ ID NO: 81.

E114. An isolated nucleic acid molecule encoding the HC of an antibody, or antigen-binding fragment thereof, that specifically binds human CD1a, comprising a nucleic acid at least 90%, 91%, 92%, 93%, 94%, 95%, 96%, 97%, 98% or 99% identical to a nucleic acid sequence of SEQ ID NO: 82 or SEQ ID NO: 85.

E115. An isolated nucleic acid molecule encoding the LC of an antibody, or antigen-binding fragment thereof, that specifically binds human CD1a, comprising a nucleic acid at least 90%, 91%, 92%, 93%, 94%, 95%, 96%, 97%, 98% or 99% identical to a nucleic acid sequence of SEQ ID NO: 83.

E116. A vector comprising the nucleic acid molecule of any one of E101-E115.

E117. A host cell comprising the nucleic acid molecule of any one of E101-115, or the vector of E116.

E118. A host cell comprising a nucleic acid molecule comprising the nucleic acid sequence of SEQ ID NO: 80 and/or the nucleic acid sequence of SEQ ID NO: 81.

E119. A host cell comprising a nucleic acid molecule comprising the nucleic acid sequence of SEQ ID NO: 82 and/or the nucleic acid sequence of SEQ ID NO: 83.

E120. The host cell of any one of E117-E119, wherein the cell is a mammalian cell or an insect cell.

E121. The host cell of E120, wherein the host cell is a mammalian cell selected from the group consisting of a CHO cell, an HEK-293 cell, an NS0 cell, a PER.C6® cell, or a Sp2.0 cell.

E122. A method of making an antibody or antigen-binding fragment thereof, comprising culturing the host cell of any one of E117-E121, under a condition wherein said antibody, or antigen-binding fragment, is expressed by the host cell.

E123. The method of E122, further comprising isolating said antibody or antigen-binding fragment thereof.

E124. A pharmaceutical composition comprising an antibody, or antigen-binding fragment thereof, of any one of E1-E100, and a pharmaceutically acceptable carrier or excipient.

E125. The pharmaceutical composition of E124, wherein the composition comprises 1.12 mg/mL L-histidine, 2.67 mg/mL L-histidine hydrochloride monohydrate, 85 mg/mL sucrose, 0.05 mg/mL EDTA disodium dihydrate, 0.2 mg/mL polysorbate 80 at pH 5.8.

E126. The pharmaceutical composition of E124 or E125, wherein the composition comprises 20 mM histidine, 8.5% sucrose, and 0.02% polysorbate 80, 0.005% EDTA at pH 5.8.

E127. The pharmaceutical composition of any one of E124-E126, wherein the composition comprises about 2 mg/mL, 5 mg/mL, 10 mg/mL, 15 mg/mL, 20 mg/mL, 25 mg/mL, 50 mg/mL, 75 mg/mL, 100 mg/mL, 125 mg/mL, 150 mg/mL antibody, or antigen binding fragment thereof.

E128. The pharmaceutical composition of E127, wherein the composition comprises about 100 mg/mL antibody, or antigen binding fragment thereof.

E129. The pharmaceutical composition of any one of E124-E128, wherein the dose is a 1 mL dose.

E130. The pharmaceutical composition of E124-E129, wherein the composition is suitable for subcutaneous (SC) and/or intravenous (IV) administration.

E131. The pharmaceutical composition of any one of E124-E130, wherein the antibody, or antigen-binding fragment thereof, comprises i) CDR-H1, CDR-H2, and CDR-H3 sequences as set forth in SEQ ID NO:55 and CDR-L1, CDR-L2, and CDR-L3 sequences of SEQ ID NO: 28; ii) a VH domain comprising the amino acid sequence of SEQ ID NO: 55 and a VL domain comprising the amino acid sequence of SEQ ID NO: 28; or iii) a HC comprising the amino acid sequence of SEQ ID NO: 54 and a LC comprising the amino acid sequence of SEQ ID NO: 24.

E132. The pharmaceutical composition of any one of E124-E131 further comprising an additional therapeutically active compound.

E133. The pharmaceutical composition of E132, wherein the additional therapeutically active compound comprises antagonists to one or more of IL-1a, IL-1b, IL-2, IL-3, IL-4, IL-5, IL-6, IL-8, IL-9, IL-10, IL-12, IL-13, IL-17, IL-18, IL-21, IL-23, IL-25, IL-26, IL-31, IL36, IFNα, IFNγ, or antagonists of their respective receptors, anti-inflammatory agents, recombinant interferon gamma, NSAIDs, steroids, calcineurin inhibitors, and/or corticosteroids.

E134. The pharmaceutical composition of E132, wherein the additional therapeutically active compound comprises dupilumab.

E135. A method of reducing or inhibiting CD1a activity, comprising administering to a subject in need thereof a therapeutically effective amount of the antibody, or antigen-binding fragment thereof, of any one of E1-E100, or the pharmaceutical composition of any one of E124-E134.

E136. The method of E135, further comprising comparing the activity of CD1a before administration with the level of CD1a activity after administration of the antibody.

E137. The method of any one of E135-E136, wherein reducing or inhibiting CD1a activity treats a disease, disorder, or condition which is improved, ameliorated, inhibited, or prevented by removal, inhibition, or reduction of CD1a activity.

E138. The method of any one of E135-E137, wherein the activity of CD1a is selected from the group consisting of:

(a) CD1a binding to T cell receptors;
(b) CD1a-mediated lipid presentation to T cells and their subsequent activation;
(c) CD1a-dependent CD69 expression;
(d) CD1a-dependent IL-2 production;
(e) CD1a-dependent increase in serum IgE levels;
(f) CD1a-dependent increase in antigen-specific IgE antibodies; and
(g) CD1a-dependent increase in expression levels of atopic dermatitis-associated genes (e.g., but not limited to, TSLP, FLG, IL-33, CCL-26, IL-23p40, CCL-20, and/or CCL-20).

E139. A method of reducing the level of CD1a in a subject in need thereof, the method comprising administering to a subject a therapeutically effective amount of the antibody, or antigen-binding fragment thereof, of any one of E1-E100, or the pharmaceutical composition of any one of E124-E134.

E140. A method of reducing or inhibiting CD1a binding to T-cell receptors in a subject in need thereof, the method comprising administering to a subject a therapeutically effective amount of the antibody, or antigen-binding fragment thereof, of any one of E1-E100, or the pharmaceutical composition of any one of E124-E134.

E141. A method of treating and/or preventing a disease, disorder and/or condition associated with, or mediated by, CD1a expression and/or CD1a binding to a ligand, comprising administering to a subject in need thereof a therapeutically effective amount of the antibody, or antigen-binding fragment thereof, of any one of E1-E100, or the pharmaceutical composition of any one of E124-E134.

E142. The method of E141, wherein the disease, disorder, and/or condition is selected from the group consisting of inflammatory bowel disease, allergies, allergic rhinitis, allergic conjunctivitis, vernal keratoconjunctivitis, a seasonal allergy, pet allergy, asthma, food allergy, peanut allergy, atopic dermatitis, contact dermatitis, chronic rhinosinusitis with nasal polyps (CRSwNP), allergic rhinitis, bronchitis, chronic obstructive pulmonary disease (COPD), viral exacerbations of respiratory disease, viral infection in children and adults, (respiratory syncytial virus (RSV), rhinovirus, influenza), urticarias, eosinophilic esophagitis, chronic fibrosis, liver fibrosis, non-alcoholic steatohepatitis (NASH), chronic kidney disease, idiopathic pulmonary fibrosis (IPF), scleroderma, systemic sclerosis, acute kidney injury, sepsis, pancreatitis, type 1 diabetes, graft-versus-host disease (GVHD), tissue transplant, Alzheimer's, rheumatoid arthritis, irritable bowel syndrome (IBS), Crohns disease, ulcerative colitis, multiple sclerosis, psoriasis, celiac disease and Raynaud's disease or phenomenon.

E143. A method of treating an inflammatory disease, comprising administering to a subject in need thereof a therapeutically effective amount of the antibody, or antigen-binding fragment thereof, of any one of E1-E100, or the pharmaceutical composition of any one of E124-E134.

E144. A method of treating atopic dermatitis, comprising administering to a subject in need thereof a therapeutically effective amount of the antibody, or antigen-binding fragment thereof, of any one of E1-E100, or the pharmaceutical composition of any one of E124-E134.

E145. A method of treating inflammatory bowel disease (IBD), comprising administering to a subject in need thereof a therapeutically effective amount of the antibody, or antigen-binding fragment thereof, of any one of any one of E1-E100, or the pharmaceutical composition of any one of E124-E134.

E146. The method of any one of E135-E145, wherein the treatment is a prophylactic treatment.

E147. The method of any one of E135-E146, wherein the subject is a human.

E148. The method of any one of E135-E147, wherein the subject is a patient with an inflammatory disease (for example, but not limited to, atopic dermatitis or IBD).

E149. The method of any one of E135-E148, wherein the antibody or antigen-binding fragment thereof, or pharmaceutical composition, is administered subcutaneously.

E150. The method of any one of E135-E149, wherein the antibody or antigen-binding fragment thereof, or pharmaceutical composition, is administered intravenously.

E151. The method of any one of E135-E150, wherein the antibody, or antigen-binding fragment thereof, or pharmaceutical composition, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, once every four months, once every five months, once every six months, once every seven months, once every eight months, once every nine months, once every ten months, once every eleven months or once every twelve months.

E152. The method of any one of E135-E151, wherein the antibody or antigen-binding fragment thereof, or pharmaceutical composition, is administered once a month or once every four weeks.

E153. The method of any one of E135-E152, wherein the antibody, or antigen-binding fragment thereof, or pharmaceutical composition, is administered once a week.

E154. The method of any one of E135-E153, wherein the therapeutically effective amount comprises a dose of about 1 mg to about 1000 mg of the anti-CD1a antibody, or antigen binding fragment thereof.

E155. The method of E154, wherein the dose is an initial fixed dose.

E156. The method of any one of E154-E155, wherein the dose is about 1 mg to about 10 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, about 90 mg to about 100 mg, about 100 mg to about 150 mg, about 150 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 to about 900 mg, or about 900 to about 1000 mg of the anti-CD1a antibody, or antigen binding fragment thereof.

E157. The method of any one of E154-E156, wherein the dose is about 15 mg, 20 mg, 25 mg, 30 mg, 35 mg, 40 mg, 100 mg, 150 mg, 300 mg, 500 mg or 600 mg of an anti-CD1a antibody, or antigen binding fragment thereof.

E158. The method of any one of E154-E157, wherein the dose is about 30 mg of the anti-CD1a antibody, or antigen binding fragment thereof.

E159. The method of any one of E154-E158, comprising administering the dose once a week, once every 2 weeks, once every three weeks, once every four weeks, once a month, once every two months, or a combination thereof.

E160. The method of any one of E154-E159, wherein the antibody or antigen-binding fragment thereof, or pharmaceutical composition, is administered at a dose of about 30 mg once every four weeks and the antibody is antibody Ab571 or Ab673.

E161. The method of any one of E154-E160, wherein the administration is subcutaneous or intravenous administration.

E162. The method of any one of E154-E161 comprising administering an antibody, or antigen-binding fragment thereof, comprising i) CDR-H1, CDR-H2, and CDR-H3 sequences as set forth in SEQ ID NO: 55 and CDR-L1, CDR-L2, and CDR-L3 sequences as set forth in SEQ ID NO: 28; ii) a VH domain comprising the amino acid sequence of SEQ ID NO:55 and a VL domain comprising the amino acid sequence of SEQ ID NO: 28; or iii) a HC comprising the amino acid sequence of SEQ ID NO: 54 and a LC comprising the amino acid sequence of SEQ ID NO: 24.

E163. The method of any one of E154-E161 comprising administering an antibody, or antigen-binding fragment thereof, comprising i) CDR-H1, CDR-H2, and CDR-H3 sequences as set forth in SEQ ID NO:74 and CDR-L1, CDR-L2, and CDR-L3 sequences as set forth in SEQ ID NO:28; ii) a VH domain comprising the amino acid sequence of SEQ ID NO: 74 and a VL domain comprising the amino acid sequence of SEQ ID NO: 28; or iii) a HC comprising the amino acid sequence of SEQ ID NO: 73 and a LC comprising the amino acid sequence of SEQ ID NO: 24.

E164. The method of any one of E154-E163, wherein the subject has atopic dermatitis.

E165. A method of treating atopic dermatitis, comprising administering to a subject in need thereof a therapeutically effective amount an anti-CD1a antibody, or antigen-binding fragment thereof, comprising i) CDR-H1, CDR-H2, and CDR-H3 sequences as set forth in SEQ ID NO: 55 and CDR-L1, CDR-L2, and CDR-L3 sequences as set forth in SEQ ID NO: 28; ii) a VH domain comprising the amino acid sequence of SEQ ID NO: 55 and a VL domain comprising the amino acid sequence of SEQ ID NO: 28; or iii) a HC comprising the amino acid sequence of SEQ ID NO: 54 and a LC comprising the amino acid sequence of SEQ ID NO: 24, and a pharmaceutically acceptable carrier or excipient.

E166. A method of treating atopic dermatitis, comprising administering to a subject in need thereof a therapeutically effective amount an anti-CD1a antibody, or antigen-binding fragment thereof, comprising i) CDR-H1, CDR-H2, and CDR-H3 sequences as set forth in SEQ ID NO: 74 and CDR-L1, CDR-L2, and CDR-L3 sequences as set forth in SEQ ID NO: 28; ii) a VH domain comprising the amino acid sequence of SEQ ID NO: 74 and a VL domain comprising the amino acid sequence of SEQ ID NO:28; or iii) a HC comprising the amino acid sequence of SEQ ID NO: 73 and a LC comprising the amino acid sequence of SEQ ID NO: 24, and a pharmaceutically acceptable carrier or excipient.

E167. The method of any one of E135-E166, wherein the antibody, or antigen-binding fragment thereof, is administered in combination with a therapeutically effective amount of one or more additional therapeutically active compounds or treatment modalities effective in treating and/or preventing at least one sign and/or symptom of atopic dermatitis.

E168. The method of E167, wherein the amount of the anti-CD1a antibody, or antigen-binding fragment thereof, and the amount of the therapeutically active compound or treatment modality effective in treating and/or preventing at least one sign and/or symptom of atopic dermatitis, are administered in amounts that together achieve synergistic effects in the treatment and/or prevention of at least one sign and/or symptom of atopic dermatitis.

E169. The method of E167, wherein the amount of the anti-CD1a antibody, or antigen-binding fragment thereof, and/or the amount of the therapeutically active compound or treatment modality effective in treating and/or preventing at least one sign and/or symptom of atopic dermatitis, are each administered at a dosage that is lower than would be administered if not in combination.

E170. The method of any one of E167-E169, wherein the additional therapeutically active compound comprises antagonists to one or more of IL-1a, IL-1b, IL-2, IL-3, IL-4, IL-5, IL-6, IL-8, IL-9, IL-10, IL-12, IL-13, IL-17, IL-18, IL-21, IL-23, IL-25, IL-26, IL-31, IL36 IFNα, IFNγ, or antagonists of their respective receptors, anti-inflammatory agents, recombinant interferon gamma, NSAIDs, steroids, calcineurin inhibitors, and/or corticosteroids.

E171. The method of any one of E167-E169, wherein the additional therapeutically active compound comprises dupilumab.

E172. The method of any one of E167-E171, wherein the anti-CD1a antibody, or antigen-binding fragment thereof, and the therapeutically active compound or treatment modality which is effective in treating and/or preventing at least one sign and or symptom of atopic dermatitis, are co-administered.

E173. The method of any one of E167-E172, wherein the combination therapies are administered according to the same dosing regimen (e.g., both therapies are administered daily) or according to different dosing regimens (e.g., one therapy is administered daily, the other therapy is administered weekly).

E174. The method of any one of E167-E173, wherein the combination therapies are administered to a subject by the same or different routes of administration.

E175. Use of the pharmaceutical composition of any one of E124-134 in the manufacture of a medicament for treating a disease, disorder or condition associated with, or mediated by, CD1a expression, activity and/or CD1a binding to T-cell receptors.

E176. Use of an antibody, or antigen-binding fragment thereof, of any one of E1-E100 in the manufacture of a medicament for treating and/or preventing a disease, disorder or condition associated with, or mediated by, CD1a expression, activity and/or CD1a binding to T-cell receptors.

E177. An antibody, or antigen-binding fragment thereof, of any one of E1-E100, or the pharmaceutical composition of E124-E134, for use as a medicament.

E178. An antibody, or antigen binding fragment thereof, of any one of E1-E100, or the pharmaceutical composition of any one of E124-E134 for use in the treatment and/or prevention of at least one sign and/or symptom of an inflammatory disease (e.g., but not limited to atopic dermatitis).

E179. An antibody, or antigen binding fragment thereof, that specifically binds to human CD1a, comprising:

(a) a CDR-H1 comprising the amino acid sequence of SEQ ID NO:96;
(b) a CDR-H2 comprising the amino acid sequence of SEQ ID NO:97;
(c) a CDR-H3 comprising the amino acid sequence of SEQ ID NO:98;
(d) a CDR-L1 comprising the amino acid sequence of SEQ ID NO:99;
(e) a CDR-L2 comprising the amino acid sequence of SEQ ID NO:100; or
(f) a CDR-L3 comprising the amino acid sequence of SEQ ID NO:101.

E180. An antibody, or antigen binding fragment thereof, that specifically binds to human CD1a, comprising:

(a) a CDR-H1 comprising the amino acid sequence of SEQ ID NO:96;
(b) a CDR-H2 comprising the amino acid sequence of SEQ ID NO:97;
(c) a CDR-H3 comprising the amino acid sequence of SEQ ID NO:98;
(d) a CDR-L1 comprising the amino acid sequence of SEQ ID NO:99;
(e) a CDR-L2 comprising the amino acid sequence of SEQ ID NO:100; and
(f) a CDR-L3 comprising the amino acid sequence of SEQ ID NO:101.

E181. An antibody, or antigen binding fragment thereof, of any of E1-E100, comprising:

(a) a CDR-H1 comprising the amino acid sequence of SEQ ID NO:96;
(b) a CDR-H2 comprising the amino acid sequence of SEQ ID NO:97;
(c) a CDR-H3 comprising the amino acid sequence of SEQ ID NO:98;
(d) a CDR-L1 comprising the amino acid sequence of SEQ ID NO:99;
(e) a CDR-L2 comprising the amino acid sequence of SEQ ID NO:100; and/or
(f) a CDR-L3 comprising the amino acid sequence of SEQ ID NO:101.

E182. A pharmaceutical composition comprising any antibody, or antigen binding fragment thereof, comprising E181.

E183. Any method of E135-E174 or any use of an antibody, or antigen binding fragment thereof, of any of E1-E100, or any pharmaceutical composition of any of E124-E134, wherein (a) a CDR-H1 comprises the amino acid sequence of SEQ ID NO:96;

(b) a CDR-H2 comprises the amino acid sequence of SEQ ID NO:97;
(c) a CDR-H3 comprises the amino acid sequence of SEQ ID NO:98;
(d) a CDR-L1 comprises the amino acid sequence of SEQ ID NO:99;
(e) a CDR-L2 comprises the amino acid sequence of SEQ ID NO:100; and/or
(f) a CDR-L3 comprises the amino acid sequence of SEQ ID NO:101.

BRIEF DESCRIPTION OF THE SEVERAL VIEWS OF THE DRAWINGS

In FIG. 3A, CD1a is shown in black in foreground (beta sheet and interface-distal domain removed for clarity), while Ab138 is shown in shaded white in background. In FIG. 3B, CD1a is shown in black on top, while Ab138 is shown in shaded white on bottom.

FIG. 5 depicts HTRF assay screen of primary scFv clones from optimization libraries. The lower HTRF signal correlates to higher binding affinity to human CD1a. An arbitrary cut-off threshold was selected for clones that bind better than parental Ab138. The negative control mAb does not bind human CD1a.

DETAILED DESCRIPTION

Figure 1A:
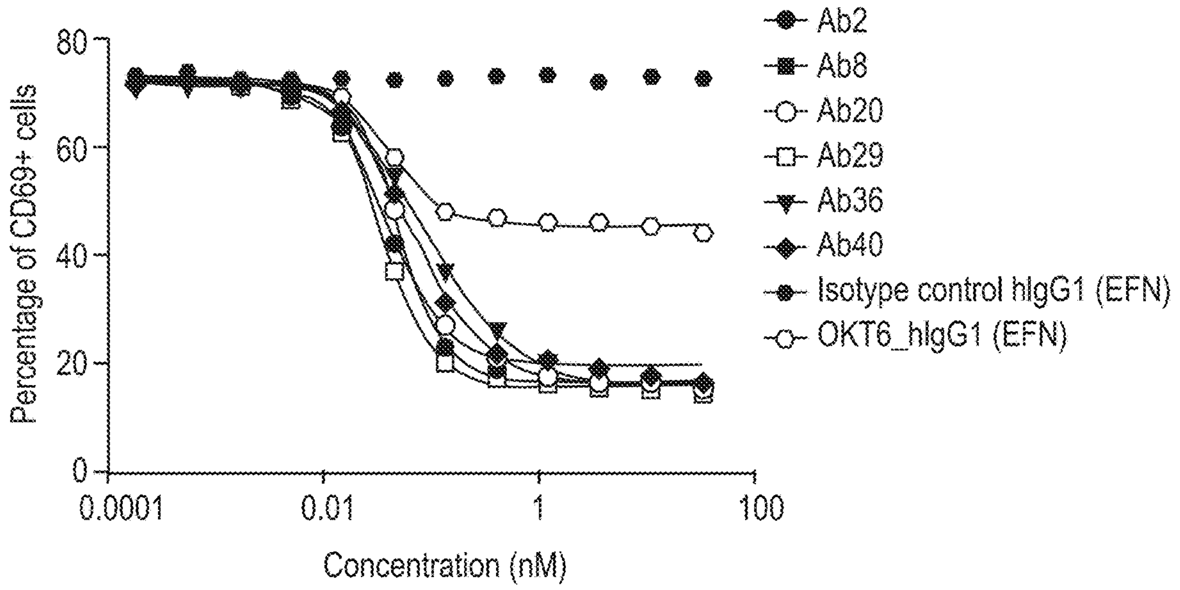
FIG. 1A depicts the effects of chimeric anti-CD1a antibodies on CD69 expression in a T-cell activation assay. OKT6 is a commercial CD1a-blocking antibody. OKT6 sequences were cloned from hybridoma obtained from ATCC and made as chimeric human IgG1.

The present disclosure provides antibodies, and antigen-binding fragments thereof, that specifically bind to Cluster of Differentiation 1a (CD1a) and reduce or inhibit CD1a activity, including but not limited to, the ability of CD1a to bind to T cell receptors and their subsequent activation. The disclosure also provides processes for making, preparing, or producing anti-CD1a antibodies. Antibodies of the disclosure are useful in the diagnosis, prophylaxis, and/or treatment of disorders or conditions mediated by, or associated with, CD1a activity (e.g., binding to T cell receptors and their subsequent activation), including, but not limited to, inflammatory disorders and conditions such as (but not limited to) inflammatory bowel disease, allergies, allergic rhinitis, allergic conjunctivitis, vernal keratoconjunctivitis, a seasonal allergy, pet allergy, asthma, food allergy, peanut allergy, atopic dermatitis, contact dermatitis, chronic rhinosinusitis with nasal polyps (CRSwNP), allergic rhinitis, bronchitis, chronic obstructive pulmonary disease (COPD), viral exacerbations of respiratory disease, viral infection in children and adults, (respiratory syncytial virus (RSV), rhinovirus, influenza), urticarias, eosinophilic esophagitis, chronic fibrosis, liver fibrosis, non-alcoholic steatohepatitis (NASH), chronic kidney disease, idiopathic pulmonary fibrosis (IPF), scleroderma, systemic sclerosis, acute kidney injury, sepsis, pancreatitis, type 1 diabetes, graft-versus-host disease (GVHD), tissue transplant, Alzheimer's disease, rheumatoid arthritis, irritable bowel syndrome (IBS), Crohns disease, ulcerative colitis, multiple sclerosis, psoriasis, celiac disease and Raynaud's disease or phenomenon. The disclosure further encompasses expression of antibodies, and preparation and manufacture of compositions comprising antibodies of the disclosure, or antigen-binding fragments thereof, such as medicaments for the use of the antibodies. Polynucleotides encoding antibodies that bind CD1a, or antigen-binding fragments thereof, are provided, including but not limited to, polynucleotides encoding antibody heavy chains or light chains, or both. Host cells that express anti-CD1a antibodies are also provided.

CD1a, an MHC class I like molecule, is predominantly expressed on Langerhans cells and presents skin-derived lipid antigens which can be recognized by antigen-specific T cells, leading to subsequent T cell activation. Without wishing to be bound by any particular theory, recent work using human CD1a transgenic mice has suggested that CD1a may be a key driver of inflammatory skin diseases, such as contact dermatitis, psoriasis, and AD (Kim J H, Yongqing T, Kim J, et al. CD1a on Langerhans cells controls inflammatory skin disease. Nat Immunol 2016; 17(10):1159-66). CD1a, an MHC class I like molecule, is predominantly expressed on Langerhans cells, a specialized type of dendritic cell in the skin (Igyarto B Z, Kaplan D H. Antigen presentation by Langerhans cells. Curr Opin Immunol 2013; 25(1):115-9; Merad M, Ginhoux F, Collin M. Origin, homeostasis and function of Langerhans cells and other langerin-expressing dendritic cells. Nat Rev Immunol 2008; 8(12):935-47). CD1a presents lipid antigens found in the skin which are recognized by antigen-specific T cells, leading to subsequent T cell activation (de Jong A, Cheng T Y, Huang S, et al. CD1a-autoreactive T cells recognize natural skin oils that function as headless antigens. Nat Immunol 2014; 15(2):177-85). Thus, CD1a may have an important role driving inflammatory skin diseases, and antibodies, and antigen-binding fragments thereof, that bind CD1a and inhibit subsequent T cell activation are hypothesized to reduce skin inflammation associated with AD. As disclosed in the Examples herein, antibodies, and antigen-binding fragments thereof, of the disclosure, reduce CD1a-dependent T cell activation as demonstrated by the potent inhibition of CD1a-dependent Cluster of Differentiation 69 (CD69) expression and interleukin-2 (IL-2) production in Jurkat 76 (J76) cells expressing T-cell receptor (TCR) allele BK6. Moreover, administration of anti-CD1a antibodies to a human CD1a transgenic house dust mite (HDM) mouse model resulted in a reduction of the dermatitis score, total serum IgE levels and HDM-specific IgE antibody titer, thereby demonstrating the ability of these CD1a neutralizing antibodies to markedly suppress AD disease activity.

An anti-CD1a antibody, or antigen-binding fragment thereof, including a humanized antibody, can be used, alone or in combination with a second therapy, in the prevention, treatment, and/or amelioration of at least one sign and/or symptom of inflammatory disorders and conditions such as (but not limited to) inflammatory bowel disease, allergies, allergic rhinitis, allergic conjunctivitis, vernal keratoconjunctivitis, a seasonal allergy, pet allergy, asthma, food allergy, peanut allergy, atopic dermatitis, contact dermatitis, chronic rhinosinusitis with nasal polyps (CRSwNP), allergic rhinitis, bronchitis, chronic obstructive pulmonary disease (COPD), viral exacerbations of respiratory disease, viral infection in children and adults, (respiratory syncytial virus (RSV), rhinovirus, influenza), urticarias, eosinophilic esophagitis, chronic fibrosis, liver fibrosis, non-alcoholic steatohepatitis (NASH), chronic kidney disease, idiopathic pulmonary fibrosis (IPF), scleroderma, systemic sclerosis, acute kidney injury, sepsis, pancreatitis, type 1 diabetes, graft-versus-host disease (GVHD), tissue transplant, Alzheimer's, rheumatoid arthritis, irritable bowel syndrome (IBS), Crohns disease, ulcerative colitis, multiple sclerosis, psoriasis, celiac disease and Raynaud's disease or phenomenon.

The section headings used herein are for organizational purposes only and are not to be construed as limiting the subject matter described.

All references cited herein, including patent applications, patent publications, UniProtKB accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al, Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds); Gene Transfer Vectors for Mammalian Cells (J. M. Miller and M. P. Calos, eds., 1987); PCR: The Polymerase Chain Reaction, (Mullis et al, eds., 1994); Current Protocols in Immunology (J. E. Coligan et al, eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty, ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999)); The Antibodies (M. Zanetti and J. D. Capra, eds., Harwood Academic Publishers, 1995); and updated versions thereof.

The present disclosure may be understood more readily by reference to the following detailed description of exemplary embodiments of the invention and the Examples included therein.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Definitions

Unless otherwise defined, all technical and scientific terms used herein have the same meaning as commonly understood by one of ordinary skill in the art to which this invention belongs. In case of conflict, the present specification, including definitions, will control.

Further, unless otherwise required by context or expressly indicated, singular terms shall include pluralities and plural terms shall include the singular.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

As used herein, the singular form "a", "an", and "the" includes plural references unless indicated otherwise.

As used herein, the term "and/or" refers to and encompasses any and all possible combinations of one or more of the associated listed items, as well as the lack of combinations when interpreted in the alternative, "or".

As used herein, the term "about," or "approximately" refers to a measurable value such as an amount of the biological activity, length of a polynucleotide or polypeptide sequence, content of G and C nucleotides, codon adaptation index, number of CpG dinucleotides, dose, time, temperature, and the like, and is meant to encompass variations of 25%, 20%, 19%, 18%, 17%, 16%, 15%, 14%, 13%, 12%, 11%, 10%, 9%, 8%, 7%, 6%, 5%, 4%, 3%, 2% 1%, 0.5% or even 0.1%, in either direction (greater than or less than) of the specified amount unless otherwise stated, otherwise evident from the context, or except where such number would exceed 100% of a possible value.

As used herein, the term "ameliorate" means a detectable or measurable improvement in a subject's disease, disorder or condition, (e.g., atopic dermatitis) or symptom thereof (e.g., severe pruritus), or an underlying cellular response (e.g., CD1a-dependent T cell activation). A detectable or measurable improvement includes a subjective or objective decrease, reduction, inhibition, suppression, limit or control in the occurrence, frequency, severity, progression or duration of, complication caused by or associated with, improvement in a symptom of, or a reversal of the disease, disorder or condition.

As used herein "another" may mean at least a second or more. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular.

As used herein, the term "associated with" refers to with one another, if the presence, level and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example, by means of hydrogen bonds, van der Waals interaction, hydrophobic interactions, magnetism, and a combination thereof.

As used herein, the term "coding sequence" refers to a sequence which encodes a particular protein or "encoding nucleic acid," denotes a nucleic acid sequence which is transcribed (in the case of DNA) and translated (in the case of mRNA) into a polypeptide in vitro or in vivo when placed under the control of (operably linked to) appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences.

Throughout this specification and claims, the word "comprise," or variations such as "comprises" or "comprising," and the words "having/including" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting. It is understood that wherever embodiments are described herein with the language "comprising," otherwise analogous embodiments described in terms of "consisting of" and/or "consisting essentially of" are also provided.

As used herein, the term "conservative substitution" refers to replacement of one amino acid by a biologically, chemically or structurally similar residue. Biologically similar means that the substitution does not destroy a biological activity. Structurally similar means that the amino acids have side chains with similar length, such as alanine, glycine and serine or a similar size. Chemical similarity means that the residues have the same charge or are both hydrophilic or hydrophobic. Particular examples include the substitution of a hydrophobic residue, such as isoleucine, valine, leucine or methionine with another, or the substitution of one polar residue for another, such as the substitution of arginine for lysine, glutamic acid for aspartic acid or glutamine for asparagine, serine for threonine, and the like. Particular examples of conservative substitutions include the substitution of a hydrophobic residue such as isoleucine, valine, leucine or methionine for one another, the substitution of a polar residue for another, such as the substitution of arginine for lysine, glutamic acid for aspartic acid, or glutamine for asparagine, and the like. Conservative amino acid substitutions typically include, for example, substitutions within the following groups: glycine, alanine, valine, isoleucine, leucine; aspartic acid, glutamic acid; asparagine, glutamine; serine, threonine; lysine, arginine; and phenylalanine, tyrosine. A "conservative substitution" also includes the use of a substituted amino acid in place of an unsubstituted parent amino acid.

As used herein, the term "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, the term an "effective dosage" or "effective amount" of drug, compound, or pharmaceutical composition is an amount sufficient to affect any one or more beneficial or desired results. In more specific aspects, an effective amount prevents, alleviates and/or ameliorates at least one sign and/or symptom of a disease, e.g., AD. For prophylactic use, beneficial or desired results include eliminating or reducing the risk, lessening the severity, or delaying the outset of the disease, including biochemical, histological and/or a behavioral symptom of the disease, its complications and intermediate pathological phenotypes presenting during development of the disease. For therapeutic use, beneficial or desired results include clinical results such as reducing at least one sign and/or symptom of a CD1a-mediated disease, disorder or condition, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "functional" refers to a biological molecule in a form in which it exhibits a property and/or activity by which it is characterized. A biological molecule may have two functions (i.e., bifunctional) or many functions (i.e., multifunctional).

As used herein, the term "homologous" or "homology" refer to two or more reference entities (e.g., nucleotide or polypeptide sequences) that share at least partial identity over a given region or fragment. For example, when an amino acid position in two peptides is occupied by identical amino acids, the peptides are homologous at that position. Notably, a homologous peptide will retain activity or function associated with the unmodified or reference peptide and the modified peptide will generally have an amino acid sequence "substantially homologous" with the amino acid sequence of the unmodified sequence. When referring to a polypeptide, nucleic acid or fragment thereof, "substantial homology" or "substantial similarity," means that when optimally aligned with appropriate insertions or deletions with another polypeptide, nucleic acid (or its complementary strand) or fragment thereof, there is sequence identity in at least about 95% to 99% of the sequence. The extent of homology (identity) between two sequences can be ascertained using computer program or mathematical algorithm. Such algorithms that calculate percent sequence homology (or identity) generally account for sequence gaps and mismatches over the comparison region or area. Exemplary programs and algorithms are provided below.

As used herein, the terms "host cell," "host cell line," and "host cell culture" are used interchangeable and mean an individual cell or cell culture that can be or has been a recipient for vector(s) for incorporation of polynucleotide inserts. Host cells include "transformants," "transformed cells," and "transduced cells," which include the primary transformed or transduced cell and progeny derived therefrom without regard to the number of passages. Host cell progeny may not necessarily be completely identical (in morphology or in genomic DNA complement) to the original parent cell due to natural, accidental, or deliberate mutation. A host cell includes cells transfected and/or transformed in vivo with a polynucleotide of this invention (e.g., a polynucleotide encoding an amino acid sequence of an anti-CD1a antibody).

As used herein, the term "identity" or "identical to" refers to the overall relatedness between polymeric molecules, e.g., between nucleic acid molecules (e.g., DNA molecules and/or RNA molecules) and/or between polypeptide molecules. "Identity" measures the percent of identical matches between two or more sequences with gap alignments addressed by a particular mathematical model of computer programs (i.e. "algorithms").

In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, 98% or 99% identical.

Calculation of the percent identity of two nucleic acid or polypeptide sequences, for example, can be performed by aligning the two sequences for optimal comparison purposes (e.g., gaps can be introduced in one or both of a first and a second sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm.

To determine percent identity, sequences can be aligned using the methods and computer programs, including BLAST, available over the world wide web at ncbi.nlm.nih.gov/BLAST/. Other alignment programs include MegAlign® program in the Lasergene® suite of bioinformatics software (DNASTAR®, Inc., Madison, WI). Another alignment algorithm is FASTA, available in the Genetics Computing Group (GCG) package, from Madison, Wis., USA. Other techniques for alignment are described in Methods in Enzymology, vol. 266: Computer Methods for Macromolecular Sequence Analysis (1996), ed. Doolittle, Academic Press, Inc. Of particular interest are alignment programs that permit gaps in the sequence. Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

Also, of interest is the BestFit program using the local homology algorithm of Smith and Waterman (1981, Advances in Applied Mathematics 2: 482-489) to determine sequence identity. The gap generation penalty will generally range from 1 to 5, usually 2 to 4 and in some embodiments will be 3. The gap extension penalty will generally range from about 0.01 to 0.20 and in some instances will be 0.10. The program has default parameters determined by the sequences inputted to be compared. Preferably, the sequence identity is determined using the default parameters determined by the program. This program is available also from Genetics Computing Group (GCG) package, from Madison, WI, USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters: Mismatch Penalty: 1.00; Gap Penalty: 1.00; Gap Size Penalty: 0.33; and Joining Penalty: 30.0.

The term "similarity" is a related concept, but in contrast to "identity," refers to a measure of similarity which includes both identical matches and conservative substitution matches. Since conservative substitutions apply to polypeptides and not nucleic acid molecules, similarity only applies to polypeptide sequence comparisons. If two polypeptide sequences have, for example, 10 out of 20 identical amino acids, and the remainder are all nonconservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

As used herein, the terms "increase," improve," "decrease" or "reduce" indicate values that are relative to a baseline measurement, such as a measurement in the same individual prior to initiation of treatment described herein, or a measurement in a control individual (or multiple control individuals) in the absence of the treatment described herein. In some embodiments, a "control individual" is an individual afflicted with the same form of disease or injury as an individual being treated. In some embodiments, a "control individual" is an individual that is not afflicted with the same form of disease or injury as an individual being treated.

As used herein, the term "isolated molecule" (where the molecule is, for example, a polypeptide, a polynucleotide, or an antibody or antigen-binding fragment thereof) means a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

As used herein, the terms "leader peptide" or "leader sequence" or "leader signal sequence" or "signal sequence", (used interchangeably herein) mean any nucleic acid sequence, or amino acid sequence encoded thereby, that may be present on the 5' end of a nucleic acid molecule and/or at or near the N-terminus of a polypeptide, that when present may mediate the transport of the polypeptide to an organelle of destination, including, but not limited to, the secretion of the polypeptide from a cell. Such leader sequences include, but are not limited to, nucleic acid sequences comprising nucleotides 1-16 of SEQ ID NO: 1. Embodiments encompass this and any other leader signals (nucleic and amino acid sequences) known in the art or to be identified which can result in the transport of a polypeptide to the desired organelle, e.g., the endoplasmic reticulum, and/or secreted from the cell. Generally, the signal peptide is removed from and/or is not present in the mature polypeptide.

As used herein, the term "residue" means a position in a protein and its associated amino acid identity. For example, asparagine 297 (also referred to as Asn297, also referred to as N297) is a residue in a human antibody IgG1.

As used herein, the term "subject" means a mammal, more preferably, a human. Mammals also include, but are not limited to, farm animals (e.g., cows, pigs, horses, chickens, etc.), pets, primates, horses, dogs, cats, mice and rats. In some embodiments, a subject is a patient. In some embodiments, a subject is at risk for a disease, disorder or condition mediated by or associated with CD1a binding to and subsequent activation of T cell receptors. In some embodiments, a subject is a patient who has a disease, disorder or condition as described herein, e.g., an inflammatory disorder or condition. In some embodiments, a subject (e.g., a patient) has atopic dermatitis, contact dermatitis, inflammatory bowel disease, non-alcoholic steatohepatitis (NASH), chronic kidney disease, irritable bowel syndrome (IBS), Crohns disease, ulcerative colitis, multiple sclerosis, and psoriasis.

As used herein, the term "substantially pure" means an object species is the predominant species present (i.e., on a molar basis it is more abundant than any other individual species in the composition), and preferably a substantially purified fraction is a composition wherein the object species (e.g., a glycoprotein, including an antibody or receptor) comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species. In certain embodiments, a substantially pure material is at least 50% pure (i.e., free from contaminants), more preferably, at least 90% pure, more preferably, at least 95% pure, yet more preferably, at least 98% pure, and most preferably, at least 99% pure.

Polypeptide or antibody "fragments" or "portions" according to the invention may be made by truncation, e.g. by removal of one or more amino acids from the N and/or C-terminal ends of a polypeptide. One, 2, 3, 4, 5, up to 10, up to 20, up to 30, up to 40 or more amino acids may be removed from the N and/or C terminus in this way. Fragments may also be generated by one or more internal deletions.

As used herein, the terms "nucleic acid sequence" and "nucleotide sequence," refer interchangeably to any molecule composed of or comprising monomeric nucleotides. A nucleic acid may be an oligonucleotide or a polynucleotide. A nucleotide sequence may be a DNA or RNA (e.g., genomic DNA, cDNA, antisense DNA, mRNA, tRNA, rRNA, etc.). A nucleotide sequence may be chemically modified or artificial. Nucleotide sequences include peptide nucleic acids (PNA), morpholinos and locked nucleic acids (LNA), as well as glycol nucleic acids (GNA) and threose nucleic acids (TNA). Each of these sequences is distinguished from naturally-occurring DNA or RNA by changes to the backbone of the molecule. Also, phosphorothioate nucleotides may be used. Other deoxynucleotide analogs include methylphosphonates, phosphoramidates, phosphorodithioates, N3'-P5'-phosphoramidates, and oligoribonucleotide phosphorothioates and their 2'-0-allyl analogs and 2'-0-methylribonucleotide methylphosphonates which may be used in a nucleotide sequence of the disclosure.

As used here, the term "nucleic acid construct," refers to a non-naturally occurring nucleic acid molecule resulting from the use of recombinant DNA technology (e.g., a recombinant nucleic acid). A nucleic acid construct is a nucleic acid molecule, either single or double stranded, which has been modified to contain segments of nucleic acid sequences, which are combined and arranged in a manner not found in nature. A nucleic acid construct may be a "vector" (e.g., a plasmid), that is, a nucleic acid molecule designed to deliver exogenously created DNA into a host cell.

As used herein, the term "operably linked" refers to a linkage of polynucleotide (or polypeptide) elements in a functional relationship. A nucleic acid is operably linked when it is placed into a functional relationship with another nucleic acid sequence. For instance, a promoter or other transcription regulatory sequence (e.g., an enhancer) is operably linked to a coding sequence if it affects the transcription of the coding sequence. In some embodiments, operably linked means that the nucleic acid sequences being linked are contiguous. In some embodiments, operably linked does not mean that the nucleic acid sequences are contiguously linked, rather intervening sequences are between those nucleic acid sequences that are linked.

As used herein, the term "polynucleotide" (also referred to herein as a "nucleic acid molecule") refers to a sequence of nucleotides connected by phosphodiester linkages. Polynucleotides are presented herein in the direction from the 5' to the 3' direction. A polynucleotide of the present disclosure can be a deoxyribonucleic acid (DNA) molecule or ribonucleic acid (RNA) molecule and refers to all forms of a nucleic acid such as, double stranded molecules, single stranded molecules, small or short hairpin RNA (shRNA), micro RNA, small or short interfering RNA (siRNA), trans-splicing RNA, antisense RNA. Where a polynucleotide is a DNA molecule, that molecule can be a gene, a cDNA, an antisense molecule or a fragment of any of the foregoing molecules. Nucleotide bases are indicated herein by a single letter code: adenine (A), guanine (G), thymine (T), cytosine (C), inosine (I) and uracil (U). A polynucleotide of the present disclosure can be prepared using standard techniques well known to one of skill in the art.

As used herein, the terms "polypeptide," "protein" and "peptide" encoded by a polynucleotide (nucleic acid sequence or nucleotide sequence) refer to full-length native sequences, as with naturally occurring proteins, as well as functional subsequences, modified forms or sequence variants so long as the subsequence, modified form or variant retains some degree of functionality of the native full-length protein. In methods and uses of the disclosure, such polypeptides, proteins and peptides encoded by the polynucleotide sequences can be but are not required to be identical to the endogenous protein that is defective, or whose expression is insufficient, or deficient in a subject treated with gene therapy.

As used herein, the term "prevent" or "prevention" refers to delay of onset, and/or reduction in frequency and/or severity of at least one sign and/or symptom (e.g., severe pruritus) of a particular disease, disorder or condition (e.g., AD). In some embodiments, prevention is assessed on a population basis such that an agent is considered to "prevent" a particular disease, disorder or condition if a statistically significant decrease in the development, frequency and/or intensity of one or more symptoms of the disease, disorder or condition is observed in a population susceptible to the disease, disorder or condition. Prevention may be considered complete when onset of disease, disorder or condition has been delayed for a predefined period of time.

As used herein, the term "recombinant," refers to a vector, polynucleotide, polypeptide or cell that is the product of various combinations of cloning, restriction or ligation steps (e.g. relating to a polynucleotide or polypeptide comprised therein), and/or other procedures that result in a construct that is distinct from a product found in nature.

As used herein, the terms "treat" or "treatment" means to administer a therapy that partially or completely alleviates, ameliorates, relieves, inhibits, delays onset of, reduces severity of, and/or reduces incidence of one or more symptoms, features and causes of a particular disease, disorder and/or condition (e.g., AD). For purposes of this invention, beneficial or desired clinical results include, but are not limited to, one or more of the following: improved Eczema Area and Severity Index (EASI), improved pruritus numerical rating scale (NRS), reduction in affected body surface area (BSA), improved Patient-Oriented Eczema Measure (POEM), improved Dermatology Life Quality Index (DLQI), improved Investigator's Global Assessment (IGA), improved Physician's Global Assessment (PGA), improved Six Area Six Sign Atopic Dermatitis (SASSAD), improved Scoring Atopic Dermatitis (SCORAD), improved Visual Analogue Scale (VAS), reduction in the dermatitis score (which may, for example, but not limited to, be calculated as the sum of two or more of the following scores: erythema, scarring/dryness, edema and skin erosion), reduction in total serum IgE levels, reduction in antigen-specific IgE titers, and a decrease in suppression of atopic dermatitis associated gene signature. In some embodiments, beneficial or desired clinical results include decreased extent of damage from the disease, decreased duration of the disease, and/or reduction in the number, extent, or duration of a symptom related to the disease. In some embodiments, the term includes the administration of a compound or agent of the present invention to prevent or delay the onset of a symptom, complication, or biochemical indicia of a disease, alleviating a symptom or arresting or inhibiting further development of a disease, condition, or disorder. Treatment may be prophylactic (to prevent or delay the onset of the disease, or to prevent the manifestation of a clinical or subclinical symptom thereof) or therapeutic suppression or alleviation of a symptom after the manifestation of the disease. In some embodiments, the term does not include prophylactic administration (i.e, the term does not include preventing or delaying the onset of the disease or preventing the manifestation of a clinical or subclinical symptom thereof). In some embodiments, the disease, condition or disorder is AD.

Antibodies

An "antibody" or "Ab" is an immunoglobulin molecule capable of recognizing and binding to a specific target or antigen (Ag), such as a carbohydrate, polynucleotide, lipid, polypeptide, etc., through at least one antigen recognition site, located in the variable region of the immunoglobulin molecule. As used herein, the term "antibody" can encompass any type of antibody, including but not limited to monoclonal antibodies, polyclonal antibodies, antigen-binding fragments (or portion), of intact antibodies that retain the ability to specifically bind to a given antigen (e.g., CD1a), and any other modified configuration of the immunoglobulin molecule that comprises an antigen recognition site.

An antibody includes an antibody of any class, such as IgG, IgA, or IgM (or sub-class thereof), and the antibody need not be of any particular class. Depending on the antibody amino acid sequence of the constant region of its heavy chains (HC), immunoglobulins can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$ and $IgA_2$. In some embodiments, an anti-CD1a antibody of the present disclosure is an IgG1 antibody. The heavy chain constant regions that correspond to the different classes of immunoglobulins are called alpha, delta, epsilon, gamma, and mu, respectively. The subunit structures and three-dimensional configurations of different classes of immunoglobulins are well known.

Antibodies may be derived from any mammal, including, but not limited to, humans, monkeys, pigs, horses, rabbits, dogs, cats, mice, rats (e.g., a Sprague Dawley rat) etc., or other animals such as birds (e.g. chickens), fish (e.g., sharks) and camelids (e.g., llamas).

The term "antigen" refers to the molecular entity used for immunization of an immunocompetent vertebrate to produce the antibody that recognizes the antigen or to screen an expression library (e.g., phage, yeast or ribosome display library, among others). Herein, antigen is termed more broadly and is generally intended to include target molecules that are specifically recognized by the antibody, thus including fragments or mimics of the molecule used in an immunization process for raising the antibody or in library screening for selecting the antibody. Thus, for antibodies of the invention binding to CD1a, full-length CD1a from mammalian species (e.g., human, monkey (including cynomolgus monkey), dog and rabbit), including monomers and multimers, such as dimers, trimers, etc. thereof, truncated and other variants of CD1a (e.g., extracellular domain), as well as soluble CD1a and cell-surface expressed CD1a, are referred to herein as an antigen.

An "antigen-binding fragment" of an antibody refers to a one or more fragments of a full-length antibody that retains the ability to specifically bind to an antigen (preferably with substantially the same binding affinity). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 1989; 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et al., Science 1988; 242:423-426 and Huston et al., Proc. Natl. Acad. Sci. 1988 USA 85:5879-5883. Other forms of single chain antibodies, such as diabodies are also encompassed. Such single chain antibodies are also intended to be encompassed within the term "antigen-binding fragment" of an antibody. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al, Proc. Natl. Acad. Sci. USA 1993; 90:6444-6448; Poljak et al., Structure 1994; 2:1121-1123).

An antibody "variable domain" refers to the variable region of the antibody light chain (VL) or the variable region of the antibody heavy chain (VH), either alone or in combination. As known in the art, the variable regions of the heavy and light chains each consist of four framework regions (FR) connected by three "complementarity determining regions" (CDRs) and contribute to the formation of the antigen-binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J. Mol. Biol. 1987; 196(4): 901-917).

Residues in a variable domain are typically numbered according Kabat, which provides a numbering system used for heavy chain variable domains or light chain variable domains of the compilation of antibodies. See, Kabat et al., 1991, Sequences of Proteins of Immunological Interest, 5th Ed. Public Health Service, National Institutes of Health, Bethesda, MD. Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. For example, the algorithm implemented in the version 2.3.3 release of Abysis (www.abysis.org) can be used to assign Kabat numbering to variable regions CDR-L1, CDR-L2, CDR-L3, CDR-H2, and CDR-H3, and the AbM definition can then be used for CDR-H1.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition, the contact definition, and the conformational definition.

"Complementarity Determining Regions" (CDRs) can be identified according to the definitions of Kabat, Chothia, the accumulation of both Kabat and Chothia, AbM, contact, North, and/or conformational definitions or any method of CDR determination well known in the art. See, e.g., Kabat et al., 1991, Sequences of Proteins of Immunological Interest, 5th ed. (hypervariable regions); Chothia et al., Nature 1989; 342:877-883 (structural loop structures). The identity of the amino acid residues in a particular antibody that make up a CDR can be determined using methods well known in the art. The AbM definition of CDRs is a compromise between Kabat and Chothia and uses Oxford Molecular AbM antibody modeling software (Accelrys®).

The "contact" definition of CDRs is based on observed antigen contacts, set forth in MacCallum et al., J. Mol. Biol. 1996; 262:732-745. The "conformational" definition of CDRs is based on residues that make enthalpic contributions to antigen binding (see, e.g., Makabe et al., J. Biol. Chem., 2008; 283:1156-1166). North has identified canonical CDR conformations using a different preferred set of CDR definitions (North et al., J. Mol. Biol. 2011; 406: 228-256). In another approach, referred to herein as the "conformational definition" of CDRs, the positions of the CDRs may be identified as the residues that make enthalpic contributions to antigen binding (Makabe et al., J. Biol. Chem. 2008, 283:1156-1166). Still other CDR boundary definitions may not strictly follow one of the above approaches but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, North, extended, AbM, contact, and/or conformational definitions.

"Contact residue" as used herein with respect to an antibody or the antigen specifically bound thereby, refers to an amino acid residue present on an antibody/antigen comprising at least one heavy atom (i.e., not hydrogen) that is within 4 Å or less (e.g., 3.8 Å) of a heavy atom of an amino acid residue present on the cognate antibody/antigen.

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4.

As known in the art, a "constant region" of an antibody refers to the constant region of the antibody light chain or the constant region of the antibody heavy chain, either alone or in combination.

The terms "Ig Fc region," "Fc region," "Fc domain" and "Fc," as interchangeably used herein, refer to the portion of an immunoglobulin (Ig) molecule that correlates to a crystallizable fragment obtained by papain digestion of an Ig molecule. As used herein, the terms relate to the constant region of an antibody excluding the first constant region immunoglobulin domain and further relates to portions of that region. Thus, Fc refers to the last two constant region immunoglobulin domains of IgA, IgD, and IgG, and the last three constant region immunoglobulin domains of IgE and IgM, and the flexible hinge N-terminal to these domains, or portions thereof. For IgA and IgM, Fc may include the J chain.

In certain embodiments, the antibody, or antigen-binding fragment thereof, described herein comprises an Fe domain. The Fe domain can be derived from IgA (e.g., $IgA_1$ or $IgA_2$), IgD, IgE, IgM, or IgG (e.g., $IgG_1$, $IgG_2$, $IgG_3$, or $IgG_4$). In some embodiments, an anti-CD antibody is an IgG antibody. In some embodiments, an anti-CD1a antibody (e.g., Ab571 or Ab673) is an $IgG_1$ antibody.

For IgG, Fc comprises immunoglobulin domains Cγ2 and Cγ3 (C gamma 2 and C gamma 3) and the hinge between Cγ1 (C gamma 1) and Cγ2 (C gamma 2). Although the boundaries of the Fc region may vary, the human IgG heavy chain Fc region is usually defined to comprise residues C226 or P230 to its carboxyl-terminus, wherein the numbering is according to the EU index of Edelman et al., Proc. Natl. Acad. Sci. USA 1969; 63(1):78-85 and as described in Kabat et al., 1991. Typically, the Fc domain comprises from about amino acid residue 236 to about 447 of the human IgG1 constant domain. An exemplary human wild type IgG1 Fc domain amino acid sequence is set forth in SEQ ID NO: 86 (including an optional terminal lysine (K) residue and effector mutations). Fc polypeptide may refer to this region in isolation, or this region in the context of an antibody, or an antigen-binding fragment thereof, or Fc fusion protein.

The heavy chain constant domain comprises the Fc region and further comprises the CH1 domain and hinge as well as the CH2 and CH3 (and, optionally, CH4 of IgA and IgE) domains of the IgG heavy chain.

As used herein, "Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Daeron, Annu. Rev. Immunol. 1997; 15:203-234). FcRs are reviewed, for example, in Ravetch and Kinet, Annu. Rev. Immunol 1991; 9:457-92; Capel et al., Immunomethods 1994; 4:25-34; and de Haas et al., J. Lab. Clin. Med. 1995; 126:330-41. Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 1976; 117:587 and Kim et al., J. Immunol. 1994; 24:249) and regulation of homeostasis of immunoglobulins. Methods of measuring binding to FcRn are known (see, e.g., Ghetie and Ward, Immunol. Today 1997; 18(12):592-598; Ghetie et al., Nature Biotechnology, 1997; 15(7):637-640; Hinton et al., J. Biol. Chem. 2004; 279(8):6213-6216; WO 2004/92219).

In some embodiments, where an anti-CD1a antibody comprises a C-terminal lysine (K) amino acid residue on a heavy chain polypeptide (e.g., human IgG1 heavy chain comprises a terminal lysine), one skilled in the art would understand that the lysine residue may be clipped resulting in an antibody with a heavy chain lacking the C-terminal lysine residue. Additionally, the antibody heavy chain may be produced using a nucleic acid that does not encode the lysine. Thus, in some embodiments, an anti-CD1a antibody comprises a heavy chain where the terminal lysine otherwise present is not present. Accordingly, the present disclosure includes compositions comprising an anti-CD1a antibody with a heavy chain lacking the C-terminal lysine residue. In some embodiments, the present disclosure includes compositions comprising an anti-CD1a antibody with a heavy chain having a C-terminal lysine residue and an anti-CD1a antibody with a heavy chain lacking the C-terminal lysine residue. In some embodiments, the present disclosure includes compositions comprising an anti-CD1a antibody lacking the C-terminal lysine residue.

An "Fc fusion" protein is a protein wherein one or more polypeptides are operably linked to an Fc polypeptide. An Fc fusion combines the Fc region of an immunoglobulin with a fusion partner.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. In some embodiments, the variant Fc region retains at least one effector function of the native sequence Fc region. In some embodiments, the variant Fc region does not retain any effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably, at least about 90% sequence identity therewith, more preferably, at least about 95%, at least about 96%, at least about 97%, at least about 98%, at least about 99% sequence identity therewith.

An "epitope" refers to the area or region of an antigen to which an antibody specifically binds, e.g., an area or region comprising residues that interact with the antibody, as determined by any method well known in the art, for example, by conventional immunoassays or as described in Example 4 of the present disclosure. There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, New York, 1999. In an additional example, epitope mapping can be used to determine the sequence to which an anti-CD1a antibody binds. Epitope mapping is commercially available from various sources, for example, Pepscan Systems (Edelhertweg 15, 8219 PH Lelystad, The Netherlands). Alternatively, during the discovery process, the generation and characterization of antibodies may elucidate information about desirable epitopes. From this information, it is then possible to competitively screen antibodies for binding to the same epitope. An approach to achieve this is to conduct competition and cross-competition studies to find antibodies that compete or cross-compete with one another for binding to CD1a, e.g., the antibodies compete for binding to the antigen.

In addition, the epitope to which the anti-CD1a antibody binds can be determined in a systematic screening by using overlapping peptides derived from the CD1a (e.g., a human CD1a sequence) and determining binding by the antibody. According to the gene fragment expression assays, the open reading frame encoding CD1a can be fragmented either randomly or by specific genetic constructions and the reactivity of the expressed fragments of CD1a with the antibody to be tested is determined. The gene fragments may, for example, be produced by PCR and then transcribed and translated into protein in vitro, in the presence of radioactive amino acids. The binding of the antibody to the radioactively labeled CD1a fragments is then determined by immunoprecipitation and gel electrophoresis.

Certain epitopes can also be identified by using large libraries of random peptide sequences displayed on the surface of phage particles (phage libraries) or yeast (yeast display). Alternatively, a defined library of overlapping peptide fragments can be tested for binding to the test antibody in simple binding assays. In an additional example, mutagenesis of an antigen, domain swapping experiments and alanine scanning mutagenesis can be performed to identify residues required, sufficient, and/or necessary for epitope binding.

At its most detailed level, the epitope for the interaction between the antigen and the antibody can be defined by the spatial coordinates defining the atomic contacts present in the antigen-antibody interaction, as well as information about their relative contributions to the binding thermodynamics. At a less detailed level, the epitope can be characterized by the spatial coordinates defining the atomic contacts between the antigen and antibody. At a further less detailed level the epitope can be characterized by the amino acid residues that it comprises as defined by a specific criterion, e.g., by distance between atoms (e.g., heavy, i.e., non-hydrogen atoms) in the antibody and the antigen. At a further less detailed level the epitope can be characterized through function, e.g., by competition binding with other antibodies. The epitope can also be defined more generically as comprising amino acid residues for which substitution by another amino acid will alter the characteristics of the interaction between the antibody and antigen (e.g. using alanine scanning).

From the fact that descriptions and definitions of epitopes, dependent on the epitope mapping method used, are obtained at different levels of detail, it follows that comparison of epitopes for different antibodies on the same antigen can similarly be conducted at different levels of detail.

Epitopes described at the amino acid level, e.g., determined from an X-ray crystallography, Nuclear Magnetic Resonance (NMR) spectroscopy, hydrogen/deuterium exchange Mass Spectrometry (H/D-MS), are said to be identical if they contain the same set of amino acid residues. Epitopes are said to overlap if at least one amino acid is shared by the epitopes. Epitopes are said to be separate (unique) if no amino acid residue is shared by the epitopes.

Yet another method which can be used to characterize an anti-CD1a antibody is to use competition assays (e.g., as described in Example 12 of the present disclosure) with other antibodies known to bind to the same antigen, to determine if an anti-CD1a antibody binds to the same epitope as other antibodies. Competition assays are well known to those of skill in the art. Epitopes characterized by competition binding are said to be overlapping if the binding of the corresponding antibodies are mutually exclusive, i.e., binding of one antibody excludes simultaneous or consecutive binding of the other antibody. The epitopes are said to be separate (unique) if the antigen is able to accommodate binding of both corresponding antibodies simultaneously.

Epitopes can be linear or conformational. In a linear epitope, all of the points of interaction between the protein and the interacting molecule (such as an antibody) occur linearly along the primary amino acid sequence of the protein. A "nonlinear epitope" or "conformational epitope" comprises noncontiguous polypeptides (or amino acids) within the antigenic protein to which an antibody specific to the epitope binds.

The binding affinity of an antibody can be expressed as $K_D$ value, which refers to the dissociation rate of a particular antigen-antibody interaction. $K_D$ is the ratio of the rate of dissociation, also called the "off-rate ($k_{off}$)," to the association rate, or "on-rate ($k_{on}$)." Thus, $K_D$ equals $k_{off}/k_{on}$ and is expressed as a molar concentration (M), and the smaller the $K_D$, the stronger the affinity of binding. $K_D$ values for antibodies can be determined using methods well established in the art. One exemplary method for measuring $K_D$ is surface plasmon resonance (SPR), typically using a biosensor system such as a BIACORE® system. BIAcore kinetic analysis comprises analyzing the binding and dissociation of an antigen from chips with immobilized molecules (e.g. molecules comprising epitope binding domains), on their surface. Another method for determining the $K_D$ of an antibody is by using Bio-Layer Interferometry, typically using OCTET technology (Octet QKe system, ForteBio). Alternatively, or in addition, a KinExA (Kinetic Exclusion Assay) assay, available from Sapidyne Instruments (Boise, ID) can also be used.

An antibody that "preferentially binds" or "specifically binds" (used interchangeably herein) to an epitope is a term well understood in the art, and methods to determine such specific or preferential binding are also well known in the art. A molecule (e.g., a protein, a nucleic acid, an antibody, and the like) is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CD1a epitope is an antibody that binds a particular CD1a epitope with greater affinity, avidity, more readily, and/or with greater duration than it binds to other CD1a epitopes or non-CD1a epitopes, including CD1b and/or CD1c epitopes. Thus, under designated assay conditions, the specified binding moiety (e.g., an antibody or an antigen-binding fragment thereof or a receptor or a ligand binding fragment thereof) binds preferentially to a particular target molecule and does not bind in a significant amount to other components present in a test sample. Generally, but not necessarily, reference to binding means preferential binding.

A variety of assay formats may be used to select an antibody or peptide that specifically binds a molecule of interest. For example, solid-phase ELISA immunoassay (including a competition binding ELIA), AlphaLISA® immunoassay (Perkin-Elmer), immunoprecipitation, BIAcore™ (GE Healthcare, Piscataway, NJ), fluorescence-activated cell sorting (FACS), Octet™ (ForteBio, Inc., Menlo Park, CA) and Western blot analysis are among many assays that may be used to identify an antibody that specifically reacts with an antigen or a receptor, or ligand binding fragment thereof, that specifically binds with a cognate ligand or binding partner. Typically, a specific or selective reaction will be at least twice background signal or noise and more typically more than 10 times background, more than 50 times background, more than 1000 times background or more. An antibody is said to "specifically bind" an antigen when the equilibrium dissociation constant ($K_D$) is ≤1 μM, ≤100 nM, ≤10 nM, ≤1 nM or ≤100 pM. In some embodiments, an anti-CD1a antibody binds CD1a (e.g., human CD1a) with a $K_D$ of <250 pM (e.g., 181.38+/−11.92 pM). In some embodiments, an anti-CD1a antibody binds CD1a (e.g., cynomolgus monkey CD1a) with a $K_D$ of <100 pM (e.g., 60.35+/−11.04 pM).

In some embodiments, an anti-CD1a antibody binds human CD1a with a $K_D$ selected from the group consisting of about 250 pM, 245 pM, 240 pM, 235 pM, 230 pM, 225 pM, 220 pM, 215 pM, 210 pM, 205 pM, 200 pM, 195 pM, 190 pM, 185 pM, 180 pM, 175 pM, 170 pM, 165 pM, 160 pM, 155 pM, 150 pM, 140 pM, 130 pM, 120 pM, 110 pM and 100 pM. In some embodiments, an anti-CD1a antibody binds human CD1a with a $K_D$ selected from the group consisting of about 3.87 nM, 0.62 nM, 0.77 nM, 0.53 nM, 0.28 nM, 0.27 nM, 0.17 nM, and 0.1 nM.

The term "compete," as used herein with regard to an antibody, means that binding of a first antibody, or an antigen-binding fragment thereof, to an antigen reduces the subsequent binding of the same antigen by a second antibody or an antigen-binding fragment thereof. The alternative, where the binding of the second antibody to an antigen is also detectably decreased in the presence of the first antibody, can, but need not be the case. That is, a first antibody can inhibit the binding of a second antibody to an antigen without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or fragment thereof), the skilled artisan would appreciate, based upon the teachings provided herein, that such competing and/or cross-competing antibodies are encompassed and can be useful for the methods disclosed herein.

Standard competition assays may be used to determine whether two antibodies compete with each other. One suitable assay for antibody competition involves the use of the Biacore technology, which can measure the extent of interactions using surface plasmon resonance (SPR) technology, typically using a biosensor system (such as a BIACORE system). For example, SPR can be used in an in vitro competitive binding inhibition assay to determine the ability of one antibody to inhibit the binding of a second antibody. Another assay for measuring antibody competition uses an ELISA-based approach.

Furthermore, a high throughput process for "binning" antibodies based upon their competition is described in International Patent Application No. WO2003/48731. Competition is present if one antibody (or fragment) reduces the binding of another antibody (or fragment) to CD1a. For example, a sequential binding competition assay may be used, with different antibodies being added sequentially. The first antibody may be added to reach binding that is close to saturation. Then, the second antibody is added. If the binding of second antibody to CD1a is not detected, or is significantly reduced (e.g., at least about 10%, at least about 20%, at least about 30%, at least about 40%, at least about 50%, at least about 60%, at least about 70%, at least about 80%, or at least about 90% reduction) as compared to a parallel assay in the absence of the first antibody (which value can be set as 100%), the two antibodies are considered as competing with each other.

The definition of the term "paratope" is derived from the above definition of "epitope" by reversing the perspective. Thus, the term "paratope" refers to the area or region on the antibody which specifically binds an antigen, i.e., the amino acid residues on the antibody which make contact with the antigen (CD1a, or a fragment thereof) as "contact" is defined elsewhere herein. The paratope for a given antibody/antigen pair may be identified by routine methods. For example, the antibody and target molecule may be combined, and the antibody/antigen complex may be crystallized. The crystal structure of the complex may be determined and used to identify specific sites of interaction between the antibody and its target.

In some embodiments, an antibody is a "variant antibody". A variant antibody may comprise 1, 2, 3, 4, 5, up to 10, up to 20, up to 30 or more amino acid substitutions and/or deletions and/or insertions from the specific sequences and fragments disclosed herein, and in particular in Table 9. "Deletion" variants may comprise the deletion of individual amino acids, deletion of small groups of amino acids such as 1, 2, 3, 4 or 5 amino acids, or deletion of larger amino acid regions, such as the deletion of specific amino acid domains or other features. "Insertion" variants may comprise the insertion of individual amino acids, insertion of small groups of amino acids such as 1, 2, 3, 4 or 5 amino acids, or insertion of larger amino acid regions, such as the insertion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 16. If such substitutions result in a change in biological activity, then more substantial changes, denominated "exemplary substitutions" shown below, or as further described below in reference to amino acid classes, may be introduced and the products screened.

TABLE 16

Amino Acids and Substitutions

| Original Residue | Conservative Substitutions | Exemplary Substitutions |
|---|---|---|
| alanine Ala (A) | Val | Val; Leu; Ile |
| arginine Arg (R) | Lys | Lys; Gln; Asn |
| asparagine Asn (N) | Gln | Gln; His; Asp, Lys; Arg |
| aspartic Asp (D) | Glu | Glu; Asn |
| cysteine Cys (C) | Ser | Ser; Ala |
| glutamine Gln (Q) | Asn | Asn; Glu |
| glutamic Glu (E) | Asp | Asp; Gln |
| glycine Gly (G) | Ala | Ala |
| histidine His (H) | Arg | Asn; Gln; Lys; Arg |
| isoleucine Ile (I) | Leu | Leu; Val; Met; Ala; Phe; Norleucine |
| leucine Leu (L) | Ile | Norleucine; Ile; Val; Met; Ala; Phe |
| lysine Lys (K) | Arg | Arg; Gln; Asn |
| methionine Met (M) | Leu | Leu; Phe; Ile |
| phenylalanine Phe (F) | Tyr | Leu; Val; Ile; Ala; Tyr |
| proline Pro (P) | Ala | Ala |
| serine Ser (S) | Thr | Thr |
| threonine Thr (T) | Ser | Ser |
| tryptophan Trp (W) | Tyr | Tyr; Phe |
| tyrosine Tyr (Y) | Phe | Trp; Phe; Thr; Ser |
| valine Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a beta-sheet or helical conformation, (b) the charge or hydrophobicity of the molecule at the target site, or (c) the bulk of the side chain. Naturally occurring residues are divided into groups based on common side-chain properties:

Non-polar: Norleucine, Met, Ala, Val, Leu, Ile;

Polar without charge: Cys, Ser, Thr, Asn, Gln;

Acidic (negatively charged): Asp, Glu;

Basic (positively charged): Lys, Arg;

Residues that influence chain orientation: Gly, Pro; and

Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

In a process known as "germlining," certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. As used herein, the term "germline" refers to the nucleotide sequences and amino acid sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation. An antibody that "utilizes" a particular germline has a nucleotide or amino acid sequence that most closely aligns with that germline nucleotide sequence or with the amino acid sequence that it specifies. Such antibodies frequently are mutated compared with the germline sequence. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., J. Mol. Biol. 1992; 227:776-798; and Cox et al., Eur. J. Immunol. 1994; 24:827-836).

Antibodies to CD1a

In some embodiments, the disclosure provides antibodies, and antigen-binding fragments thereof, that bind to Cluster of Differentiation 1a (CD1a). This protein is a member of the CD1 family of transmembrane glycoproteins, which are structurally related to the major histocompatibility complex (MHC) proteins and form heterodimers with beta-2-microglobulin. The CD1 proteins mediate the presentation of primarily lipid and glycolipid antigens of self or microbial origin to T cells. The human genome contains five CD1 family genes organized in a cluster on chromosome 1. The CD1 family members are thought to differ in their cellular localization and specificity for particular lipid ligands. The protein encoded by the CD1a gene localizes to the plasma membrane and to recycling vesicles of the early endocytic system.

As used herein, the term "CD1a" includes variants, isoforms, homologs, orthologs and paralogs of human CD1a. In some embodiments, an antibody, or antigen-binding fragment thereof, disclosed herein cross-reacts with CD1a from species other than human, such as CD1a of cynomolgus monkey, as well as different forms of CD1a. In some embodiments, an antibody, or antigen binding fragment thereof, may be completely specific for human CD1a and may not exhibit species cross-reactivity (e.g., does not bind monkey CD1a) or other types of cross-reactivity (e.g., does not bind CD1b, CD1c and/or CD1d). As used herein the term CD1a refers to naturally occurring human CD1a unless contextually dictated otherwise. Therefore, an "CD1a antibody, or antigen-binding fragment thereof," "anti-CD1a antibody, or antigen-binding fragment thereof" or other similar designation means any antibody, or antigen-binding fragment thereof, (as defined herein) that specifically and/or preferentially associates, binds or reacts with CD1a, an isoform, fragment or derivative thereof. The full length, mature form of human CD1a, as represented by UniProtKB/Swiss-Prot accession number P06126 (amino acids 17-327) is herein provided as SEQ ID NO:1.

CD1 glycoproteins can be classified primarily into three groups which differ in their lipid anchoring: Group 1 CD1 molecules, which include CD1a, CD1b and CD1c and are expressed on cells specialized for antigen presentation, Group 2 CD1 molecules, which includes CD1d that is expressed in a wider variety of cells and Group 3 CD1 which include CD1e (Zajonc D M, Wilson I A (2007). "Architecture of CD1 proteins". Curr. Top. Microbiol. Immunol. Current Topics in Microbiology and Immunology. 314: 27-50; Sköld M, Behar S M (2005). "The role of group 1 and group 2 CD1-restricted T cells in microbial immunity". Microbes Infect. 7 (3): 544-51). Group 1 CD1 molecules mainly present lipid antigens to clonally diverse T cells that mediate adaptive immunity to the vast range of microbial lipid antigens. By contrast, CD1d (group 2) molecules present lipid antigens to natural killer T (NKT) cells, a subset of which, the invariant NKT (iNKT) cells, expresses an invariant T-cell receptor (TCR) α-chain, responds rapidly en masse following antigen recognition and is a potent effector of innate immunity.

CD1 proteins are comprised of a heavy chain with three extracellular domains that are non-covalently associated with $\beta_2$-microglobulin ($\beta_2$m). Similar to MHC class I molecules, CD1 heavy chains consist of α1 and α2 domains that form the antigen-binding region, contained within two anti-parallel α-helical structures that are situated on a β-pleated sheet. The α1 and α2 antigen-binding region is linked to an immunoglobulin-like α3 domain, which is attached to the membrane by a transmembrane segment, followed by a short cytoplasmic tail. Group 1 CD1 isoforms have structurally diverse antigen-binding grooves that allow them to bind very different lipid classes.

CD1a molecules are highly expressed on skin resident dendritic cells, or Langerhans cells (Wollenberg A, Kraft S, Hanau D, Bieber T. Immunomorphological and ultrastructural characterization of Langerhans cells and a novel, inflammatory dendritic epidermal cell (IDEC) population in lesional skin of atopic eczema. *J Invest Dermatol* (1996) 106(3):446-53). CD1b is most highly expressed on a subset of migrating lymph dendritic cells and myeloid-derived dendritic cells (Olivier M, Foret B, Le Vern Y, Kerboeuf D, Guilloteau L A. Plasticity of migrating CD1b+ and CD1b− lymph dendritic cells in the promotion of Th1, Th2 and Th17 in response to *Salmonella* and helminth secretions. *PLoS One* (2013) 8(11):e79537). CD1c is the most ubiquitously expressed group 1 CD1 molecule, being found on monocyte-derived DCs, B cells, and Langerhans cells under steady-state conditions (Sugita M, van Der Wel N, Rogers R A, Peters P J, Brenner M B. CD1c molecules broadly survey the endocytic system. *Proc Natl Acad Sci USA* (2000) 97(15):8445-50; Milne P, Bigley V, Gunawan M, Haniffa M, Collin M. CD1c+ blood dendritic cells have Langerhans cell potential. *Blood* (2015) 125(3):470-3). CD1e is the only CD1 isoform that is not expressed on the surface of APCs (Angenieux C, Salamero J, Fricker D, Cazenave J P, Goud B, Hanau D, et al. Characterization of CD1e, a third type of CD1 molecule expressed in dendritic cells. *J Biol Chem* (2000) 275(48):37757-64).

Preferably, antibodies, and antigen binding fragments thereof, of the present disclosure bind to CD1a but do not bind, or bind at a lower affinity, to other CD1 molecules (e.g., CD1b, CD1c, CD13 and/or CD1e). In some embodiments, antibodies, or antigen-binding fragments thereof, of the present disclosure specifically bind CD1a, and more preferably, specifically bind human and/or cynomolgus monkey CD1a. The disclosure also provides for compositions comprising such antibodies, and antigen-binding fragments thereof, as well as uses for such antibodies, including therapeutic and pharmaceutical uses.

Antibodies, and antigen-binding fragments thereof, of the disclosure have the potential to specifically bind CD1a and inhibit binding of CD1a to T cell receptors, such as but not limited to BK6, and their subsequent activation. Without wishing to be bound by any particular theory, recent work using human CD1a transgenic mice has suggested that CD1a may be a key driver of inflammatory skin diseases, such as contact dermatitis, psoriasis, and AD (Kim J H, Yongqing T, Kim J, et al. CD1a Langerhans cells controls inflammatory skin disease. Nat Immunol 2016; 17(10):1159-66). Antibodies, and antigen-binding fragments thereof, that bind CD1a and inhibit subsequent T cell activation are hypothesized to reduce skin inflammation associated with diseases such as AD, contact dermatitis and psoriasis.

Accordingly, in some embodiments, an isolated antibody, or antigen-binding fragment thereof, that specifically binds to CD1a is provided. In some embodiments, the CD1a is human, cynomolgus monkey, dog and/or rabbit CD1a. In some embodiments, an antibody, or antigen-binding fragment thereof, that binds an epitope on CD1a is provided. The epitope comprises Glu82 and/or His170, according to the numbering of SEQ ID NO: 1. In some embodiments, the epitope further comprises Ile92 and/or Arg93, according to the numbering of SEQ ID NO: 1. In some embodiments, the epitope comprises at least one or more of the following residues: Glu82, His170, Arg93, Glu78, Lys81, Thr85, Ile89, Arg93, Asp173, and Asn177, according to the numbering of SEQ ID NO: 1. In some embodiments, the epitope comprises at least one or more of the following residues: Glu82, His170, Arg93, Glu78, Lys81, Thr85, Ile89, Arg93, Asp173, Asn177, Leu86, Asn146, Asn168, Ile174, His176, Asp181, and Arg185, according to the numbering of SEQ ID NO: 1. In some embodiments, the epitope comprises at least one or more of the following residues: Glu78, Glu79, Lys81, Glu82, Leu83, Glu84, Thr85, Leu86, Arg88, Ile89, Ile92, Arg93, Asn146, Gln167, Asn168, Gln169, His170, Asp173, Ile174, His176, Asn177, Leu178, Ser180, Asp181, Thr182 and Arg185, according to the numbering of SEQ ID NO: 1. In some embodiments, the epitope does not comprise Asn146 and/or Asn168 according to the numbering of SEQ ID NO: 1.

A "neutralizing" or "blocking" antibody refers to an antibody whose binding to CD1a (i) interferes with, limits, or inhibits the interaction between CD1a, or a CD1a fragment, and a T cell receptor such as BK6; and/or (ii) results in reduction or inhibition of at least one biological function of CD1a. Assays to determine neutralization by an antibody of the disclosure are described elsewhere herein and are well-known in the art.

"Biological function" or "biological activity" of CD1a is meant to include (a) CD1a binding to T cell receptors; (b) CD1a-mediated lipid presentation to T cells and their subsequent activation; (c) CD1a-dependent CD69 expression; (d) CD1a-dependent IL-2 production; (e) CD1a-dependent increase in serum IgE levels; (f) CD1a-dependent increase in antigen-specific IgE antibodies; (g) CD1a-dependent increase in expression levels of atopic dermatitis-associated genes (e.g., but not limited to TSLP, FLG, IL-33, CCL-26, IL-23p40, CCL-20, and/or CCL-20).

Accordingly, the disclosure includes a neutralizing or blocking antibody, or antigen-binding fragment thereof. That is, embodiments include an isolated antibody, or antigen-binding fragment thereof, that (i) specifically binds CD1a and interferes with, limits, or inhibits the interaction between CD1a, or a CD1a fragment, and a T cell receptor such as BK6; and/or (ii) results in reduction or inhibition of at least one biological function of CD1a such as, but not limited to, (a) CD1a binding to T cell receptors; (b) CD1a-mediated lipid presentation to T cells and their subsequent activation; (c) CD1a-dependent CD69 expression; (d) CD1a-dependent IL-2 production; (e) CD1a-dependent increase in serum IgE levels; (f) CD1a-dependent increase in antigen-specific IgE antibodies; (g) CD1a-dependent increase in expression levels of atopic dermatitis-associated genes (e.g., but not limited to TSLP, FLG, IL-33, CCL-26, IL-23p40, CCL-20, and/or CCL-20).

The biological activity of CD1a can be assessed in an in vitro T cell activation assays using CD1a or CD1a expressing cells and T cell receptors (e.g., Jurkat 76 cells expressing T cell receptor allele BK6). Binding of CD1a can also be assessed using soluble or cell surface expressed proteins in physiological flow assays know in the art and set forth in the Examples section of the present disclosure. The ability of neutralizing antibodies to prevent CD1a binding can also be assessed by incubating cells expressing CD1a (e.g., human, cynomolgus monkey) with a cell surface expressed T cell receptor (e.g., on J76 cells expressing BK6) in the absence or presence of increasing concentrations of the anti-CD1a antibody, or antigen-binding fragment thereof.

Anti-CD1a antibodies of the present disclosure can encompass monoclonal antibodies, polyclonal antibodies, antibody fragments (e.g., Fab, Fab', $F(ab')_2$, Fv, Fc, etc.), chimeric antibodies, bispecific antibodies, heteroconjugate antibodies, single chain (ScFv), mutants thereof, fusion proteins comprising an antibody fragment (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some embodiments, an anti-CD1a antibody is a monoclonal antibody. In some embodiments, an anti-CD1a antibody is a human or humanized antibody. In some embodiments, an anti-CD1a antibody is a chimeric antibody.

In some embodiments, an anti-CD1a antibody, or antigen-binding fragment thereof, comprises or consists of a CDR-H1, CDR-H2, CDR-H3, CDR-L1, CDR-L2, CDR-L3, CH1, CH2, CH1-CH2 Hinge, CH3, CL, VH, VL, VH FW4, and/or VL FW4, or any combination thereof, including, but not limited to, any of the sequences set forth in Tables 14 and 15 for these regions.

In some embodiments, the disclosure includes chimeric and humanized anti-CD1a antibodies as described in Table 15. Generally, unless specifically indicated, anti-CD1a antibodies of the disclosure can include any combination of one or more CDRs. In some embodiments, anti-CD1a antibodies of the disclosure can include any combination of one or more VH and/or VL sequences as set forth in Table 15, with particular antibodies defined by SEQ ID NO: in Table 14. The CDRs of the anti-CD1a VHs and VLs were defined using the Kabat definition with the extended H1. For CDR-H1, the last residue includes any insert before the H36 position (i.e. H35a, H35b, H35c, etc.). The CDRs were defined as follows: CDR-H1 (H26 to H35c), CDR-H2 (H50 to H65), CDR-H3 (H95 to H102), CDR-L1 (L24 to L34), CDR-L2 (L50 to L56), and CDR-L3 (L89 to L87) (see also Tables 4 and 5).

In some embodiments, the disclosure includes an anti-CD1a antibody, or antigen-binding fragment thereof, comprising a heavy chain complementarity determining region-three (CDR-H3), wherein the CDR-H3 comprises the amino acid sequence selected from the group consisting of SEQ ID NO: 17, 49, and 52. In some embodiments, the anti-CD1a antibody, or antigen-binding fragment thereof, comprises a CDR-H3, wherein the CDR-H3 comprises the amino acid sequence of SEQ ID NO: 17 or 49. In some embodiments, the anti-CD1a antibody, or antigen-binding fragment thereof, comprises a CDR-H3, wherein the CDR-H3 comprises the amino acid sequence of SEQ ID NO: 17.

In some embodiments, the disclosure includes an anti-CD1a antibody, or antigen-binding fragment thereof, comprising (i) a heavy chain complementarity determining region-one (CDR-H1) comprising the amino acid sequence selected from the group consisting of SEQ ID NO: 15, 30, 40, 62, and 66; (ii) a CDR-H2 comprising the amino acid sequence selected from the group consisting of SEQ ID NO: 16, 31, 41, 48, 59, 63 and 76; and/or (iii) a CDR-H3 comprising the amino acid sequence selected from the group consisting of SEQ ID NO: 17, 49 and 52.

In some embodiments, the disclosure includes an anti-CD1a antibody, or antigen-binding fragment thereof, comprising a light chain complementarity determining region-one (CDR-L1) comprising the amino acid sequence of SEQ ID NO: 8, wherein one or more amino acids may be substituted by a different amino acid. In some embodiments, one or two amino acid residues in SEQ ID NO: 8 are substituted. The one or more amino acid substitutions may involve a conservative or a non-conservative amino acid substitution as disclosed herein. In some embodiments, the one or more (e.g., one or two) amino acid substitutions is selected from the group consisting of (i) Ser at position 7 (corresponding to L30 according to Kabat) is substituted by Tyr, Leu, Arg, or Trp and (ii) Asn at position 8 (corresponding to L31 according to Kabat) is substituted by Phe, Glu, Ile, Lys, Leu, Met, Gln, Arg, Trp or Tyr.

In some embodiments, the disclosure includes an anti-CD1a antibody, or antigen-binding fragment thereof, comprising (i) a light chain complementarity determining region-one (CDR-L1) comprising the amino acid sequence selected from the group consisting of SEQ ID NO: 8 and 25, (ii) a CDR-L2 comprising the amino acid sequence selected from the group consisting of SEQ ID NO: 9, 26, 37, 44, and 71, and/or (iii) a CDR-L3 comprising the amino acid sequence selected from the group consisting of SEQ ID NO: 10, 27, 34, and 45.

In some embodiments, the disclosure includes an anti-CD1a antibody, or antigen-binding fragment thereof, comprising (i) a CDR-H1 comprising the amino acid sequence selected from the group consisting of SEQ ID NO: 15, 30, 40, 62, and 66, (ii) a CDR-H2 comprising the amino acid sequence selected from the group consisting of SEQ ID NO: 16, 31, 41, 48, 59, 63 and 76, (iii) a CDR-H3 comprising the amino acid sequence selected from the group consisting of SEQ ID NO: 17, 49 ad 52, (iv) a CDR-L1 comprising the amino acid sequence selected from the group consisting of SEQ ID NO: 8 and 25, (v) a CDR-L2 comprising the amino acid sequence selected from the group consisting of SEQ ID NO: 9, 26, 37, 44, and 71, and/or (vi) a CDR-L3 comprising the amino acid sequence selected from the group consisting of SEQ ID NO: 10, 27, 34, and 45.

In some embodiments, the disclosure includes an anti-CD1a antibody, or antigen-binding fragment thereof, comprising (i) a CDR-H1 comprising the amino acid sequence selected from the group consisting of SEQ ID NO: 15, 30 and 40, (ii) a CDR-H2 comprising the amino acid sequence selected from the group consisting of SEQ ID NO: 16, 41 and 63, (iii) a CDR-H3 comprising the amino acid sequence selected from the group consisting of SEQ ID NO: 17 and 49, (iv) a CDR-L1 comprising the amino acid sequence selected from the group consisting of SEQ ID NO: 8 and 25, (v) a CDR-L2 comprising the amino acid sequence selected from the group consisting of SEQ ID NO: 9, and 26, and/or (vi) a CDR-L3 comprising the amino acid sequence selected from the group consisting of SEQ ID NO: 10 and 27.

In some embodiments, the disclosure includes an anti-CD1a antibody, or antigen-binding fragment thereof, comprising (i) a CDR-H1 comprising the amino acid sequence of SEQ ID NO: 15, (ii) a CDR-H2 comprising the amino acid sequence of SEQ ID NO: 16, (iii) a CDR-H3 comprising the amino acid sequence of SEQ ID NO: 17, (iv) a CDR-L1 comprising the amino acid sequence of SEQ ID NO: 8, (v) a CDR-L2 comprising the amino acid sequence of SEQ ID NO: 9, and (vi) a CDR-L3 comprising the amino acid sequence of SEQ ID NO: 10.

In some embodiments, the disclosure includes an anti-CD1a antibody, or antigen-binding fragment thereof, comprising (i) a CDR-H1 comprising the amino acid sequence of SEQ ID NO: 30, (ii) a CDR-H2 comprising the amino acid sequence of SEQ ID NO: 41, (iii) a CDR-H3 comprising the amino acid sequence of SEQ ID NO: 17, (iv) a CDR-L1 comprising the amino acid sequence of SEQ ID NO: 25, (v) a CDR-L2 comprising the amino acid sequence of SEQ ID NO: 26, and (vi) a CDR-L3 comprising the amino acid sequence of SEQ ID NO: 27.

In some embodiments, the disclosure includes an anti-CD1a antibody, or antigen-binding fragment thereof, comprising (i) a CDR-H1 comprising the amino acid sequence of SEQ ID NO: 40, (ii) a CDR-H2 comprising the amino acid sequence of SEQ ID NO: 63, (iii) a CDR-H3 comprising the amino acid sequence of SEQ ID NO: 49, (iv) a CDR-L1 comprising the amino acid sequence of SEQ ID NO: 25, (v) a CDR-L2 comprising the amino acid sequence of SEQ ID NO: 26, and (vi) a CDR-L3 comprising the amino acid sequence of SEQ ID NO: 27.

In some embodiments, the disclosure includes an anti-CD1a antibody, or antigen-binding fragment thereof, comprising (i) a CDR-H1 comprising the amino acid sequence of SEQ ID NO: 96, (ii) a CDR-H2 comprising the amino acid sequence of SEQ ID NO: 97, (iii) a CDR-H3 comprising the amino acid sequence of SEQ ID NO: 98, (iv) a CDR-L1 comprising the amino acid sequence of SEQ ID NO: 99, (v) a CDR-L2 comprising the amino acid sequence of SEQ ID NO: 100, and/or (vi) a CDR-L3 comprising the amino acid sequence of SEQ ID NO: 101.

Any embodiment referring to CDR-H1 or any of SEQ ID NOs: 15, 30, 40, 62, or 66 can be implemented with SEQ ID NO: 96. It is specifically contemplated that any alternative amino acid in SEQ ID NO:96 may be excluded in an embodiment. Any embodiment referring to CDR-H2 or any of SEQ ID NOs: 16, 31, 41, 48, 59, 63, or 76 can be implemented with SEQ ID NO: 97. It is specifically contemplated that any alternative amino acid in SEQ ID NO:97 may be excluded in an embodiment. Any embodiment referring to CDR-H3 or any of SEQ ID NOs: 17, 49, or 52 can be implemented with SEQ ID NO: 98. It is specifically contemplated that any alternative amino acid in SEQ ID NO:99 may be excluded in an embodiment. Any embodiment referring to CDR-L1 or any of SEQ ID NOs: 8 or 25 can be implemented with SEQ ID NO: 99. It is specifically contemplated that any alternative amino acid in SEQ ID NO:99 may be excluded in an embodiment. Any embodiment referring to CDR-L2 or any of SEQ ID NOs: 9, 26, 37, 44 or 71 can be implemented with SEQ ID NO: 100. It is specifically contemplated that any alternative amino acid in SEQ ID NO:100 may be excluded in an embodiment. Any embodiment referring to CDR-L3 or any of SEQ ID NOs: 10, 27, 34, or 45 can be implemented with SEQ ID NO: 101. It is specifically contemplated that any alternative amino acid in SEQ ID NO:101 may be excluded in an embodiment. Such embodiments include an antibody, or antigen binding fragment thereof, further comprising a CH1, CH1_CH2 hinge, CH2, and/or CH3 or embodied in a VH or VL region described herein.

Germline Substitutions

A wide variety of acceptor human germline sequences are available and the process for "humanizing" a non-human species antibody to use in humans is well-known in the art and also discussed elsewhere herein. Therefore, the skilled artisan would appreciate that the above CDR sequences from a mouse, rat, etc., can be placed in the context of human variable domain amino acid sequences. In doing so, changes to the acceptor human germline sequences are generally made to preserve antibody binding and other desirable characteristics of the original parent (i.e., donor) antibody. Both the CDRs and framework regions (FW) may be engineered as follows.

In certain embodiments, a substitution is a human germline substitution in which a (donor) CDR residue is replaced with the corresponding human germline (acceptor) residue, to increase the human amino acid content and potentially reduce immunogenicity of the antibody as described in, e.g., U.S. Patent Application Publication No. 2017/0073395 and Townsend et al., Proc. Nat. Acad. Sci. USA 2015; 112(50): 15354-15359, both of which are herein incorporated by reference in their entirety.

An antibody, or antigen-binding fragment thereof, may comprise a VH framework comprising a human germline VH framework sequence. In some aspects, a VH framework from the following germlines may be used: IGHV1-2*02, IGHV1-3*01, IGHV1-46*01, IGHV1-69*01, IGHV1-69*02, IGHV1-8*01, IGHV3-7*01, IGHV3-13*01, IGHV3-23*01, IGHV3-23*04, IGHV3-30*01, IGHV3-30*18, IGHV5-10-1*01, IGHV5-10-1*04, or IGHV5-51*01 (germline names are based on IMGT germline definition). In some embodiments, an anti-CD1a antibody, or antigen binding fragment thereof, uses the VH framework from germline IGHV3-7*01.

Preferred human germline light chain frameworks are frameworks derived from VK or Vλ germlines. In some aspects, a VL framework from the following germlines may be used: IGKV1-12*01, IGKV1-13*02, IGKV1-33*01, IGKV1-39*01, IGKV1-5*01, IGKV3-11*01, IGKV3-15*01, IGKV3-20*01, IGKV3D-20*02, and IGKV4-1*01 (germline names are based on IMGT germline definition). In some embodiments, an anti-CD1a antibody, or antigen-binding fragment thereof, uses the VL framework from germline IGHV1-39*01.

Alternatively, or in addition, the framework sequence may be a human germline consensus framework sequence, such as the framework of human Vλ1 consensus sequence, VK1 consensus sequence, VK2 consensus sequence, VK3 consensus sequence, VH3 germline consensus sequence, VH1 germline consensus sequence, VH5 germline consensus sequence, or VH4 germline consensus sequence. Sequences of human germline frameworks are available from various public databases, such as V-base, IMGT, NCBI, or Abysis.

An anti-CD1a antibody, or antigen-binding fragment thereof, may comprise a VL framework comprising a human germline VL framework sequence. A VL framework may comprise one or more amino acid substitutions, additions, or deletions, while still retaining functional and structural similarity with the germline from which it was derived. In some aspects, a VL framework is at least 90%, at least 91%, at least 92%, at least 93%, at least 94%, at least 95%, at least 96%, at least 97%, at least 98%, at least 99%, or 100% identical to a human germline VL framework sequence. In some embodiments, an antibody, or antigen binding fragment thereof, comprises a VL framework comprising 1, 2, 3, 4, 5, 6, 7, 8, 9, 10 amino acid substitutions, additions or deletions relative to the human germline VL framework sequence. In some embodiments, the 1, 2, 3, 4, 5, 6, 7, 8, 9, or 10 amino acid substitutions, additions or deletions are only in the framework regions. In some embodiments, the percent identity is based on similarity with VL domain excluding those portions herein defined as CDRs.

It is contemplated that a region or fragment of a polypeptide of the disclosure may have an amino acid sequence that has, has at least or has at most 1, 2, 3, 4, 5, 6, 7, 8, 9, or 10 amino acid substitutions, contiguous amino acid additions, or contiguous amino acid deletions with respect to any of SEQ ID NOs: 7-79, 86, and 96-102. In some embodiments, an anti-CD1a antibody, or antigen-binding fragment thereof, comprises or consists of an amino acid sequence that is, is at least, or is at most 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% (or any range derivable therein) identical to any of SEQ ID NOs: 7-79, 86, and 96-102. Moreover, in some embodiments, a region or fragment comprises an amino acid region of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more contiguous amino acids starting at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 in any of SEQ ID NOS: 7-79, 86, and 96-102 (where position 1 is at the N-terminus of the SEQ ID NO). An anti-CD1a antibody, or antigen-binding fragment thereof, of the disclosure may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more variant amino acids or amino acid substitutions. In some embodiments, a variant or amino acid substitution is at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, and/or 500 in any of SEQ ID NOS: 7-79, 86, and 96-102 (where position 1 is at the N-terminus of the SEQ ID NO), and the anti-CD1a antibody, or antigen-binding fragment thereof may be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to or homologous with at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 600, or more contiguous amino acids, or any range derivable therein, of any of SEQ ID NOs: 7-79, 86, and 96-102. It is specifically contemplated that any one or more of SEQ ID NOs: 7-79, 86, or 96-102 may be excluded from an embodiment disclosed herein.

A human germline VL framework may be, for example, the framework of IGKV1-39*01. A human germline VL framework may be, for example, the framework of IGKV1-33*01. A human germline VL framework may be the framework of any one of human consensus sequence including: Vλ, Vλ1, Vλ3, VK, VK1, VK2 or VK3.

In some embodiments, a VL framework is IGK-39*01_IGKJ1*01. Other similar framework regions are also predicted to deliver advantageous antibodies comprising CDRs of SEQ ID NOs: 8-10, 25-27, 34, 37, 44, 45, 71; and CDRs specified by the following VL amino acid sequences: SEQ ID NOs: 12, 28, 35, 38, 46, 72 and 79, which may comprise 99%, 97%, 97%, 96%, 80%, 76%, 74% and 66%, identity respectively to the framework region of any one of IGKV1-12*01, IGKV1-13*02, IGKV1-33*01, IGKV1-39*01, IGKV1-5*01, IGKV3-11*01, IGKV3-15*01, IGKV3-20*01, IGKV3D-20*02, and IGKV4-1*01. In some embodiments, the percent identity is based on similarity with VL excluding those portions herein defined as CDRs.

An anti-CD1a antibody, or antigen-binding fragment thereof, may comprise a VH framework comprising a human germline VH framework sequence. A VH framework may comprise one or more amino acid substitutions, additions, or deletions, while still retaining functional and structural similarity with the germline from which it was derived. In some aspects, a VH framework is at least 90%, at least 91%, at least 92%, at least 93%, at least 94%, at least 95%, at least 96%, at least 97%, at least 98%, at least 99%, or 100% identical to a human germline VH framework sequence. In some embodiments, an antibody, or antigen binding fragment thereof, comprises a VH framework comprising 1, 2, 3, 4, 5, 6, 7, 8, 9, 10 amino acid substitutions, additions or deletions relative to the human germline VH framework sequence. In some embodiments, the 1, 2, 3, 4, 5, 6, 7, 8, 9, or 10 amino acid substitutions, additions or deletions are only in the framework regions. In some embodiments, the percent identity is based on similarity with VH domain excluding those portions herein defined as CDRs.

A human germline VH framework may be, for example, the framework of IGHV3-7*01. A human germline VH framework may be, for example, the framework of IGHV1-46*01. A human germline VH framework may be, for example, IGHV1-69*01. A human germline VH framework may be the framework of human VH germline consensus sequence. The human germline VH framework may be the framework of a human germline consensus sequence including: VH3, VH5, VH1 or VH4.

In some embodiments, a VH framework is IGHV3-7*01 Other similar framework regions are also predicted to deliver advantageous antibodies comprising CDRs of SEQ ID NOs:15-17, 30, 31, 40, 41, 48, 49, 52, 59, 62, 63, 66, 76 and CDRs specified by any of the following VH amino acid sequences: SEQ ID NOs: 22, 32, 42, 50, 53, 55, 57, 60, 64, 67, 69, 74 and 77, including IGHV1-2*02, IGHV1-3*01, IGHV1-46*01, IGHV1-69*01, IGHV1-69*02, IGHV1-8*01, IGHV3-7*01, IGHV3-13*01, IGHV3-23*01, IGHV3-23*04, IGHV3-30*01, IGHV3-30*18, IGHV5-10-1*01, IGHV5-10-1*04, or IGHV5-51*01, which may comprise 92, 93, 94, 95, 96, 97, 98, 99% identity respectively to the FW region of DP-54 and one or fewer amino acid differences in common structural features (Kabat Numbering) In some aspects, the percent identity is based on similarity with VH domain excluding those portions herein defined as CDRs.

In some embodiments, the antibody, or antigen binding fragment thereof, comprises: (i) a heavy chain variable region (VH) comprising the amino acid sequence selected from the group consisting of SEQ ID NO: 22, 32, 42, 50, 53, 55, 57, 60, 64, 67, 69, 74 and 77; and/or (ii) a light chain variable region (VL) comprising the amino acid sequence selected from the group consisting of SEQ ID NO: 12, 28, 35, 38, 46, 72 and 79. Any combination of these VL and VH sequences is also encompassed by various embodiments.

In some embodiments, (i) the VH comprises an amino acid sequence at least 90%, at least 91%, at least 92%, at least 93%, at least 94%, at least 95%, at least 96%, at least 97%, at least 98%, at least 99%, or 100% identical to SEQ ID NO: 22, 32, 42, 50, 53, 55, 57, 60, 64, 67, 69, 74 or 77; and/or (ii) the VL comprises an amino acid sequence at least 90%, at least 91%, at least 92%, at least 93%, at least 94%, at least 95%, at least 96%, at least 97%, at least 98%, at least 99%, or 100% identical to SEQ ID NO: 12, 28, 35, 38, 46, 72 or 79. Any combination of these VL and VH sequences is also encompassed by various embodiments.

In some embodiments, the antibody, or antigen binding fragment thereof, of the present disclosure comprises: (i) a VH comprising the amino acid sequence of SEQ ID NO: 22 and a VL comprising the amino acid sequence of SEQ ID NO: 12; (ii) a VH comprising the amino acid sequence of SEQ ID NO: 55 and a VL comprising the amino acid sequence of SEQ ID NO: 28; (iii) a VH comprising the amino acid sequence of SEQ ID NO: 74 and a VL comprising the amino acid sequence of SEQ ID NO: 28; (iv) a VH comprising an amino acid sequence at least 90%, at least 91%, at least 92%, at least 93%, at least 94%, at least 95%, at least 96%, at least 97%, at least 98%, at least 99%, or 100% identical to SEQ ID NO: 22 and a VL comprising an amino acid sequence at least 90%, at least 91%, at least 92%, at least 93%, at least 94%, at least 95%, at least 96%, at least 97%, at least 98%, at least 99%, or 100% identical to SEQ ID NO: 12; (v) a VH comprising an amino acid sequence at least 90%, at least 91%, at least 92%, at least 93%, at least 94%, at least 95%, at least 96%, at least 97%, at least 98%, at least 99%, or 100% identical to SEQ ID NO: 55 and a VL comprising an amino acid sequence at least 90%, at least 91%, at least 92%, at least 93%, at least 94%, at least 95%, at least 96%, at least 97%, at least 98%, at least 99%, or 100% identical to SEQ ID NO: 28; or (vi) a VH comprising an amino acid sequence at least 90%, at least 91%, at least 92%, at least 93%, at least 94%, at least 95%, at least 96%, at least 97%, at least 98%, at least 99%, or 100% identical to SEQ ID NO: 74 and a VL comprising an amino acid sequence at least 90%, at least 91%, at least 92%, at least 93%, at least 94%, at least 95%, at least 96%, at least 97%, at least 98%, at least 99%, or 100% identical to SEQ ID NO: 28.

In some embodiments, the disclosure includes an anti-CD1a antibody, or antigen binding fragment thereof, comprising: (i) the CDR-H1, CDR-H2, and CDR-H3 sequences as set forth in SEQ ID NO: 22 and the CDR-L1, CDR-L2, and CDR-L3 sequences as set forth in SEQ ID NO: 12, (ii) the CDR-H1, CDR-H2, and CDR-H3 sequences as set forth in SEQ ID NO: 55 and the CDR-L1, CDR-L2, and CDR-L3 sequences as set forth in SEQ ID NO: 28, or (iii) the CDR-H1, CDR-H2, and CDR-H3 sequences as set forth in SEQ ID NO: 74 and the CDR-L1, CDR-L2, and CDR-L3 sequences as set forth in SEQ ID NO: 28.

The antibody, or antigen-binding fragment thereof, of the disclosure may comprise a human kappa ($V_K$) or lambda ($V_\lambda$) light chain constant domain. In some embodiments, the antibody, or antigen-binding fragment thereof, comprises a human $V_K$ light chain constant domain.

In some embodiments, an anti-CD1a antibody, or antigen-binding fragment thereof, comprises a light chain comprising a VL domain comprising the amino acid sequence of any one of SEQ ID NOs: 12, 28, 35, 38, 46, 72 and 79 and further comprises a kappa constant domain. In some embodiments, an anti-CD1a antibody, or antigen-binding fragment thereof, comprises a light chain comprising a VL domain consisting of the amino acid sequence of SEQ ID NO: 28 and further comprises a kappa constant domain.

The antibody, or antigen-binding fragment thereof, of the disclosure, wherein the antibody, or antigen-binding fragment thereof, comprises a heavy chain constant domain. The heavy chain constant domain comprises an IgA (for example $IgA_1$ or $IgA_2$), IgD, IgE, IgM, or IgG (for example $IgG_1$, $IgG_2$, $IgG_3$, or $IgG_4$). In some embodiments, the heavy chain constant domain comprises an IgG. In some embodiments, the IgG is selected from the group consisting of $IgG_1$, $IgG_2$, $IgG_3$, and $IgG_4$. In some embodiments, the IgG is $IgG_1$.

In some embodiments, an anti-CD1a antibody, or antigen-binding fragment thereof, may comprise a heavy chain comprising a VH domain comprising the amino acid sequence of any one of SEQ ID NOs: 22, 32, 42, 50, 53, 55, 57, 60, 64, 67, 69, 74 and 77, and further comprising an IgG1 constant domain comprising the amino acid sequence of SEQ ID NO: 86. In some embodiments, an anti-CD1a antibody, or antigen-binding fragment thereof, may comprise a heavy chain comprising a VH domain comprising the amino acid sequence of SEQ ID NO: 55, and further comprising an IgG1 constant domain comprising the amino acid sequence of SEQ ID NO: 86. In some embodiments, an anti-CD1a antibody, or antigen-binding fragment thereof, may comprise a heavy chain comprising a VH domain comprising the amino acid sequence of SEQ ID NO: 74, and further comprising an IgG1 constant domain comprising the amino acid sequence of SEQ ID NO: 86.

In some embodiments, the constant region of an anti-CD1a antibody, or antigen-binding fragment thereof, can be altered, e.g., mutated, to modify the properties of the antibody (e.g., to increase or decrease one or more of: Fc receptor binding, antibody glycosylation, the number of cysteine residues, effector cell function, and/or complement function). In some embodiments, an anti-CD1a antibody, or antigen-binding fragment thereof, lacks effector function (i.e., is effector null).

In some embodiments, the antibody, or antigen-binding fragment thereof, comprises an Fc domain. The Fc domain may comprise an IgG1 heavy chain $CH_2$ domain and an IgG heavy chain $CH_3$ domain.

In some embodiments, the antibody, or antigen-binding fragment thereof, comprises: (i) a heavy chain (HC) comprising the amino acid sequence selected from the group consisting of SEQ ID NO: 14, 29, 39, 47, 51, 54, 56, 58, 61, 65, 68, 73, and 75; and (ii) a light chain (LC) comprising the amino acid sequence selected from the group consisting of SEQ ID NO: 7, 24, 33, 36, 43, 70 and 78.

In some embodiments, the antibody, or antigen-binding fragment thereof, comprises: (i) a HC comprising an amino acid sequence at least 90%, at least 91%, at least 92%, at least 93%, at least 94%, at least 95%, at least 96%, at least 97%, at least 98%, at least 99%, or 100% identical to SEQ ID NO: 14, 29, 39, 47, 51, 54, 56, 58, 61, 65, 68, 73, and 75; and (ii) a LC comprising an amino acid sequence at least 90%, at least 91%, at least 92%, at least 93%, at least 94%, at least 95%, at least 96%, at least 97%, at least 98%, at least 99%, or 100% identical to SEQ ID NO: 7, 24, 33, 36, 43, 70 and 78.

In some embodiments, the antibody, or antigen-binding fragment thereof, comprises: (i) a HC comprising, or consisting of, the amino acid sequence of SEQ ID NO: 14 and a LC comprising, or consisting of, the amino acid sequence of SEQ ID NO: 7; (ii) a HC comprising, or consisting of, the amino acid sequence of SEQ ID NO: 54 and a LC comprising, or consisting of, the amino acid sequence of SEQ ID NO: 24; (iii) a HC comprising, or consisting of, the amino acid sequence of SEQ ID NO: 73 and a LC comprising, or consisting of, the amino acid sequence of SEQ ID NO: 24; (iv) a HC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 14 and a LC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 7; (v) a HC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 54 and a LC comprising, or consisting of, an amino acid sequence of SEQ ID NO: 24; or (vi) a HC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 73 and a LC comprising, or consisting of, an amino acid sequence at least 90%, at least 91%, at least 92%, at least 93%, at least 94%, at least 95%, at least 96%, at least 97%, at least 98%, at least 99%, or 100% identical to SEQ ID NO: 24.

In some embodiments, the disclosure provides an antibody, or antigen binding fragment thereof, comprising a HC comprising, or consisting of, the amino acid sequence of SEQ ID NO: 54 and a LC comprising, or consisting of, the amino acid sequence of SEQ ID NO: 24. In some embodiments, the disclosure provides an antibody, or antigen binding fragment thereof, comprising a HC comprising, or consisting of, the amino acid sequence of SEQ ID NO: 73 and a LC comprising, or consisting of, the amino acid sequence of SEQ ID NO: 24.

In some embodiments, the antibody, or antigen-binding fragment thereof, comprises the amino acid sequence encoded by the insert of the plasmid deposited at the ATCC and having ATCC Accession No. PTA-126810. In some embodiments, the antibody, or antigen-binding fragment thereof, comprises the amino acid sequence encoded by the insert of the plasmid deposited at the ATCC and having ATCC Accession No. PTA-126811. In some embodiments, the disclosure provides an antibody, or antigen-binding fragment thereof, comprising the amino acid sequence encoded by the insert in the plasmid deposited at the ATCC and having ATCC Accession No. PTA-126810 and comprising the amino acid sequence encoded by the insert in the plasmid deposited at the ATCC and having ATCC Accession No. PTA-126811.

In some aspects, an antibody, or antigen-binding fragment, variant comprises 1, 2, 3, 4, 5, 6, 7, 8, 9, 10, 11, 12, 13, 14, or 15 conservative or non-conservative substitutions, and/or 1, 2, 3, 4, 5, 6, 7, 8, 9, 10, 11, 12, 13, 14, or 15 additions and/or deletions to the full length heavy chain (e.g., a HC of the amino acid sequence of SEQ ID NO: 54 or 73) and/or the full length light chain (e.g., a LC of the amino acid sequence of SEQ ID NO: 24). In a further aspect, a variant antibody shares at least 65%, at least 75%, at least 85%, at least 90%, at least 95%, at least 96%, at least 97%, at least 98%, or at least 99% sequence identity with the full length heavy chain (e.g., a HC of the amino acid sequence of SEQ ID NO: 54 or 73) and, and wherein said antibody or antigen-binding fragment specifically binds CD1a. In a further aspect, a variant antibody shares at least 65%, at least 75%, at least 85%, at least 90%, at least 95%, at least 96%, at least 97%, at least 98%, or at least 99% sequence identity with the full length light chain (e.g., a LC of the amino acid sequence of SEQ ID NO: 24), and wherein said antibody or antigen-binding fragment specifically binds CD1a.

In some embodiments, the antibody, or antigen-binding fragment thereof, is an Fc fusion protein, a monobody, a maxibody, a bifunctional antibody, an scFab, an scFv, a peptibody.

Anti-CD1a Antibody Properties

In some embodiments, an anti-CD1a antibody, or antigen-binding fragment thereof, binds to at least one, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or more amino acid residues of human CD1a. The human CD1a amino acid residues may be selected from the group consisting of: Glu78, Glu79, Lys81, Glu82, Leu83, Glu84, Thr85, Leu86, Arg88, Ile89, Ile92, Arg93, Asn146, Gln167, Asn168, Gln169, His170, Asp173, Ile174, His176, Asn177, Leu178, Ser180, Asp181, Thr182 and Arg185, according to the numbering of SEQ ID NO: 1.

In some embodiments, an anti-CD1a antibody, or antigen-binding fragment thereof, interacts with at least one of the following human CD1a amino acid residues: Glu78, Lys81, Thr85, Ile89, Arg93, Asp173, and Asn177, according to the numbering of SEQ ID NO: 1. In some embodiments, the anti-CD1a antibody or antigen-binding fragment thereof, interacts with human CD1a amino acid residues: Glu78, Lys81, Thr85, Ile89, Arg93, Asp173, and Asn177, according to the numbering of SEQ ID NO: 1. In some embodiments, the anti-CD1a antibody or antigen-binding fragment thereof, interacts with human CD1a amino acid residues: Glu78, Lys81, Thr85, Ile89, Arg93, Asp173, and Asn177, according to the numbering of SEQ ID NO: 1, with (i) >80 $Å^2$ of accessible surface area (ASA) buried by the interaction with CD1a, and/or (ii) >90% of ASA in free state buried by the interface and >30 $Å^2$ of ASA buried by the interaction with CD1a. In some embodiments, the anti-CD1a antibody or antigen-binding fragment thereof, interacts with human CD1a amino acid residues: Glu78, Lys81, Thr85, Ile89, Arg93, Asp173, and Asn177, according to the numbering of SEQ ID NO: 1, within 3.8 Å, via either a salt bridge or via a hydrogen bond.

In some embodiments, an anti-CD1a antibody, or antigen-binding fragment thereof, interacts with at least one of the following human CD1a amino acid residues: Glu78, Lys81, Leu86, Glu82, Thr85, Ile89, Arg93, Asn146, Asn168, His170, Asp173, Ile174, His176, Asn177, Asp181, and Arg185, according to the numbering of SEQ ID NO: 1. In some embodiments, an anti-CD1a antibody, or antigen-binding fragment thereof, interacts with the following human CD1a amino acid residues: Glu78, Lys81, Leu86, Glu82, Thr85, Ile89, Arg93, Asn146, Asn168, His170, Asp173, Ile174, His176, Asn177, Asp181, and Arg185, according to the numbering of SEQ ID NO: 1. In some embodiments, the anti-CD1a antibody, or antigen-binding fragment thereof, interacts with the following human CD1a amino acid residues: Glu78, Lys81, Leu86, Glu82, Thr85, Ile89, Arg93, Asn146, Asn168, His170, Asp173, Ile174, His176, Asn177, Asp181, and Arg185, according to the numbering of SEQ ID NO: 1 with (i) >40 $Å^2$ of accessible surface area (ASA) buried by the interaction with CD1a, and/or (ii) >50% of ASA in free state buried by the interaction with CD1a. In some embodiments, the anti-CD1a antibody, or antigen-binding fragment thereof, interacts with the following human CD1a amino acid residues: Glu78, Lys81, Leu86, Glu82, Thr85, Ile89, Arg93, Asn146, Asn168, His170, Asp173, Ile174, His176, Asn177, Asp181, and Arg185, according to the numbering of SEQ ID NO: 1, within 3.8 Å, via a salt bridge, and/or via a hydrogen bond.

In some embodiments, an anti-CD1a antibody, or antigen-binding fragment thereof, interacts with at least one of the following human CD1a amino acid residues: Glu78, Glu79, Lys81, Glu82, Leu83, Glu84, Thr85, Leu86, Arg88, Ile89, Ile92, Arg93, Asn146, Gln167, Asn168, Gln169, His170, Asp173, Ile174, His176, Asn177, Leu178, Ser180, Asp181, Thr182 and Arg185, according to the numbering of SEQ ID NO: 1. In some embodiments, an anti-CD1a antibody, or antigen-binding fragment thereof, interacts with the following human CD1a amino acid residues: Glu78, Glu79, Lys81, Glu82, Leu83, Glu84, Thr85, Leu86, Arg88, Ile89, Ile92, Arg93, Asn146, Gln167, Asn168, Gln169, His170, Asp173, Ile174, His176, Asn177, Leu178, Ser180, Asp181, Thr182 and Arg185, according to the numbering of SEQ ID NO: 1. In some embodiments, an anti-CD1a antibody, or antigen-binding fragment thereof, interacts with the following human CD1a amino acid residues: Glu78, Glu79, Lys81, Glu82, Leu83, Glu84, Thr85, Leu86, Arg88, Ile89, Ile92, Arg93, Asn146, Gln167, Asn168, Gln169, His170, Asp173, Ile174, His176, Asn177, Leu178, Ser180, Asp181, Thr182 and Arg185, according to the numbering of SEQ ID NO: 1, with (i) >20 $Å^2$ of accessible surface area (ASA) buried by the interaction with CD1a, and which reciprocally buries >10 $Å^2$ of accessible surface area (ASA) of the CD1a epitope. In some embodiments, an anti-CD1a antibody, or antigen-binding fragment thereof, interacts with the following human CD1a amino acid residues: Glu78, Glu79, Lys81, Glu82, Leu83, Glu84, Thr85, Leu86, Arg88, Ile89, Ile92, Arg93, Asn146, Gln167, Asn168, Gln169, His170, Asp173, Ile174, His176, Asn177, Leu178, Ser180, Asp181, Thr182 and Arg185, according to the numbering of SEQ ID NO: 1, within 3.8 Å, via a salt bridge, via a water-mediated hydrogen bond and/or via a hydrogen bond.

In some embodiments, the anti-CD1a antibody, or antigen-binding fragment thereof, does not interact with human CD1a amino acid residue Asn146 and/or Asn168 according to the numbering of SEQ ID NO: 1.

In some embodiments, the disclosure provides an antibody, or antigen-binding fragment thereof, that specifically binds to CD1a, wherein the antibody, or antigen-binding fragment thereof, is selected from the group consisting of: Ab138, Ab491, Ab492, Ab504, Ab514, Ab555, Ab556, Ab559, Ab560, Ab571, Ab572, Ab579, Ab585, Ab599, Ab609, Ab610, Ab616, Ab623, Ab624, Ab656, Ab657, Ab660, Ab673, Ab681, and Ab689 (e.g., as disclosed in Table 14).

In some embodiments, an anti-CD1a antibody of the disclosure encompasses an antibody that competes for binding to human CD1a with, and/or binds substantially the same epitope as, an antibody, or antigen-binding fragment described herein. In some embodiments, an anti-CD1a antibody of the disclosure encompasses an antibody that competes for binding to human CD1a with, and/or binds substantially the same epitope as, Ab138, Ab571, and Ab673 (e.g., as disclosed in Table 14). In some embodiments, an anti-CD1a antibody of the disclosure encompasses an antibody that competes for binding to human CD1a with, and/or binds the same epitope as Ab571 (e.g., disclosed in Table 14).

In some embodiments, the antibody, or antigen-binding fragment thereof, of the disclosure, binds CD1a with a binding affinity, expressed as $K_D$, that is about or less than a value selected from the group consisting of: 500 nM, 400 nM, 300 nM, 200 nM, 175 nM, 150 nM, 125 nM, 100 nM, 90 nM, 80 nM, 70 nM, 60 nM, 50 nM, 40 nM, 30 nM, 20 nM, 10 nM, 5 nM, 2 nM, 1 nM, 900 pM, 800 pM, 700 pM, 600 pM, 500 pM, 400 pM, 300 pM, 200 pM, 180 pM, 160 pM, 140 pM, 120 pM, 100 pM, 80 pM, 60 pM, 40 pM, 20 pM and 10 pM. In some embodiments, the antibody, or antigen-binding fragment thereof, binds CD1a with a $K_D$ value of or less than 500 pM, 400 pM, 300 pM, 200 pM, 190 pM, 180 pM, 181 pM, 170 pM, 160 pM, 150 pM, 140 pM, 130 pM, 120 pM, 110 pM, 100 pM, 90 pM, 80 pM, 70 pM, 60 pM, 50 pM, 40 pM, 30 pM, 20 pM or 10 pM. CD1a may be human CD1a, cyno CD1a, dog CD1a and/or rabbit CD1a.

In some embodiments, the antibody, or antigen binding fragment thereof, binds human CD1a with a $K_D$ value of about 250 pM to about 100 pM, about 200 pM to about 150 pM, or about 190 pM to about 170 pM. In some embodiments, the antibody, or antigen binding fragment thereof, (e.g., Ab571) binds human CD1a with a $K_D$ value of about 181.39+/−11.92 pM. In some embodiments, the antibody, or antigen binding fragment thereof, binds cynomolgus monkey CD1a with a $K_D$ value of about 100 pM to about 30 pM, about 80 pM to about 40 pM, or about 70 pM to about 50 pM. In some embodiments, the antibody, or antigen binding fragment thereof, (e.g., Ab571) binds cynomolgus monkey CD1a with a $K_D$ value of about 60.35+/−11.04 pM.

In some embodiments, the disclosure provides an isolated antibody, or antigen-binding fragment thereof that binds human CD1a with a $K_D$ value of about 2-4 nM, about 250 pM to about 100 pM, about 200 pM to about 150 pM or about 190 pM to about 170 pM, and wherein the antibody, or antigen binding fragment thereof, comprises a heavy chain complementarity determining region-three (CDR-H3) comprising the amino acid sequence selected from the group consisting of SEQ ID NO: 17 and 49. In some embodiments, the disclosure provides an isolated antibody, or antigen-binding fragment thereof that binds human CD1a with a $K_D$ value of about 250 pM to about 150 pM, and wherein the antibody, or antigen binding fragment thereof, comprises a heavy chain complementarity determining region-three (CDR-H3) comprising the amino acid sequence selected from the group consisting of SEQ ID NO: 17 and 49. In some embodiments, the disclosure provides an isolated antibody, or antigen-binding fragment thereof that binds human CD1a with a $K_D$ value of about 190 pM to about 170 pM, and wherein the antibody, or antigen binding fragment thereof, comprises a heavy chain complementarity determining region-three (CDR-H3) comprising the amino acid sequence of SEQ ID NO: 17.

As described herein, the $K_D$ value may be measured by surface plasmon resonance (SPR), optionally using a Biacore T200 or a Biacore 8K instrument. In some embodiments, the $K_D$ value is measured by bio-layer interferometry (BLI), optionally using a ForteBio Octet instrument.

In some embodiments, the anti-CD1a antibody, or antigen-binding fragment thereof, has weak or no binding to cyno or human CD1b, to cyno or human CD1c and/or to cyno, rat, mouse or human CD1d.

In some embodiments, the anti-CD1a antibody, or antigen-binding fragment thereof, inhibits CD1a-dependent Cluster of Differentiation 69 (CD69) expression with an $IC_{50}$ value of no more than about 50 nM, 40 nM, 20 nM, 10 nM, 5 nM, 4 nM, 3 nM, 2 nM, or 1 nM, as measured, for example, using a T cell activation assay as described in Examples 1 and 9. In some embodiments, the anti-CD1a antibody, or antigen-binding fragment thereof, inhibits CD1a-dependent CD69 expression with an $IC_{50}$ value of no more than about 5 nM, 4 nM, 3 nM, 2 nM, 1.97 nM, 1.9 nM, 1.8 nM, 1.7 nM, 1.6 nM, 1.5 nM, 1.4 nM, 1.3 nM, 1.2 nM, 1.1 nM, 1 nM, 0.9 nM, 0.8 nM, 0.7 nM, 0.6 nM, 0.5 nM, 0.4 nM, 0.3 nM, 0.2 nM, or 0.1 nM. In some embodiments, the anti-CD1a antibody, or antigen-binding fragment thereof, inhibits CD1a-dependent CD69 expression with an $IC_{50}$ value of no more than about 2000 pM, 1970 pM, 1500 pM, 1110 pM, 1000 pM, 500 pM, 400 pM, 300 pM, 200 pM, 100 pM, 90 pM, 80 pM, 70 pM, 60 pM, 50 pM, 40 pm, 30 pM, 20 pM, 10 pM, 9 pM, 8 pM, 7 pM, 6 pM, 5 pM, 4 pM, 3 pM, 2 pM, or 1 pM. In some embodiments, the anti-CD1a antibody, or antigen-binding fragment thereof (e.g., Ab571), inhibits CD1a-dependent CD69 expression with an $IC_{50}$ value of about 1.11 nM. In some embodiments, the anti-CD1a antibody, or antigen-binding fragment thereof (e.g., Ab673), inhibits CD1a-dependent CD69 expression with an $IC_{50}$ value of about 0.3 nM. In some embodiments, the anti-CD1a antibody, or antigen-binding fragment thereof (e.g., Ab138), inhibits CD1a-dependent CD69 expression with an $IC_{50}$ value of about 1.97 nM.

In some embodiments, the anti-CD1a antibody, or antigen-binding fragment thereof, inhibits CD1a-dependent interleukin-2 (IL-2) production with an $IC_{50}$ value of no more than 5 nM, 4 nM, 3 nM, 2 nM, 1.9 nM, 1.8 nM, 1.7 nM, 1.6 nM, 1.5 nM, 1.4 nM, 1.3 nM, 1.2 nM, 1.1 nM, 1 nM, 0.9 nM, 0.8 nM, 0.7 nM, 0.6 nM, 0.5 nM, 0.4 nM, 0.3 nM, 0.22 nM, 0.2 nM, 0.18 nM, or 0.1 nM, as measured, for example, using a T cell activation assay as described in Examples 1 and 9. In some embodiments, the anti-CD1a antibody, or antigen-binding fragment thereof, inhibits CD1a-dependent IL-2 production with an $IC_{50}$ value of no more than about 500 pM, 400 pM, 300 pM, 220 pM, 200 pM, 100 pM, 90 pM, 80 pM, 70 pM, 60 pM, 50 pM, 40 pm, 30 pM, 20 pM, 10 pM, 9 pM, 8 pM, 7 pM, 6 pM, 5 pM, 4 pM, 3 pM, 2 pM, or 1 pM. In some embodiments, the anti-CD1a antibody, or antigen-binding fragment thereof, inhibits CD1a-dependent IL-2 production with an $IC_{50}$ value of about 0.18 nM.

As described, for example in Example 1, the $IC_{50}$ values may be determined using CD1a-restricted T cell receptor BK6-expressing Jurkat 76 (J76) cells.

Immunogenicity

Immunogenicity is a major barrier to the development and utilization of protein therapeutics, including antibodies and Fc fusion proteins. Several factors can contribute to protein immunogenicity, including but not limited to the protein sequence, the route and frequency of administration, and the patient population. Although immune responses are typically most severe for non-human proteins, such as murine antibodies, even therapeutics with mostly or entirely human sequence content may be immunogenic. Immunogenicity is a complex series of responses to a substance that is perceived as foreign and may include production of neutralizing and non-neutralizing antibodies, formation of immune complexes, complement activation, mast cell activation, inflammation, and anaphylaxis. Unwanted immune responses may reduce the efficacy of antibody and Fc fusion protein therapeutics by directly interfering with antigen recognition, altering interactions with effector molecules, or perturbing the serum half-life or tissue distribution of the therapeutic.

Protein therapeutics can be analyzed to predict the presence of potential immunogenic epitopes using commercially available services such as provided by Epivax, Inc. of Providence, R.I. Potential immunogenic epitopes may also be predicted using methods such as the IEDB Consensus method. In some embodiments, in silico algorithms can predict epitopes that bind to Class II MHC molecules. Analysis of a data set of the polypeptide with such algorithms provides predicted epitopes. Predicted epitopes are used to make peptides prepared by standard methods of automated peptide synthesis or recombinant DNA techniques. Scoring information provided from Epivax can provide an indication of how widespread a predicted epitope is recognized in the population. A lower score predicts a lower immunogenic potential.

As used herein, "Tregitopes" are amino acid sequences within the monoclonal antibody framework region that can potentially activate natural regulatory T cells and reduce unwanted immune responses. In some embodiments, an anti-CD1a antibody, or antigen binding-fragment thereof, comprises 8, 7, 6, 5, 4, 3, 2, 1 or 0 non-germline T-cell epitopes. In some embodiments, an anti-CD1a antibody, or antigen-binding fragment thereof, has a low immunogenicity risk, e.g., has a T-reg Adjusted Score that is less than or equal to −15, −20, −30, −35, −40, −45, −50, −55, −60, −65, −70, −75, −80, −85, −90, −95, or −100. In some embodiments, the predicted immunogenic potential of the antibody, or antigen-binding fragment thereof, as indicated by the Tregitope (T-reg) adjusted score, is less than or equal to about −35. In some embodiments, the predicted immunogenic potential of the antibody, or antigen-binding fragment thereof, as indicated by the Tregitope (T-reg) adjusted score, is less than or equal to about −52. In some embodiments, the predicted immunogenic potential of the antibody, or antigen-binding fragment thereof, as indicated by the Tregitope (T-reg) adjusted score, is less than or equal to about −69.

In some embodiments, the anti-CD1a antibody (e.g., Ab138) has a T-reg adjusted score that is less than or equal to about −35 and 8 or less than 8 non-germline T cell epitopes. In some embodiments, the anti-CD1a antibody (e.g., Ab138) has a T-reg adjusted score that is less than or equal to about −35 (e.g., −37.94) and 8 or less than 8 non-germline T cell epitopes. In some embodiments, the anti-CD1a antibody (e.g., Ab571) has a T-reg adjusted score that is less than or equal to about −52 (e.g., −57.37) and 3 or less than 3 non-germline T cell epitopes. In some embodiments, the anti-CD1a antibody (e.g., Ab673) has a T-reg adjusted score that is less than or equal to about −69 (e.g., −72.89) and 1 or less than 1 non-germline T cell epitopes.

In some embodiments, the antibody, or antigen-binding fragment thereof, is at low risk for polyreactivity, as measured by, for example an AC-SINS assay, a DNA binding assay and/or an insulin binding assay. In some embodiments, the antibody, or antigen-binding fragment thereof, does not induce anti-drug antibodies.

In some embodiments, treatment with a neutralizing anti-CD1a antibody, or antigen-binding fragment thereof, improves one or more parameters associated with inflammatory diseases such as but not limited to AD. For example, in some embodiments, treatment with a neutralizing anti-CD1a antibody, or antigen-binding fragment thereof, improves (e.g., reduces) one or more AD-associated parameters such as but not limited to: Eczema Area and Severity Index (EASI), pruritus numerical rating scale (NRS), affected body surface area (BSA), Patient-Oriented Eczema Measure (POEM), Dermatology Life Quality Index (DLQI), Investigator's Global Assessment (IGA), Physician's Global Assessment (PGA), Six Area Six Sign Atopic Dermatitis (SASSAD), Scoring Atopic Dermatitis (SCORAD), Visual Analogue Scale (VAS), dermatitis score (which may, for example, but not limited to, be calculated as the sum of two or more of the following scores: erythema, scarring/dryness, edema and skin erosion), total serum IgE levels, antigen-specific IgE titers, and atopic dermatitis associated gene signature. Treatment with an anti-CD1a antibody, or antigen-binding fragment thereof, may improve (e.g., reduce) one or more of these parameters by 5%, 10%, 20%, 30%, 40%, 50%, 60%, 70%, 80%, 90%, 95%, 98%, or 100% as compared to these parameters in untreated patients.

In some embodiments, the anti-CD1a antibody, or antigen-binding fragment thereof, reduces dermatitis score in patients with atopic dermatitis by at least 5%, 10%, 20%, 30%, 40%, 50%, 60%, 70%, 80%, 90%, 95%, 98%, or 100% as compared to the dermatitis score in untreated patients. In some embodiments, the anti-CD1a antibody, or antigen-binding fragment thereof, reduces dermatitis score in patients with atopic dermatitis by 70%, 75%, 80%, 85%, 90%, 95%, 98%, or 100% as compared to the dermatitis score in untreated patients.

In some embodiments, the anti-CD1a antibody, or antigen-binding fragment thereof, reduces dermatitis score in a human CD1a transgenic house dust mite (HDM) induced dermatitis mouse model by at least 5%, 10%, 20%, 30%, 40%, 50%, 60%, 70%, 80%, 90%, 95%, 98%, or 100% as compared to the dermatitis score in untreated or isotype treated controls. In some embodiments, the anti-CD1a antibody, or antigen-binding fragment thereof, reduces dermatitis score in a human CD1a transgenic house dust mite (HDM) induced dermatitis mouse model by at least 70%, 75%, 80%, 85%, 90%, 95%, 98%, or 100% as compared to the dermatitis score in untreated or isotype treated controls.

In some embodiments, the anti-CD1a antibody, or antigen-binding fragment thereof, reduces serum IgE levels in a human CD1a transgenic house dust mite (HDM) induced dermatitis mouse model by at least 5%, 10%, 20%, 30%, 40%, 50%, 60%, 70%, 80%, 90%, 95%, 98%, or 100% as compared to the serum IgE levels in untreated or isotype treated controls. In some embodiments, the anti-CD1a antibody, or antigen-binding fragment thereof, reduces serum IgE levels in a human CD1a transgenic house dust mite (HDM) induced dermatitis mouse model by at least 70%, 75%, 80%, 85%, 90%, 95%, 98%, or 100% as compared to the serum IgE levels in untreated or isotype treated controls.

In some embodiments, the anti-CD1a antibody, or antigen-binding fragment thereof, reduces HDM-specific IgE antibody titer in a human CD1a transgenic house dust mite HDM induced dermatitis mouse model by at least 5%, 10%, 20%, 30%, 40%, 50%, 60%, 70%, 80%, 90%, 95%, 98%, or 100% as compared to the serum IgE levels in untreated or isotype treated controls. In some embodiments, the anti-CD1a antibody, or antigen-binding fragment thereof, reduces HDM-specific IgE antibody titer in a human CD1a transgenic HDM induced dermatitis mouse model by at least 70%, 75%, 80%, 85%, 90%, 95%, 98%, or 100% as compared to the HDM-specific IgE antibody titer in untreated or isotype treated controls.

In some embodiments, the anti-CD1a antibody, or antigen-binding fragment thereof, reduces expression levels of one or more atopic dermatitis-associated genes. Examples of atopic dermatitis associated genes include, but are not limited to, Thymic Stromal Lymphopoietin (TSLP), filaggrin (FLG), interleukin-33 (IL-33), C—C motif chemokine ligand 26 (CCL-26), IL-23p40, C—X—C chemokine ligand 1 (CXCL-1) and CCL-20. In some embodiments, the anti-CD1a antibody, or antigen-binding fragment thereof, reduces expression levels of two or more, three or more, four or more, five or more, six or more or seven or more atopic dermatitis-associated genes. In some embodiments, the anti-CD1a antibody, or antigen-binding fragment thereof, reduces expression levels of one or more (e.g., two or more, three or more, four or more, five or more, six or more, seven or more) atopic dermatitis-associated genes in a human CD1a transgenic house dust mite (HDM) induced dermatitis mouse model by at least 5%, 10%, 20%, 30%, 40%, 50%, 60%, 70%, 80%, 90%, 95%, 98%, or 100% as compared to the expression levels of atopic dermatitis-associated genes in untreated or isotype treated controls. In some embodiments, the anti-CD1a antibody, or antigen-binding fragment thereof, reduces expression levels of one or more (e.g., two or more, three or more, four or more, five or more, six or more, seven or more) atopic dermatitis-associated genes in a human CD1a transgenic house dust mite (HDM) induced dermatitis mouse model by at least 70%, 75%, 80%, 85%, 90%, 95%, 98%, or 100% as compared to the expression levels of atopic dermatitis-associated genes in untreated or isotype treated controls.

Nucleic Acids Encoding Anti-CD1a Antibodies

The disclosure also provides polynucleotides encoding any of the antibodies of the invention, including antibody portions and modified antibodies described herein. The invention also provides a method of making any of the polynucleotides described herein. Polynucleotides can be made and the proteins expressed by procedures known in the art.

A sequence of a desired antibody, or antigen-binding fragment thereof, and nucleic acid encoding such antibody, or antigen-binding fragment thereof, can be determined using standard sequencing techniques. A nucleic acid molecule encoding a desired antibody, or antigen-binding fragment thereof, may be inserted into various vectors (such as cloning and expression vectors) for recombinant production and characterization. A nucleic acid molecule encoding the heavy chain, or an antigen-binding fragment of the heavy chain, and a nucleic acid molecule encoding the light chain, or an antigen-binding fragment of the light chain, can be cloned into the same vector, or different vectors.

In some embodiments, the disclosure provides polynucleotides encoding the amino acid sequences of any of the following anti-CD1a antibodies and antigen-binding fragments thereof: Ab138, Ab491, Ab492, Ab504, Ab514, Ab555, Ab556, Ab559, Ab560, Ab571, Ab572, Ab579, Ab585, Ab599, Ab609, Ab610, Ab616, Ab623, Ab624, Ab656, Ab657, Ab660, Ab673, Ab681, and Ab689 (e.g., as disclosed in Table 14). In one embodiment, there are polynucleotides encoding the amino acid sequences of any of the following anti-CD1a antibodies, and antigen-binding fragments thereof: Ab138, Ab571 and Ab673. In some embodiments, the disclosure includes polynucleotides encoding the amino acid sequence of Ab571.

In some embodiments, the disclosure provides polynucleotides encoding one or more anti-CD1a antibody HC polypeptides comprising an amino acid sequence selected from the group consisting of: SEQ ID NOs: 14, 29, 39, 47, 51, 54, 56, 58, 61, 65, 68, 73, and 75. In some embodiments, the disclosure provides a polynucleotide encoding an anti-CD1a antibody HC polypeptide comprising, or consisting of, the amino acid sequence of SEQ ID NO: 54 or SEQ ID NO:73.

In some embodiments, the disclosure provides polynucleotides encoding one or more anti-CD1a antibody LC polypeptides comprising an amino acid sequence selected from the group consisting of: SEQ ID NOs: 7, 24, 33, 36, 43, 70 and 78. In some embodiments, the disclosure provides a polynucleotide encoding an anti-CD1a antibody LC polypeptide comprising, or consisting of, the amino acid sequence of SEQ ID NO: 24.

In some embodiments, the disclosure provides polynucleotides encoding one or more anti-CD1a antibody VH domain polypeptides comprising an amino acid sequence selected from the group consisting of: SEQ ID NOs: 22, 32, 42, 50, 53, 55, 57, 60, 64, 67, 69, 74 and 77. In some embodiments, the disclosure provides a polynucleotide encoding an anti-CD1a antibody VH domain polypeptide comprising, or consisting of, the amino acid sequence of SEQ ID NO: 55 or SEQ ID NO: 74.

In some embodiments, the disclosure provides polynucleotides encoding one or more anti-CD1a antibody VL domain polypeptides comprising an amino acid sequence selected from the group consisting of: SEQ ID NOs: 12, 28, 35, 38, 46, 72 and 79. In some embodiments, the disclosure provides a polynucleotide encoding an anti-CD1a antibody VL domain polypeptide comprising, or consisting of, the amino acid sequence of SEQ ID NO: 28.

In some embodiments, the disclosure provides an isolated nucleic acid molecule encoding an antibody, or antigen-binding fragment thereof, that specifically binds human CD1a, wherein said nucleic acid molecule comprises one or more nucleic acid sequences selected from the group consisting of: (i) the nucleic acid sequence of SEQ ID NO: 80, (ii) the nucleic acid sequence of SEQ ID NO: 81, (iii) the nucleic acid sequence of SEQ ID NO: 82, (iv) the nucleic acid sequence of SEQ ID NO: 83, (v) the nucleic acid sequence of SEQ ID NO: 84, (vi) the nucleic acid sequence of SEQ ID NO: 85, (vii) the nucleic acid sequence of the insert of the vector deposited as Ab571-VH under ATCC Accession No. PTA-126810, and the nucleic acid sequence of the insert of the vector deposited as Ab571-VL under ATCC Accession No. PTA-126811.

In some embodiments, the disclosure provides an isolated nucleic acid molecule comprising, or consisting of, the nucleic acid sequence of SEQ ID NO: 80, the nucleic acid sequence of SEQ ID NO: 81, or both.

In some embodiments, the disclosure provides an isolated nucleic acid molecule comprising, or consisting of, the nucleic acid sequence of SEQ ID NO: 82, the nucleic acid sequence of SEQ ID NO: 83, or both.

In some embodiments, the disclosure provides an isolated nucleic acid molecule encoding an antibody, or an antigen-binding fragment thereof, that specifically binds human CD1a, wherein said nucleic acid molecule comprises the nucleic acid sequence of the insert of the plasmid deposited with the ATCC and having the Accession No. PTA-126810.

In some embodiments, the disclosure provides an isolated nucleic acid molecule encoding an antibody, or an antigen-binding fragment thereof, that specifically binds human CD1a, wherein said nucleic acid molecule comprises the nucleic acid sequence of the insert of the plasmid deposited with the ATCC and having the Accession No. PTA-126811.

In some embodiments, the disclosure provides an isolated nucleic acid molecule encoding an antibody, or an antigen-binding fragment thereof, that specifically binds human CD1a, wherein said nucleic acid comprises the nucleic acid sequence of the insert of the plasmid deposited with the ATCC and having the Accession No. PTA-126810 and the nucleic acid sequence of the insert of the plasmid deposited with the ATCC and having the Accession No. PTA-126811.

In some embodiments, the disclosure provides an isolated nucleic acid molecule comprising the nucleic acid sequence of the insert of the plasmid deposited with the ATCC and having the Accession No. PTA-126810. In some embodiments, the disclosure provides an isolated nucleic acid molecule comprising the nucleic acid sequence of the insert of the plasmid deposited with the ATCC and having the Accession No. PTA-126811. In some embodiments, the disclosure provides an isolated nucleic acid molecule comprising the nucleic acid sequence of the insert of the plasmid deposited with the ATCC and having the Accession No. PTA-126810, and the nucleic acid sequence of the insert of the plasmid deposited with the ATCC and having the Accession NO. PTA-126811.

In some embodiments, the disclosure provides a polypeptide comprising the amino acid sequence encoded by the DNA insert of the plasmid deposited with the ATCC and having Accession No. PTA-126810, encoding the VH domain of Ab571. The disclosure further provides a polypeptide comprising the amino acid sequence encoded by the insert of the plasmid deposited with the ATCC and having Accession No. PTA-126811 encoding the VL domain of Ab571.

In some embodiments, the disclosure also provides a polynucleotide comprising the nucleic acid sequence of the insert of the plasmid deposited with the ATCC and having Accession No. PTA-126810, encoding the HCDR-1, HCDR-2 and HCDR-3 of Ab571 and the nucleic acid sequence of the insert of the plasmid deposited with the ATCC and having Accession No. PTA-126811, encoding the LCDR-1, LCDR-2 and LCDR-3 of Ab571.

In some embodiments, the disclosure also provides a polynucleotide comprising the nucleic acid sequence of the insert of the plasmid deposited with the ATCC and having Accession No. PTA-126810, encoding the VH domain of Ab571 and the nucleic acid sequence of the insert of the plasmid deposited with the ATCC and having Accession No. PTA-126811, encoding the VL domain of Ab571.

In some embodiments, the disclosure provides an isolated nucleic acid molecule encoding the VH of an antibody, or antigen-binding fragment thereof, that specifically binds human CD1a, comprising a nucleic acid at least 90%, 91%, 92%, 93%, 94%, 95%, 96%, 97%, 98% or 99% identical to a nucleic acid sequence of SEQ ID NO: 80 or SEQ ID NO: 84.

In some embodiments, the disclosure provides an isolated nucleic acid molecule encoding the VL of an antibody, or antigen-binding fragment thereof, that specifically binds human CD1a, comprising a nucleic acid at least 90%, 91%, 92%, 93%, 94%, 95%, 96%, 97%, 98% or 99% identical to a nucleic acid sequence of SEQ ID NO: 81.

In some embodiments, the disclosure provides an isolated nucleic acid molecule encoding the HC of an antibody, or antigen-binding fragment thereof, that specifically binds human CD1a, comprising a nucleic acid at least 90%, 91%, 92%, 93%, 94%, 95%, 96%, 97%, 98% or 99% identical to a nucleic acid sequence of SEQ ID NO: 82 or SEQ ID NO: 85.

In some embodiments, the disclosure provides an isolated nucleic acid molecule encoding the LC of an antibody, or antigen-binding fragment thereof, that specifically binds human CD1a, comprising a nucleic acid at least 90%, 91%, 92%, 93%, 94%, 95%, 96%, 97%, 98% or 99% identical to a nucleic acid sequence of SEQ ID NO: 83.

In some embodiments, the disclosure provides polynucleotides and variants thereof encoding an anti-CD1a antibody, wherein such variant polynucleotides share at least 70%, at least 75%, at least 80%, at least 85%, at least 87%, at least 89%, at least 90%, at least 91%, at least 92%, at least 93%, at least 94%, at least 95%, at least 96%, at least 97%, at least 98%, or at least 99% nucleic acid sequence identity to any of the nucleic acid sequences disclosed in Table 14. These amounts are not meant to be limiting and increments between the recited percentages are specifically envisioned as part of the disclosure.

In one embodiment, the VH and VL domains, or antigen-binding fragment thereof, or full-length HC or LC, are encoded by separate polynucleotides. Alternatively, both VH and VL, or antigen-binding fragment thereof, or HC and LC, are encoded by a single polynucleotide.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a nucleic acid sequence that encodes an antibody or a fragment thereof or may comprise a variant of such a sequence. Polynucleotide variants contain one or more substitutions, additions, deletions and/or insertions such that the binding characteristics of the encoded polypeptide is not diminished relative to a native antibody molecule. The effect on the binding characteristics of the polypeptide encoded by the variant nucleic acid sequence may generally be assessed as described herein. In some embodiments, polynucleotide variants exhibit at least about 70% identity, at least about 80% identity, at least about 90% identity, at least about 95% identity, at least 98% identity or at least 99% identity to a polynucleotide sequence that encodes the original (parent) antibody not comprising any substitution, addition, deletion and/or insertion, or a fragment thereof. These percent identities are not meant to be limiting and increments between the recited percentages are specifically envisioned as part of the disclosure.

Two polynucleotide or polypeptide sequences are said to be "identical" if the sequence of nucleotides or amino acids in the two sequences is the same when aligned for maximum correspondence as described herein. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned. In some embodiments, a polynucleotide is at least 70%, 75%, 80%, 85%, 90%, 95%, 98%, 99% identical to a polynucleotide disclosed herein.

Polynucleotide variants may also, or alternatively, be substantially homologous to a gene, or a fragment or complement thereof. Such polynucleotide variants are capable of hybridizing under moderately stringent conditions to a naturally occurring DNA sequence encoding an antibody (or a complementary sequence).

Suitable "moderately stringent conditions" include prewashing in a solution of 5×SSC, 0.5% SDS, 1.0 mM EDTA (pH 8.0); hybridizing at about 50° C. to 65° C., 5×SSC (0.75 M NaCl, 0.075 M sodium citrate), overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC, 50 mM sodium phosphate (pH 6.8), 0.1% sodium pyrophosphate, 5×Denhardt's solution, sonicated salmon sperm DNA (50 pg/mL), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode the amino acid sequence of a polypeptide as described herein. Some of these polynucleotides bear minimal homology to the nucleotide sequence of any native gene. That is, there are 64 different codons to encode 20 natural amino acids, with some amino acids having multiple codons that encode it (e.g., 6 different codons encode leucine). Therefore, a large number of nucleic acid sequences can encode the same protein sequence such that two nucleic acids encoding the same polypeptide amino acid sequence can share very low nucleic acid sequence identity. Therefore, polynucleotides that vary due to differences in codon usage are specifically contemplated by the present disclosure.

Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, for example.

As used herein, the term "vector" means a construct, which is capable of delivering, and, preferably, expressing, one or more gene(s) or sequence(s) of interest (e.g., a nucleic acid encoding a HC, a LC, a VH, a VL and/or a fragment thereof, of an anti-CD1a antibody) in a host cell. Examples of vectors include, but are not limited to, viral vectors (e.g. AAV), naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

Suitable cloning and expression vectors can include a variety of components, such as promoter, enhancer, and other transcriptional regulatory sequences. The vector may also be constructed to allow for subsequent cloning of an antibody variable domain into different vectors. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors are further provided. Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

In some embodiments, a cell (e.g., isolated or within an organism) is transduced with a recombinant AAV (rAAV) comprising a recombinant nucleic acid encoding a heterologous polynucleotide (e.g., a HC, a LC, a VH domain, a VL domain, or an antigen-binding fragment thereof, of an anti-CD1a antibody) and an AAV capsid. A recombinant nucleic acid may further comprise regulatory elements (e.g., a promoter, an enhancer, an intron, an exon, polyA) for expression of the heterologous polynucleotide within a transduced cell. A recombinant nucleic acid may further comprise viral inverted tandem repeat (ITR) sequences. In some embodiments, an AAV capsid is an AAV1, AAV2, AAV3, AAV4, AAV5, AAV6, AAV7, AAV8, AAV9, AAV10, or any other wild type or recombinant AAV capsid known in the art. ITR sequences may be AAV1, AAV2, AAV3, AAV4, AAV5, AAV6, AAV7, AAV8, AAV9, AAV10, or any other wild type or recombinant ITR sequences (e.g., AAV2) known in the art. In some embodiments, a rAAV comprises a recombinant nucleic acid encoding a HC, a LC, a VH domain, a VL domain, or an antigen-binding fragment thereof, of an anti-CD1a antibody, a promoter, an AAV ITR and a viral capsid. Such rAAV is suitable for expression of an anti-CD1a antibody, or antigen-binding fragment thereof in a cell to treat or prevent a disease, disorder or condition (e.g., AD) mediated by CD1a in a subject (e.g., a patient).

The vectors containing the polynucleotides of interest and/or the polynucleotides themselves, can be introduced into a host cell by any of a number of appropriate means, including electroporation, transfection employing calcium chloride or polyethylenimine (PEI), rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

In some embodiments, a vector comprises a polynucleotide comprising a nucleic acid sequence selected from the group consisting of SEQ ID NO: 80, 81, 82, 83, 84 and 85. In some embodiments, a vector comprises a polynucleotide comprising a nucleic acid sequence at least 70%, 80%, 85%, 90%, 95%, 98% or 99% identical to the nucleic acid sequence selected from the group consisting of SEQ ID NO: 80, 81, 82, 83, 84 and 85.

In some embodiments, a vector comprises a polynucleotide comprising i) a nucleic acid sequence of SEQ ID NO: 80; ii) a nucleic acid of SEQ ID NO:81; or iii) both. In some embodiments, a vector comprises a polynucleotide comprising i) a nucleic acid sequence of SEQ ID NO: 82; ii) a nucleic acid of SEQ ID NO:83; or iii) both. In some embodiments, a vector comprises a polynucleotide comprising i) a nucleic acid sequence of SEQ ID NO: 84; ii) a nucleic acid of SEQ ID NO:81; or iii) both. In some embodiments, a vector comprises a polynucleotide comprising i) a nucleic acid sequence of SEQ ID NO: 85; ii) a nucleic acid of SEQ ID NO:83; or iii) both.

As used herein, the terms "host cell," "host cell line," and "host cell culture" are used interchangeable and mean an individual cell or cell culture that can be or has been a recipient for a polynucleotide and/or vector(s) for incorporation of polynucleotide inserts. Host cells include "transformants," "transformed cells," and "transduced cells," which include the primary transformed or transduced cell and progeny derived therefrom without regard to the number of passages. Host cell progeny may not necessarily be completely identical (in morphology or in genomic DNA complement) to the original parent cell due to natural, accidental, or deliberate mutation. A host cell includes cells transfected and/or transformed in vivo with a polynucleotide of this disclosure (e.g., a polynucleotide encoding an amino acid sequence of an anti-CD1a antibody) or a vector comprising the same.

Host cells may be prokaryotic cells or eukaryotic cells. Exemplary eukaryotic cells include mammalian cells, such as primate or non-primate animal cells; fungal cells, such as yeast; plant cells; and insect cells.

An antibody, or antigen-binding fragment thereof, may be made recombinantly using a suitable host cell. A nucleic acid encoding an anti-CD1a antibody, or antigen-binding fragment thereof, of the present disclosure can be cloned into an expression vector, which can then be introduced into a host cell, where the cell does not otherwise produce an immunoglobulin protein, to obtain the synthesis of an antibody in the recombinant host cell. Any host cell susceptible to cell culture, and to expression of protein or polypeptides, may be utilized in accordance with the disclosure. In certain embodiments, the host cell is mammalian. Mammalian cell lines available as hosts for expression are well known in the art and include many immortalized cell lines available from the American Type Culture Collection (ATCC). Nonlimiting exemplary mammalian cells include, but are not limited to, NS0 cells, HEK 293 and Chinese hamster ovary (CHO) cells, and their derivatives, such as 293-6E and CHO DG44 cells, CHO DXB11, and Potelligent® CHOK1SV cells (BioWa/Lonza, Allendale, NJ). Mammalian host cells also include, but are not limited to, human cervical carcinoma cells (HeLa, ATCC CCL 2), baby hamster kidney (BHK, ATCC CCL 10) cells, monkey kidney cells (COS), and human hepatocellular carcinoma cells (e.g., Hep G2). Other non-limiting examples of mammalian cells that may be used in accordance with the present disclosure include human retinoblasts (PER.C6®; CruCell, Leiden, The Netherlands); monkey kidney CV1 line transformed by SV40 (COS-7, ATCC CRL 1651); human embryonic kidney line 293 (HEK 293) or 293 cells subcloned for growth in suspension culture (Graham et al., J. Gen Virol. 1997; 36:59); mouse sertoli cells (TM4, Mather, Biol. Reprod. 1980; 23:243-251); monkey kidney cells (CV1 ATCC CCL 70); African green monkey kidney cells (VERO-76, ATCC CRL-1 587); canine kidney cells (MDCK, ATCC CCL 34); buffalo rat liver cells (BRL 3 Å, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 1982; 383:44-68); MRC 5 cells; FS4 cells; a human hepatoma line (Hep G2); and numerous myeloma cell lines, including, but not limited to, BALB/c mouse myeloma line (NS0/1, ECACC No: 85110503), NS0 cells and Sp2/0 cells.

Additionally, any number of commercially and non-commercially available cell lines that express polypeptides or proteins may be utilized in accordance with the present disclosure. One skilled in the art will appreciate that different cell lines might have different nutrition requirements and/or might require different culture conditions for optimal growth and polypeptide or protein expression and will be able to modify conditions as needed.

Methods of Treatment

In some embodiments, the disclosure provides therapeutic methods for reducing or inhibiting CD1a activity, wherein the therapeutic method comprises administering a therapeutically effective amount of an anti-CD1a antibody or antigen-binding fragment thereof, or a pharmaceutical composition comprising an antibody or antigen-binding fragment thereof. The disorder treated is any disease or condition which is improved, ameliorated, inhibited or prevented by removal, inhibition or reduction of CD1a activity (e.g., AD).

Examples of CD1a activity includes, but is not limited to (a) CD1a binding to T cell receptors; (b) CD1a-mediated lipid presentation to T cells and their subsequent activation; (c) CD1a-dependent CD69 expression; (d) CD1a-dependent IL-2 production; (e) CD1a-dependent increase in serum IgE levels; (f) CD1a-dependent increase in antigen-specific IgE antibodies; and/or (g) CD1a-dependent increase in expression levels of atopic dermatitis-associated genes (e.g., but not limited to TSLP, FLG, IL-33, CCL-26, IL-23p40, CCL-20, and/or CCL-20).

In some embodiments, the disclosure provides methods wherein the activity of CD1a before administration of the antibody, or antigen-binding fragments thereof, is compared to the level of CD1a activity after administration.

In some embodiments, the disclosure provides methods for reducing the level of CD1a in a subject in need thereof, the method comprising administering to a subject a therapeutically effective amount of the antibody, or antigen-binding fragment thereof, or a pharmaceutical composition comprising an antibody or antigen-binding fragment thereof.

In some embodiments, the disclosure provides methods for treating and/or preventing a disease, disorder and/or condition associated with, or mediated by, CD1a expression and/or CD1a binding to a ligand, the method comprising administering to a subject in need thereof a therapeutically effective amount of the antibody, or antigen-binding fragment thereof, or a pharmaceutical composition comprising an antibody or antigen-binding fragment thereof.

Examples of diseases, disorders, and/or conditions that can be treated, prevented, improved, ameliorated, or inhibited by anti-CD1a antibodies, or antigen-binding fragments thereof include, but are not limited to: inflammatory bowel disease, allergies, allergic rhinitis, allergic conjunctivitis, vernal keratoconjunctivitis, a seasonal allergy, pet allergy, asthma, food allergy, peanut allergy, atopic dermatitis, contact dermatitis, chronic rhinosinusitis with nasal polyps (CRSwNP), allergic rhinitis, bronchitis, chronic obstructive pulmonary disease (COPD), viral exacerbations of respiratory disease, viral infection in children and adults, (respiratory syncytial virus (RSV), rhinovirus, influenza), urticarias, eosinophilic esophagitis, chronic fibrosis, liver fibrosis, non-alcoholic steatohepatitis (NASH), chronic kidney disease, idiopathic pulmonary fibrosis (IPF), scleroderma, systemic sclerosis, acute kidney injury, sepsis, pancreatitis, type 1 diabetes, graft-versus-host disease (GVHD), tissue transplant, Alzheimer's, rheumatoid arthritis, irritable bowel syndrome (IBS), Crohns disease, ulcerative colitis, multiple sclerosis, psoriasis, celiac disease and Raynaud's disease or phenomenon.

In some embodiments, the disclosure provides a method of treating an inflammatory disease, the method comprising administering to a subject in need thereof a therapeutically effective amount of the antibody, or antigen-binding fragment thereof, or a pharmaceutical composition comprising an antibody or antigen-binding fragment thereof.

In some embodiments, the disclosure provides a method of treating atopic dermatitis, the method comprising administering to a subject in need thereof a therapeutically effective amount of the antibody, or antigen-binding fragment thereof, or a pharmaceutical composition comprising an antibody or antigen-binding fragment thereof.

In some embodiments, the disclosure provides a method of treating inflammatory bowel disease (IBD), the method comprising administering to a subject in need thereof a therapeutically effective amount of the antibody, or antigen-binding fragment thereof, or a pharmaceutical composition comprising an antibody or antigen-binding fragment thereof.

Methods of treating using an anti-CD1a antibody, or antigen-binding fragment thereof, of the present disclosure includes prophylactic and/or therapeutic treatments. If a treatment is administered prior to clinical manifestation of a condition, the treatment is considered prophylactic. For example, administration of an anti-CD1a antibody, or antigen-binding fragment thereof, may be used to prevent severe pruritus when utilized as a prophylactic treatment (e.g., one or more doses, over a period of time) for AD. Therapeutic treatment includes, e.g., ameliorating or reducing the severity of a disease, or shortening the length of the disease. For example, administration of an anti-CD1a antibody, or antigen-binding fragment thereof, may be used to treat severe pruritus in patients with AD by decreasing the duration, intensity and/or severity of the pruritus. In some embodiments, the methods described herein are not prophylactic.

In some embodiments, a subject to be treated may be mammal, and in particular a human patient, for example, a patient with an inflammatory disease such as but not limited to, AD, contact dermatitis, psoriasis, or IBD). In some embodiments, the antibody or antigen-binding fragment thereof, or pharmaceutical composition, is administered subcutaneously. In some embodiments, the antibody or antigen-binding fragment thereof, or pharmaceutical composition, is administered intravenously.

The disclosure further encompasses an anti-CD1a antibody, or antigen-binding fragment thereof, or pharmaceutical composition, as defined herein for use as a medicament. In some embodiments, the disclosure encompasses an anti-CD1a antibody, or antigen-binding fragment thereof, or pharmaceutical composition, as defined herein for use in the defined methods of treatment and/or prevention. In some embodiments, the disclosure encompasses an anti-CD1a antibody, or antigen-binding fragment thereof, or pharmaceutical composition, as defined herein for use in the defined methods of treatment and/or prevention of at least one sign and/or symptom of an inflammatory disease (e.g, but not limited to atopic dermatitis).

The disclosure also includes use of an anti-CD1a antibody, or antigen binding fragment thereof, or pharmaceutical composition, as defined herein, in the manufacture of a medicament for treating a disease, disorder or condition associated with, or mediated by, CD1a expression, activity and/or CD1a binding to T-cell receptors.

Combination Therapies

An antibody, or antigen-binding fragment thereof of the present disclosure, may be administered in combination with one or more additional therapeutically active compounds or treatment modalities which are effective in treating and/or preventing at least one sign and/or symptom of diseases, disorders or condition associated with, or mediated by, CD1a expression, activity and/or CD1a binding to T-cell receptors. In some embodiments, the anti-CD1a antibody, or antigen-binding fragment thereof, or pharmaceutical composition as defined here, may be administered in combination with one or more additional therapeutically active compounds or treatment modalities which are effective in treating and/or preventing at least one sign and/or symptom of inflammatory disease (e.g, but not limited to atopic dermatitis).

Embodiments also encompass a method of treating and/or preventing at least one sign and/or symptom of AD comprising administering to a patient in need thereof an amount of an anti-CD1a antibody, or antigen-binding fragment thereof and an amount of a therapeutically active compound or treatment modality which is effective in treating and/or preventing at least one sign and/or symptom of AD, wherein the amounts together are effective in treating and/or preventing at least one sign and/or symptom of AD.

In some embodiments, the disclosure includes a method of treating and/or preventing at least one sign and/or symptom of AD comprising administering to a patient in need thereof an amount of an anti-CD1a antibody, or antigen-binding fragment thereof, and an amount of a therapeutically active compound or treatment modality which is effective in treating and/or preventing at least one sign and/or symptom of AD, wherein the amounts together achieve synergistic effects in the treatment and/or prevention of at least one sign and/or symptom of AD, that is, the combination is "synergistic," (i.e., the combination provides an effect greater than a merely additive effect of two or more individual therapies). Such synergistic combination therapies may advantageously utilize lower dosages of the administered therapeutic agents, thus avoiding possible toxicities or complications associated with the various monotherapies.

Additional therapeutically active compounds useful for the treatment and/or prevention of at least one sign and/or symptom of AD include, for example, antagonists to one or more of IL-1a, IL-1b, IL-2, IL-3, IL-4, IL-5, IL-6, IL-8, IL-9, IL-10, IL-12, IL-13, IL-17, IL-18, IL-21, IL-23, IL-25, IL-26, IL-31, IL36 IFNα, IFNγ, or antagonists of their respective receptors, anti-inflammatory agents, recombinant interferon gamma, NSAIDs, steroids, calcineurin inhibitors, and/or corticosteroids. In some embodiments, the additional therapeutically active compound comprises dupilumab.

The present disclosure encompasses a pharmaceutical composition comprising an anti-CD1a antibody, or antigen-binding fragment thereof, a therapeutically active compound or treatment modality which is effective in treating and/or preventing at least one sign and/or symptom of AD, and a pharmaceutically acceptable carrier for use in the treatment and/or prevention of at least one sign and/or symptom of AD. The disclosure encompasses a pharmaceutical composition comprising a synergistic, therapeutically effective amount of an anti-CD1a antibody, a synergistic, therapeutically effective amount of a therapeutically active compound or treatment modality which is effective in treating and/or preventing at least one sign and/or symptom of AD and a pharmaceutically acceptable carrier for use in the treatment and/or prevention of at least one sign and/or symptom of AD. The composition can further comprise an additional therapeutic agent, such as, but not limited to at least one other therapeutically active compound or treatment modality which is effective in treating and/or preventing at least one sign and/or symptom of AD.

One skilled in the art would understand, based on the disclosure provided therein, that the method of treating and/or preventing at least one sign and/or symptom of AD encompasses administering a synergistic, therapeutically effective amount of an anti-CD1a antibody and a synergistic, therapeutically effective amount of a therapeutically active compound or treatment modality which is effective in treating and/or preventing at least one sign and/or symptom of AD, to a patient either previously treated with, or currently receiving, at least one additional therapeutic agent to treat and/or prevent at least one sign and/or symptom of AD.

Such additional therapeutic agent encompasses an agent that is standard of care to treat and/or prevent at least one sign and/or symptom of AD. That is, combination therapy may be added to the therapeutic regimen of an AD patient already receiving a different therapy including, but not limited to, dupilumab and any other therapy known in the art.

Those skilled in the art will be able to determine, according to known methods, the appropriate amount, dose or dosage of each compound, as used in the combination of the present disclosure, to administer to a patient with AD, taking into account factors such as age, weight, general health, the compound administered, the route of administration, the nature and advancement of the treatment of AD, and the presence of other medications.

A prophylactic or therapeutic agent of the combination therapies, including an anti-CD1a antibody, or antigen-binding fragment thereof, can be administered to a subject in the same pharmaceutical composition (e.g., the therapies are co-formulated). Alternatively, a prophylactic or therapeutic agent of the combination therapies can be administered concurrently to a subject in separate pharmaceutical compositions (e.g., the therapies are co-administered). Prophylactic or therapeutic agent of the combination therapies can be administered according to the same dosing regimen (e.g., both therapies are administered daily) or according to different dosing regimens (e.g., one therapy is administered daily, the other therapy is administered weekly). Prophylactic or therapeutic agents may be administered to a subject by the same or different routes of administration.

The disclosure further encompasses a prophylactic or therapeutic agent of the combination therapies, including an anti-CD1a antibody, or antigen-binding fragment thereof, as defined herein for use in the defined methods of treatment and/or prevention. In embodiments that refer to a method of treatment and/or prevention as described herein, such embodiments are also include further embodiments concerning a combination therapy, including an anti-CD1a antibody, or antigen binding fragment thereof, or pharmaceutical composition, for use in that treatment and/or prevention, or alternatively for the manufacture of a medicament for use in that treatment and/or prevention of at least one sign and/or symptom of AD.

The disclosure provides protocols for the administration of pharmaceutical composition comprising anti-CD1a antibodies, or antigen-binding fragments thereof, of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently. The term “concurrently” is not limited to the administration of therapies (e.g., prophylactic or therapeutic agents) at exactly the same time, but rather it is meant that a pharmaceutical composition comprising anti-CD1a antibodies, or antigen-binding fragments thereof, of the disclosure are administered to a subject in a sequence and within a time interval such that the antibodies of the disclosure or conjugates thereof can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

Prophylactic or therapeutic agents of a combination therapy can be administered to a subject in the same pharmaceutical composition. Alternatively, a prophylactic or therapeutic agent of a combination therapy can be administered concurrently to a subject in separate pharmaceutical compositions. Prophylactic or therapeutic agents may be administered to a subject by the same or different routes of administration.

Diagnostic Uses

The anti-CD1a antibodies, antibody compositions, and methods described herein have in vitro and in vivo utilities including immunoassays and use for the diagnosis and assessment of treatment of CD1a mediated disorders. The methods are particularly suitable for diagnosing, assessing, and treating human patients having a disorder associated with the existence of CD1a. This disorder associated with the existence of CD1a includes, but is not limited to, inflammatory diseases such as AD, contact dermatitis, psoriasis, and IBD.

In some embodiments there is a method for detecting the presence of CD1a in a sample, the method comprising contacting a sample suspected of comprising CD1a with an antibody specific for CD1a and detecting the presence of CD1a bound with the antibody thereby detecting CD1a in the sample. Methods for detecting CD1a bound with the antibody are well-known in the art including, but not limited to, an assay where CD1a is bound to a solid support and a sample is added thereto allowing the antibody to bind CD1a in the sample. A second CD1a antibody that is either the same or different from the antibody bound to the solid support is added and can be detected by either direct labeling (i.e., the second antibody is conjugated to a detectable label) or by adding a third antibody, e.g., from another species which reacts with the constant domain of the second antibody and which comprises a detectable label. Thus, the assay can be used to detect the presence or absence of CD1a in a sample.

In some embodiments there is a method for determining the concentration of CD1a in a sample, said method comprising providing a labeled competitor comprising CD1a coupled to a detectable label; providing an antibody, or antigen binding fragment thereof, that specifically binds CD1a; combining the sample, the antibody, and the labeled competitor, wherein the CD1a in the sample competes with the labeled competitor for binding to the antibody; and determining the concentration of CD1a in said sample by measuring the amount of labeled competitor not bound to antibody by detection of the label. The amount of labeled competitor bound to the antibody in the absence of the sample is compared with the amount of labeled competitor bound to the antibody when the sample is added. The amount of decrease of bound labeled-competitor in the presence of the sample is an indicator of the amount of non-labeled CD1a present in the sample such that the assay can be used to assess the presence and level of CD1a in a sample. In some embodiments, CD1a is soluble CD1a. In some embodiments, CD1a is membrane bound E CD1a.

In one embodiment, there is a method for assessing the effectiveness of a treatment for a disease or disorder associated with an increased level of CD1a in a subject, the method comprising administering a treatment to the subject and comparing the level of CD1a in a sample obtained from the subject prior to the treatment with the level of CD1a in an otherwise identical sample obtained from the subject after the treatment, wherein the level of CD1a in a sample is assessed using a CD1a specific antibody, and further wherein a lower, level of CD1a in the sample collected from the subject after the treatment compared with the level of CD1a in a sample collected from the subject prior to treatment is an indication of the effectiveness of the course of treatment.

The term "labeled" with regard to the CD1a specific antibody or labeled competitor, includes direct labeling by coupling (i.e., physically linking) a detectable substance to the antibody or labeled competitor, as well as indirect labeling of the antibody or labeled competitor by coupling it with another reagent that is directly labeled. An example of indirect labeling includes detection of a primary antibody using a fluorescent-labeled secondary antibody. In vitro techniques for detection of polypeptides include enzyme linked immunosorbent assays (ELISAs), Western blots, immunoprecipitation, and immunofluorescence.

The term "sample" is intended to include tissues, cells, and biological fluids (e.g., blood, CSF, urine, etc.) isolated from a subject, as well as tissues, cells, and fluids present within a subject.

The antibodies, labeled competitors, and potential therapeutic compounds described herein are also suitable for use with any of a number of other homogeneous and heterogeneous immunoassays with a range of detection systems.

Compositions

An anti-CD1a antibody, or antigen-binding fragment thereof, of the disclosure may be formulated as a pharmaceutical composition. The pharmaceutical composition may further comprise a pharmaceutically acceptable carrier, excipient, and/or stabilizer (Remington: The Science and practice of Pharmacy 21st Ed., 2005, Lippincott Williams and Wilkins, Ed. K. E. Hoover), in the form of lyophilized formulation or aqueous solution. As used herein, the term "pharmaceutically acceptable carrier" or "pharmaceutically acceptable excipient" includes any material which, when combined with an active ingredient, allows the ingredient to retain biological activity and is non-reactive with the subject's immune system.

Examples include, but are not limited to, any of the standard pharmaceutical carriers such as phosphate buffered saline (PBS), water, normal saline (0.9%), emulsions (e.g., oil/water emulsions) and various types of wetting agents. Preferred diluents for aerosol or parenteral administration are PBS and normal saline.

Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™, polysorbate (e.g., polysorbate 80 (PS80), polysorbate 60 (PS60), polysorbate 20 (PS20)), or polyethylene glycol (PEG). Pharmaceutically acceptable excipients are further described herein.

Pharmaceutical compounds of the disclosure may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A pharmaceutical composition of the present disclosure may be prepared, packaged, or sold in a formulation suitable for ophthalmic administration. Such formulations may, for example, be in the form of eye drops including, for example, a 0.1%-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Remington's Pharmaceutical Sciences, Genaro, ed., Mack Publishing Co., Easton, PA (1985), which is incorporated herein by reference.

In some embodiments, an anti-CD1a antibody, or antigen-binding fragment thereof is formulated in a vial containing 100 mg of an anti-CD1a antibody (e.g., AB571), or an antigen binding fragment thereof, in 1 mL of an aqueous buffered solution. In some embodiments, an anti-CD1a antibody, or antigen-binding fragment thereof is formulated in a vial containing 150 mg of an anti-CD1a antibody (e.g., AB571), or an antigen binding fragment thereof, in 1 mL of an aqueous buffered solution. In some embodiments, an anti-CD1a antibody, or antigen-binding fragment thereof is formulated in a vial containing 15 mg, 40 mg, 100 mg, 300 mg, or 600 mg of an anti-CD1a antibody (e.g., Ab571), or an antigen binding fragment thereof, in 1 mL of an aqueous buffered solution, optionally for subcutaneous administration. In some embodiments, an anti-CD1a antibody, or antigen-binding fragment thereof is formulated in a vial containing 500 mg of an anti-CD1a antibody (e.g., Ab571), or an antigen binding fragment thereof, in 1 mL of an aqueous buffered solution, optionally for intravenous administration.

In some embodiments, a pharmaceutical composition comprises about 25 mg/mL, 50 mg/mL, 75 mg/mL, 100 mg/mL, 125 mg/mL, 150 mg/mL antibody, or antigen binding fragment thereof. In some embodiments, a pharmaceutical composition comprises about 100 mg/mL antibody, or antigen binding fragment thereof. In some embodiments, a pharmaceutical composition suitable for SC and/or IV administration comprises about 100 mg/mL anti-CD1a antibody (e.g., Ab571), or antigen binding fragment thereof.

In some embodiments, an anti-CD1a antibody, or antigen-binding fragment thereof, is administered in an intravenous or subcutaneous formulation as a sterile aqueous solution comprising a polypeptide comprising the amino acid sequence of SEQ ID NO: 54 or SEQ ID NO: 73. In some embodiments, an anti-CD1a antibody, or antigen-binding fragment thereof, is administered in an intravenous or subcutaneous formulation as a sterile aqueous solution comprising a polypeptide comprising the amino acid sequence of SEQ ID NO: 24. In some embodiments, an anti-CD1a antibody, or antigen-binding fragment thereof, is administered in an intravenous or subcutaneous formulation as a sterile aqueous solution comprising a polypeptide comprising the amino acid sequence of SEQ ID NO: 54 or SEQ ID NO: 73 and polypeptide comprising the amino acid sequence of SEQ ID NO: 24.

In some embodiments, an anti-CD1a antibody (e.g., Ab571), or antigen-binding fragment thereof, is administered as an intravenous or subcutaneous formulation that is a sterile aqueous solution containing about 5 mg/mL, about 10 mg/mL, about 15 mg/mL, about 20 mg/mL of antibody, about 25 mg/mL, about 50 mg/mL, about 75 mg/mL, about 100 mg/mL, about 125 mg/mL, or about 150 mg/mL of antibody or antigen-binding fragment thereof. In some embodiments, an intravenous or subcutaneous formulation is a sterile aqueous solution comprising sodium acetate, polysorbate 80, and sodium chloride at a pH ranging from about 5 to 6. In some embodiments, an intravenous formulation is a sterile aqueous solution containing 5 or 10 mg/mL of antibody, with 20 mM sodium acetate, 0.2 mg/mL polysorbate 80, and 140 mM sodium chloride at pH 5.5. Further, a solution comprising an antibody, or antigen-binding fragment thereof, can comprise, among many other compounds, glutamic acid, histidine, mannitol, sucrose, trehalose, glycine, poly(ethylene) glycol, EDTA, methionine, polysorbate 80 and any combination thereof, and many other compounds known in the relevant art.

In one embodiment, a pharmaceutical composition of the present disclosure comprises the following components: 50 mg/mL or 100 mg/mL of an anti-CD1a antibody (e.g., Ab571) or antigen-binding fragment of the present disclosure, 20 mM histidine, 8.5% sucrose, and 0.02% polysorbate 80, 0.005% EDTA at pH 5.8. In one embodiment, a pharmaceutical composition comprises the following components: 100 mg/mL anti-CD1a antibody (e.g., Ab571) or antigen-binding fragment of the present disclosure, 10 mM histidine, 5% sucrose, and 0.01% polysorbate 80 at pH 5.8.

In some embodiments, a pharmaceutical composition comprises an anti-CD1a antibody, or antigen-binding fragment thereof (e.g., Ab571) at a concentration of 100 mg/mL, 1.12 mg/mL L-histidine, 2.67 mg/mL L-histidine hydrochloride monohydrate, 85 mg/mL sucrose, 0.05 mg/mL edetate disodium dihydrate and 0.2 mg/mL polysorbate 80 at pH 5.8 in a nominal fill volume of 1.0 mL. Such pharmaceutical composition is suitable for SC or IV administration.

Such pharmaceutical compositions may be provided as a liquid formulation or as a lyophilized powder. When a powder is reconstituted at full volume, the composition retains the same formulation. Alternatively, a powder may be reconstituted at half volume, in which case the composition comprises the same components but at twice the concentration.

With regard to a therapeutic agent, where the agent is, e.g., a small molecule to be used in a combination therapy, it can be present in a pharmaceutical composition in the form of a physiologically acceptable ester or salt, such as in combination with a physiologically acceptable cation or anion, as is well known in the art.

Formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In some embodiments, a composition of the disclosure is a pyrogen-free formulation which is substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. These substances can cause fever, hypotension and shock if administered to humans. Due to the potential harmful effects, it is advantageous to remove even low amounts of endotoxins from intravenously administered pharmaceutical drug solutions. The Food and Drug Administration ("FDA") has set an upper limit of 5 endotoxin units (EU) per dose per kilogram body weight in a single one-hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg. In another embodiment, endotoxin and pyrogen levels in the composition are less than about 10 EU/mg, or less than about 5 EU/mg, or less than about 1 EU/mg, or less than about 0.1 EU/mg, or less than about 0.01 EU/mg, or less than about 0.001 EU/mg.

Dosing and Administration

To prepare a pharmaceutical or sterile composition including an anti-CD1a antibody, or antigen-binding fragment thereof, of the disclosure, the antibody is mixed with a pharmaceutically acceptable carrier or excipient (see above). Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N. Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of a symptom, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, 1996, Antibody Therapy, Bios Scientific Pub. Ltd, Oxfordshire, UK; Kresina (ed.), 1991, Monoclonal Antibodies, Cytokines and Arthritis, Marcel Dekker, New York, N.Y.; Bach (ed.), 1993, Monoclonal Antibodies and Peptide Therapy in Autoimmune Diseases, Marcel Dekker, New York, N. Y.; Baert, et al., New Engl. J. Med. 2003; 348:601-608; Milgrom, et al., New Engl. J. Med. 1999; 341:1966-1973; Slamon, et al., New Engl. J. Med. 2001; 344:783-792; Beniaminovitz, et al., New Engl. J. Med. 2000; 342:613-619; Ghosh, et al., New Engl. J. Med. 2003; 348:24-32; Lipsky, et al., New Engl. J. Med. 2000; 343:1594-1602).

Determination of the appropriate dose is made by a clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. A specific dose protocol may be one involving the maximal dose or dose frequency that avoids significant undesirable side effects.

In some embodiments, an effective dose of an anti-CD1a antibody is administered to reduce, neutralize, inhibit CD1a functional activity, such as (a) CD1a binding to T cell receptors; (b) CD1a-mediated lipid presentation to T cells and their subsequent activation; (c) CD1a-dependent CD69 expression; (d) CD1a-dependent IL-2 production; (e) CD1a-dependent increase in serum IgE levels; (f) CD1a-dependent increase in antigen-specific IgE antibodies; and (g) CD1a-dependent increase in expression levels of atopic dermatitis-associated genes (e.g., but not limited to TSLP, FLG, IL-33, CCL-26, IL-23p40, CCL-20, and/or CCL-20).

As used herein, an "effective dosage," "effective dose," "effective amount," or "therapeutically effective amount" of a drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include detectable clinical results such as reducing, or decreasing the rate of, weight loss or reducing one or more symptoms resulting from expression of CD1a, decreasing the dose of other medications required to treat the disease, enhancing the effect of another medication, and/or delaying the progression of the disease of patients. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

In some embodiments, an effective dose of an anti-CD1a antibody is administered to a patient with an inflammatory disease, such as but not limited to AD, contact dermatitis, psoriasis and IBD.

In some embodiments, an effective dose on an anti-CD1 antibody (e.g., Ab571) is administered to treat and/or prevent diseases, disorders and conditions associated with, or mediated by, CD1a expression and/or CD1a activity, including, but not limited to, inflammatory disease, such as but not limited to AD, contact dermatitis, psoriasis and IBD.

In some embodiments, an effective dose on an anti-CD1a antibody (e.g., Ab571) is administered to prevent, or reduce the occurrence of a sign or symptom of AD. In some embodiments, prophylactic administration of an anti-CD1a antibody (e.g., Ab571) is administered one time. In some embodiments, prophylactic administration of an anti-CD1a antibody (e.g., Ab571) is administered on an on-going basis (e.g., one or more than one dose, over a period of time).

In some embodiments, the method or use comprises administering a dose of about 1 mg to about 1000 mg. In some embodiments, the method or use comprises administering a dose of about 1 mg to 1000 mg as an initial fixed dose. In some embodiments, the method or use comprises administering a dose of about 1 mg to about 2 mg, about 2 mg to about 5 mg, about 5 mg to about 10 mg, about 10 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, about 90 mg to about 100 mg, about 100 mg to about 150 mg, about 150 mg to about 200 mg, about 200 mg to about 300 mg, about 300 mg to about 400 mg, about 400 mg to about 500 mg, about 500 mg to about 600 mg, about 600 mg to about 700 mg, about 700 mg to about 800 mg, about 800 mg to about 900 mg or about 900 mg to about 1000 mg optionally as an initial fixed dose. In some embodiments, the method or use comprises administering a dose of about 15 mg, 30 mg, 40 mg, 50 mg, 75 mg, 100 mg, 150 mg, 300 mg, 500 mg, 600 mg, 700 mg, 800 mg, 900 mg or 1000 mg of an anti-CD1a antibody, or antigen binding fragment thereof, or a pharmaceutical composition thereof. In some embodiments, the dose is an initial fixed dose.

In some embodiments, the method or use comprises administering a dose of about 2 mg, 10 mg, 20 mg, 30 mg, 40 mg, 50 mg, 75 mg, 100 mg, 125 mg, or 150 mg of an anti-CD1a antibody, or antigen binding fragment thereof, or a pharmaceutical composition thereof, of the invention. In some embodiments, the method or use comprises administering a dose of about 2 mg, 10 mg, 30 mg, 50 mg, 75 mg, 100 mg, 125 mg, or 150 mg of an anti-CD1a antibody, or antigen binding fragment thereof, or a pharmaceutical composition thereof, of the invention on a weekly basis. In some embodiments, the method or use comprises administering a dose of about 2 mg, 10 mg, 20 mg, 30 mg, 40 mg, 50 mg, 75 mg, 100 mg, 125 mg, or 150 mg of an anti-CD1a antibody (e.g., Ab571), or antigen binding fragment thereof, or a pharmaceutical composition thereof, subcutaneously, on a weekly basis.

In some embodiments, the method or use comprises administering dose of about 0.01 mg/kg to about 300 mg/kg, about 1 mg/kg to about 250 mg/kg, about 10 mg/kg to about 200 mg/kg, about 50 mg/kg to about 150 mg/kg, or about 75 mg/kg to about 100 mg/kg of an antibody, or antigen binding fragment thereof, or a pharmaceutical composition, optionally as an initial dose. The initial dose may be followed by one or more subsequent doses. In some embodiments, one or more subsequent dose may be administered at least any of weekly, every other week, every three weeks, every four weeks, every five weeks, every six weeks, every seven weeks, every eight weeks, every nine weeks, every ten weeks, every eleven weeks, or every twelve weeks.

An initial dose may be followed by one or more subsequent doses. In some embodiments, a subsequent dose is the same dose, a lower dose or a higher dose of anti-CD1a antibody as compared to the initial dose. In some embodiments, one or more subsequent dose may be administered at least any of weekly, every other week, every three weeks, every four weeks, every five weeks, every six weeks, every seven weeks, every eight weeks, every nine weeks, every ten weeks, every eleven weeks, or every twelve weeks. A specific dose protocol is one involving the maximal dose or dose frequency that avoids significant undesirable side effects.

A pharmaceutical composition of the present disclosure may also be administered via one or more routes of administration using one or more of a variety of methods known in the art. As will be appreciated by the skilled artisan, the route and/or mode of administration will vary depending upon the desired results. Selected routes of administration for antibodies of the disclosure include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the disclosure can be administered via a non-parenteral route, such as a topical, epidermal or mucosal route of administration, for example, intranasally, orally, vaginally, rectally, sublingually or topically.

In some embodiments, an anti-CD1a antibody, or antigen-binding fragment thereof of the disclosure is administered intravenously. In some embodiments, an anti-CD1a antibody, or antigen-binding fragment thereof of the disclosure is administered subcutaneously. In some embodiments, an anti-CD1a antibody, or antigen-binding fragment thereof of the disclosure is administered topically.

In some embodiments, an anti-CD1a antibody, or antigen-binding fragment thereof of the disclosure is administered intravenously or subcutaneously on a weekly basis. In some embodiments, an anti-CD1a antibody, or antigen-binding fragment thereof of the disclosure is administered at a unit dose of about 15 mg, about 30 mg, about 40 mg, about 100 mg, about 150 mg, about 300 mg, or about 600 mg subcutaneously on a weekly basis. In some embodiments, an anti-CD1a antibody, or antigen-binding fragment thereof of the disclosure is administered at a unit dose of about 150 mg or about 500 mg intravenously on a weekly basis.

In some embodiments, a subject is administered an anti-CD1a antibody, or antigen-binding fragments thereof, of the disclosure on a weekly basis and a therapeutically active compound or treatment modality which is effective in treating and/or preventing at least one sign and/or symptom of a disease (e.g., AD) on a daily, weekly, biweekly, monthly, or on an as needed basis. The disclosure provides protocols for the administration of pharmaceutical composition comprising anti-CD1a antibodies, or antigen-binding fragments thereof, of the disclosure alone or in combination with other therapies to a subject in need thereof. The therapies (e.g., prophylactic or therapeutic agents) of the combination therapies of the present disclosure can be administered concomitantly or sequentially to a subject. The therapy (e.g., prophylactic or therapeutic agents) of the combination therapies of the present disclosure can also be cyclically administered.

In some embodiments, an anti-CD1a antibody, or antigen-binding fragment thereof, or a pharmaceutical composition comprising the same, is administered about twice a week, once a week, once every two weeks, once every three weeks, once every four weeks, once every five weeks, once every six weeks, once every seven weeks, once every eight weeks, once every nine weeks, once every ten weeks, twice a month, once a month, once every two months, once every three months, once every four months, once every five months, once every six months, once every seven months, once every eight months, once every nine months, once every ten months, once every eleven months or once every twelve months. In some embodiments, an anti-CD1a antibody, or antigen-binding fragment thereof, or a pharmaceutical composition comprising the same, is administered about once every four weeks.

In some embodiments, an anti-CD1a antibody, or antigen-binding fragment thereof of the disclosure is administered intravenously or subcutaneously once every two weeks, once every three weeks, once every four weeks or once every five weeks. In some embodiments, an anti-CD1a antibody, or antigen-binding fragment thereof of the disclosure is administered at a unit dose of about 15 mg, about 30 mg, about 40 mg, about 100 mg, about 150 mg, about 300 mg, or about 600 mg subcutaneously once every two weeks, once every three weeks or once every four weeks. In some embodiments, an anti-CD1a antibody, or antigen-binding fragment thereof of the disclosure is administered at a unit dose of about 30 mg subcutaneously once every four weeks (Q4W).

In some embodiments, part of a dose is administered by an intravenous bolus and the rest of the dose is administered by infusion of the antibody formulation. For example, a 0.01 mg/kg intravenous injection of the anti-CD1a antibody, or antigen-binding fragment thereof, may be given as a bolus, and the rest of the antibody dose may be administered by intravenous injection. A predetermined dose of the anti-CD1a antibody, or antigen-binding fragment thereof, may be administered, for example, over a period of an hour and a half to two hours to five hours.

Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

Kits

The disclosure also provides a kit comprising any or all of the anti-CD1a antibodies or antigen-binding fragments thereof described herein. A kit of the disclosure includes one or more containers comprising an anti-CD1a antibody, or antigen-binding fragment thereof, described herein and instructions for use in accordance with any of the methods of the disclosure described herein. Generally, these instructions comprise a description of administration of an antibody for the above described therapeutic treatments. In some embodiments, a kit is provided for producing a single-dose administration unit. In certain embodiments, a kit can contain both a first container having a dried protein and a second container having an aqueous formulation. In certain embodiments, a kit containing an applicator, e.g., single and multi-chambered pre-filled syringe or device (e.g., liquid syringes and lyosyringes), is included.

In some embodiments, a kit contains an applicator comprising an anti-CD1a antibody, or antigen-binding fragment thereof, wherein the applicator is designed, or acceptable for self-administration, by a patient (e.g., a patient with AD). In some embodiments, self-administration is by subcutaneous administration.

Instructions relating to use of an anti-CD1a antibody, or antigen-binding fragment thereof, generally include information as to dosage, dosing schedule, and route of administration (e.g., SC or IV) for the intended treatment. A container may be a unit dose, a bulk package (e.g., a multi-dose package) or a sub-unit dose. Instructions supplied in a kit of the disclosure are typically written instructions on a label or package insert (e.g., a paper sheet included in the kit), but machine-readable instructions (e.g., instructions carried on a magnetic or optical storage disk) are also acceptable.

A kit of this disclosure is in suitable packaging. Suitable packaging includes, but is not limited to, a vial, bottle, jar, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example a container may be an intravenous solution bag or a vial having a stopper pierceable by a hypodermic injection needle). A container may also have a sterile access port (for example a container may be an intravenous solution bag or a vial having a stopper pierceable by a hypodermic injection needle). At least one active agent in the composition is an anti-CD1a antibody of the disclosure. A container may further comprise an additional therapeutic agent.

In one embodiment, there is a kit further comprising a second therapeutically active compound, or treatment modality, which is effective in treating or preventing symptoms of inflammatory diseases such as but not limited to AD, wherein the amount of the anti-CD1a antibody and the second compound or modality together achieve synergistic effects in the treatment or prevention of symptoms of the inflammatory disease, that is, the combination is "synergistic," (i.e., the combination provides an effect greater than a merely additive effect of two or more individual therapies). Such a kit comprising synergistic combination therapies may advantageously utilize lower dosages of the administered therapeutic agents, thus avoiding possible toxicities or complications associated with the various monotherapies.

In some embodiments, a kit may further comprise at least one additional therapeutically active compound useful for the treatment or prevention of a sign and/or symptom of AD including, for example, antagonists to one or more of IL-1a, IL-1b, IL-2, IL-3, IL-4, IL-5, IL-6, IL-8, IL-9, IL-10, IL-12, IL-13, IL-17, IL-18, IL-21, IL-23, IL-25, IL-26, IL-31, IL36 IFNα, IFNγ, or antagonists of their respective receptors, anti-inflammatory agents, recombinant interferon gamma, NSAIDs, steroids, calcineurin inhibitors, dupilumab and/or corticosteroids.

A kit may optionally provide additional components such as a buffer and interpretive information. Normally, a kit comprises a container and a label or package insert(s) on, or associated with, the container.

The disclosure also provides a diagnostic kit comprising any or all of the antibodies, or antigen-binding fragments thereof, described herein. A diagnostic kit is useful for, for example, detecting the presence of CD1a in a sample. In some embodiments, a diagnostic kit can be used to identify an individual with a latent disease, disorder or condition that may put them at risk of developing a CD1a-mediated disease, disorder or condition. In some embodiments, a diagnostic kit can be used to detect the presence and/or level of CD1a in an individual suspected of having a CD1a mediated disease, disorder or condition.

Diagnostic kits of the disclosure include one or more containers comprising an anti-CD1a antibody, or antigen-binding fragment thereof, described herein and instructions for use in accordance with any of the methods of the disclosure described herein. Generally, the instructions comprise a description of use of a CD1a antibody, or antigen-binding fragment thereof, to detect the presence of CD1a in individuals at risk for, or suspected of having, an CD1a mediated disease, disorder or condition, such as AD. In some embodiments, an exemplary diagnostic kit can be configured to contain reagents such as, for example, a CD1a antibody, or antigen-binding fragment thereof, a negative control sample, a positive control sample, and directions for using the kit.

Biological Deposits

The heavy and light chains of anti-CD1a Ab571 were deposited under terms in accordance with the Budapest Treaty with the American Type Culture Collection (ATCC), 10801 University Boulevard, Manassas, Va. 20110-2209, USA, on Jul. 29, 2020.

| Antibody | Description | SEQ ID NO: | ATCC Accession No. |
|---|---|---|---|
| Ab571 | Ab571-VH (heavy chain variable region of Ab571) | 55 | PTA-126810 |
| Ab571 | Ab571-VL (light chain variable region of Ab571) | 28 | PTA-126811 |

The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

General Techniques

It is to be understood that this invention is not limited to specific synthetic methods of making that may of course vary. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Sambrook and Russell, Molecular Cloning: A Laboratory Manual, 3rd. ed., Cold Spring Harbor Laboratory Press, Cold Spring Harbor, N Y (2001); Ausubel et al., Current Protocols in Molecular Biology, John Wiley & Sons, N Y (2002); Harlow and Lane Using Antibodies: A Laboratory Manual, Cold Spring Harbor Laboratory Press, Cold Spring Harbor, N Y (1998); Coligan et al., Short Protocols in Protein Science, John Wiley & Sons, N Y (2003); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Enzymatic reactions and purification techniques are performed according to manufacturer's specifications, as commonly accomplished in the art or as described herein. The nomenclatures used in connection with, and the laboratory procedures and techniques of, analytical chemistry, biochemistry, immunology, molecular biology, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

EQUIVALENTS

The foregoing description and following Examples detail certain specific embodiments of the disclosure and describes the best mode contemplated by the inventors. It will be appreciated, however, that no matter how detailed the foregoing may appear in text, the disclosure may be practiced in many ways and the disclosure should be construed in accordance with the appended claims and any equivalents thereof.

Although the disclosed teachings have been described with reference to various applications, methods, kits, and compositions, it will be appreciated that various changes and modifications can be made without departing from the teachings herein and the claimed disclosure below. The following examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

EXAMPLES

In order that this invention may be better understood, the following examples are set forth. These examples are for purposes of illustration only and are not to be construed as limiting the scope of the invention in any manner.

Example 1: Identification of Anti-CD1a Antibodies from Rat Hybridoma and Testing Chimeric IgGs Female Sprague Dawley rats were immunized with human single-chain CD1a-$\beta_2$M recombinant protein (SEQ ID NO: 2) along with RIBI adjuvant twice per week for 4 weeks. The antigen-adjuvant mixture was given to the animals through intraperitoneal injections. At the end of the dosing period, test bleeds were collected from the immunized animals and the titers against human and cynomolgus CD1a-β2M recombinant proteins were determined by ELISA. In addition, the reactivity of the test bleeds was also examined by flow cytometry on CHO cells stably expressing human or cynomolgus CD1a protein on the cell surface, as well as on parental CHO that do not express CD1a.

Animals with strong titers on both the recombinant and the cell-surface CD1a proteins were selected for hybridoma production. Briefly, spleens were harvested from the immunized animal and the isolated splenocytes were fused with mouse P3X63Ag8.653 myeloma cells (ATCC, cat #is CRL-1580). Resulting fusions were selected by growing them in medium containing HAT (sodium hypoxanthine, aminopterin and thymidine). Successfully fused hybridomas were first screened for reactivity against human or cynomolgus CD1a-$\beta_2$M recombinant proteins. To eliminate hybridomas that specifically recognized the $\beta_2$M portion of the fusion proteins, they were counter-screened on human FcRn protein, which contains the $\beta_2$M polypeptide. The human and cynomolgus CD1a reactive hybridomas were further screened for reactivity on CHO/human CD1a and CHO/cyno CD1a cells in order to identify those specifically recognizing cell surface CD1a. In addition, to further eliminate hybridomas that exhibited cross reactivity against other CD1 family members, they were also screened on CHO cells stably expressing human CD1b or CD1c proteins. The final panel of hybridomas that produced CD1a-specific monoclonal antibodies was then tested for its ability to inhibit CD1a-dependent activation of an engineered T cell line in vitro as described below.

For the T-cell activation assay, human CD1a-transfected C1R cells (C1R-huCD1a cells) were incubated with Jurkat 76 (J76) cells expressing T-cell receptor (TCR) allele BK6 that specifically recognizes CD1a (Birkinshaw et al. Nature Immunol 2015 March; 16(3):258-66). The activation of J76-BK6 cells in the absence or presence of hybridoma supernatants and control antibodies was assessed by measuring interleukin 2 (IL-2) secretion into the culture media by a Mesoscale Discovery (MSD, K151QQD-4) assay and cell-surface Cluster of Differentiation-69 (CD69) expression (% CD69$^+$ cells) by flow cytometry, as described below. Antibodies that blocked CD1a binding to BK6 TCR caused suppression of both IL-2 secretion and CD69 expression.

C1R-huCD1a cells were pre-incubated with titrated amounts of hybridoma supernatant or purified antibody, then co-cultured with J76-BK6 cells overnight at 37° C. The next day the assay plate was centrifuged, supernatant was removed, frozen at −20° C. and later analyzed for the presence of IL-2 using an MSD assay. Remaining cells were resuspended in buffer and stained for cell surface expression of CD3, CD1a, and CD69 using specific antibodies (BioLegend 344816, 300110 and 310920, respectively). Cells were stained for 30 minutes, washed and run on the flow cytometer. The variable heavy (VH) and variable light (VL) chain genes from the hybridomas that inhibited the CD1a-dependent T cell activation (i.e., suppressed both IL-2 secretion and CD69 expression) were then chosen for molecular cloning and subsequent analysis.

Example 2: Cloning of Rat Anti-CD1a Antibody Heavy and Light Chain Variable Regions Heavy chain and light chain variable regions of the anti-CD1a antibodies were cloned using the SMART® cDNA synthesis system (Clontech Laboratories Inc.) followed by PCR amplification. The cDNA was synthesized from 1 pg total RNA isolated from approximately 500,000 hybridoma cells using the RNEasy kit (Qiagen) and the SMART® IIA oligo (Clontech Laboratories Inc.) with Superscript™ III reverse transcriptase (Invitrogen). The cDNA was then amplified by PCR using a primer that anneals to the SMART® IIA oligo sequence and rat constant region-specific primer (rat Kappa for the light chain and rat IgG1 for the heavy chain) with Q5® High-Fidelity 2× Master Mix (New England Biolabs Inc.). Heavy and light chain PCR products were subcloned into the pCR4-TOPO vector (Invitrogen) and the nucleic acid sequence was determined. The variable heavy regions were then cloned into the pTT5 mammalian expression vector containing the human IgG1 constant region (SEQ ID NO: 86) that was mutated to abolish effector function (Leu234Ala, Leu235Ala and Gly237Ala, EU numbering; U.S. Pat. No. 5,624,821), producing chimeric heavy chains. Variable light regions were cloned into the pTT5 mammalian expression vectors containing the constant region of human kappa (SEQ ID NO: 11) to produce chimeric light chains.

Figure 1B:
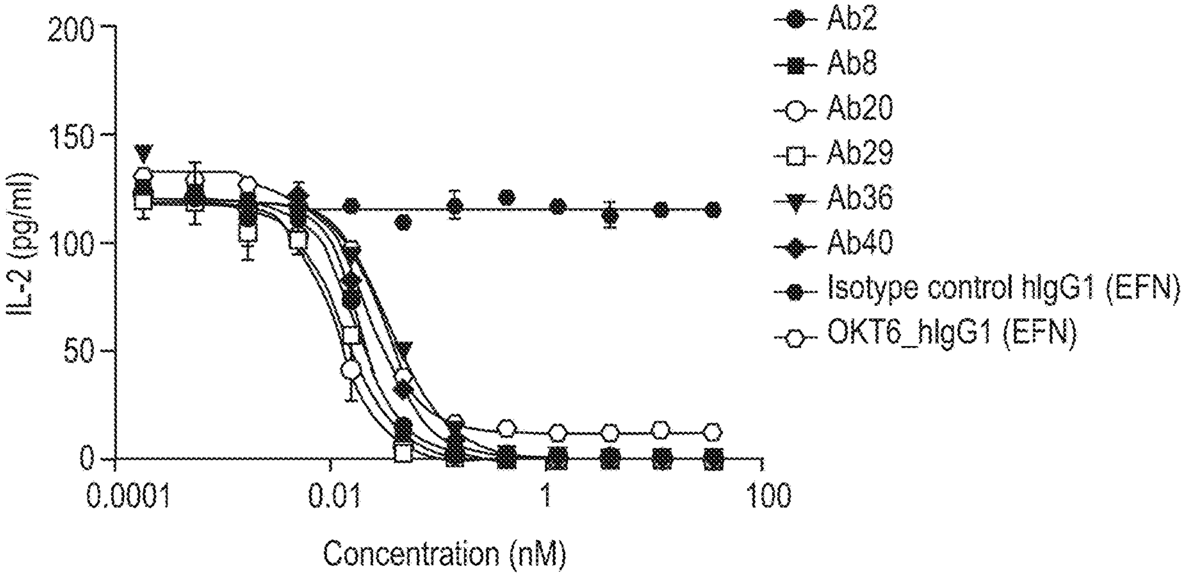
FIG. 1B depicts the effects of chimeric anti-CD1a antibodies on IL-2 secretion in a T-cell activation assay.

The chimeric antibodies were then expressed in and purified from human embryonic kidney (HEK) cells using standard techniques and their activity was re-tested in the T cell activation assay described above. A representative result of a T-cell activation assay is shown in FIGS. 1A, 1B and Table 1. The chimeric anti-CD1a antibodies potently inhibited CD1a-dependent T cell activation as demonstrated by the decrease in CD1a-dependent CD69 expression (FIG. 1A) and the inhibition of IL-2 production by BK6-expressing J76 cells (FIG. 1B). The $IC_{50}$ values from the experiment shown in FIGS. 1A and 1B are shown in Table 1. OKT6 is a commercially available CD1a-blocking antibody. OKT6 sequences were cloned from hybridoma obtained from ATCC (CRL8020™) and made as chimeric human IgG1.

TABLE 1

$IC_{50}$ values from the experiment shown in FIG. 1A and FIG. 1B.

| Antibody | CD69 expression, $IC_{50}$ (nM) | IL-2 secretion, $IC_{50}$ (nM) |
|---|---|---|
| Ab2 | 0.043 | 0.018 |
| Ab8 | 0.051 | 0.018 |
| Ab20 | 0.040 | 0.012 |
| Ab29 | 0.036 | 0.013 |
| Ab36 | 0.093 | 0.031 |
| Ab40 | 0.069 | 0.022 |
| Human IgG1 (EFN) isotype control | >100 | >100 |
| OKT6-human IgG1 (EFN) | 0.042 | 0.028 |

EFN = effector function null

Example 3: Humanization of Rat Anti-CD1a Antibodies

Humanization of variable regions of four rat anti-CD1a antibodies (Ab8, Ab36, Ab40 and Ab80) was performed using a CDR grafting strategy known in the art (e.g. Hwang et al., 2005; Methods 36, p35-42). Complementarity-determining regions (CDRs) of anti-CD1a antibodies were determined based on Kabat definition (Kabat E A, Wu T T, Perry H M, Gottesman K S, Foeller C. *Sequences of Proteins of Immunological Interest. US Department of Health and Human Services, NIH Publication No.* 91-3242, 1991), with the exception of CDR-H1 where the start of the loop was extended from H31 (Kabat) to H26. CDRs of parental rat Ab were inserted (grafted) into human acceptor framework sequences, IGHV3-7*01 for the heavy chain and IGKV1-39*01 for the light chain, and synthesized in vectors containing human IgG1 (mutated to abolish effector function as follows: Leu234Ala, Leu235Ala and Gly237Ala, EU numbering; U.S. Pat. No. 5,624,821) or human kappa constant regions, respectively. Limited back-mutations toward parental rat sequences in the framework regions of both the VH and the VL domains were introduced based on structural modeling. The Ab variants were produced in HEK cells, and the retention of their binding activity was measured using competition ELISA against parental chimeric (non-CDR grafted) antibody, as described below.

For competition ELISA, high-binding Costar ELISA plates were coated with 0.1 pg per well (100 μL of 1 μg/mL) CD1a protein in PBS buffer overnight at 4° C. Plates were then washed and blocked for 3 hours with PBS+3% bovine serum albumin (BSA) at room temperature. Antibody variants were pre-mixed at various concentrations (typically at 3-fold dilutions) with a fixed concentration of biotinylated parental (chimeric) antibody, and the mixtures added to wells of blocked plates. After 2 hours incubation, plates were washed and incubated for 1 hour with streptavidin-HRP secondary reagent. After washing, plates were incubated with one-component HRP substrate and the developed color measured at 450 nm using Envision plate reader (Perkin Elmer).

Figure 2:
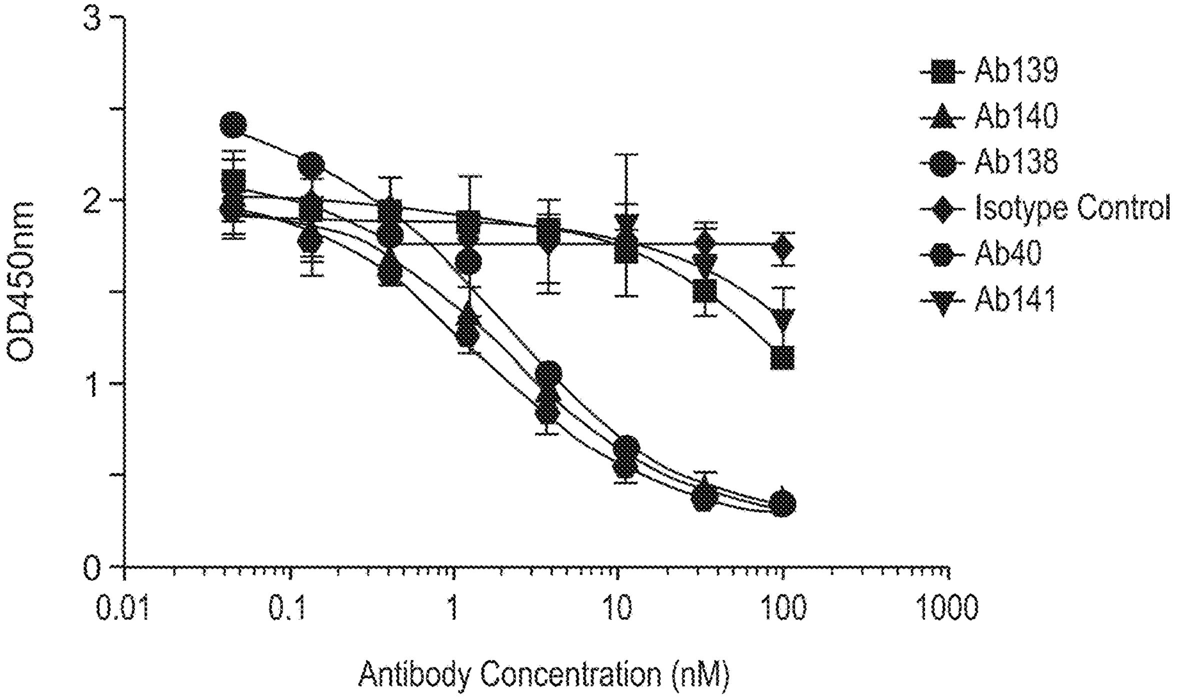
FIG. 2 depicts competition ELISA with Ab138, Ab139 and Ab140—the humanized antibody variants of chimeric antibody Ab40. Humanized clones Ab138 (circle) and Ab140 (upright triangle) demonstrate very similar activity to the parental chimeric Ab40 in this assay, suggesting good retention of their binding affinity.

As shown in FIG. 2, humanized clones Ab138 and Ab140 demonstrate very similar activity to the parental chimeric (non-CDR grafted) Ab40 in this assay, suggesting good retention of their binding affinity. Ab138 was chosen for further optimization based on its overall acceptable human/cyno CD1a affinity & parity, reasonable number of predicted T-cell epitopes and chemical liability sites as compared to the other clones.

Example 4: Determination of Co-Crystal Structure of Ab138 Fab with Human CD1a The Fab fragment of the anti-CD1a antibody Ab138 (Fab138) was obtained by cleaving the full-length IgG with papain and removing the Fc using a Protein A resin. Human β2M-CD1a-His6 protein (SEQ ID NO:95) was expressed in HEK cells and purified using standard techniques. X-ray crystallography was used to determine the structure of the Fab domain of Ab138 in complex with human CD1a protein.

For crystallization trials, human β2M-CD1a-His6 protein was mixed with Fab138 at 1:1.5 molar ratio, and the complex was concentrated to 10 mg/ml in TBS buffer, pH 7.5. The crystals were obtained by hanging-drop vapor-diffusion method under conditions containing 100 mM sodium cacodylate pH 6.5, 100 mM magnesium acetate, and 15% PEG 6000. The crystals had symmetry consistent with monoclinic space group $P2_1$ with unit cell parameters a=42.23 Å; b=174.13 Å; c=120.16 Å, β=90.1° and with two copies of CD1a-Fab138 complexes in the crystallographic asymmetric unit. A data set to a 2.14 Å resolution was collected from a single frozen crystal at IMCA beamline 17-ID at the Argonne National Laboratory.

Figure 3A:
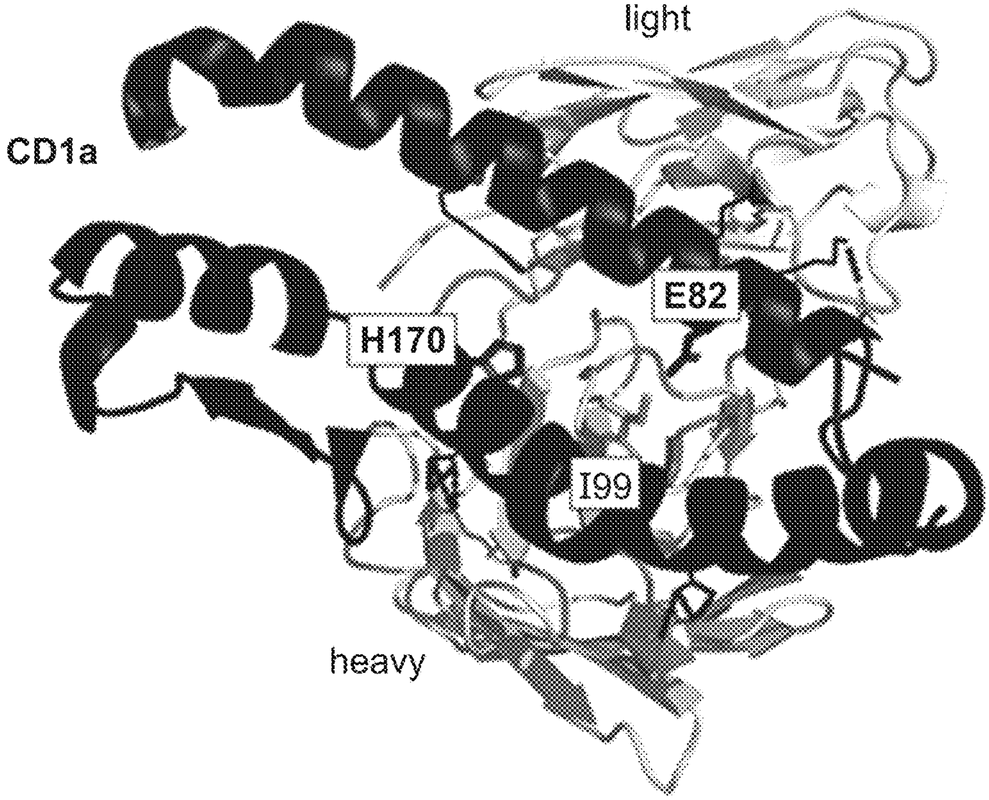
FIG. 3A and FIG. 3B depict two views of CD1a/Ab138 interface. Antibody heavy and light chains are labeled. Backbone trace is shown as ribbons. 3 highly buried interface residues (Ab138-heavy-I99, CD1a-E82, CD1a-H170) are labeled and have side chains highlighted (thick lines). Residue side chains making cross-interface salt bridges are also shown (thin lines), with salt bridge contacts shown in dashed lines.
Figure 3B:
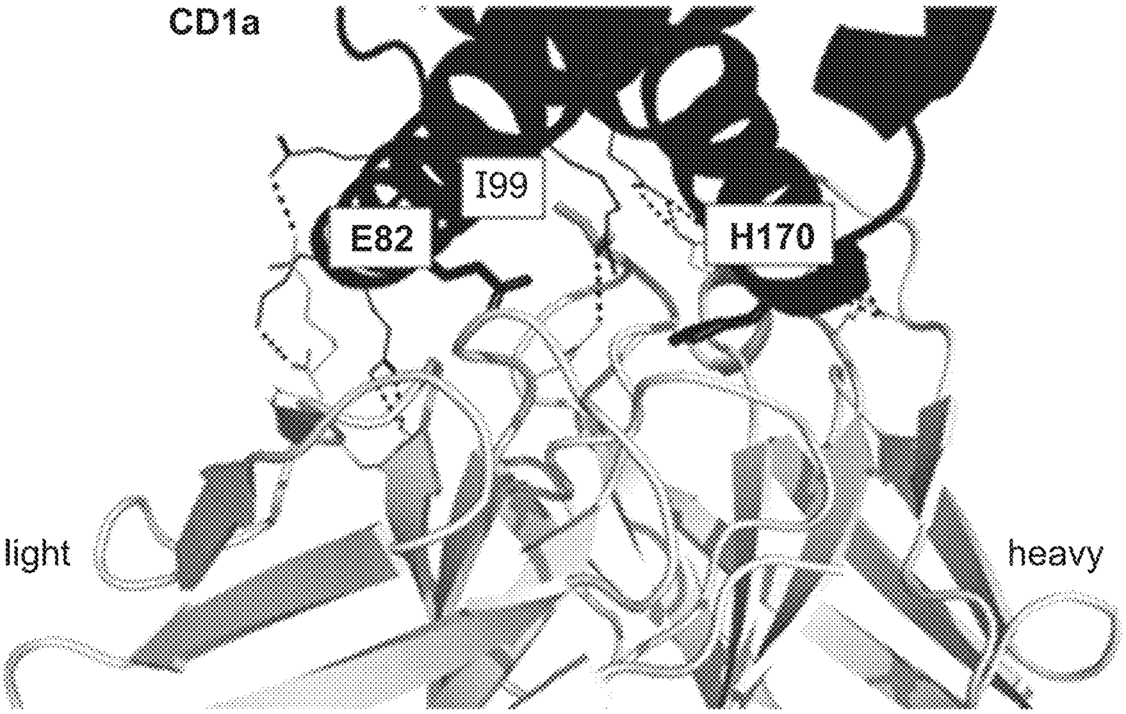

The data were processed and scaled using autoPROC. The structure was solved by molecular replacement with PHASER starting with the CD1a model from pdb=4x6f and the homology model of Fab138 built based on the closest homologous structure from our internal structure database. The solution was obtained by searching for the two copies of CD1a and two copies of Fab138. The resulting electron density maps calculated with the two copies of complexes as a model were of unambiguous quality. Several iterative rounds of manual adjustment and model rebuilding using COOT and crystallographic refinement using autoBUSTER yielded the final model of CD1a-Fab138 with a crystallographic $R_{work}$ of 21.1% and $R_{free}$ of 25.8%, where $R_{work}=||F_{obs}|-|F_{calc}||/|F_{obs}|$ and $R_{free}$ is equivalent to $R_{work}$, but calculated for a randomly chosen 5% of reflections omitted from the refinement process. The co-crystal structure reveals the interactions between CD1a and Ab138 (FIG. 3). Interacting residue pairs were identified as interacting if they met any of 5 criteria: 1) cross-interface heavy atom-heavy atom (non-hydrogen) contacts within 3.8 Angstroms; 2) cross-interface salt bridge contact; 3) cross-interface hydrogen-bond contact; 4) polar contacts within 3.8 Angstroms to a shared water molecule spanning the interface; 5) reduction of residue accessible surface area (ASA) by more than 20 square Angstroms between free and bound state AND a corresponding inducement of a reduction of ASA of at least 10 square Angstroms between free and bound state on a residue across the interface. 56 CD1a/Ab138 residue pair interactions were identified, comprising 54 total amino acid residues: 26 on the CD1a antigen, 14 on the Ab138 heavy chain, and 14 on the antibody light chain.

The interacting residues are further separated into three tiers based on their contributions to the interface. Tier 1 residues (listed in Table 2) meet at least one of 3 criteria: 1)>80 square Angstroms of ASA buried by the interface; 2) >90% of ASA in free state buried by the interface, AND >30 square Angstroms of ASA buried by the interface; 3) >6 cross-interface heavy atom-heavy atom contacts within 3.8 Angstroms AND >1 cross-interface salt bridge or hydrogen-bond contacts. Tier 2 residues do not meet any of the Tier 1 criteria, but do meet at least one of 4 looser criteria: 1) >40 square Angstroms of ASA buried by the interface; 2) >50% of ASA in free state buried by the interface; 3) >4 cross-interface heavy atom-heavy atom contacts within 3.8 Angstroms; 4) >1 cross-interface salt bridge or hydrogen-bond contacts. Interacting residues that do not meet the Tier 1 or Tier 2 criteria are categorized as Tier 3. The Tier 1 interface residues and their interaction properties are summarized in Table 2, along with properties of the entire interface. Residues from all 3 Tier categories are highlighted in the sequences in Table 3.

TABLE 2

List of 18 Tier 1 interacting residues within the CD1a/Ab138 interface. Values in the "specific interactions" columns represent summations of all observations of each interaction type involving the given residue. Values in the three "Accessible/buried surface area" columns represent, in square Angstroms (Å$^2$), the accessible surface area (ASA) of the given residue in the free state, the ASA of the residue in the bound state, and the difference of the two: the residue's buried surface area (BSA). The last column records the percentage of the residue's free state ASA that is buried upon complex formation. Relevant values for the full interface are included in the final row of the table.

| Residue | | | Specific interactions | | | | Accessible/buried surface area (Å$^2$) | | | |
|---|---|---|---|---|---|---|---|---|---|---|
| Chain (A: CD1a, H: heavy, L: light) | Position | Amino acid | Heavy atoms within 3.8 Å | Salt bridge | H-bond (excluding salt bridge) | Shared water | ASA, Free state | ASA, Bound state | BSA | BSA as % of ASA, free state |
| A | 78 | GLU | 14 | 1 | 1 | 2 | 140.9 | 26.9 | 114.0 | 80.9 |
| A | 81 | LYS | 8 | 1 | 1 | | 125.0 | 51.6 | 73.4 | 58.7 |
| A | 82 | GLU | 9 | | 1 | 1 | 112.7 | 1.6 | 111.1 | 98.6 |
| A | 85 | THR | 4 | | 2 | | 63.7 | 2.8 | 60.8 | 95.5 |
| A | 89 | ILE | 1 | | | 1 | 79.6 | 7.6 | 72.0 | 90.4 |
| A | 93 | ARG | 10 | 1 | 1 | | 111.9 | 36.7 | 75.2 | 67.2 |
| A | 170 | HIS | 18 | | 2 | | 118.8 | 2.8 | 116.0 | 97.6 |
| A | 173 | ASP | 13 | 1 | 2 | | 74.3 | 1.5 | 72.8 | 98.0 |
| A | 177 | ASN | 6 | | 1 | | 75.1 | 3.8 | 71.3 | 95.0 |
| H | 99 | ILE | 5 | | | | 109.7 | 9.1 | 100.6 | 91.7 |
| H | 100 | PRO | 8 | | 1 | | 51.7 | 0.2 | 51.5 | 99.6 |
| H | 100A | THR | 2 | | | 1 | 31.3 | 0.0 | 31.3 | 100.0 |
| H | 100C | TRP | 2 | | | | 46.7 | 1.0 | 45.7 | 97.9 |
| L | 30 | SER | 7 | | 1 | 1 | 61.1 | 14.8 | 46.2 | 75.7 |
| L | 49 | TYR | 3 | | | 1 | 61.6 | 1.5 | 60.1 | 97.5 |
| L | 53 | ARG | 14 | 1 | 3 | | 146.2 | 32.8 | 113.3 | 77.5 |
| L | 56 | ASP | 10 | 1 | 1 | | 135.9 | 75.8 | 60.1 | 44.2 |
| L | 94 | TYR | 12 | | 1 | | 107.4 | 49.9 | 57.6 | 53.6 |
| Full interface BSA | | | 115 | 6 | 15 | 5 | | | 2397.1 | |

TABLE 3

Partial sequence table with Tier 1, Tier 2, and Tier 3 interacting residues of CD1a and Ab138 highlighted. Tier 1 residues (also shown in Table 2) are bolded and underlined, Tier 2 residues are bolded without an underline, and Tier 3 residues are in italics. CD1a includes 9 Tier 1 residues, 7 Tier 2 residues, and 10 Tier 3 residues. The Ab138 light chain includes 5 Tier 1 residues, 6 Tier 2 residues, and 3 Tier 3 residues. The Ab138 heavy chain includes 4 Tier 1 residues, 8 Tier 2 residues, and 2 Tier 3 residues.

| SEQ ID NO | Description | Sequence |
|---|---|---|
| 1 | Human CD1a protein (with signal peptide) | MLFLLLPLLA VLPGDGNADG LKEPLSFHVT<br>WIASFYNHSW KQNLVSGWLS DLQTHTWDSN<br>SSTIVFLCPW SRGNFSN**E***EW* **KE***LE***TL**F*R***I**R T*I***R**SFEGIRR |

TABLE 3-continued

Partial sequence table with Tier 1, Tier 2, and Tier 3 interacting residues of CD1a and Ab138 highlighted. Tier 1 residues (also shown in Table 2) are bolded and underlined, Tier 2 residues are bolded without an underline, and Tier 3 residues are in italics. CD1a includes 9 Tier 1 residues, 7 Tier 2 residues, and 10 Tier 3 residues. The Ab138 light chain includes 5 Tier 1 residues, 6 Tier 2 residues, and 3 Tier 3 residues. The Ab138 heavy chain includes 4 Tier 1 residues, 8 Tier 2 residues, and 2 Tier 3 residues.

| SEQ ID NO | Description | Sequence |
|---|---|---|
| | | YAHELQFEYP FEIQVTGGCE LHSGKVSGSF LQLAYQGSDF |
| | | VSFQNNSWLP YPVAGNMAKH FCKVLNQNQH |
| | | ENDITHNLLS DTCPRFILGL LDAGKAHLQR QVKPEAWLSH |
| | | GPSPGPGHLQ LVCHVSGFYP KPVWVMWMRG |
| | | EQEQQGTQRG DILPSADGTW YLRATLEVAA |
| | | GEAADLSCRV KHSSLEGQDI VLYWEHHSSV GFIILAVIVP |
| | | LLLLIGLALW FRKRCFC |
| 7 | Ab138_full LC | DIQMTQSPSS LSASVGDRVT ITCLASEDIS NDLAWYQQKP |
| | | GKAPKLLIYG ANRLKDGVPS RESGSGSGTD YTLTISSLQP |
| | | EDFATYYCQQ SYKYPYTFGQ GTKLEIKRTV AAPSVFIFPP |
| | | SDEQLKSGTA SVVCLLNNFY PREAKVQWKV |
| | | DNALQSGNSQ ESVTEQDSKD STYSLSSTLT LSKADYEKHK |
| | | VYACEVTHQG LSSPVTKSEN RGEC |
| 14 | Ab138_full HC | EVQLVESGGG LVQPGGSLRL SCAASGFTFT |
| | | DFYMNWVRQA PGKGLEWVAF IRNKANGYTT |
| | | ESNPSVKGRF TISRDNAKNS LYLQMNSLRA |
| | | EDTAVYYCAR ETTGIPTGWF AYWGQGTLVT |
| | | VSSASTKGPS VFPLAPSSKS TSGGTAALGC LVKDYFPEPV |
| | | TVSWNSGALT SGVHTFPAVL QSSGLYSLSS VVTVPSSSLG |
| | | TQTYICNVNH KPSNTKVDKK VEPKSCDKTH TCPPCPAPEA |
| | | AGAPSVFLFP PKPKDTLMIS RTPEVTCVVV DVSHEDPEVK |
| | | FNWYVDGVEV HNAKTKPREE QYNSTYRVVS |
| | | VLTVLHQDWL NGKEYKCKVS NKALPAPIEK |
| | | TISKAKGQPR EPQVYTLPPS REEMTKNQVS LTCLVKGFYP |
| | | SDIAVEWESN GQPENNYKTT PPVLDSDGSF FLYSKLTVDK |
| | | SRWQQGNVFS CSVMHEALHN HYTQKSLSLS PG(K) |

The epitope region on CD1a (the residues that interact with Ab138) is largely confined to the 1$^{st}$ and 3$^{rd}$ helical regions of the protein, which together comprise 23 of the 26 interacting residues and all 9 of the Tier 1 interacting residues. The only other CD1a residues at the antibody-antigen interface are Q167 & N168 (according to the numbering of SEQ ID NO: 1), which are capping residues for the 3$^{rd}$ helical region, and N146, which lies in the final beta turn before the 2$^{nd}$ helical region (the last turn in the N-terminal domain's beta sheet). The corresponding paratope region on Ab138 includes contributing residues from all 6 CDRs, as well as from framework-L2 residue Y49. All CDRs except the H1 and L1 contribute at least 5 residues to the paratope, with the H3 (7 interacting residues, 4 Tier 1 interacting residues) being the most involved.

Within the Tier 1 interacting residues, 3 residues are notably involved in the interface interaction, with a BSA >100 square Angstroms and >90% of residue ASA buried upon binding. On the antibody side, 199 on the heavy chain is highly exposed in the free state and embedded between the 1$^{st}$ and 3$^{rd}$ CD1a helices near the center of the interface in the bound state. On the antigen side, H170 mimics this behavior; it is also highly exposed in the free state, and embedded between the Ab-heavy and Ab-light chain in the bound state, making 18 total cross-chain contacts within 3.8 Angstroms, 2 of which are hydrogen bonds. Additionally, on the antigen side, E82 is encircled by the antibody H3 loop, interacting with 4 residues within the loop; it also interacts with one residue from the antibody light chain.

Figure 4:
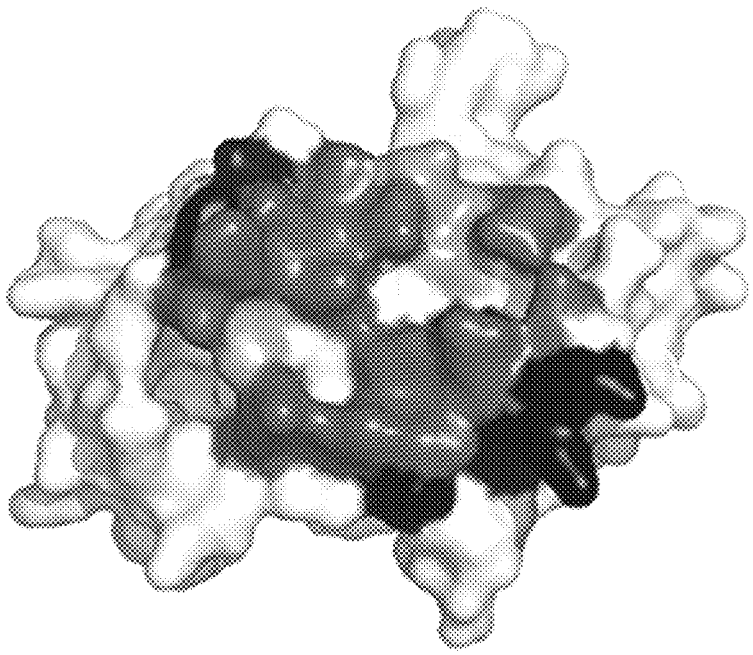
FIG. 4 depicts surface view of CD1a epitope, with residues contacting anti-CD1a Ab138 and/or BK6 TCR shown. BK6-exclusive residues (E171, D181, T182) are in light gray, Ab138-exclusive residues (E78, K81, L83, E84, R88, N146, Q167, Q169, S180) are in black, residues that contact both (E79, E82, T85, L86, I89, R93, N168, H170, D173, I174, H176, N177, R185) are in dark gray, and non-contacting residues are in shaded white. View represents a similar orientation as FIG. 3A, but flipped 180 degrees about the vertical page axis.

There are 6 salt bridges across the interface, with 5 of the 6 at the periphery of the interface; the 6$^{th}$, A-R93/L-D32, is more central. Apart from those concurrent with salt bridges, there are also 20 hydrogen bonds bridging the interface; 5 of these are mediated by a shared water molecule. In total, the interface buries 2397 square Angstroms of surface area between CD1a and Ab138. The CD1a/Ab138 interface is similar to the CD1a/BK6 TCR interface, as revealed by Protein Data Base crystal structure 4X6C (described in Birkinshaw et al., Nature Immunol. 16 (3), 258-266, 2015). The overlap of Ab138 and BK6 epitopes on CD1a is illustrated in FIG. 4. The BK6 alpha chain occupies a similar relative position to CD1a as Ab138's heavy chain; the BK6 beta chain and Ab138's light chain are not as similar, but do overlap somewhat, particularly within the CDR3. BK6 makes 3.8 Angstrom contacts to 16 CD1a residues. Of these, 13 also make 3.8 Angstrom contacts to Ab138; 2 of the remaining 3 CD1a residues from the set are not within 3.8 Angstroms of Ab138 but are interacting by other means; the last remaining residue (Glu-171) does not interact with Ab138. The BK6 alpha chain is the more involved of the two TCR chains, with 9 residues across all 3 CDRs making contact with CD1a. The BK6 beta chain only has 5 residues that contact CD1a, all within the CDR3.

Example 5: Affinity Maturation and Sequence Optimization of Ab138 by Phage Display Using Crystal Structure-Based Rational Design Next, sequence optimization of Ab138 was performed to reduce potential immunogenicity risks as described below.

Immunogenicity Risk Prediction

Immunogenicity risk of the humanized anti-CD1a antibody Ab138 was predicted using in silico tools for prediction of MHCII peptide binding. These tools were used: (1) for epitope identification of potential MHCII binding for each individual peptide in the sequence, (2) for epitope classification, to assess the risk of potential MHCII peptide binders and (3) for overall sequence score, to predict the overall risk of the entire sequence having MHCII binding associated immunogenicity risk. The methods are described below.

Epitope Identification

Sequences were analyzed using two protocols (labeled "Protocol 1" and "Protocol 2" described below) to identify epitopes. Any sequence flagged by the rules described herein for either protocol was considered an epitope. The identification methods examine sequences primarily at the level of amino acid 9-mers.

Protocol 1: ISPRI/EpiMatrix

Sequences were submitted for EpiMatrix analysis in the ISPRI software package (ISPRI v 1.8.0, EpiVax Inc., Providence, RI (2017). Schafer J R A, Jesdale B M, George J A, Kouttab N M, De Groot A S. Prediction of well-conserved HIV-1 ligands using a matrix-based algorithm, EpiMatrix. Vaccine 16(19), 1880-84 (1998)). The raw results provided rankings of likelihood of binding (as a percentile on a standardized scale) of each 9-mer amino acid fragment against 8 different HLA types. Thus, there are 8 predictions ("observations") for each 9-mer. The 9-mers are generated starting at each individual linear numbering position of the sequence (thus, it is possible for the same 9-mer to occur more than once in the same sequence). If any 4 observations indicate that the 9-mer is in the top 5% of binders (meaning it is predicted to be in the top 5% of binders for at least 4 HLA types), the 9-mer is considered a predicted epitope ("epitope"). Alternatively, if any 1 of the 8 predictions indicate that the 9-mer is in the top 1% of binders, the 9-mer is also considered a predicted epitope.

Protocol 2: IEDB Consensus Method

Sequences were submitted for analysis using the MHC-II binding Consensus method (Wang P, Sidney J, Kim Y, Sette A, Lund O, Nielsen M, Peters B. Peptide binding predictions for HLA DR, DP and DQ molecules. BMC Bioinformatics 11, 568 (2010); Wang P, Sidney J, Dow C, Mothé B, Sette A, Peters B. A systematic assessment of MHC class II peptide binding predictions and evaluation of a consensus approach. PLoS Comput Biol. 4(4), e1000048 (2008).) in IEDB (Vita R, Overton J A, Greenbaum J A, Ponomarenko J, Clark J D, Cantrell J R, Wheeler D K, Gabbard J L, Hix D, Sette A, Peters B. The immune epitope database (IEDB) 3.0. Nucleic Acids Res. January 28 (43), D405-12 (2015). IEDB MHC-II Binding Predictions, http://www.iedb.org). The output of the software arranged results by 15-mer. A consensus score and percentile ranking were provided for each combination of 15-mer and HLA type. The individual scores from which each 15-mer's consensus was derived were rankings of certain 9-mers found in the 15-mer: each method used for the consensus reported a percentile rank for the 9-mer with the tightest predicted HLA binding within the 15-mer. The consensus taken as the value for the overall 15-mer was the prediction for the 9-mer having the median score across all methods used for the consensus. A 9-mer was classified as an epitope if (a) it was chosen as the consensus representative for the 15-mer AND (b) had a percentile ranking in the top 10% of binders for the HLA type being considered, AND if criteria (a) and (b) occurred for three or more distinct HLA types for the same 9-mer (i.e., three observations). The HLA types considered were DRB1*01, 1*03, 1*04, 1*07, 1*08, 1*11, 1*13, and 1*15, which are the same HLA types in a standard ISPRI/EpiMatrix report. Thus, although the primary output of the method was a ranking of 15-mers, the data was reinterpreted to obtain a list of predicted 9-mer epitopes, for ease of comparison with Protocol 1.

Epitope Classification

Each epitope was classified as a germline or non-germline epitope. For antibodies, we further classified each epitope based on its location within the antibody (CDR or non-CDR).

We filtered sequences of human V domains obtained from IMGT (www.imgt.org) to remove germlines annotated as pseudogenes or open reading frames (ORFs). Any predicted 9-mer epitope found in the remaining sequences was considered a germline epitope. Epitopes found in the J or C regions (including IgG1, IgG2, IgG3, and IgG4) or the junctions between these regions were also classified as germline epitopes. Otherwise, an epitope is classified as a non-germline epitope. Variable domain residues were numbered based on the numbering system of Kabat (Kabat E A, Wu T T, Perry H M, Gottesman K S, Foeller C. Sequences of Proteins of Immunological Interest. US Department of Health and Human Services, NIH Publication No. 91-3242 (1991).). After numbering, CDRs are defined to include the following residues: CDR-H1 (H26-H35 including insertions such as H35A, up to but not including H36), CDR-H2 (H50-H65 inclusive), CDR-H3 (H95-H102 inclusive) CDR-L1 (L24-L34 inclusive), CDR-L2 (L50-L56 inclusive), CDR-L3 (L89-L97, inclusive). A predicted 9-mer epitope is a CDR epitope if any one of its amino acids is part of a CDR region. Note that our chosen start position (H26) for CDR-H1 differs from some other publications using Kabat annotation.

Overall Sequence Immunogenicity Score (Tregitope Adjusted Score)

For an individual chain, or for a pairing of an antibody VH and VL domain, an overall score can be calculated by summing over each of the constituent 9-mers as follows:

all individual combinations of 9-mer and HLA type ("observations") are examined, regardless of whether the 9-mer is an epitope. If a particular observation indicates the peptide is in the top 5% of binders for the given HLA type, the EpiMatrix Z-score for this observation is added to a running total associated with the entire protein sequence. The total number of observations examined is also recorded. The only exception is that all observations on 9-mers identified by ISPRI as "Tregitopes" (T-reg) are assumed to have EpiMatrix scores of zero.

In the running total, a baseline score of 0.05*2.2248 is subtracted from each observation (including Tregitopes). The final score is computed as follows:

$$T\text{-reg Adjusted Score}=(\text{Running total})*1000/(\text{Number of observations})$$

Lower scores indicate lower predicted immunogenic potential. Note that the score only includes predictions from ISPRI/EpiMatrix and does not include information from IEDB. Therefore, any strong HLA binders predicted by IEDB, but not ISPRI, do not contribute to the score. In theory, sequences may contain many IEDB-predicted HLA binders and still have a favorable T-reg Adjusted Score if EpiMatrix does not also predict the same sequences to be likely binders.

Immunogenicity Risk Mitigation

The above protocol identified 8 non-germline T-cell epitopes in the anti-CD1a antibody Ab138 sequence-4 in the VH (beginning at residues H29, H32, H47 and H50) and 4 in the VL (beginning at residues L45, L46, L48 and L86). The 9-mer amino acid sequences of these 8 epitopes are as follows: FTDFYMNWV (Seq ID No. 87), FYMNWVRQA (SEQ ID NO: 88), WVAFIRNKA (SEQ ID NO: 89), FIRNKANGY (SEQ ID NO: 90), KLLIYGANR (SEQ ID NO: 91) LLIYGANRL (SEQ ID NO: 92), IYGANRLKD (SEQ ID NO: 93) and YYCQQSYKY (SEQ ID NO: 94). Additionally, the overall sequence immunogenicity (Epivax) score was −37.94. Reduction in the number of epitopes and the overall sequence score is predicted to decrease the overall immunogenicity risk of the sequence.

To reduce the immunogenicity risk, mutations were introduced in some of the 8 identified non-germline T cell epitopes such that the mutated sequences no longer registered as a T-cell epitope in our in silico protocol. The mutation sets that remove the non-germline T-cell epitopes were derived either by 1) rational structure-based design, or 2) as screened output of a semi-random mutagenesis through a rationally designed phage display library (described below).

Rational Structure-Based Design

The co-crystal structure of CD1a/anti-CD1a antibody Ab138 was used to identify mutations that would not disrupt the binding interaction and could therefore be used to modulate T-cell epitopes. Two computational protocols were used to predict the effect on CD1a/Ab138 binding (ΔΔG) of all possible point mutations within the Ab138 CDRs: 1) Rosetta ddG (v. 3.5) was used to predict the change in stability of the mutant complex relative to the CD1a/Ab138 complex; 2) foldX was used to predict the change in free energy of binding between the mutant complex and the CD1a/Ab138 complex. Mutations were designated as "tolerated" if they recorded a ΔΔG value below 1 kcal/mol in Rosetta ddG, or below 0.75 kcal/mol in foldX; otherwise, they were discarded. The set of tolerated mutations was then permuted to generate alternate sequences for each epitope region containing up to 2 mutations from the Ab138 sequence, which were tested against our in silico immunogenicity protocol; sequences that did not remove the T-cell epitope of interest were discarded.

Optimization Strategy Using Phage Display

Based on the obtained structural information, rational design and phage-based library selection strategies were applied to isolate variants of anti-CD1a Ab138 with increased affinity, further humanized CDR regions, improved biophysical properties and reduced sequence liabilities, as described below.

In the first, phage library-based approach, DNA sequences of VH and VL domains of humanized Ab138 were combined to produce a single chain variable fragment (scFv) with added C-terminal 6×His (SEQ ID NO: 102) and Myc tags in a phage expression vector. Soft-randomized mutations and/or degenerate codons were designed at the structurally important sites in VH and VL CDRs of Ab138. Oligonucleotides to selectively mutate these residues were synthesized and then used to generate mutant sequence libraries in the scFv nucleic acid template.

In the second, rational design approach, point mutants were designed at defined sites of Ab138 CDRs and then expressed and purified in hIgG1 format in a high-throughput manner. Binding affinities of the engineered variants were evaluated using competition ELISA and/or Biacore.

In the phage library based-approach, selections were performed using biotinylated CD1a proteins. Aliquots of phage pools described above and magnetic streptavidin beads (Dynabeads M-280 streptavidin) were blocked separately in 3% milk/PBS for 1 hour at room temperature in a rotary mixer (20 rpm). Blocked phage pools were centrifuged at 4000 rpm for 10 minutes, supernatants were transferred to fresh tubes and mixed with 6% blocking buffer. Blocked phages were incubated with excess molar concentrations of the de-selection reagents (e.g. dsDNA, Insulin and/or membrane extracts), incubated at room temperature for 1 hour on a rotary shaker (20 rpm), mixed with blocked streptavidin-magnetic beads and incubated for 1 hour. The de-selected library was collected by pelleting the beads using a magnetic separator.

Using a Kingfisher magnetic purification instrument (ThermoFisher) biotinylated human or cyno CD1a was incubated at various concentrations with the de-selected phage library in a 96-deep well plate for 1 hour at room temp with periodic mixing. Beads were separated using a magnetic separator on the Kingfisher instrument and washed 7 times with PBS/0.1% Tween-20 and 11 times with PBS in separate 96-deep well plates. Bound phages were eluted by incubating with 100 mM triethylamine (TEA) for 8 minutes in a fresh 96-well plate followed by separation from the magnetic beads. Eluted phages were neutralized with 2 M Tris-HCl pH 7.5. Eluted phage were used to infect 10 mL of *E. coli* ER2738 (Lucigen, cat #NC0292392) culture that had been grown to mid-logarithmic phase (corresponding to an $OD_{600}$ of ~0.5). Bacteria were infected with phage for 1 hour at 37° C. with shaking at 150 rpm, concentrated following a centrifugation step and plated on 2×YT agar plates containing 2% glucose and 100 pg/mL ampicillin (2×YTAG). Various dilutions of *E. coli* culture infected with either input or output phage were also plated on 2×YTAG agar to determine phage titers. Following overnight growth at 30° C., 10 mL of 2×YTAG medium was added to each bioassay plate and the cells were re-suspended by scraping the bacterial lawn. Glycerol was added to this cell suspension to give a final concentration of 17% and stored in aliquots at −80° C. until further use. In order to rescue phage for the next round of selection, 100 mL of this cell suspension was used to inoculate 20 mL 2×YTAG medium, which was grown at 37° C. (300 rpm) to an $OD_{600}$ of 0.3-0.5. Cells were then super-infected with 3.3 mL of MK13K07 helper phage and incubated at 37° C. (150 rpm) for 1 hour. The cells were then centrifuged, and the pellet re-suspended in a kanamycin/non-glucose containing medium (2×YT with 50 mg/mL kanamycin and 100 pg/mL ampicillin). This culture was grown overnight at 30° C. (300 rpm). Phage were harvested in the supernatant following centrifugation and were ready to use in the next round of selection as described above.

After phage panning, the output phage clones were evaluated using scFv expressed and extracted from peri-prep by HTRF (Homogeneous Time Resolved Fluorescence) assay as described below.

Example 6: Homogeneous Time Resolved Fluorescence (HTRF) Assay

Preparation of Periprep Material for Use in HTRF Assays

ScFv can be expressed either on the surface of a phage particle or in solution in the bacterial periplasmic space, depending upon the growth conditions used. To induce release of scFv into the periplasm, 96-deep well plates containing 2×YT media with 0.1% glucose/100 mg/mL ampicillin were inoculated from thawed glycerol stocks (one clone per well) using the QPix Colony picker (Molecular Devices) and grown at 37° C. (850 rpm) for ~4 hours. Cultures were induced with Isopropyl β-D-1-thiogalactopyranoside (IPTG) at a final concentration of 0.1 mM and grown overnight at 30° C. (850 rpm). The contents of the bacterial periplasm (i.e. peripreps) were released by osmotic shock. Briefly, plates were centrifuged and pellets were resuspended in 150 mL HEPES periplasmic buffer (50 mM HEPES, 0.5 mM EDTA, 20% sucrose, pH 7.4), followed by the addition of 150 mL 1:5 HEPES:water and incubated on ice for 30 minutes. Plates were centrifuged for 20 minutes at 4000 rpm and the scFv-containing supernatant was harvested.

HTRF Assay

Figure 5:
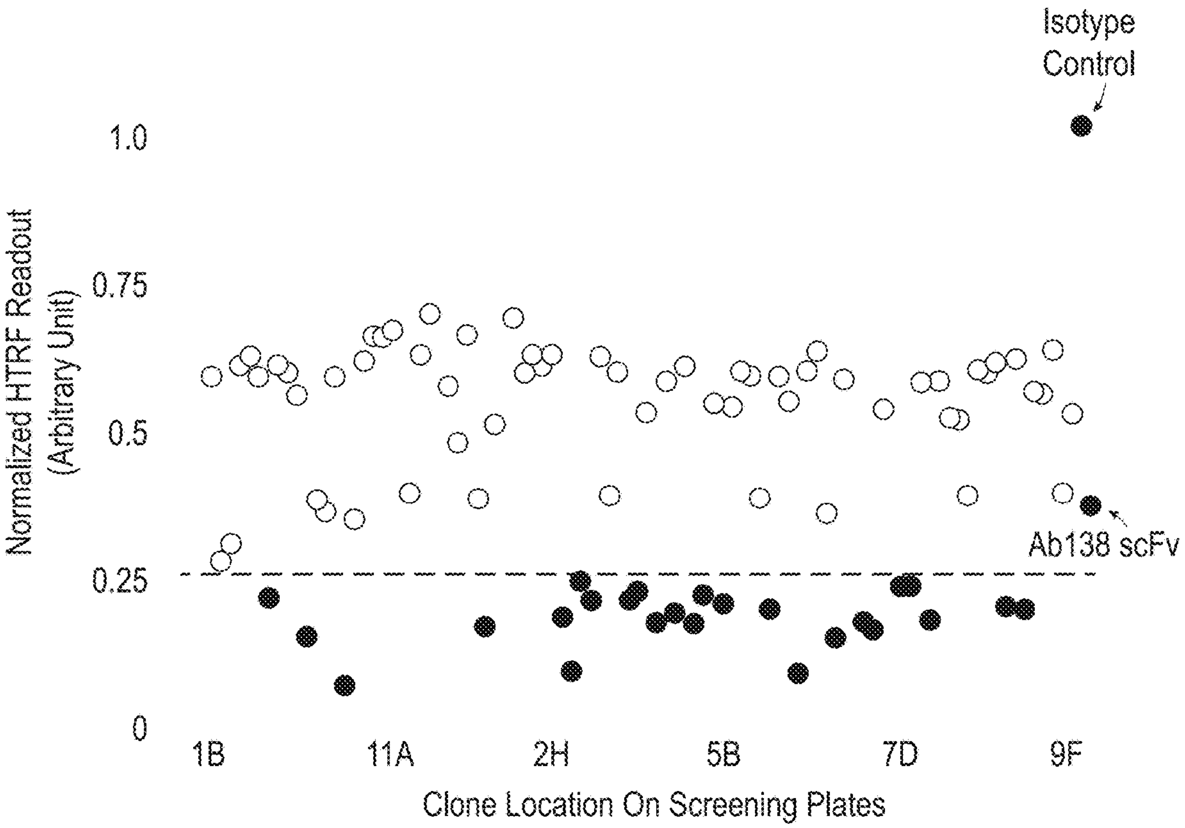

A high-throughput competition HTRF assay was established to facilitate the identification of affinity improved clones. The parental antibody Ab138 was labeled with fluorescence donor terbium (Tb) using a labeling kit (CisBio) according to the manufacturer's instructions. The CD1a antigen was biotinylated and then labeled with fluorescence acceptor d2 by the addition of streptavidin-d2. The final assay mixture consisted of biotinylated human CD1a and Tb-labeled parental antibody at a certain concentration ratio, which was derived from a cross-titration to achieve the maximum signal-noise ratio. Periprep extracts containing the scFvs of interest were added to this binding system at four different dilutions (up to 10-fold), in a total reaction volume of 20 μL in 1× assay buffer (50 mM sodium phosphate, pH 7.5, 400 mM potassium fluoride, 0.1% BSA). After an hour incubation, fluorescence at 665 nm and 620 nm was measured on an Envision multi-label plate reader (Perkin Elmer). The HTRF Ratio was calculated as fluorescence at 665 nm/fluorescence at 620 nm×10,000. Maximal signal was defined as the HTRF ratio of Tb-labeled Ab138 with d2-labeled CD1a in the absence of scFvs, the minimum maximal signal was defined as the HTRF ratio of d2-labeled CD1a only. If the tested scFv gave lower signal than parental Ab138, it suggested this antibody may have higher affinity than parental Ab138. Unique scFv clones which showed potentially higher affinity than parental Ab138 were identified (FIG. 5) and reformatted into full length human IgG. The assay was then repeated as above using the purified IgG and the resulting data was compared with that of the parental antibody.

Selected antibodies with strong competition against Ab138 were further confirmed using competition ELISA, with similar procedure as described before.

In the next step, the advantageous mutations from several individual clones were combined using mix-and-match methods. The combinatorial mix-and-match mutants were purified in batches; a total of 305 different clones were made in 7 batches and tested by competition ELISA and Biacore. In silico sequence analysis was performed to estimate potential immunogenicity of these variants by calculating the number of predicted T-cell epitopes and overall Epivax scores, using the protocols described above. In addition, sequence liabilities, such as potential sites for post-translational modifications (e.g. deamidation, isomerization, oxidation), were identified. Additional assays were performed to further characterize physicochemical properties of new antibody variants. Specifically, a polyreactivity ELISA binding assay on DNA and insulin, and a self-interaction AC-SINS assay were conducted (described below). These assays evaluated the chances of non-specific or self-interactions of these IgG molecules, which are expected to correlate with their in vivo behavior (e.g. clearance rate).

Example 7: DNA and Insulin Polyreactivity ELISA Assay

Three hundred eighty-four well ELISA plates (Nunc Maxisorp) were coated overnight at 4° C. with 10 mg/mL DNA from salmon testes (Sigma-Aldrich, D1626) or 5 mg/mL human insulin (Sigma-Aldrich, 19278) in PBS pH 7.5. The ELISA was carried out on a PerkinElmer Janus Automated Workstation liquid handling robot. Wells were washed with water, blocked with 50 μL of Polyreactivity ELISA Buffer (PBS containing 0.05% Tween-20, 1 mM EDTA) for 1 hour at room temperature and rinsed three times with water. Serially diluted mAbs in 25 μL were added in quadruplicate to the wells and incubated for 1 h at room temperature. Plates were washed three times with water, and 25 μL of 10 ng/mL goat anti-human IgG (Fc specific) conjugated to horseradish peroxidase (Jackson ImmunoResearch, 109-035-008) were added to each well. Plates were incubated for 1 h at room temperature, washed three times with 80 μL of water, and 25 μL of TMB substrate (Sigma-Aldrich, T-0440) added to each well. Reactions were stopped after approximately 7 minutes by adding 25 μL of 0.18 M ortho-phosphoric acid to each well, and absorbance was read at 450 nm. DNA- and insulin-binding scores (shown in Table 5) were calculated as the ratio of the ELISA signal of the antibody at 10 mg/mL to the signal of a well containing buffer instead of the primary antibody.

As shown in Table 5, the DNA and insulin ELISA scores for Ab138 were 5 and 7, respectively. A score of 5 or below is considered low/favorable. Ab571 showed an improvement in both scores (4 and 3, respectively). Furthermore, all other optimized variants of Ab138 that were tested in this polyreactivity assay demonstrated favorable scores of <5 (Table 5).

Example 8: Affinity-Capture Self-Interaction Nanoparticle Spectroscopy (AC-SINS) Assay The AC-SINS assay was standardized in a 384-well format on a Perkin-Elmer Janus liquid handling robot. 20 nm gold nanoparticles (Ted Pella, Inc., 15705) were coated with a mixture of 80% goat anti-human Fc (Jackson ImmunoResearch Laboratories, Inc. 109-005-098) and 20% non-specific goat polyclonal antibodies (Jackson ImmunoResearch Laboratories, Inc. 005-000-003) that were buffer exchanged into 20 mM sodium acetate pH 4.3 and diluted to 0.4 mg/mL. After an hour incubation at room temperature, sites unoccupied on the gold nanoparticles were blocked with thiolated polyethylene glycol (2 kD). The coated nanoparticles were then concentrated 10-fold using a syringe filter and 10 μL were added to 100 μL of mAb at 0.05 mg/mL in PBS pH 7.2. The coated nanoparticles were incubated with the antibody of interest for 2 hours in a 96-well polypropylene plate and then transferred to a 384-well polystyrene plate and read on a Tecan M1000 spectrophotometer. The absorbance was read from 450-650 nm in 2 nm increments, and a Microsoft Excel macro was used to identify the max absorbance, smooth the data, and fit the data using a second-order polynomial. The smoothed max absorbance of the average blank (PBS alone) was subtracted from the smoothed max absorbance of the antibody sample to determine the antibody AC-SINS score (shown in Table 5).

An AC-SINS score of <5 is considered favorable/low. Ab138 showed an AC-SINS score of −1, whereas Ab571 had a score of +1. All optimized antibodies tested in this assay showed scores of less than or equal to 5 (Table 5).

The effects of the specific changes in VH and VL domains are as follows (numbering based on Kabat): In the VH domain, F32H and N35H/T mutations removed a potential T-cell epitope and improve the binding affinity to CD1a. Mutations F50H, I51T and N52aD together removed 2 T-cell epitopes. Mutation N53G removed a deamidation site and S62 Å removed a glycosylation site. G98R/T mutation largely improved the antibody binding affinity to CD1a.

In the VL domain, S30Y and N31F mutations removed a deamidation site and improved the binding affinity to CD1a. Mutations A51G, N52D/S, L54P and D56E together removed 2 T-cell epitopes, 1 isomerization site and improved CD1a binding. Y92E and K93S removed 1 T-cell epitope. Finally, VH mutations T28D, T30E, R52S, K52BS and light chain mutations R53T, K55Q were designed to reduce antibody polyreactivity (e.g. in the DNA and insulin ELISA assays).

TABLE 4

Sequence alignment of VH domain CDRs (numbering according to Kabat) (Table 4 discloses SEQ ID NOS 15, 30, 30, 40, 40, 40, 40, 40, 40, 30, 30, 30, 40, 40, 62, 66, 62, 62, 66, 66, 40, 40, 40, 40, 40, 16, 31, 31, 41, 48, 48, 48, 41, 41, 41, 41, 48, 59, 59, 63, 63, 59, 63, 63, 63, 63, 76, 63, 63, 63, 17, 17, 17, 17, 49, 49, 49, 52, 52, 17, 17, 49, 49, 49, 49, 49, 49, 49, 49, 49, 49, 49, 49, 49, and 49, all respectively, in order of columns).
VH CDR alignment:

| | CDR-H1 | | | | | | | | | | CDR-H2 | | | | | | | | | | | |
|---|---|---|---|---|---|---|---|---|---|---|---|---|---|---|---|---|---|---|---|---|---|---|
| Antibody | 26 | 27 | 28 | 29 | 30 | 31 | 32 | 33 | 34 | 35 | 50 | 51 | 52 | 52a | 52b | 52c | 53 | 54 | 55 | 56 | 57 | 58 |
| Ab138 | G | F | T | F | T | D | F | Y | M | N | F | I | R | N | K | A | N | G | Y | T | T | E |
| Ab491 | | | | | | | H | | | T | | | | | | | | | | | | |
| Ab492 | | | | | | | H | | | T | | | | | | | | | | | | |
| Ab504 | | | | | | | H | | | H | | | | | | | G | | | | | |
| Ab514 | | | | | | | H | | | H | | | | | S | | G | | | | | |
| Ab555 | | | | | | | H | | | H | | | | | S | | G | | | | | |
| Ab556 | | | | | | | H | | | H | | | | | S | | G | | | | | |
| Ab559 | | | | | | | H | | | H | | | | | | | G | | | | | |
| Ab560 | | | | | | | H | | | H | | | | | | | G | | | | | |
| Ab571 | | | | | | | H | | | T | | | | | | | G | | | | | |
| Ab572 | | | | | | | H | | | T | | | | | | | G | | | | | |
| Ab579 | | | | | | | H | | | T | | | | | S | | G | | | | | |
| Ab585 | | | | | | | H | | | H | H | | S | G | S | | G | | | | | |
| Ab599 | | | | | | | H | | | H | H | | S | G | S | | G | | | | | |
| Ab609 | | | | | E | | H | | | H | H | T | | D | | | G | | | | | |
| Ab610 | | | D | | | | H | | | H | H | T | | D | | | G | | | | | |
| Ab616 | | | | | E | | H | | | H | H | | S | G | S | | G | | | | | |
| Ab623 | | | | | E | | H | | | H | H | T | | D | | | G | | | | | |
| Ab624 | | | D | | | | H | | | H | H | T | | D | | | G | | | | | |
| Ab656 | | | D | | | | H | | | H | H | T | | D | | | G | | | | | |
| Ab657 | | | | | | | H | | | H | H | T | | D | | | G | | | | | |
| Ab660 | | | | | | | H | | | H | H | | | | A | | G | | | | | |
| Ab673 | | | | | | | H | | | H | H | T | | D | | | G | | | | | |
| Ab681 | | | | | | | H | | | H | H | T | | D | | | G | | | | | |
| Ab689 | | | | | | | H | | | H | H | T | | D | | | G | | | | | |

| | CDR-H2 | | | | | | | CDR-H3 | | | | | | | | | | | |
|---|---|---|---|---|---|---|---|---|---|---|---|---|---|---|---|---|---|---|---|
| Antibody | 59 | 60 | 61 | 62 | 63 | 64 | 65 | 95 | 96 | 97 | 98 | 99 | 100 | 100a | 100b | 100c | 100d | 101 | 102 |
| Ab138 | S | N | P | S | V | K | G | E | T | T | G | I | P | T | G | W | F | A | Y |
| Ab491 | | | | A | | | | | | | | | | | | | | | |
| Ab492 | | | | A | | | | | | | | | | | | | | | |
| Ab504 | | | | A | | | | | | | | | | | | | | | |
| Ab514 | | | | A | | | | | | | R | | | | | | | | |
| Ab555 | | | | A | | | | | | | R | | | | | | | | |
| Ab556 | | | | A | | | | | | | R | | | | | | | | |
| Ab559 | | | | A | | | | | | | T | | | | | | | | |
| Ab560 | | | | A | | | | | | | T | | | | | | | | |
| Ab571 | | | | A | | | | | | | | | | | | | | | |
| Ab572 | | | | A | | | | | | | | | | | | | | | |
| Ab579 | | | | A | | | | | | | R | | | | | | | | |
| Ab585 | | | | A | | | | | | | R | | | | | | | | |
| Ab599 | | | | A | | | | | | | R | | | | | | | | |
| Ab609 | | | | A | | | | | | | R | | | | | | | | |
| Ab610 | | | | A | | | | | | | R | | | | | | | | |
| Ab616 | | | | A | | | | | | | R | | | | | | | | |
| Ab623 | | | | A | | | | | | | R | | | | | | | | |
| Ab624 | | | | A | | | | | | | R | | | | | | | | |
| Ab656 | | | | A | | | | | | | R | | | | | | | | |
| Ab657 | | | | A | | | | | | | R | | | | | | | | |
| Ab660 | | | | A | | | | | | | R | | | | | | | | |

TABLE 4-continued

Sequence alignment of VH domain CDRs (numbering according to Kabat) (Table 4 discloses SEQ ID NOS 15, 30, 30, 40, 40, 40, 40, 40, 40, 30, 30, 30, 40, 40, 62, 66, 62, 62, 66, 66, 40, 40, 40, 40, 40, 40, 16, 31, 31, 41, 48, 48, 48, 41, 41, 41, 41, 48, 59, 59, 63, 63, 59, 63, 63, 63, 63, 76, 63, 63, 63, 17, 17, 17, 17, 49, 49, 49, 52, 52, 17, 17, 49, 49, 49, 49, 49, 49, 49, 49, 49, 49, 49, 49, 49, and 49, all respectively, in order of columns).
VH CDR alignment:

| | | |
|---|---|---|
| Ab673 | A | R |
| Ab681 | A | R |
| Ab689 | A | R |

TABLE 5

Sequence alignment of VL domain CDRs (numbering according to Kabat) and key properties of antibodies tested (Table 5 discloses SEQ ID NOS 8, 25, 25, 25, 25, 25, 25, 25, 25, 25, 25, 25, 25, 25, 25, 25, 25, 25, 25, 25, 25, 25, 25, 25, 25, 25, 9, 26, 26, 37, 44, 26, 26, 26, 26, 26, 26, 26, 44, 26, 26, 26, 26, 26, 26, 71, 44, 44, 26, 71, 71, 10, 27, 34, 34, 45, 27, 34, 27, 34, 27, 34, 27, 45, 34, 34, 34, 27, 27, 27, 27, 45, 45, 27, 34, and 27, all respectively, in order of columns)

| | CDR-L1 | | | | | | | | | | | CDR-L2 | | | | | | | CDR-L3 | | | |
|---|---|---|---|---|---|---|---|---|---|---|---|---|---|---|---|---|---|---|---|---|---|---|
| Antibody | 24 | 25 | 26 | 27 | 28 | 28 | 30 | 31 | 32 | 33 | 34 | 50 | 51 | 52 | 53 | 54 | 55 | 56 | 89 | 90 | 91 | 92 |
| Ab138 | L | A | S | E | D | I | S | N | D | L | A | G | A | N | R | L | K | D | Q | Q | S | Y |
| Ab491 | | | | | | | Y | F | | | | | G | D | | | | E | | | | |
| Ab492 | | | | | | | Y | F | | | | | G | D | | | | E | | | | E |
| Ab504 | | | | | | | Y | F | | | | | G | D | | | | | | | | E |
| Ab514 | | | | | | | Y | F | | | | | | S | T | P | | | | | | E |
| Ab553 | | | | | | | Y | F | | | | | G | D | | | | E | | | | |
| Ab556 | | | | | | | Y | F | | | | | G | D | | | | E | | | | E |
| Ab559 | | | | | | | Y | F | | | | | G | D | | | | E | | | | |
| Ab560 | | | | | | | Y | F | | | | | G | D | | | | E | | | | E |
| Ab571 | | | | | | | Y | F | | | | | G | D | | | | E | | | | |
| Ab572 | | | | | | | Y | F | | | | | G | D | | | | E | | | | E |
| Ab579 | | | | | | | Y | F | | | | | G | D | | | | E | | | | |
| Ab585 | | | | | | | Y | F | | | | | | S | T | P | | | | | | E |
| Ab599 | | | | | | | Y | F | | | | | G | D | | | | E | | | | E |
| Ab609 | | | | | | | Y | F | | | | | G | D | | | | E | | | | E |
| Ab610 | | | | | | | Y | F | | | | | G | D | | | | E | | | | E |
| Ab616 | | | | | | | Y | F | | | | | G | D | | | | E | | | | |
| Ab623 | | | | | | | Y | F | | | | | G | D | | | | E | | | | |
| Ab624 | | | | | | | Y | F | | | | | G | D | | | | E | | | | |
| Ab656 | | | | | | | Y | F | | | | | G | D | | | Q | E | | | | |
| Ab657 | | | | | | | Y | F | | | | | | S | T | P | | | | | | E |
| Ab660 | | | | | | | Y | F | | | | | | S | T | P | | | | | | E |
| Ab673 | | | | | | | Y | F | | | | | G | D | | | | E | | | | |
| Ab681 | | | | | | | Y | F | | | | | G | D | | | Q | E | | | | E |
| Ab689 | | | | | | | Y | F | | | | | G | D | | | Q | E | | | | |

| | CDR-L3 | | | | | Number of T-cell | Number of | Biacore | DNA ELISA | Insulin ELISA | AC-SINS | Epivax |
|---|---|---|---|---|---|---|---|---|---|---|---|---|
| Antibody | 93 | 94 | 95 | 96 | 97 | epitopes | liabilities | KD (nM) | score | score | score | score |
| Ab138 | K | Y | P | Y | T | 8 | 4 | 3.87 | 5 | 7 | −1 | −37.94 |
| Ab491 | S | | | | | 3 | 2 | 0.62 | | | 1 | −54.36 |
| Ab492 | S | | | | | 3 | 2 | 0.77 | | | 1 | −56.18 |
| Ab504 | S | | | | | 3 | 2 | 0.53 | | | 0 | −60.54 |
| Ab514 | | | | | | 2 | 3 | 0.28 | 5 | 4 | 1 | −61.07 |
| Ab553 | S | | | | | 3 | 2 | 0.27 | 4 | 4 | 3 | −58.8 |
| Ab556 | S | | | | | 3 | 2 | 0.1 | 5 | 3 | 5 | −60.62 |
| Ab559 | S | | | | | 3 | 1 | 0.39 | | | 0 | −57.43 |
| Ab560 | S | | | | | 3 | 1 | 0.35 | | | 0 | −59.25 |

TABLE 5-continued

Sequence alignment of VL domain CDRs (numbering according to Kabat) and key properties of antibodies tested (Table 5 discloses SEQ ID NOS 8, 25, 25, 25, 25, 25, 25, 25, 25, 25, 25, 25, 25, 25, 25, 25, 25, 25, 25, 25, 25, 25, 25, 25, 25, 9, 26, 26, 37, 44, 26, 26, 26, 26, 26, 26, 26, 44, 26, 26, 26, 26, 26, 26, 71, 44, 44, 26, 71, 71, 10, 27, 34, 34, 45, 27, 34, 27, 34, 27, 34, 27, 45, 34, 34, 34, 27, 27, 27, 27, 45, 45, 27, 34, and 27, all respectively, in order of columns)

| | | | | | | | | |
|---|---|---|---|---|---|---|---|---|
| Ab571 | S | 3 | 1 | 0.17 | 4 | 3 | 1 | −57.37 |
| Ab572 | S | 3 | 1 | 0.39 | 3 | 3 | 0 | −59.19 |
| Ab579 | S | 3 | 2 | 0.27 | | | 4 | −58.74 |
| Ab585 | | 1 | 2 | 0.32 | 3 | 2 | −1 | −76.11 |
| Ab599 | S | 2 | 1 | 0.52 | 2 | 1 | 2 | −75.66 |
| Ab609 | S | 1 | 1 | 0.56 | 3 | 2 | −1 | −75.98 |
| Ab610 | S | 1 | 1 | 0.21 | 3 | 2 | −1 | −77.04 |
| Ab616 | S | 2 | 1 | 0.46 | 3 | 2 | −1 | −75.11 |
| Ab623 | S | 1 | 1 | 0.56 | 3 | 1 | −1 | −74.16 |
| Ab624 | S | 1 | 1 | 1.3 | 3 | 2 | −1 | −75.22 |
| Ab656 | S | 1 | 1 | 0.54 | 3 | 1 | −1 | −75.56 |
| Ab657 | | 0 | 2 | 0.41 | 3 | 3 | 0 | −75.16 |
| Ab660 | | 1 | 2 | 0.57 | 5 | 2 | 1 | −67.36 |
| Ab673 | S | 1 | 1 | 0.21 | 2 | 3 | 1 | −72.89 |
| Ab681 | S | 1 | 1 | 1.22 | 3 | 2 | 1 | −75.05 |
| Ab689 | S | 1 | 1 | 3.59 | 3 | 2 | 0 | −73.23 |

Example 9: Activity of Optimized Antibodies in Inhibition of CD1a-Dependent Jurkat T Cell Activation Cells expressing CD1a were pre-incubated with titrated amounts of antibodies then co-cultured with BK6 T cell receptor expressing Jurkat (J76-BK6) cells. After overnight incubation, cells were assessed for expression of CD69 and the presence of IL-2 in the culture supernatants, as described in detail in Example 1. Potent inhibition of CD69 expression and IL-2 production was observed with the optimized Abs. Their potency was comparable to or better than the parental Ab138 (Table 6).

TABLE 6

Antibody-dependent inhibition of CD1a-dependent Jurkat T cell activation.

| Antibody | Inhibition of CD69 expression, $IC_{50}$ (nM) | Inhibition of IL-2 production, $IC_{50}$ (nM) |
|---|---|---|
| Ab138 | 1.97 | N.T. |
| Ab491 | 1.18 | N.T. |
| Ab492 | 1.18 | N.T. |
| Ab504 | 1.69 | N.T. |
| Ab514 | 0.99 | N.T. |
| Ab555 | 0.99 | N.T. |
| Ab556 | 0.73 | N.T. |
| Ab559 | 1.29 | N.T. |
| Ab560 | 1.61 | N.T. |
| Ab571 | 1.11 | N.T. |
| Ab572 | 0.85 | N.T. |
| Ab579 | 0.73 | N.T. |
| Ab585 | 0.38 | 0.14 |
| Ab599 | 0.30 | 0.08 |
| Ab609 | 0.39 | 0.12 |
| Ab610 | 0.44 | 0.09 |
| Ab616 | 0.41 | 0.11 |
| Ab623 | 0.35 | 0.17 |
| Ab624 | 0.35 | 0.17 |
| Ab656 | 0.48 | 0.22 |
| Ab657 | 0.51 | 0.19 |
| Ab660 | 0.33 | 0.15 |
| Ab673 | 0.30 | 0.18 |
| Ab681 | 0.42 | 0.12 |
| Ab689 | 0.41 | 0.17 |

$IC_{50}$ = concentration necessary to inhibit 50% of the maximal response;
nM = nanomolar;
N.T. = not tested

Example 10: Determination of Antibody Ab571 Affinity to CD1a by Surface Plasmon Resonance (Biacore)

Figure 6A:
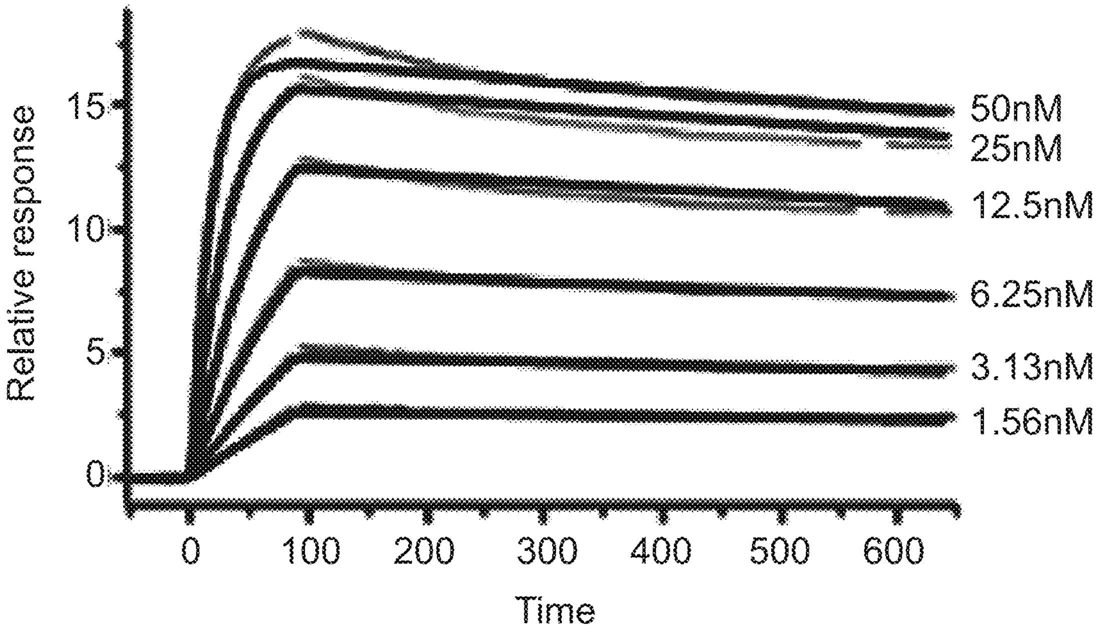
FIG. 6A and FIG. 6B depicts representative kinetic data SPR sensorgrams with 1:1 Langmuir Fit for Ab571 Binding to Human and Cyno CD1a. The gray lines are the raw Biacore data generated for each injection. The black fit lines that overlay the sensorgram are generated by the Biacore analysis software. Association was monitored for 90 seconds and dissociation monitored for 550 seconds, measured in terms of resonance units (y-axis) over time in seconds (x-axis). Data for 6 concentrations of human CD1a and 8 concentrations of cyno CD1a are shown. Relative response is measured in RU=Resonance units; s=Seconds.
Figure 6B:
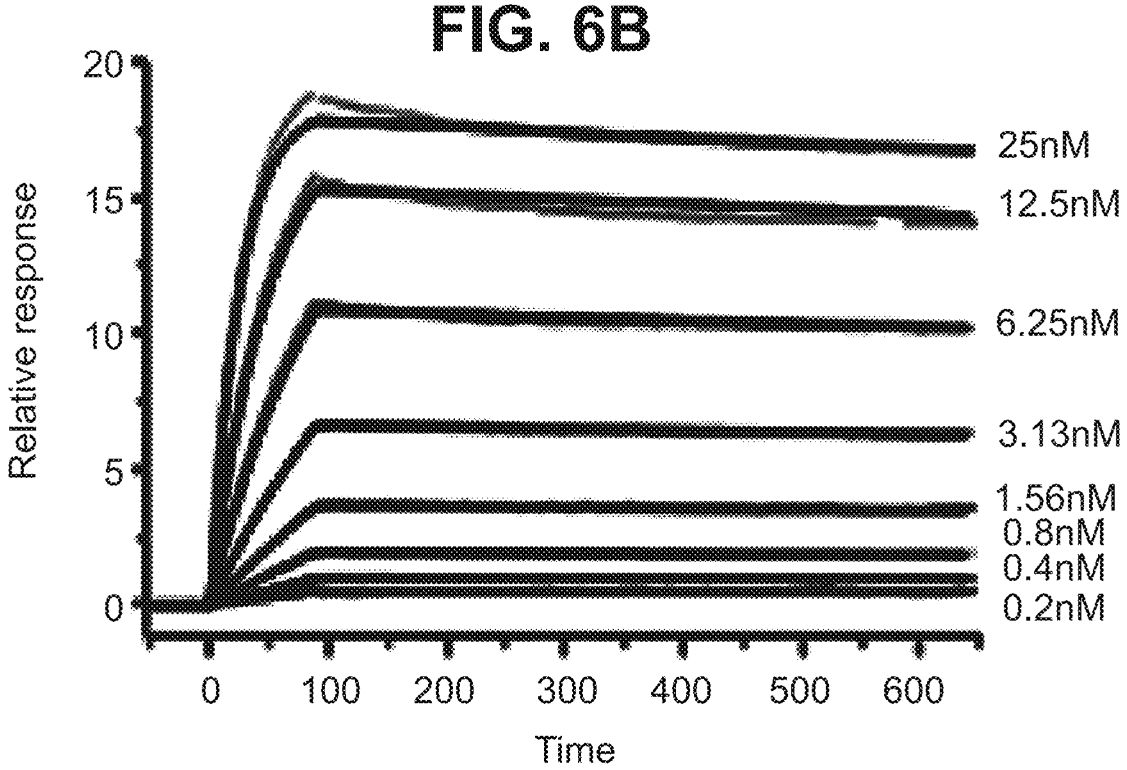

SPR kinetic assays were conducted at 37° C. with a collection rate of 10 Hz on a Biacore 8K instrument (GE Healthcare). Antibody Ab571 was captured by an anti-human IgG (Fc specific) antibody (GE Healthcare, BR-1008-39) covalently coupled onto a CM5 sensor chip (GE Healthcare, 29-1496-03,) according to the manufacturer's protocol. The final capture levels of Ab571 were less than 35 resonance units (RU). HBS-EP+ pH 7.4 (10 mM HEPES pH 7.4, 150 mM NaCl, 3 mM EDTA, 0.05% Tween 20) was used as sample and running buffer. Flow cell 1 was used as a reference flow cell. Two-fold serial dilutions of human CD1a (lot SJ_20180420_01) and cynomolgus (cyno) monkey CD1a (lot SJ_20160901_001) were prepared with concentrations of human CD1a ranging from 50 nM to 1.56 nM and 25 nM to 0.2 nM for cyno CD1a. Dilutions were prepared in triplicate, both manually and with the Janus automated workstation (Perkin Elmer). The dilutions were injected over all flow cells for 90 s at flow rate of 50 μL per minute. Dissociation was monitored for 900 s and the surface was regenerated with three 30 s injections of 3M $MgCl_2$. Rate constants and affinities were determined by fitting the resulting sensorgram data to a Langmuir 1:1 model using Biacore Insight Evaluation software version 2.0.15.12933 (GE Healthcare) (see FIG. 6 and Table 7).

TABLE 7

| Summary of Biacore Results for Ab571. | | | | | |
|---|---|---|---|---|---|
| Compound (ligand) | Analyte | ka (1/Ms) | kd (1/s) | $K_D$, +/− SD (pM) | n |
| Ab571 | Human CD1a | 1.26E+06 | 2.28E−04 | 181.38 ± 11.92 | 6 |
| Ab571 | Cyno CD1a | 1.64E+06 | 9.80E−05 | 60.35 ± 11.04 | 6 |

Biacore was used to determine the binding affinity ($K_D$) of Ab571 to human and cynomolgus monkey CD1a. The data shown is the average of 6 independent dilutions, 3 performed manually and 3 using a Janus liquid handler, done in parallel.
Cyno = cynomolgus monkey;
ka = association constant;
kd = dissociation constant;
$K_D$ = equilibrium dissociation constant;
n = number of determinations

Example 11: Comparison of the Lead Optimized Antibody Ab571 with the Parental Ab138

Figure 7:
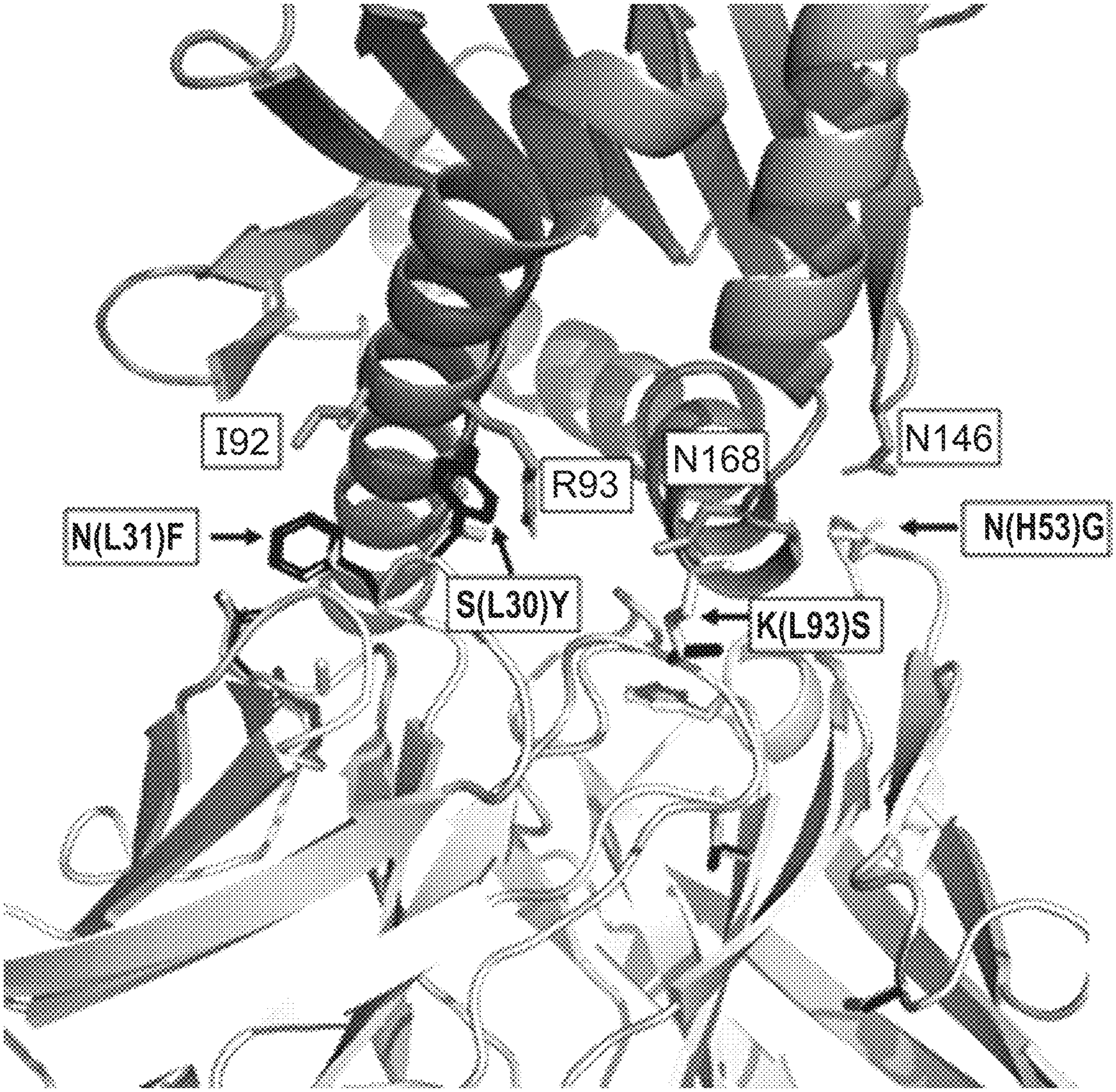
FIG. 7 depicts mutations in Ab571 and their effect on CD1a interaction. Ab571 mutations N(L31)F, S(L30)Y, K(L93)S and N(H53)G are modeled based on Ab138 crystal structure shown in FIG. 3. CD1a residues 192, R93, N168 and N146 that interact with these positions in Ab138/Ab571 are illustrated in CD1a crystal structure shown in FIG. 3B.

Several amino acid changes in Ab571 in comparison to Ab138 (see Tables 4 and 5) resulted in affinity gains to CD1a for Ab571 as compared to Ab138. In particular, based on molecular modeling, it was determined that (antibody numbering is based on Kabat, while CD1a positions are according to the numbering of SEQ ID NO: 1): a) Mutation S(L30)Y strengthened an existing contact with CD1a Arg93, and b) Mutation N(L31)F strengthened an existing contact with CD1a Ile92. At the same time, the changes of K(L93)S and N(H53)G weakened or eliminated existing contacts with CD1a residues Asn168 and Asn146, respectively. These changes are illustrated in FIG. 7.

Based on these studies, alternate mutations at VL positions L30 and L31 are also expected to result in affinity gains similar to mutations S(L30)Y and N(L31)F. Specifically, mutation to Leu, Arg, or Trp at position L30 (corresponding to position 7 in SEQ ID NO: 8) or mutation to Glu, Ile, Lys, Leu, Met, Gln, Arg, Trp, or Tyr at position L31 (corresponding to position 8 in SEQ ID NO: 8) is expected to create a similar affinity effect as observed in Ab571.

Example 12: Comparison of Epitopes of Antibodies Ab571, Ab673 and OKT6 on Human CD1a Using Octet Assay A competitive Octet binding assay was used to compare the binding epitopes of antibodies Ab571, Ab673 and OKT6 on human CD1a. OKT6 is a mouse monoclonal antibody to human CD1a described in U.S. Pat. No. 4,364,933 (Kung P C and Goldstein G. Monoclonal antibody to a human thymocyte antigen and methods of preparing same), and is available as hybridoma line ATCC® CRL-8020™.

Briefly, the competitive Octet assay involves covalently coupling a first antibody (Ab1) to an Octet biosensor tip, followed by adding the antigen (CD1a), then adding a second antibody (Ab2). If the epitopes of Ab1 and Ab2 overlap (i.e. the antibodies complete with each other for CD1a binding), Ab2 is not able to bind. The studies described herein demonstrated that Ab571 and Ab673 recognize a distinct/non-competitive epitope on CD1a from OKT6.

An Octet RED384 instrument was used to perform this experiment, using the reagents provided by the manufacturer (ForteBio). For the competitive Octet assay, the 1$^{st}$ antibody was diluted in loading buffer at 100 nM, then covalently immobilized (coupled) on amine reactive AR2G sensor tips. The tips were first activated by dipping into activation solution for 300 seconds, then reacted with the 1$^{st}$ antibody for 480 seconds, and quenched in quenching buffer for 240 seconds. After quenching, baseline was established by dipping the Ab-coupled tips into 1× kinetic buffer for 120 seconds, followed by capture of human CD1a at 200 nM in kinetic buffer for 480 seconds. A brief 30 sec dissociation was performed by dipping sensor tips into kinetic buffer. Finally, the 2$^{nd}$ antibody's binding was measured by dipping sensor tips into 100 nM Ab for 300 seconds, followed by final dissociation in kinetic buffer for 100 seconds. All binding curves were generated at a shaking speed of 1000/s. In parallel experiments, either Ab571 or OKT6 were used as 1$^{st}$ antibody immobilized on AR2G sensor tips. Antibodies Ab571, Ab673, OKT6, or an isotype control IgG were used as the 2$^{nd}$ antibody.

Figure 8A:
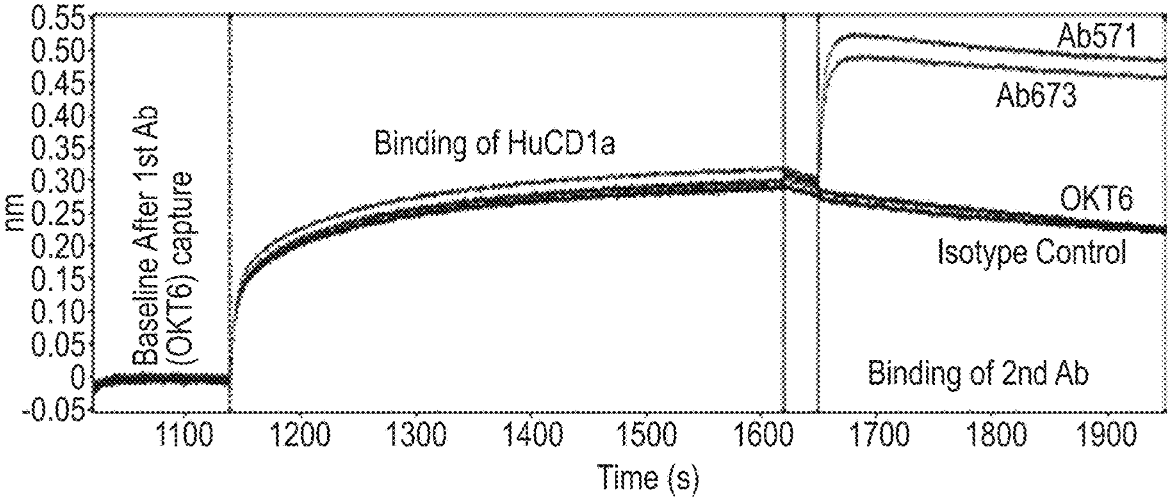
FIG. 8A and FIG. 8B depict Octet sensorgrams of CD1a binding followed by antibody binding for sensor tips first coupled to OKT6 (FIG. 8A) or Ab571 (FIG. 8B). The coupling step is not shown.

As shown in FIG. 8A, after CD1a protein is bound by sensor coupled OKT6, it can be further bound by Ab571 or Ab673, but not OKT6 or an isotype control IgG. This result demonstrates that Ab571 and Ab673 recognize a distinct, non-competing epitope from OKT6.

Figure 8B:
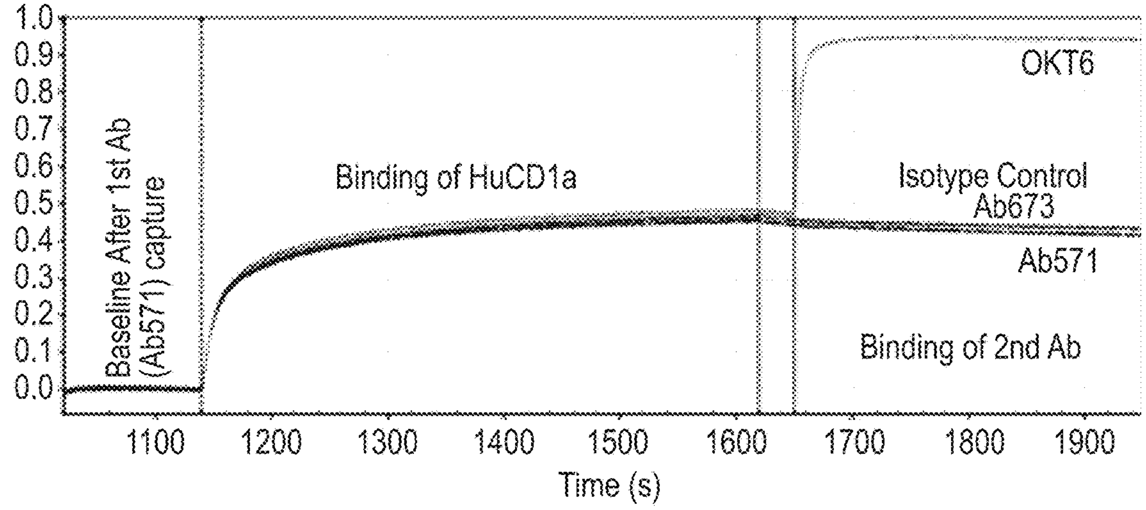

As shown in FIG. 8B, after CD1a protein is bound by sensor coupled Ab571, it can be further bound by OKT6 but not Ab571 itself, Ab673 or an isotype control IgG. This result confirms that Ab571 and Ab673 recognize a distinct epitope from OKT6 but compete with each other for CD1a binding.

Example 13: In Vivo Efficacy Using House Dust Mite AD Model in Human CD1a TG Mice Sex- and age-matched CD1a transgenic mice (Kobayashi, C. et al. GM-CSF-independent CD1a expression in epidermal Langerhans cells: evidence from human CD1A genome-transgenic mice. J. Invest. Dermatol. 132, 241-244 (2012)) between 8 and 10 weeks of age were shaved 4 days before house dust mite (HDM) antigen (Greer Laboratories, XPB81D3A2.5) sensitization. A day prior to sensitization, mice received an injection of the relevant antibody (anti-CD1a antibodies Ab571 or Ab673, or an isotype control) and then additional doses every 2 days over 9 days total. For HDM antigen sensitization, a 4% sodium dodecyl sulfate (SDS) solution was applied to the shaved skin and 3 hours later crude HDM antigen was applied on the skin. Additional exposures to HDM antigen were done following the same procedure every 4 days over a 16-day period. Mice were monitored for pathology prior to each round of antigen sensitization and the dermatitis score was calculated as the sum of the following scores: erythema, scarring/dryness, edema and skin erosion (FIG. 9).

Figure 9:
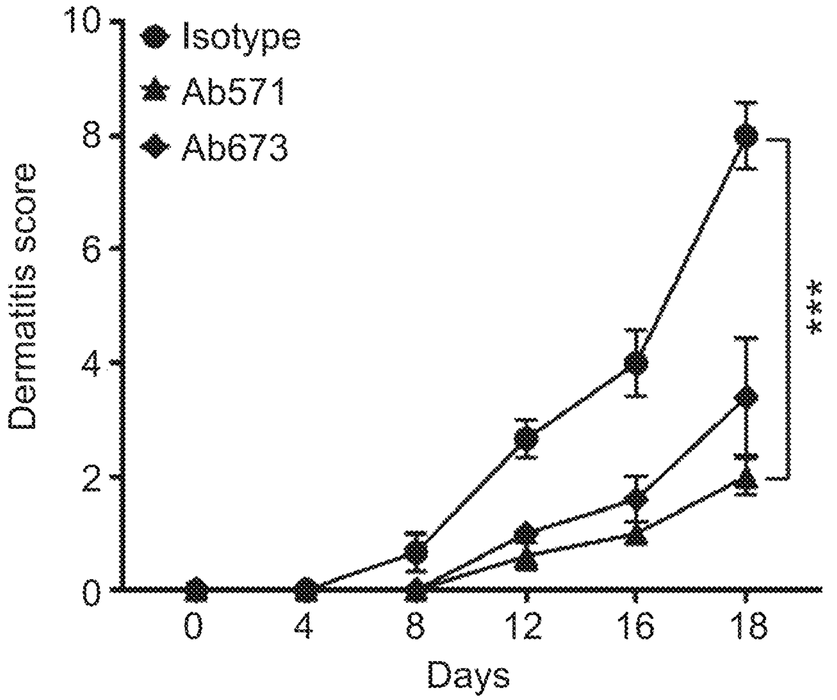
FIG. 9 depicts in vivo antibody administration leads to the suppression of HDM antigen-induced dermatitis. Mice were administered antibody and the following day sensitized with house dust mite (HDM) antigen. Antibody injections continued every other day over a total of 10 days and sensitized with HDM antigen every 4 days over a total of 16 days. Dermatitis scores were assessed prior to antigen sensitization and at completion of the study (day 18). Increasing skin inflammation was observed in sensitized mice given isotype control antibody (circles), whereas Ab571 (triangles) and Ab673 (rhombi) significantly suppressed dermatitis. *** represents a P value of <0.005.

As shown in FIG. 9, administration of Ab571 or Ab673 resulted in significant reduction of the dermatitis score over the 18-day course of the experiment as compared to isotype control. Ab571 treatment led to decreased inflammation and lower dermatitis scores over the course of the study and at the completion of the study (Day 18); the average dermatitis score of the isotype control treated mice was 8 (SD±1), whereas Ab571 led to significant suppression with a dermatitis score of 2 (SD±0.71, p value=$4\times10^4$).

Figure 10:
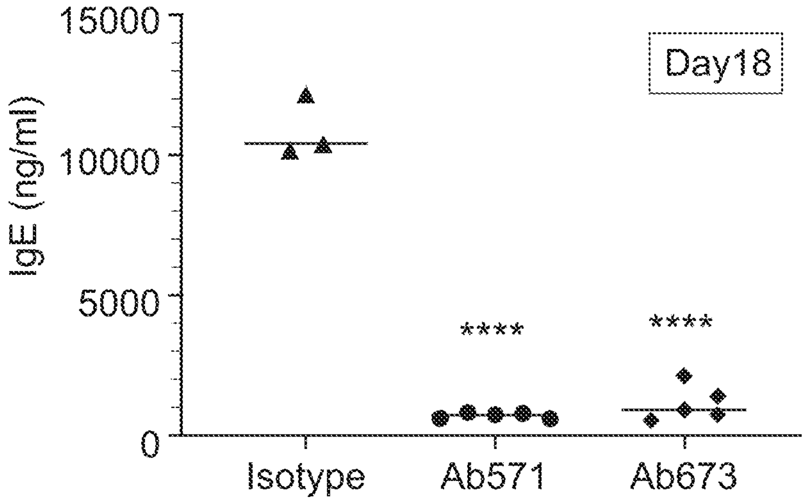
FIG. 10 depicts in vivo antibody administration leads to a reduction in serum IgE levels after sensitization with HDM antigen. Levels of total IgE were determined in serum isolated from mice sensitized with HDM antigen in the presence of isotype control or CD1a neutralizing antibodies. Administration of neutralizing antibodies led to a significant reduction in total serum IgE levels. **** represents a p-value of <0.0001.
Figure 11:
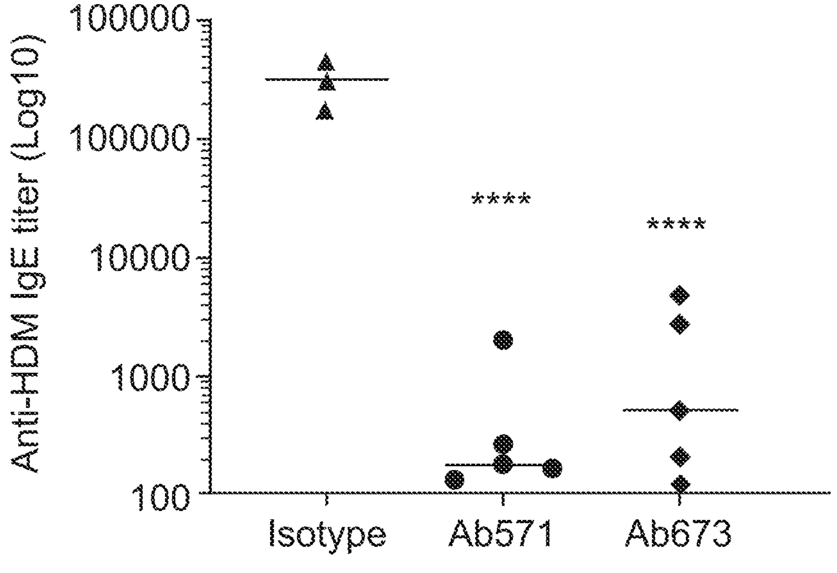
FIG. 11 depicts in vivo antibody administration leads to a reduction in HDM-specific IgE titers after sensitization with HDM antigen. Levels of HDM-specific IgE were determined in serum isolated from mice sensitized with HDM antigen in the presence of isotype control or CD1a neutralizing antibodies. Administration of neutralizing antibodies led to a significant reduction in anti-HDMI IgE titers. **** represents a p-value of <0.0001.

At the end of this in vivo experiment, mouse serum was collected to monitor the levels of total IgE and antigen specific IgE antibodies. The total IgE levels in serum samples were quantified using the BD OptEIA Mouse IgE ELISA set (BD Biosciences, 555248) following the manufacturer's instructions (FIG. 10), while HDM specific IgE antibodies were quantified by coating ELISA plates with HDM extract (FIG. 11). After plate wash and blocking, diluted serum samples were added. After incubation, the presence of bound antibodies was detected by horse radish peroxidase (HRP)-conjugated goat anti-mouse IgE antibodies (Southern Biotech, 1110-05). Plates were washed and visualized by addition of TMB substrate. After the reaction was stopped by the addition of sulfuric acid, optical density was read at 450 nm. Endpoint titers were calculated using a cutoff of 3× the optical density of the background. Administration of neutralizing antibodies (Ab571 and Ab673) led to a significant reduction in total serum IgE levels (FIG. 10), and in anti-HDM IgE titers (FIG. 11).

Total IgE levels were significantly reduced; sensitized CD1aTg mice treated with isotype control antibody had high levels of total serum IgE with an average of $1.10\times10^4$ ng/mL (SD±$1.08\times10^3$ ng/mL), whereas Ab571 treated mice had significantly lower levels of total IgE with a mean of 719 ng/mL (SD±105 ng/mL, p value $<1\times10^4$). Similar to total IgE levels, HDM-specific IgE titers were significantly lower as Ab571 treated mice had an average titer of 556 (SD±832) compared with an average titer of $3.18\times10^5$ (SD±$1.45\times10^5$, p value $<1\times10^4$) in isotype control treated mice.

To assess what cytokines were being secreted in the skin, single cell preparations, obtained from the mice skin samples, were suspended in cRPMI medium and $2\times10^6$ cells were stimulated with 50 ng/ml PMA (Sigma Aldrich P8139), 1 μM ionomycin and 10 μg/mL of Brefeldin A in cRPMI for 4 hr in a $CO_2$ incubator set at 37° C. After incubation, cells were washed twice, resuspended in 200 μL of cRPMI and were stained with Viability dye (1:1000 diluted in PBS) for 5 min. Thereafter, cells were centrifuged at 500×g for 5 minutes and resuspended in 100 μL of FACS buffer (PBS containing 5% BSA) and were incubated with 1 μg of anti-CD16/32 antibody (used at 1 μg/$2\times10^6$ cells) for 10 minutes at 4° C. Thereafter, anti-CD4-Pacific Blue (1:100 final dilution) antibody was added to the cells and incubated for 15 min at 4° C. Next, cells were washed with 200 μL of FACS buffer, centrifuged at 500×g for 5 minutes and were fixed by resuspending the cells in 200 μL of cytofix/cytoperm buffer for 20 minutes at 4° C. Thereafter, cells were washed twice with 200 μL of 1× wash/perm buffer (1:10 diluted in $H_2O$) and centrifuged as previously described. Cells were resuspended in 200 μL of 1× wash/perm buffer then equally divided into two tubes and stained with anti-mouse IL-4 PE-Cy7 and IL-13-PerCP-eFluor 710 ($1^{st}$ tube), or IFNγ-PE and GM-CSF-PerCP antibodies ($2^{nd}$ tube) for 30 minutes at 4° C. All antibodies were used at 1:100 final dilution. After incubation, cells were washed by addition of 200 μL of FACS buffer 2 times and centrifuged as described above. After washing, cells were resuspended in 200 μL of FACS buffer to be analyzed on the FACS Canto II flow cytometer. To enumerate the percentage of granulocytes, in separate tube, $2\times10^6$ cells from mouse skin samples were incubated for 10 minutes with 1 μg of anti-CD16/32 antibody (used at 1 μg/$2\times10^6$ cells) for 10 minutes at 4° C., followed by viability dye staining in PBS for 5 min, as described above. Thereafter, cells were stained with a cocktail of the following antibodies added at a final dilution of 1:100: anti-mouse CD45-PerCP, CD11b-FITC, and Gr-1-Pacific Blue for 20 minutes at 4° C. Cells were washed twice as described above with FACS buffer and suspended in 200 μL of FACS buffer for data acquisition. The data was first acquired on a BD Canto flow cytometer then analyzed by using Flowjo software.

Skin inflammation can result from either the expansion of resident immune cells or infiltration of circulating cells. Skin samples were treated as described and assessed by flow cytometry for the presence of inflammatory ($CD11b^+Gr\text{-}1^+$) cells. After HDM sensitization, isotype control treated animals had a higher average percentage of inflammatory cells in the skin (28.8%±4.36%) relative to Ab571 treated animals (13.7%±3.34%). Skin was also assessed for the presence of cytokine secreting cells that would drive allergic responses and promote secretion of IgE, such as $IL\text{-}13^+$ cells. Isotype control treated mice had an average of 12.2%±2.70% $IL\text{-}13^+$ cells, whereas Ab571 treated animals had a significantly lower percentage of $IL\text{-}13^+$ cells with an average of 3.19%±1.86%.

Figure 12:
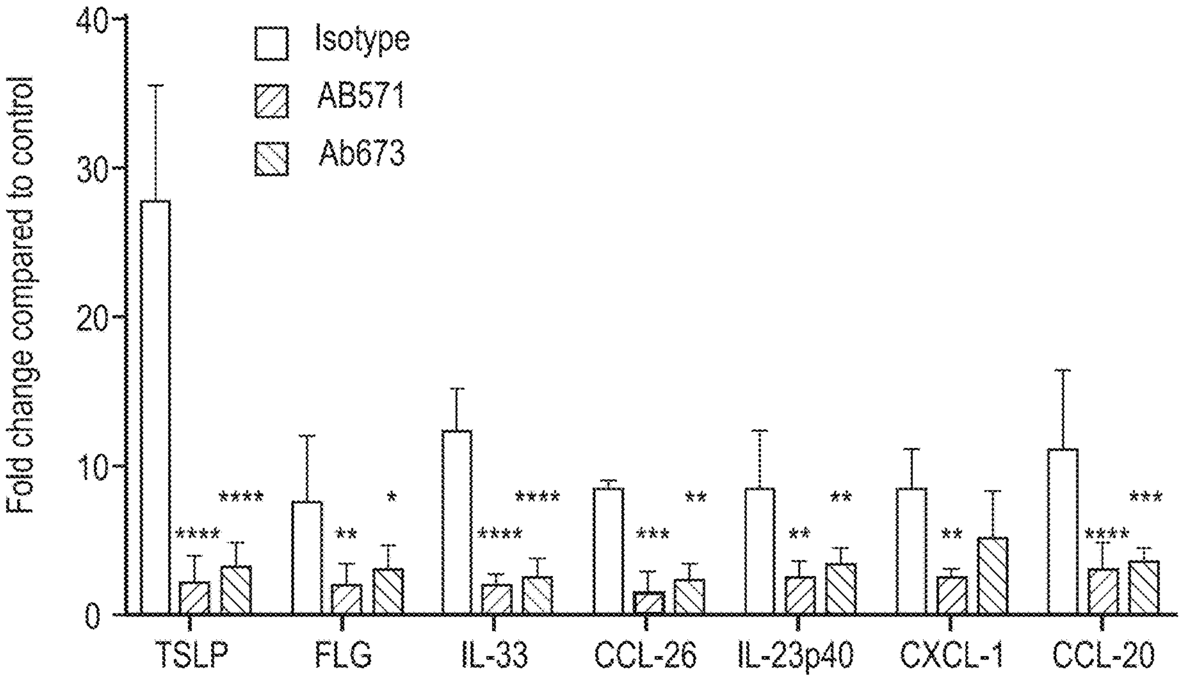
FIG. 12 depicts in vivo antibody administration leads to suppression of atopic dermatitis gene signature. After antibody treatment, RNA was isolated from sensitized skin and assessed for expression of genes associated with an atopic dermatitis (AD) gene signature. Administration of CD1a neutralizing antibodies, Ab571 and Ab673 resulted in a significant suppression of the AD gene signature relative to the isotype control treated animals.

In the same in vivo experiment, total RNA from mouse skin was isolated using Trizol reagent by following manufacturer's instructions. RNA was quantified using NanoDrop 2000 spectrophotometer and processed for reverse transcription and real-time RT-PCR analysis as per manufacturer's instructions. Reactions were run on an Ab7300 real time PCR system using the SYBR green master mix. β-Actin was used as the reference gene, and the mean fold changes were calculated using the $2^{\wedge\Delta\Delta CT}$ method (Livak K J, Schmittgen T D. Analysis of relative gene expression data using real-time quantitative PCR and the 2(−Delta Delta C(T)) Method. Methods 2001; 25(4):402-8). Expression of genes making up an atopic dermatitis (AD) signature, including TSLP, FLG, IL-33, CCL-26, CCL-20 and CXCL-1 were determined (FIG. 12). Isotype control treated animals had an elevation of all genes interrogated with the lowest being an 8.60±0.60-fold increase in CCL-26 expression and the highest, a 28.0±7.55 fold increase in TSLP gene expression. Administration of CD1a neutralizing antibodies, Ab571 and Ab673 resulted in a significant suppression of the AD gene signature relative to the isotype control treated animals. Gene expression in Ab571-treated animals was significantly suppressed for every gene assessed. For example, CCL-26 only had a 1.63±1.40-fold increase (p value=$6\times10^{-4}$ whereas TSLP expression was increased only 2.30±1.69-fold (p value $<1\times10^{-4}$). Combined these data demonstrate the ability of these CD1a neutralizing antibodies to markedly suppress CD1a-dependent inflammation and AD disease activity in vivo.

Example 14: Nonclinical Pharmacology

In vitro primary pharmacodynamic studies indicate that Ab571 is a high affinity, selective mAb against CD1a that binds both human and cynomolgus monkey CD1a. In vitro studies demonstrate dose-dependent binding to recombinant human or cynomolgus monkey CD1a protein; when CD1a is transfected and expressed on CHO cells and when endogenously expressed on primary monocyte-derived dendritic cells. Ab571 inhibits CD1a-dependent upregulation of CD69, a marker of T cell activation, and IL-2 secretion by Jurkat-BK6 T cells in a dose-dependent manner. Additionally, Ab571 suppresses CD1a-dependent IL-17 secretion by primary peripheral blood CD3+ cells isolated from cynomolgus monkeys, healthy volunteers, AD patients, or healthy volunteer human skin.

In vivo studies in a mouse model of AD using human CD1a transgenic mice were used to assess the efficacy of Ab571 to suppress HDM-induced inflammation. Prophylactic administration of Ab571 led to a statistically significant suppression of CD1a-dependent, HDM-induced inflammation.

Binding Specificity of Ab571 to Recombinant Human CD1a as Determined by ELISA

To assess the specificity of Ab571, ELISA plates were coated with recombinant forms of CD1a or 1 of 3 related family members, CD1b, CD1c or CD1d. After plates were blocked to prevent non-specific binding, coated plates were incubated with titrated amounts of Ab571. Bound test article was detected by incubation with a relevant secondary HRP conjugated antibody. Bound antibody was visualized by the addition of TMB substrate. The colorimetric reaction was stopped by the addition of sulfuric acid and the absorbance was read at 450 nm. The $EC_{50}$ was determined by transforming the data (Ab concentration X=log [X]), then a nonlinear regression analysis was performed using a 4-parameter variable slope of log [Ab] versus OD450 nm. The $EC_{50}$ of Ab571 for human CD1a was determined to be $6.52\times10^{-3}$ nM. When plates were coated with CD1b, CD1c or CD1d no binding to Ab571 was detected demonstrating that Ab571 specifically binds to CD1a.

Binding of Ab571 to Human or Cynomolgus Monkey CD1a Overexpressed on CHO Cells

To assess binding of Ab571 to cell surface expressed CD1a, CHO cells were stably transfected with either human or cynomolgus monkey CD1a and were incubated with titrated amounts of Ab571. Incubation of cells with secondary goat anti-human IgG-Rhodamine Red-X antibody was used to detect bound test article. Stained cells were analyzed by flow cytometry and the geometric mean fluorescence intensity was determined. Ab571 had little binding to untransfected parental CHO cells with the gMFI-ranging from $4.98\times10^{2}$ to $5.60\times10^{2}$ in the tested range of antibody concentrations. Ab571 demonstrated dose-dependent binding to CHO cells expressing either human or cynomolgus monkey CD1a protein. Ab571 binding to human CD1a CHO cells produced gMFI-values ranging between $4.67\times10^{5}$ to $1.95\times10^{6}$. Ab571 binding to CHO/cyCD1a cells yielded gMFI values ranging between $1.45\times10^{5}$ to $2.52\times10^{5}$. Combined these data demonstrate that Ab571 bound to cell surface expressed CD1a.

Binding of Ab571 to Human CD1a on Primary Monocyte-Derived Dendritic Cells

To assess the binding of Ab571 to endogenous cell surface expressed CD1a, whole blood was obtained from healthy volunteers and PBMCs were isolated by density gradient centrifugation. Monocytes were then purified from the PBMCs by positive selection using the Miltenyi Pan Monocyte Isolation kit according to the manufacturer's directions. Monocytes were cultured for 5 days in vitro with 20 ng/mL IL-4 and 25 ng/mL GM-CSF to promote dendritic cell differentiation. On day 2, fresh IL-4 and GMCSF were added to cultures at the same final concentrations. On day 5, cells were harvested, washed and resuspended in TruStain FcX™ receptor blocking solution. Dendritic cells were then incubated with titrated amounts of AF-647-conjugated human IgG1 or Ab571. Cells were analyzed on a BD LSRFortessa flow cytometer. Exported data was analyzed and EC50 was determined by curve fitting the gMFI of the AF-647 signal using a 4-parameter logistic regression curve. The average $EC_{50}$ was 7.83±6.75 nM with values ranging from 3.67 nM to 15.6 nM. These demonstrate Ab571 binds with high affinity to endogenously expressed human CD1a.

Binding of Ab571 to Cynomolgus Monkey CD1a on Primary Monocyte-Derived Dendritic Cells To assess the binding of Ab571 to endogenous cell surface expressed CD1a, cynomolgus monkey whole blood was obtained and PBMCs were isolated by density gradient centrifugation. Monocytes were then purified from the PBMCs by positive selection using the Miltenyi anti-CD14 beads according to the manufacturer's directions. Monocytes were cultured for 7 days in vitro with 40 ng/mL IL-4 and 25 ng/mL GM-CSF to promote dendritic cell differentiation. Every 3 days, ⅓ of the culture media was removed and replaced with fresh media containing a 3× concentration of IL-4 and GM-CSF. On day 7, cells were harvested, washed and incubated with titrated amounts of FITC-conjugated human IgG1 or Ab571. Cells were analyzed on a Novocyte flow cytometer. Non-linear regression analysis of the concentration response of FITC-Ab571 binding was done to calculate the $EC_{50}$ values for Ab571. The average $EC_{50}$ was 2.06±1.58 nM. These demonstrate Ab571 binds with high affinity to endogenously expressed cynomolgus monkey CD1a.

Inhibition of CD1a-Dependent Activation of Jurkat BK6 Cells as Assessed by CD69 Upregulation and IL-2 Secretion T cell activation results in the upregulation of many proteins including the surface expression of markers, like CD69, and secretion of cytokines, such as IL-2. Jurkat76-BK6 cells are a T cell line that expresses a CD1a-restricted T cell receptor (BK6) and when co-cultured in the presence of CD1a+ antigen cells, such as C1R cells expressing CD1a (C1R-CD1a), will upregulate CD69 expression and secrete IL-2.

To assess the ability of Ab571 to functionally inhibit T cell activation, C1RCD1a and Jurkat76BK6 cells were cultured in the presence of titrated amounts of Ab571. T cell activation was assessed by measuring expression of surface CD69 expression by flow cytometry and IL-2 secretion by MSD assay. C1RCD1a cells were preincubated with titrated amounts of Ab571 or isotype control antibody for 30 minutes at room temperature. After incubation, Jurkat76BK6 cells were added and co-cultured overnight. The following day, assay plates were centrifuged to pellet cells. Culture supernatants were harvested and assayed for IL-2 by MSD according to the manufacturer's instructions. Cells were resuspended in 0.5% BSA/DPBS and stained with antibodies against CD3, CD1a, and CD69; after staining was completed the cells were analyzed using a BD LSRFortessa cytometer. Exported data was analyzed for CD69 expression on CD3+CD1a− cells and a 4-parameter logistic regression curve analysis was used for $IC_{50}$ determination.

The addition of Ab571 resulted in a dose-dependent reduction of CD69 expression with an average IC50 of 0.894 (n=2) and IL-2 secretion with an average IC50 of and 0.268 (n=2).

Inhibition of CD1a− Dependent IL-17 Secretion by Primary Human CD3+ Cells as Assessed by ELISpot To confirm Ab571 can functionally inhibit primary human T cell activation, the ability of Ab571 to neutralize CD1a-induced secretion of IL-17A by CD3+ cells was assessed by ELISpot assay using K562 cells expressing human CD1a and primary CD3+ cells. CD3+ cells were purified by positive selection according to the manufacturer's instructions. CD3+ cells were isolated from PBMCs, either AD patient or healthy volunteer derived, or from healthy skin. K562 cells transfected to express human CD1a were pre-incubated with Ab571 or isotype control antibody, at a final concentration 50 μg/mL, for 30 minutes at room temperature prior to the addition of CD3+ cells. CD3+ cells also were cultured with untransfected cells to measure CD1a-independent IL-17A secretion, which was background subtracted in the subsequent analysis. ELISpot plates were incubated overnight and developed the following day according to the manufacturer's instructions. Ab571 reduced CD1a-induced spot formation between 39% and 80% in CD3+ cells isolated from both healthy donors and AD patients.

Inhibition of CD1a-Dependent IL-17 Secretion by Primary Cynomolgus Monkey CD3+ Cells as Assessed by ELISpot To support cynomolgus monkeys as a pharmacologically relevant species, the ability of Ab571 to neutralize CD1a-induced secretion of IL-17A by primary cynomolgus monkey CD3+ cells was assessed by ELISpot assay using K562 cells expressing cynomolgus monkey CD1a and primary CD3+ cells. CD3+ cells were isolated from the PBMCs of healthy cynomolgus monkeys. K562 cells stably expressing cynomolgus monkey CD1a were pre-incubated with Ab571 or isotype control antibody, at a final concentration 50 μg/mL, for 30 minutes at room temperature prior to the addition of CD3+ cells. CD3+ cells also were cultured with untransfected cells to measure CD1a-independent IL-17A secretion, which was background subtracted in the subsequent analysis. ELISpot plates were incubated overnight and developed the following day according to the manufacturer's instructions. Ab571 reduced spot formation between 19% and 53% (n 7) in CD3+ cells isolated from cynomolgus monkeys. Key pharmacologic properties for Ab571 are summarized in Table 8.

TABLE 8

Summary of Key Pharmacologic Properties of Ab571

| Assay | Pharmacodynamic Activity |
|---|---|
| **Surface Plasmon Resonance** | |
| Human CD1a | $K_D$ = 0.181 ± 0.012 nM |
| Cynomolgus Monkey CD1a | $K_D$ = 0.060 ± 0.011 nM |
| **ELISA (Binding Specificity)** | |
| Human CD1a | $EC_{50}$ = 6.52 × $10^{-3}$ nM |
| Human CD1b | No binding |
| Human CD1c | No binding |
| Human CD1d | No binding |
| **Cell Based Binding Assays (Flow cytometry)** | |
| Human CD1a Transfected CHO cells | gMFI: 4.67 × $10^5$ to 1.95 × $10^6$ RFU |
| Cynomolgus Monkey CD1a Transfected CHO cells | gMFI: 1.45 × $10^5$ to 2.52 × $10^5$ RFU |
| Primary Human Monocyte-derived Dendritic Cells | $EC_{50}$: 7.83 ± 6.75 nM |
| Primary Cynomolgus Monkey Monocyte-derived Dendritic Cells | $EC_{50}$: 2.06 ± 1.58 nM |
| **Neutralization of CD1a-dependent T cell activation** | |
| Human Jurkat T cell Activation: CD69 Expression and IL-2 secretion | $IC_{50}$ CD69 Expression: 0.894 nM<br>$IC_{50}$ IL-2: 0.268 nM |
| IL-17 Secretion by Primary Human $CD3^+$ Cells | 39-80% reduction of CD3 responses |
| IL-17 Secretion by Primary Cynomolgus Monkey $CD3^+$ Cells | 19-53% reduction of CD3 responses |
| **In vivo assay** | |
| Blockade of House Dust Mite (HDM) Model of Inflammation in CD1a transgenic mice | Pre-treatment with Ab571 significantly reduced HDM-induced inflammation |

Pharmacokinetics and Product Metabolism in Animals

The nonclinical PK of Ab571 were consistent with the PK profile for a typical IgG mAb. After single IV dosing in cynomolgus monkeys, non-linear PK was observed, consistent with TMDD. In the 13-week Good Laboratory Practice (GLP) repeat-dose toxicity study, there were no apparent sex-related differences in systemic exposure (as assessed by Cmax and AUC) following repeat SC and IV dosing. Systemic exposure increased with increasing dose and was higher after repeat SC and IV dosing. The incidence of ADA induction to Ab571 was 18% across all dose groups.

The PK of Ab571 in humans are expected to be the same as those of a typical therapeutic IgG mAb and were predicted using published human PK parameter values derived using a population-pharmacokinetic modeling approach. Based on a site of action PK/PD model, human PK predictions and targeting >95% CD1a receptor occupancy, the predicted efficacious dose of Ab571 in humans is 30 mg SC Q4W (i.e., every 4 weeks). The predicted steady-state human $AUC_{tau}$ for the efficacious dose level is 1730 μg·h/mL and the predicted $C_{max}$ and $C_{av}$ values are 3.67 and 2.58 μg/mL, respectively.

Methods of Analysis

Validated ligand binding assays (LBAs) were used to support the quantification of Ab571 and detection of ADA in the 13-week GLP repeat dose toxicity study in cynomolgus monkeys.

Quantification of Ab571 in Cynomolgus Monkeys

An LBA using the Gyrolab platform was validated for the quantification of Ab571 in cynomolgus monkey serum. In this assay, Ab571 was captured by a biotinylated recombinant protein that consists of human single chain CD1a linked to β2-microglobulin coated on the streptavidin bead column within the Gyrolab Bioaffy™ CD. The bound Ab571 was detected with an Alexa Fluor 647-labeled goat anti-human IgG H+L, monkey adsorbed antibody. Sample concentrations were determined by interpolation from calibration curves that were fit using a 5-parameter logistic regression model with a weighting factor of 1/y2. The range of quantification in 100% cynomolgus monkey serum was 0.040 to 5.12 μg/mL.

Detection of Anti-Drug Antibodies in Cynomolgus Monkeys

An LBA was validated to detect the presence of ADA in cynomolgus monkey serum using the MSD assay platform. In this method, biotin-labeled Ab571 and ruthenium-labeled Ab571 were coincubated with study samples and controls. Antibodies to Ab571 present in the samples must be bound to both the biotin- and ruthenium-labeled versions of Ab571 to be detected in this assay. ADA complexes were captured via the biotinylated Ab571 bound to streptavidin-coated MSD Multi-Array® plates. Final detection was conducted by using ruthenium-labeled Ab571 and a read buffer containing TPA to produce an ECL signal employed within the MSD instrument. Study samples were tested for ADA using a tiered strategy, and conclusions regarding the induction of ADA were made based on the comparison of the pre- and postdose sample results.

Pharmacokinetics

Single Dose Pharmacokinetics

The single-dose PK for Ab571 were evaluated in Tg32 mice, and cynomolgus monkeys. The PK data is briefly summarized in Table 9. After single IV dosing at 5 mg/kg to mice (n=4), Ab571 exhibited a mean systemic CL, mean $V_{ss}$ and mean $t_{1/2}$ of approximately 0.004 L/day/kg, 0.081 L/kg, and 17 days, respectively. Following single IV dosing at 0.1, 0.3, 1 and 3 mg/kg in cynomolgus monkeys (n=1/dose), CL values decreased from approximately 0.010 to 0.003 L/day/kg with increasing dose, and $V_{ss}$ ranged from 0.031 to 0.053 L/kg across the doses. The $t_{1/2}$ values were not reported from this study due to nonlinear PK and apparent TMDD.

TABLE 9

Pharmacokinetic Parameters following single intravenous dosing of Ab571 in Tg32 Mice and Cynomolgus Monkeys

| Species | Dose (mg/kg) | $AUC_{last}$ (μg · h/mL) | $AUC_{inf}$ (μg · h/mL) | CL (L/day/kg) | $V_{ss}$ (L/kg) | $t_{1/2}$ (h) |
|---|---|---|---|---|---|---|
| Mouse[a] | 5 | 24900 | 29100 | 0.00358 | 0.0807 | 17 |
| Monkey[b] | 0.1 | 241 | 243 | 0.00989 | 0.0425 | NR |
| | 0.3 | 745 | 747 | 0.00965 | 0.0534 | NR |
| | 1 | 3960 | 3970 | 0.00605 | 0.0431 | NR |
| | 3 | 27300 | 27300 | 0.00264 | 0.0313 | NR |

[a]n = 4 (Male/4/dose); Mean CL, $V_{ss}$ and $t_{1/2}$ values (n = 3).

[b]n = 1 (Female/1/dose).

Repeat-Dose Toxicokinetics

Toxicokinetic (TK) and ADA evaluations were conducted after once weekly SC dosing of Ab571 at 10 or 30 mg/kg/week or weekly IV dosing of Ab571 at 200 mg/kg/week for 13 weeks to cynomolgus monkeys as part of a GLP repeat-dose toxicity study. There were no apparent sex-related differences in systemic exposures (as assessed by $C_{max}$ and $AUC_{168}$) across dose groups; therefore, group mean TK parameters are discussed and presented using combined data from both male and female cynomolgus monkeys (Table 10).

Following SC dosing, mean systemic exposure increased with increasing dose in an approximately dose-proportional manner. After a single SC dose, the bioavailability was approximately 60-70%. Systemic exposure was higher after repeat dosing with mean accumulation ratios ($AUC_{168}$, Day 85/Day 1) ranging from 2.9 to 3.9 across dose groups. The overall incidence of ADA induction to Ab571 was 18% (4/22 animals) across all dose groups. Serum exposures were generally similar in ADA positive animals compared to ADA negative animals. It should be noted that circulating levels of Ab571 present in samples could interfere with the detection of ADA.

TABLE 10

Overall Mean Toxickinetic Paramter for Ab571 in Cynomolgus Monkeys

| Dose mg/kg/week (Route)[a] | Study Day | $C_{max}$ (μg/mL) | $T_{max}$ (h) | $AUC_{168}$ (μg · h/mL) |
|---|---|---|---|---|
| 10 (SC)[b] | 1 | 91.2 | 72 | 12900 |
| | 85 | 317 | 48 | 48000 |
| 30 (SC)[b] | 1 | 234 | 80 | 32800 |
| | 85 | 894 | 32 | 127000 |
| 200 (IV)[c] | 1 | 4780 | 1.5 | 361000 |
| | 85 | 10200 | 1.4 | 1060000 |

[a]Animals were dosed on Days 1, 8, 15, 22, 29, 36, 43, 50, 57, 64, 71, 78, 85, and 92.

[b]3 animals/sex/dose group.

[c]5 animals/sex/dose group

Prediction of Human Pharmacokinetics

Based on the serum PK parameter values observed for Ab571 in nonclinical species, the predicted 2-compartment PK parameter values in human are expected to be the same as those of a typical therapeutic IgG mAb. These values have been reported previously (e.g, Dirks, N. L. and B. Meibohm, Population pharmacokinetics of therapeutic monoclonal antibodies. Clin Pharmacokinet 2010; 49(10):633-59; Betts, A, et al. Linear pharmacokinetic parameters for monoclonal antibodies are similar within a species and across different pharmacological targets: A comparison between human, cynomolgus monkey and hFcRn Tg32 transgenic mouse using a population-modeling approach. MAbs 2018; 10(5): 751-764) and were used for the Ab571 human PK predictions as follows: 3.2 L for central volume, 2.2 L for peripheral volume, 0.25 L/day for central CL, 0.45 L/day for distributive clearance, 0.26 l/day for SC absorption rate constant and 60% for SC bioavailability. The predicted volume and clearance values resulted in a 17-day $t_{1/2}$ and a 5.4 L $V_{ss}$.

PK/PD and Prediction of Human Efficacious Dose and Exposure

A site of action model was used to link Ab571 exposure to CD1a receptor occupancy using the Ab571 $K_D$ and the predicted human PK parameters, CD1a concentrations in skin and CD1a internalization/turnover rate. The level of CD1a target modulation required for efficacy in atopic dermatitis is unknown; therefore, a dose that achieves >95% CD1a receptor occupancy at steady state trough concentrations at the site of action (skin) was used as the estimate of efficacious dose. Using this approach, the predicted efficacious human dose of Ab571 is estimated to be 30 mg SC Q4W. The projected AUC, $C_{av}$ and $C_{max}$ values associated with the predicted efficacious dose level are presented below in Table 11.

TABLE 11

Projected AUC, $C_{av}$ and $C_{max}$ of Ab571 in Human Serum at Efficacious and Maximum Doses

| Dose Type | Dose Route and Regimen | Dose (mg) | Bioavailability (%) | $AUC_{tau}$ (μg · h/mL) | $AUC_{inf}$ (μg · h/mL) | $C_{av}$ (μg/mL) | $C_{max}$ (μg/mL) |
|---|---|---|---|---|---|---|---|
| Efficacious[a] | SC Q4W | 30 | 60 | 1730 | NA | 2.58[b] | 3.67 |
| Maximum[c] | IV Single Dose | 1000 | 100 | NA | 96000 | 143[d] | 310 |

$AUC_{tau}$ = Area under the serum concentration-time curve over the dosing interval; $AUC_{inf}$ = Area under the serum concentration-time curve from time 0 to infinite time; $C_{av}$ = Average concentration; $C_{max}$ = Maximum observed concentration; IV = Intravenous NA = Not applicable; SC = Subcutaneous.

[a]Predicted steady-state exposures at projected efficacious clinical dose.

[b]$C_{av}$ = $AUC_{tau}$/672 hours for Q4W dose regimen, actual model output.

[c]Predicted single dose exposures at planned maximum clinical dose.

[d]$C_{av}$ = $AUC_{inf}$/672 hours; expected exposure for 1000 mg IV Q4W dose.

Toxicology

Ab571 was assessed in the nonclinical studies outlined in Table 12. Doses were administered by SC and IV injection. Rodents do not express the CD1a gene and therefore were not considered a relevant model for evaluating the potential toxicity of Ab571. Cynomolgus monkeys were selected as the toxicity species for the following reasons: Binding potency of Ab571 to cynomolgus monkey monocyte-derived dendritic cells was similar to that observed for human monocyte-derived dendritic cells (Table 8); Ab571 neutralized CD1a-dependent IL-17A production by human and cynomolgus monkey CD3+ T cells.

TABLE 12

Overview of Toxicity Testing Program

| Study | Concentration or Dose | GLP Status[a] |
|---|---|---|
| Repeat-Dose Toxicity Pivotal Studies | | |
| 13-Week (14 Dose) IV and SC Toxicity Study in Cynomolgus Monkeys with a 2-Month Recovery | 0 (IV and SC), 10 (SC), 30 (SC), 200 (IV) mg/kg/week | Yes |
| Other Studies | | |
| Tissue Cross-Reactivity Study in Normal Human and Cynomolgus Monkey Tissues | 0.1 and 0.3 μg/mL | Yes |
| In Vitro Human C1q and FcγR Binding Assays | Up to 30 μg/mL (C1q); 100 μg/mL (FcγR) | No |
| In Vitro Cytokine Release Assay (Soluble and Solid Phase) | 0.1, 1, 10, 100 μg/mL (Soluble Phase); 0.1, 1, 10, 100 μg/well (Solid Phase) | No |

[a]Study designs and parameters evaluated in the toxicity studies were consistent with accepted principles and practices as outlined in ICH, OECD guidelines, and national regulations (US FDA, European Community Directives, and Japan regulations). All definitive studies were conducted in accordance with US FDA GLP regulations in an OECD MAD member state, unless otherwise noted.

No test article-related effects or target organs were identified following once weekly administration of Ab571 to cynomolgus monkeys for 13 weeks. The NOAEL in the pivotal 13-week monkey study was therefore the highest dose tested, 200 mg/kg/week (IV). Ab571 serum concentrations and associated exposure margins are provided in Table 13. Exposure margins are calculated based on the projected $C_{max}$ and $C_{av}$ values at the predicted efficacious human dose of 30 mg (SC Q4W) and at the maximum anticipated single clinical dose of 1000 mg (IV).

Findings from other studies included staining of neuroendocrine cells with Ab71 in the human pituitary (staining not observed in the monkey pituitary) and Ab571 induced IFNγ release from human PBMCs.

Repeat-Dose Toxicity

In the pivotal repeat-dose toxicity study, Ab571 was administered once weekly to male and female cynomolgus monkeys (n=3/sex/dose) at 0 (SC and IV), 10 (SC), 30 (SC), or 200 (IV) mg/kg/week for 13 weeks (total of 14 doses). There were no test article-related clinical signs or effects on body weight, food consumption, ophthalmology, ECG parameters, hematology, coagulation, clinical chemistry, urinalysis, organ weights, or macroscopic or microscopic findings. The NOAEL was 200 mg/kg/week (IV). The incidence of ADA was 18% across the Ab571 dose groups, however, exposure was generally similar between ADA-positive and ADA-negative animals.

Local Tolerance

Local tolerance studies with Ab571 have not been conducted. However, SC and IV injection sites were evaluated macroscopically and microscopically in the pivotal 13-week repeat-dose toxicity study in cynomolgus monkeys and no Ab571-related findings were observed.

Antigenicity

The potential for Ab571 to induce an antibody response was assessed in the pivotal 13-week repeat-dose toxicity study in cynomolgus monkeys. The incidence of ADA induction was 17%, 17%, and 20% for the 10 (SC), 30 (SC), and 200 (IV) mg/kg/week dose groups, respectively. Serum Ab571 exposure was generally similar between ADA-positive and ADA-negative animals.

Immunotoxicity

Ab571 was evaluated in C1q and FcγR in vitro binding assays to determine its potential to elicit CDC or ADCC activity, respectively. No C1q or FcγR binding was observed with Ab571, suggesting a low potential to elicit CDC or ADCC activity.

Ab571 was tested in both in vitro soluble (whole blood) and solid (PBMCs) phase human CRAs. Ab571 did not induce IL-6, TNF, or IFNγ release in the soluble phase CRA. In the solid phase CRA, Ab571 induced IFNγ release in PBMC samples from 1 of 8 donors.

Tissue Cross-Reactivity

A tissue cross-reactivity study was conducted with Ab571 using human and cynomolgus monkey tissue samples. Cytoplasmic to membranous positive staining of mononuclear cells in human and monkey thymus, and of dendritic cells and epithelial cells in a comparable proportion of human and monkey tissues, was observed with FITC-Ab571.

Cytoplasmic to membranous positive staining of the neuroendocrine cells of the pituitary was observed for human only.

Staining of mononuclear cells in the thymus and dendritic cells, including Langerhans cells, in multiple tissues is consistent with the expected pattern of CD1a expression. Staining of epithelial cells in some tissues and neuroendocrine cells of the pituitary was not expected based on the reported expression of CD1a.

Relationship of Findings to Pharmacokinetics

Mean systemic exposures ($C_{max}$ and $AUC_{168}$) of Ab571 determined in the pivotal 13-week repeat-dose toxicity study in cynomolgus monkeys increased with increasing dose and were approximately dose proportional at the 2 SC doses. There were no consistent sex-related differences in Ab571 systemic exposure across the dose groups; therefore, male and female exposure data are presented together. Quantifiable concentrations of Ab571 were observed until Day 51 of the recovery phase (last samples collected) in the 200 mg/kg/week (IV) dose group. Mean accumulation ratios (based on $AUC_{16}8$) between Day 1 and Day 85 ranged from 2.9× to 3.9× across the dose groups.

TABLE 13

Relationship of Pharmacokinetics to Predicted Clinical Exposure

| Study | Dose (mg/kg/week) | $C_{max}$ (μg/mL)[a] | $AUC_{168}$ (μg · h/mL)[a] | $C_{av}$ (μg/mL)[b] | Exposure Margin Based on Predicted Human Efficacious Dose of 30 mg (SC Q4W)[c] $C_{max}$ | Exposure Margin Based on Predicted Human Efficacious Dose of 30 mg (SC Q4W)[c] $C_{av}$ | Exposure Margin Based on Highest Anticipated Single Human Dose of 1000 mg (IV)[d] $C_{max}$ | Exposure Margin Based on Highest Anticipated Single Human Dose of 1000 mg (IV)[d] $C_{av}$ |
|---|---|---|---|---|---|---|---|---|
| 13-Week (14 Dose) IV and SC | 10 (SC) | 317 | 48000 | 286 | 86 | 111 | 1 | 2 |
| Toxicity Study in Cynomolgus | 30 (SC) | 894 | 127000 | 756 | 244 | 293 | 3 | 5 |
| Monkeys with a 2-Month Recovery | 200 (IV) NOAEL | 10200 | 1060000 | 6310 | 2779 | 2446 | 33 | 44 |

[a]Exposure values on Day 85 of the 13-week toxicity study.
[b]$C_{av} = AUC_{168}/168$ hours.
[c]Exposure margins based on the projected $C_{max}$ (3.67 μg/mL) and $C_{av}$ (2.58 μg/mL) at the predicted human efficacious dose of 30 mg (SC Q4W).
[d]Exposure margins based on the projected $C_{max}$ (310 μg/mL) and $C_{av}$ (143 μg/mL) at the highest anticipated single human dose of 1000 mg (IV).

Target Organ Toxicity

No target organs were identified in the pivotal 13-week repeat-dose toxicity study. Findings from other studies included staining of neuroendocrine cells with Ab571 in the human pituitary and Ab57 1-induced IFNγ release from human PBMCs.

Neuroendocrine Cell Staining in the Human Pituitary

In the tissue cross-reactivity study, the positive staining of cell types with FITC-Ab571 was generally consistent between human and monkey tissues, with the exception of the pituitary for which staining of neuroendocrine cells was observed for human only. Based on human gene expression data available publicly at the GTEX portal (World Wide Web gtexportal.org) and the Human Protein Atlas (World Wide Web proteinatlas.org), CD1a, and other CD1 family proteins, are not expected to be expressed in the human pituitary.

No toxicity was observed in the 13-week repeat-dose monkey toxicity study for numerous tissues that showed positive FITC-Ab571 staining in the TCR study (e.g., urinary bladder, kidney, pancreas, prostate, ureter, oesophagus, duodenum, ileum, colon, lung, skin, uterus-cervix). In addition, the potential for CDC and/or ADCC of the neuroendocrine cells of the pituitary is low based on the design characteristics of the molecule (eg, Fc mutations to reduce effector function) and observed lack of C1q and FcγR binding with Ab571. Collectively, these data support that there is a low risk of pituitary toxicity in humans.

Cytokine Release from Human PBMCs

In vitro Ab571-induced IFNγ release from PBMC samples from 1 of 8 human donors was observed in the solid phase cytokine release assay (CRA). No effects of Ab571 on IL-6, TNF, or IFNγ release in the soluble phase (whole blood) CRA were observed.

The IFNγ response was limited to 1 of 8 donors and no effects on IL-6 or TNF were observed for PBMC samples from this same donor. Although cytokines were not measured in the cynomolgus monkey toxicity study, no clinical signs were observed in the animals that may have been suggestive of acute cytokine release.

These results identify the potential for Ab571-induced cytokine release. However, the clinical translation of findings from in vitro CRAs has not been established. Cytokine release syndrome and serum cytokines are monitorable in the clinic.

In the first-in-human study, single doses will be administered intravenously whereas both intravenous and subcutaneous dosing may be evaluated in the repeat dosing with the exposure limits for both single and multiple dose escalation set to 1020 μg/mL and 106000 μg·h/mL for $C_{max}$ and $AUC_{168H}$, respectively. The exposure limits were determined as 1/10th of the mean exposures observed at NOAEL in the 13-week cynomolgus monkey toxicity study. No adverse drug reactions (ADRs) for Ab571 have been identified.

The highest dose administered in nonclinical studies was 200 mg/kg/week. The dose was well-tolerated and no target organ toxicities were identified. The highest planned dose in clinical studies is 1000 mg (IV). No nonclinical findings have been identified in the 13-week GLP toxicity study that would impact subject safety. The NOAEL was 200 mg/kg/week (IV), the highest dose tested in the study. Exposure margins at the NOAEL are >30-fold to the exposures ($C_{max}$ and $C_{av}$) predicted at the highest anticipated human single IV dose of 1000 mg. Standard safety monitoring (e.g., clinical evaluation including injection/infusion reactions, clinical laboratory tests, cardiac parameters, and testing for ADA and neutralizing antibodies) will be included in the FIH study.

Ab571 was tested in both in vitro soluble (whole blood) and solid (PBMCs) phase human CRAs. Ab571 did not induce IL-6, TNF, or IFNγ release in the soluble phase CRA. In the solid phase CRA, Ab571 induced IFNγ release in PBMC samples from 1 of 8 donors. While these data suggest a potential for induction of cytokine release in human studies with Ab571, the response in only 1 of 8 donors in the solid phase only together with the mechanism of action of Ab571 being a neutralizing antibody and not an agonist, suggests that the potential risk of clinically significant cytokine release syndrome is low. To mitigate the risk of cytokine release syndrome, the starting dose in the first-in-human study will be low with respect to the safety margins and predicted target pharmacology, and sentinel dosing will be used in the single ascending dose phase of the study. Samples will be collected for measurement of cytokines in the event that cytokine release syndrome is observed or suspected.

A TCR study was conducted with FITC-conjugated Ab571 using selected human and cynomolgus monkey tissues. While FITC-Ab571 staining patterns overlapped in a variety and human and analogous monkey tissues, cytoplasmic to membranous positive staining of the neuroendocrine cells of the pituitary was observed for human only. Therefore, the 13-week GLP toxicity study in cynomolgus monkeys cannot be used to evaluate potential risk for effects on the human anterior pituitary. Based on binding assessments conducted against other CD1 family proteins Ab571 appears highly selective for CD1a. Human gene expression data demonstrates CD1a is not expected to be expressed inhuman anterior pituitary, and the potential for CDC and/or ADCC of the neuroendocrine cells due to possible off-target binding of the pituitary is low based on the design characteristics of the molecule (e.g., Fc mutations to reduce effector function) and observed lack of C1q and FcγR binding with Ab571. This is further supported by the lack of toxicity observed in the 13-week repeat-dose monkey toxicity study for numerous tissues that did show positive FITC-Ab571 staining in the TCR study (eg, urinary bladder, kidney, pancreas, prostate, ureter, oesophagus, duodenum, ileum, colon, lung, skin, uterus-cervix) in humans and monkeys. Collectively, these data support that there is a low risk of pituitary toxicity in humans. Pituitary hormone levels and hormones regulated by them may be monitored in early clinical studies to characterize any possible effects in humans. In conclusion, the nonclinical safety profile of Ab571 has been adequately characterized in vitro and in vivo in cynomolgus monkeys to support progression into clinical trials of up to 13 weeks in duration.

TABLE 14

Summary of antibody SEQ ID NOs.

| Antibody | CDR_H1 | CDR_H2 | CDR_H3 | CDR_L1 | CDR_L2 | CDR_L3 | CH1 | CH1_CH2_HINGE |
|---|---|---|---|---|---|---|---|---|
| Ab138 | 15 | 16 | 17 | 8 | 9 | 10 | 18 | 19 |
| Ab491 | 30 | 31 | 17 | 25 | 26 | 27 | 18 | 19 |
| Ab492 | 30 | 31 | 17 | 25 | 26 | 34 | 18 | 19 |
| Ab504 | 40 | 41 | 17 | 25 | 37 | 34 | 18 | 19 |
| Ab514 | 40 | 48 | 49 | 25 | 44 | 45 | 18 | 19 |
| Ab555 | 40 | 48 | 49 | 25 | 26 | 27 | 18 | 19 |
| Ab556 | 40 | 48 | 49 | 25 | 26 | 34 | 18 | 19 |

TABLE 14-continued

Summary of antibody SEQ ID NOs.

| | | | | | | | | |
|---|---|---|---|---|---|---|---|---|
| Ab559 | 40 | 41 | 52 | 25 | 26 | 27 | 18 | 19 |
| Ab560 | 40 | 41 | 52 | 25 | 26 | 34 | 18 | 19 |
| Ab571 | 30 | 41 | 17 | 25 | 26 | 27 | 18 | 19 |
| Ab572 | 30 | 41 | 17 | 25 | 26 | 34 | 18 | 19 |
| Ab579 | 30 | 48 | 49 | 25 | 26 | 27 | 18 | 19 |
| Ab585 | 40 | 59 | 49 | 25 | 44 | 45 | 18 | 19 |
| Ab599 | 40 | 59 | 49 | 25 | 26 | 34 | 18 | 19 |
| Ab609 | 62 | 63 | 49 | 25 | 26 | 34 | 18 | 19 |
| Ab610 | 66 | 63 | 49 | 25 | 26 | 34 | 18 | 19 |
| Ab616 | 62 | 59 | 49 | 25 | 26 | 27 | 18 | 19 |
| Ab623 | 62 | 63 | 49 | 25 | 26 | 27 | 18 | 19 |
| Ab624 | 66 | 63 | 49 | 25 | 26 | 27 | 18 | 19 |
| Ab656 | 66 | 63 | 49 | 25 | 71 | 27 | 18 | 19 |
| Ab657 | 40 | 63 | 49 | 25 | 44 | 45 | 18 | 19 |
| Ab660 | 40 | 76 | 49 | 25 | 44 | 45 | 18 | 19 |
| Ab673 | 40 | 63 | 49 | 25 | 26 | 27 | 18 | 19 |
| Ab681 | 40 | 63 | 49 | 25 | 71 | 34 | 18 | 19 |
| Ab689 | 40 | 63 | 49 | 25 | 71 | 27 | 18 | 19 |

| Antibody | CH2 | CH3 | CL | VH | VL | VH_FW4 | VL_FW4 | Full HC | Full LC |
|---|---|---|---|---|---|---|---|---|---|
| Ab138 | 20 | 21 | 11 | 22 | 12 | 23 | 13 | 14 | 7 |
| Ab491 | 20 | 21 | 11 | 32 | 28 | 23 | 13 | 29 | 24 |
| Ab492 | 20 | 21 | 11 | 32 | 35 | 23 | 13 | 29 | 33 |
| Ab504 | 20 | 21 | 11 | 42 | 38 | 23 | 13 | 39 | 36 |
| Ab514 | 20 | 21 | 11 | 50 | 46 | 23 | 13 | 47 | 43 |
| Ab555 | 20 | 21 | 11 | 50 | 28 | 23 | 13 | 47 | 24 |
| Ab556 | 20 | 21 | 11 | 50 | 35 | 23 | 13 | 47 | 33 |
| Ab559 | 20 | 21 | 11 | 53 | 28 | 23 | 13 | 51 | 24 |
| Ab560 | 20 | 21 | 11 | 53 | 35 | 23 | 13 | 51 | 33 |
| Ab571 | 20 | 21 | 11 | 55 | 28 | 23 | 13 | 54 | 24 |
| Ab572 | 20 | 21 | 11 | 55 | 35 | 23 | 13 | 54 | 33 |
| Ab579 | 20 | 21 | 11 | 57 | 28 | 23 | 13 | 56 | 24 |
| Ab585 | 20 | 21 | 11 | 60 | 46 | 23 | 13 | 58 | 43 |
| Ab599 | 20 | 21 | 11 | 60 | 35 | 23 | 13 | 58 | 33 |
| Ab609 | 20 | 21 | 11 | 64 | 35 | 23 | 13 | 61 | 33 |
| Ab610 | 20 | 21 | 11 | 67 | 35 | 23 | 13 | 65 | 33 |
| Ab616 | 20 | 21 | 11 | 69 | 28 | 23 | 13 | 68 | 24 |
| Ab623 | 20 | 21 | 11 | 64 | 28 | 23 | 13 | 61 | 24 |
| Ab624 | 20 | 21 | 11 | 67 | 28 | 23 | 13 | 65 | 24 |
| Ab656 | 20 | 21 | 11 | 67 | 72 | 23 | 13 | 65 | 70 |
| Ab657 | 20 | 21 | 11 | 74 | 46 | 23 | 13 | 73 | 43 |
| Ab660 | 20 | 21 | 11 | 77 | 46 | 23 | 13 | 75 | 43 |
| Ab673 | 20 | 21 | 11 | 74 | 28 | 23 | 13 | 73 | 24 |
| Ab681 | 20 | 21 | 11 | 74 | 79 | 23 | 13 | 73 | 78 |
| Ab689 | 20 | 21 | 11 | 74 | 72 | 23 | 13 | 73 | 70 |

TABLE 15

Sequence list

| SEQ | Description | Sequence |
|---|---|---|
| 1 | Human CD1a full-length (with signal peptide underlined) Source: UniProtKB, accession P06126 | MLFLLLPLLA VLPGDGNADG LKEPLSFHVT WIASFYNHSW<br>KQNLVSGWLS DLQTHTWDSN SSTIVFLCPW SRGNFSNEEW<br>KELETLFRIR TIRSFEGIRR YAHELQFEYP FEIQVTGGCE<br>LHSGKVSGSF LQLAYQGSDF VSFQNNSWLP YPVAGNMAKH<br>FCKVLNQNQH ENDITHNLLS DTCPRFILGL LDAGKAHLQR<br>QVKPEAWLSH GPSPGPGHLQ LVCHVSGFYP KPVWVMWMRG<br>EQEQQGTQRG DILPSADGTW YLRATLEVAA GEAADLSCRV<br>KHSSLEGQDI VLYWEHHSSV GFIILAVIVP LLLLIGLALW<br>FRKRCFC |
| 2 | Human B2M-CD1a ECD-Avi-His6 The Avi tag is underlined and the His6 tag (SEQ ID NO: 102) is in italic | IQRTPKIQVY SRHPAENGKS NFLNCYVSGF HPSDIEVDLL<br>KNGERIEKVE HSDLSFSKDW SFYLLYYTEF TPTEKDEYAC<br>RVNHVTLSQP KIVKWDRDMG GGGSGGGGSG GGGSGGGGSD<br>GLKEPLSFHV TWIASFYNHS WKQNLVSGWL SDLQTHTWDS<br>NSSTIVFLCP WSRGNFSNEE WKELETLFRI RTIRSFEGIR<br>RYAHELQFEY PFEIQVTGGC ELHSGKVSGS FLQLAYQGSD<br>FVSFQNNSWL PYPVAGNMAK HFCKVLNQNQ HENDITHNLL<br>SDTCPRFILG LLDAGKAHLQ RQVKPEAWLS HGPSPGPGHL<br>QLVCHVSGFY PKPVWVMWMR GEQEQQGTQR GDILPSADGT<br>WYLRATLEVA AGEAADLSCR VKHSSLEGQD IVLYWEHHSS<br>VGGGGLNDIF EAQKIEWHEG SG*HHHHHH* |

TABLE 15-continued

Sequence list

| SEQ | Description | Sequence |
|---|---|---|
| 3 | Cyno B2M-CD1a ECD-Avi-His6 The Avi tag is underlined and the His6 tag (SEQ ID NO: 102) is in italic | IQRTPKIQVY SRHPPENGKP NFLNCYVSGF HPSDIEVDLL KNGEKMGKVE HSDLSFSKDW SFYLLYYTEF TPNEKDEYAC RVNHVTLSGP RTVKWDRDMG GGGSGGGGSG GGGSGGGGSD GLKEPVSFHV IRIASFSNHS WKRNLISGYL GDLQTHTSDR NCSTIIFLWP WSRGNFSNEE WKELEMLFHI RCVRFLEGMH RYSRELQFEY PFEIQWTGGC ELHSGKESGS FYRLAYQGSD FMSFQNNSWL PSPVAGNMAK RLCKVLNQNQ HQNDIIHSLL SDTCPRLILG LLDAGKAHLQ RQVKPEAWLS RGLSPGPGRL QLVCHVSGFY PKPVWVMWMR GEQEQQGTQR GDILPNADGT WYLRATQEVA AGEAADLSCR VKHSSLEGQD IILYWEHHSS MGGGGLNDIF EAQKIEWHEG SG*HHHHHH* |
| 4 | Human B2M-CD1b ECD-His6 The His6 tag (SEQ ID NO: 102) is in italic | IQRTPKIQVY SRHPAENGKS NFLNCYVSGF HPSDIEVDLL KNGERIEKVE HSDLSFSKDW SFYLLYYTEF TPTEKDEYAC RVNHVTLSQP KIVKWDRDMG GGGSGGGGSG GGGSGGGGSS EHAFQGPTSF HVIQTSSFTN STWAQTQGSG WLDDLQIHGW DSDSGTAIFL KPWSKGNFSD KEVAELEEIF RVYIFGFARE VQDFAGDFQM KYPFEIQGIA GCELHSGGAI VSFLRGALGG LDFLSVKNAS CVPSPEGGSR AQKFCALIIQ YQGIMETVRI LLYETCPRYL LGVLNAGKAD LQRQVKPEAW LSSGPSPGPG RLQLVCHVSG FYPKPVWVMW MRGEQEQQGT QLGDILPNAN WTWYLRATLD VADGEAAGLS CRVKHSSLEG QDIILYWRNP TSIGS*HHHHH H* |
| 5 | Human B2M-CD1c ECD-His6 The His6 tag (SEQ ID NO: 102) is in italic | IQRTPKIQVY SRHPAENGKS NFLNCYVSGF HPSDIEVDLL KNGERIEKVE HSDLSFSKDW SFYLLYYTEF TPTEKDEYAC RVNHVTLSQP KIVKWDRDMG GGGSGGGGSG GGGSGGGGSN ADASQEHVSF HVIQIFSFVN QSWARGQGSG WLDELQTHGW DSESGTIIFL HNWSKGNFSN EELSDLELLF RFYLFGLTRE IQDHASQDYS KYPFEVQVKA GCELHSGKSP EGFFQVAFNG LDLLSFQNTT WVPSPGCGSL AQSVCHLLNH QYEGVTETVY NLIRSTCPRF LLGLLDAGKM YVHRQVRPEA WLSSRPSLGS GQLLLVCHAS GFYPKPVWVT WMRNEQEQLG TKHGDILPNA DGTWYLQVIL EVASEEPAGL SCRVRHSSLG GQDIILYWGH HFSM*HHHHHH* |
| 6 | Human B2M-CD1d ECD-His6 The His6 tag (SEQ ID NO: 102) is in italic | IQRTPKIQVY SRHPAENGKS NFLNCYVSGF HPSDIEVDLL KNGERIEKVE HSDLSFSKDW SFYLLYYTEF TPTEKDEYAC RVNHVTLSQP KIVKWDRDMG GGGSGGGGSG GGGSGGGGSE VPQRLFPLRC LQISSFANSS WTRTDGLAWL GELQTHSWSN DSDTVRSLKP WSQGTFSDQQ WETLQHIFRV YRSSFTRDVK EFAKMLRLSY PLELQVSAGC EVHPGNASNN FFHVAFQGKD ILSFQGTSWE PTQEAPLWVN LAIQVLNQDK WTRETVQWLL NGTCPQFVSG LLESGKSELK KQVKPKAWLS RGPSPGPGRL LLVCHVSGFY PKPVWVKWMR GEQEQQGTQP GDILPNADET WYLRATLDVV AGEAAGLSCR VKHSSLEGQD IVLYWGGSYT *SHHHHHH* |
| 7 | Ab138_Full LC | DIQMTQSPSS LSASVGDRVT ITCLASEDIS NDLAWYQQKP GKAPKLLIYG ANRLKDGVPS RFSGSGSGTD YTLTISSLQP EDFATYYCQQ SYKYPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 8 | Ab138_CDR_L1 | LASEDISNDL A |
| 9 | Ab138_CDR_L2 | GANRLKD |
| 10 | Ab138_CDR_L3 | QQSYKYPYT |
| 11 | Ab138_CL, Ab571_CL, Ab673_CL | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC |
| 12 | Ab138_VL | DIQMTQSPSS LSASVGDRVT ITCLASEDIS NDLAWYQQKP GKAPKLLIYG ANRLKDGVPS RFSGSGSGTD YTLTISSLQP EDFATYYCQQ SYKYPYTFGQ GTKLEIK |
| 13 | Ab138_VL_FW4, Ab571_VL_FW4, Ab673_VL_FW4 | FGQGTKLEIK |

TABLE 15-continued

| Sequence list | | |
|---|---|---|
| SEQ | Description | Sequence |
| 14 | Ab138_Full HC (K): Can be prepared with or without terminal lysine | EVQLVESGGG LVQPGGSLRL SCAASGFTFT DFYMNWVRQA PGKGLEWVAF IRNKANGYTT ESNPSVKGRF TISRDNAKNS LYLQMNSLRA EDTAVYYCAR ETTGIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 15 | Ab138_CDR_H1 | GFTFTDFYMN |
| 16 | Ab138_CDR_H2 | FIRNKANGYT TESNPSVKG |
| 17 | Ab138_CDR_H3, Ab571_CDR_H3 | ETTGIPTGWF AY |
| 18 | Ab138_CH1, Ab571_CH1, Ab673_CH1 | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKV |
| 19 | Ab138_CH1_CH2_ HINGE, Ab571_CH1_CH2_ HINGE, Ab673_CH1_CH2_ HINGE | EPKSCDKTHT CPPCP |
| 20 | Ab138_CH2, Ab571_CH2, Ab673_CH2 | APEAAGAPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK |
| 21 | Ab138_CH3, Ab571_CH3, Ab673_CH3 | GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG |
| 22 | Ab138_VH | EVQLVESGGG LVQPGGSLRL SCAASGFTFT DFYMNWVRQA PGKGLEWVAF IRNKANGYTT ESNPSVKGRF TISRDNAKNS LYLQMNSLRA EDTAVYYCAR ETTGIPTGWF AYWGQGTLVT VSS |
| 23 | Ab138_VH_FW4, Ab571_VH_FW4, Ab673_VH_FW4 | WGQGTLVTVS S |
| 24 | Ab571_Full LC, Ab673_Full LC | DIQMTQSPSS LSASVGDRVT ITCLASEDIY FDLAWYQQKP GKAPKLLIYG GDRLKEGVPS RFSGSGSGTD YTLTISSLQP EDFATYYCQQ SYSYPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 25 | Ab571_CDR_L1, Ab673_CDR_L1 | LASEDIYFDL A |
| 26 | Ab571_CDR_L2, Ab673_CDR_L2 | GGDRLKE |
| 27 | Ab571_CDR_L3, Ab673_CDR_L3 | QQSYSYPYT |
| 28 | Ab571_VL, Ab673_VL | DIQMTQSPSS LSASVGDRVT ITCLASEDIY FDLAWYQQKP GKAPKLLIYG GDRLKEGVPS RFSGSGSGTD YTLTISSLQP EDFATYYCQQ SYSYPYTFGQ GTKLEIK |
| 29 | Ab491_Full HC (K): Can be prepared with or without terminal lysine | EVQLVESGGG LVQPGGSLRL SCAASGFTFT DHYMTWVRQA PGKGLEWVAF IRNKANGYTT ESNPAVKGRF TISRDNAKNS LYLQMNSLRA EDTAVYYCAR ETTGIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK |

TABLE 15-continued

Sequence list

| SEQ | Description | Sequence |
| --- | --- | --- |
| | | FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 30 | Ab491_CDR_H1, Ab571_CDR_H1 | GFTFTDHYMT |
| 31 | Ab491_CDR_H2 | FIRNKANGYT TESNPAVKG |
| 32 | Ab491_VH | EVQLVESGGG LVQPGGSLRL SCAASGFTFT DHYMTWVRQA PGKGLEWVAF IRNKANGYTT ESNPAVKGRF TISRDNAKNS LYLQMNSLRA EDTAVYYCAR ETTGIPTGWF AYWGQGTLVT VSS |
| 33 | Ab492_Full LC | DIQMTQSPSS LSASVGDRVT ITCLASEDIY FDLAWYQQKP GKAPKLLIYG GDRLKEGVPS RFSGSGSGTD YTLTISSLQP EDFATYYCQQ SESYPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 34 | Ab492_CDR_L3 | QQSESYPYT |
| 35 | Ab492_VL | DIQMTQSPSS LSASVGDRVT ITCLASEDIY FDLAWYQQKP GKAPKLLIYG GDRLKEGVPS RFSGSGSGTD YTLTISSLQP EDFATYYCQQ SESYPYTFGQ GTKLEIK |
| 36 | Ab504_Full LC | DIQMTQSPSS LSASVGDRVT ITCLASEDIY FDLAWYQQKP GKAPKLLIYG GDRLKDGVPS RFSGSGSGTD YTLTISSLQP EDFATYYCQQ SESYPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 37 | Ab504_CDR_L2 | GGDRLKD |
| 38 | Ab504_VL | DIQMTQSPSS LSASVGDRVT ITCLASEDIY FDLAWYQQKP GKAPKLLIYG GDRLKDGVPS RFSGSGSGTD YTLTISSLQP EDFATYYCQQ SESYPYTFGQ GTKLEIK |
| 39 | Ab504_Full HC (K): Can be prepared with or without terminal lysine | EVQLVESGGG LVQPGGSLRL SCAASGFTFT DHYMHWVRQA PGKGLEWVAF IRNKAGGYTT ESNPAVKGRF TISRDNAKNS LYLQMNSLRA EDTAVYYCAR ETTGIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 40 | Ab673_CDR_H1 | GFTFTDHYMH |
| 41 | Ab504_CDR_H2, Ab571_CDR_H2 | FIRNKAGGYT TESNPAVKG |
| 42 | Ab504_VH | EVQLVESGGG LVQPGGSLRL SCAASGFTFT DHYMHWVRQA PGKGLEWVAF IRNKAGGYTT ESNPAVKGRF TISRDNAKNS LYLQMNSLRA EDTAVYYCAR ETTGIPTGWF AYWGQGTLVT VSS |
| 43 | Ab514_Full LC | DIQMTQSPSS LSASVGDRVT ITCLASEDIY FDLAWYQQKP GKAPKLLIYG ASTPKDGVPS RFSGSGSGTD YTLTISSLQP EDFATYYCQQ SEKYPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 44 | Ab514_CDR_L2 | GASTPKD |
| 45 | Ab514_CDR_L3 | QQSEKYPYT |

TABLE 15-continued

| Sequence list | | |
|---|---|---|
| SEQ | Description | Sequence |
| 46 | Ab514_VL | DIQMTQSPSS LSASVGDRVT ITCLASEDIY FDLAWYQQKP GKAPKLLIYG ASTPKDGVPS RESGSGSGTD YTLTISSLQP EDFATYYCQQ SEKYPYTFGQ GTKLEIK |
| 47 | Ab514_Full HC (K): Can be prepared with or without terminal lysine | EVQLVESGGG LVQPGGSLRL SCAASGFTFT DHYMHWVRQA PGKGLEWVAF IRNSAGGYTT ESNPAVKGRF TISRDNAKNS LYLQMNSLRA EDTAVYYCAR ETTRIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 48 | Ab514_CDR_H2 | FIRNSAGGYT TESNPAVKG |
| 49 | Ab673_CDR_H3 | ETTRIPTGWF AY |
| 50 | Ab514_VH | EVQLVESGGG LVQPGGSLRL SCAASGFTFT DHYMHWVRQA PGKGLEWVAF IRNSAGGYTT ESNPAVKGRF TISRDNAKNS LYLQMNSLRA EDTAVYYCAR ETTRIPTGWF AYWGQGTLVT VSS |
| 51 | Ab559_Full HC (K): Can be prepared with or without terminal lysine | EVQLVESGGG LVQPGGSLRL SCAASGFTFT DHYMHWVRQA PGKGLEWVAF IRNKAGGYTT ESNPAVKGRF TISRDNAKNS LYLQMNSLRA EDTAVYYCAR ETTTIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 52 | Ab559_CDR_H3 | ETTTIPTGWF AY |
| 53 | Ab559_VH | EVQLVESGGG LVQPGGSLRL SCAASGFTFT DHYMHWVRQA PGKGLEWVAF IRNKAGGYTT ESNPAVKGRF TISRDNAKNS LYLQMNSLRA EDTAVYYCAR ETTTIPTGWF AYWGQGTLVT VSS |
| 54 | Ab571_Full HC (K): Can be prepared with or without terminal lysine | EVQLVESGGG LVQPGGSLRL SCAASGFTFT DHYMTWVRQA PGKGLEWVAF IRNKAGGYTT ESNPAVKGRF TISRDNAKNS LYLQMNSLRA EDTAVYYCAR ETTGIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 55 | Ab571_VH | EVQLVESGGG LVQPGGSLRL SCAASGFTFT DHYMTWVRQA PGKGLEWVAF IRNKAGGYTT ESNPAVKGRF TISRDNAKNS LYLQMNSLRA EDTAVYYCAR ETTGIPTGWF AYWGQGTLVT VSS |
| 56 | Ab579_Full HC (K): Can be prepared with or without terminal lysine | EVQLVESGGG LVQPGGSLRL SCAASGFTFT DHYMTWVRQA PGKGLEWVAF IRNSAGGYTT ESNPAVKGRF TISRDNAKNS LYLQMNSLRA EDTAVYYCAR ETTRIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |

TABLE 15-continued

| Sequence list | | |
|---|---|---|
| SEQ | Description | Sequence |
| 57 | Ab579_VH | EVQLVESGGG LVQPGGSLRL SCAASGFTFT DHYMTWVRQA PGKGLEWVAF IRNSAGGYTT ESNPAVKGRF TISRDNAKNS LYLQMNSLRA EDTAVYYCAR ETTRIPTGWF AYWGQGTLVT VSS |
| 58 | Ab585_Full HC (K): Can be prepared with or without terminal lysine | EVQLVESGGG LVQPGGSLRL SCAASGFTFT DHYMHWVRQA PGKGLEWVGH ISGSAGGYTT ESNPAVKGRF TISRDNAKNS LYLQMNSLRA EDTAVYYCAR ETTRIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 59 | Ab585_CDR_H2 | HISGSAGGYT TESNPAVKG |
| 60 | Ab585_VH | EVQLVESGGG LVQPGGSLRL SCAASGFTFT DHYMHWVRQA PGKGLEWVGH ISGSAGGYTT ESNPAVKGRF TISRDNAKNS LYLQMNSLRA EDTAVYYCAR ETTRIPTGWF AYWGQGTLVT VSS |
| 61 | Ab609_Full HC (K): Can be prepared with or without terminal lysine | EVQLVESGGG LVQPGGSLRL SCAASGFTFE DHYMHWVRQA PGKGLEWVAH TRDKAGGYTT ESNPAVKGRF TISRDNAKNS LYLQMNSLRA EDTAVYYCAR ETTRIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 62 | Ab609_CDR_H1 | GFTFEDHYMH |
| 63 | Ab673_CDR_H2 | HTRDKAGGYT TESNPAVKG |
| 64 | Ab609_ VH | EVQLVESGGG LVQPGGSLRL SCAASGFTFE DHYMHWVRQA PGKGLEWVAH TRDKAGGYTT ESNPAVKGRF TISRDNAKNS LYLQMNSLRA EDTAVYYCAR ETTRIPTGWF AYWGQGTLVT VSS |
| 65 | Ab610_Full HC (K): Can be prepared with or without terminal lysine | TQTYICNVNH KPSNTKVDKK VEPKSCDKTH TCPPCPAPEA EVQLVESGGG LVQPGGSLRL SCAASGFDFT DHYMHWVRQA PGKGLEWVAH TRDKAGGYTT ESNPAVKGRF TISRDNAKNS LYLQMNSLRA EDTAVYYCAR ETTRIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 66 | Ab610_CDR_H1 | GFDFTDHYMH |
| 67 | Ab610_VH | EVQLVESGGG LVQPGGSLRL SCAASGFDFT DHYMHWVRQA PGKGLEWVAH TRDKAGGYTT ESNPAVKGRF TISRDNAKNS LYLQMNSLRA EDTAVYYCAR ETTRIPTGWF AYWGQGTLVT VSS |
| 68 | Ab616_Full HC (K): Can be prepared with or without terminal lysine | EVQLVESGGG LVQPGGSLRL SCAASGFTFE DHYMHWVRQA PGKGLEWVGH ISGSAGGYTT ESNPAVKGRF TISRDNAKNS LYLQMNSLRA EDTAVYYCAR ETTRIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL |

TABLE 15-continued

Sequence list

| SEQ | Description | Sequence |
|---|---|---|
| | | NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 69 | Ab616_VH | EVQLVESGGG LVQPGGSLRL SCAASGFTFE DHYMHWVRQA PGKGLEWVGH ISGSAGGYTT ESNPAVKGRF TISRDNAKNS LYLQMNSLRA EDTAVYYCAR ETTRIPTGWF AYWGQGTLVT VSS |
| 70 | Ab656_Full LC | DIQMTQSPSS LSASVGDRVT ITCLASEDIY FDLAWYQQKP GKAPKLLIYG GDRLQEGVPS RFSGSGSGTD YTLTISSLQP EDFATYYCQQ SYSYPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 71 | Ab656_CDR_L2 | GGDRLQE |
| 72 | Ab656_VL | DIQMTQSPSS LSASVGDRVT ITCLASEDIY FDLAWYQQKP GKAPKLLIYG GDRLQEGVPS RFSGSGSGTD YTLTISSLQP EDFATYYCQQ SYSYPYTFGQ GTKLEIK |
| 73 | Ab673_Full HC (K): Can be prepared with or without terminal lysine | EVQLVESGGG LVQPGGSLRL SCAASGFTFT DHYMHWVRQA PGKGLEWVAH TRDKAGGYTT ESNPAVKGRF TISRDNAKNS LYLQMNSLRA EDTAVYYCAR ETTRIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 74 | Ab673_VH | EVQLVESGGG LVQPGGSLRL SCAASGFTFT DHYMHWVRQA PGKGLEWVAH TRDKAGGYTT ESNPAVKGRF TISRDNAKNS LYLQMNSLRA EDTAVYYCAR ETTRIPTGWF AYWGQGTLVT VSS |
| 75 | Ab660_Full HC (K): Can be prepared with or without terminal lysine | EVQLVESGGG LVQPGGSLRL SCAASGFTFT DHYMHWVRQA PGKGLEWVGH IRNAAGGYTT ESNPAVKGRF TISRDNAKNS LYLQMNSLRA EDTAVYYCAR ETTRIPTGWF AYWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEA AGAPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PG(K) |
| 76 | Ab660_CDR_H2 | HIRNAAGGYT TESNPAVKG |
| 77 | Ab660_VH | EVQLVESGGG LVQPGGSLRL SCAASGFTFT DHYMHWVRQA PGKGLEWVGH IRNAAGGYTT ESNPAVKGRF TISRDNAKNS LYLQMNSLRA EDTAVYYCAR ETTRIPTGWF AYWGQGTLVT VSS |
| 78 | Ab681_Full LC | DIQMTQSPSS LSASVGDRVT ITCLASEDIY FDLAWYQQKP GKAPKLLIYG GDRLQEGVPS RFSGSGSGTD YTLTISSLQP EDFATYYCQQ SESYPYTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 79 | Ab681_VL | DIQMTQSPSS LSASVGDRVT ITCLASEDIY FDLAWYQQKP GKAPKLLIYG GDRLQEGVPS RFSGSGSGTD YTLTISSLQP EDFATYYCQQ SESYPYTFGQ GTKLEIK |
| 80 | Ab571_VH_DNA | GAGGTGCAGC TGGTGGAGTC TGGGGGAGGC TTGGTCCAGC CTGGGGGGTC CCTGAGACTC TCCTGTGCAG CCTCTGGATT CACCTTCACT GATCACTACA TGACCTGGGT CCGCCAGGCT CCAGGGAAGG GGCTGGAGTG GGTGGCCTTT ATTAGAAACA |

TABLE 15-continued

| SEQ | Description | Sequence |
|---|---|---|
| | | AAGCTGGTGG TTACACAACA GAGTCCAATC CGGCTGTGAA<br>GGGGCGATTC ACCATCTCCA GAGACAACGC CAAGAACTCA<br>CTGTATCTGC AAATGAACAG CCTGAGAGCC GAGGACACGG<br>CTGTGTATTA CTGTGCGAGA GAAACTACGG GTATACCTAC<br>AGGTTGGTTT GCTTACTGGG GCCAGGGAAC CCTGGTCACC<br>GTCTCCTCA |
| 81 | Ab571_VL_DNA,<br>Ab673_VL_DNA | GACATCCAGA TGACCCAGTC TCCATCCTCC CTGTCTGCAT<br>CTGTAGGAGA CAGAGTCACC ATCACTTGCC TAGCAAGTGA<br>GGACATTTAC TTTGATTTAG CGTGGTATCA GCAGAAACCA<br>GGGAAAGCCC CTAAGCTCCT GATCTATGGT GGGGACAGGT<br>TGAAAGAGGG GGTCCCATCA AGGTTCAGTG GCAGTGGATC<br>TGGGACAGAT TATACTCTCA CCATCAGCAG TCTGCAACCT<br>GAAGATTTTG CAACTTACTA CTGTCAACAG AGTTACAGTT<br>ATCCGTACAC GTTTGGCCAG GGGACCAAGC TGGAGATCAA<br>A |
| 82 | Ab571_Full<br>HC_DNA | GAGGTGCAGC TGGTGGAGTC TGGGGGAGGC TTGGTCCAGC<br>CTGGGGGGTC CCTGAGACTC TCCTGTGCAG CCTCTGGATT<br>CACCTTCACT GATCACTACA TGACCTGGGT CCGCCAGGCT<br>CCAGGGAAGG GGCTGGAGTG GGTGGCCTTT ATTAGAAACA<br>AAGCTGGTGG TTACACAACA GAGTCCAATC CGGCTGTGAA<br>GGGGCGATTC ACCATCTCCA GAGACAACGC CAAGAACTCA<br>CTGTATCTGC AAATGAACAG CCTGAGAGCC GAGGACACGG<br>CTGTGTATTA CTGTGCGAGA GAAACTACGG GTATACCTAC<br>AGGTTGGTTT GCTTACTGGG GCCAGGGAAC CCTGGTCACC<br>GTCTCCTCAG CGTCGACCAA GGGCCCATCG GTCTTCCCCC<br>TGGCACCCTC CTCCAAGAGC ACCTCTGGGG GCACAGCGGC<br>CCTGGGCTGC CTGGTCAAGG ACTACTTCCC CGAACCGGTG<br>ACGGTGTCGT GGAACTCAGG CGCCCTGACC AGCGGCGTGC<br>ACACCTTCCC GGCTGTCCTA CAGTCCTCAG GACTCTACTC<br>CCTCAGCAGC GTGGTGACCG TGCCCTCCAG CAGCTTGGGC<br>ACCCAGACCT ACATCTGCAA CGTGAATCAC AAGCCCAGCA<br>ACACCAAGGT GGACAAGAAA GTTGAGCCCA AATCTTGTGA<br>CAAAACTCAC ACATGCCCAC CGTGCCCAGC ACCTGAAGCC<br>GCTGGGGCAC CGTCAGTCTT CCTCTTCCCC CCAAAACCCA<br>AGGACACCCT CATGATCTCC CGGACCCCTG AGGTCACATG<br>CGTGGTGGTG GACGTGAGCC ACGAAGACCC TGAGGTCAAG<br>TTCAACTGGT ACGTGGACGG CGTGGAGGTG CATAATGCCA<br>AGACAAAGCC GCGGGAGGAG CAGTACAACA GCACGTACCG<br>TGTGGTCAGC GTCCTCACCG TCCTGCACCA GGACTGGCTG<br>AATGGCAAGG AGTACAAGTG CAAGGTCTCC AACAAAGCCC<br>TCCCAGCCCC CATCGAGAAA ACCATCTCCA AAGCCAAAGG<br>GCAGCCCCGA GAACCACAGG TGTACACCCT GCCCCCATCC<br>CGGGAGGAGA TGACCAAGAA CCAGGTCAGC CTGACCTGCC<br>TGGTCAAAGG CTTCTATCCC AGCGACATCG CCGTGGAGTG<br>GGAGAGCAAT GGGCAGCCGG AGAACAACTA CAAGACCACG<br>CCTCCCGTGC TGGACTCCGA CGGCTCCTTC TTCCTCTATA<br>GCAAGCTCAC CGTGGACAAG AGCAGGTGGC AGCAGGGGAA<br>CGTCTTCTCA TGCTCCGTGA TGCATGAGGC TCTGCACAAC<br>CACTACACGC AGAAGAGCCT CTCCCTGTCC CCGGGT(AAA) |
| 83 | Ab571_Full<br>LC_DNA,<br>Ab673_Full<br>LC_DNA | GACATCCAGA TGACCCAGTC TCCATCCTCC CTGTCTGCAT<br>CTGTAGGAGA CAGAGTCACC ATCACTTGCC TAGCAAGTGA<br>GGACATTTAC TTTGATTTAG CGTGGTATCA GCAGAAACCA<br>GGGAAAGCCC CTAAGCTCCT GATCTATGGT GGGGACAGGT<br>TGAAAGAGGG GGTCCCATCA AGGTTCAGTG GCAGTGGATC<br>TGGGACAGAT TATACTCTCA CCATCAGCAG TCTGCAACCT<br>GAAGATTTTG CAACTTACTA CTGTCAACAG AGTTACAGTT<br>ATCCGTACAC GTTTGGCCAG GGGACCAAGC TGGAGATCAA<br>ACGTACGGTG GCTGCACCAT CTGTCTTCAT CTTCCCGCCA<br>TCTGATGAGC AGTTGAAATC TGGAACTGCC TCTGTTGTGT<br>GCCTGCTGAA TAACTTCTAT CCCAGAGAGG CCAAAGTACA<br>GTGGAAGGTG GATAACGCCC TCCAATCGGG TAACTCCCAG<br>GAGAGTGTCA CAGAGCAGGA CAGCAAGGAC AGCACCTACA<br>GCCTCAGCAG CACCCTGACG CTGAGCAAAG CAGACTACGA<br>GAAACACAAA GTCTACGCCT GCGAAGTCAC CCATCAGGGC<br>CTGAGCTCGC CCGTCACAAA GAGCTTCAAC AGGGGAGAGT<br>GT |
| 84 | Ab673_VH_DNA | GAGGTGCAGC TGGTGGAGTC TGGGGGAGGC TTGGTCCAGC<br>CTGGGGGGTC CCTGAGACTC TCCTGTGCAG CCTCTGGATT<br>CACCTTCACT GATCACTACA TGCACTGGGT CCGCCAGGCT<br>CCAGGGAAGG GGCTGGAGTG GGTGGCCCAC ACTAGAGATA<br>AAGCTGGTGG TTACACAACA GAGTCCAATC CGGCTGTGAA<br>GGGGCGATTC ACCATCTCCA GAGACAACGC CAAGAACTCA |

TABLE 15-continued

| Sequence list | | |
|---|---|---|
| SEQ | Description | Sequence |
| | | CTGTATCTGC AAATGAACAG CCTGAGAGCC GAGGACACGG CTGTGTATTA CTGTGCGAGA GAAACTACGA GAATACCTAC AGGTTGGTTT GCTTACTGGG GCCAGGGAAC CCTGGTCACC GTCTCCTCA |
| 85 | Ab673_Full HC_DNA | GAGGTGCAGC TGGTGGAGTC TGGGGGAGGC TTGGTCCAGC CTGGGGGGTC CCTGAGACTC TCCTGTGCAG CCTCTGGATT CACCTTCACT GATCACTACA TGCACTGGGT CCGCCAGGCT CCAGGGAAGG GGCTGGAGTG GGTGGCCCAC ACTAGAGATA AAGCTGGTGG TTACACAACA GAGTCCAATC CGGCTGTGAA GGGGCGATTC ACCATCTCCA GAGACAACGC CAAGAACTCA CTGTATCTGC AAATGAACAG CCTGAGAGCC GAGGACACGG CTGTGTATTA CTGTGCGAGA GAAACTACGA GAATACCTAC AGGTTGGTTT GCTTACTGGG GCCAGGGAAC CCTGGTCACC GTCTCCTCAG CGTCGACCAA GGGCCCATCG GTCTTCCCCC TGGCACCCTC CTCCAAGAGC ACCTCTGGGG GCACAGCGGC CCTGGGCTGC CTGGTCAAGG ACTACTTCCC CGAACCGGTG ACGGTGTCGT GGAACTCAGG CGCCCTGACC AGCGGCGTGC ACACCTTCCC GGCTGTCCTA CAGTCCTCAG GACTCTACTC CCTCAGCAGC GTGGTGACCG TGCCCTCCAG CAGCTTGGGC ACCCAGACCT ACATCTGCAA CGTGAATCAC AAGCCCAGCA ACACCAAGGT GGACAAGAAA GTTGAGCCCA AATCTTGTGA CAAAACTCAC ACATGCCCAC CGTGCCCAGC ACCTGAAGCC GCTGGGGCAC CGTCAGTCTT CCTCTTCCCC CCAAAACCCA AGGACACCCT CATGATCTCC CGGACCCCTG AGGTCACATG CGTGGTGGTG GACGTGAGCC ACGAAGACCC TGAGGTCAAG TTCAACTGGT ACGTGGACGG CGTGGAGGTG CATAATGCCA AGACAAAGCC GCGGGAGGAG CAGTACAACA GCACGTACCG TGTGGTCAGC GTCCTCACCG TCCTGCACCA GGACTGGCTG AATGGCAAGG AGTACAAGTG CAAGGTCTCC AACAAAGCCC TCCCAGCCCC CATCGAGAAA ACCATCTCCA AAGCCAAAGG GCAGCCCCGA GAACCACAGG TGTACACCCT GCCCCCATCC CGGGAGGAGA TGACCAAGAA CCAGGTCAGC CTGACCTGCC TGGTCAAAGG CTTCTATCCC AGCGACATCG CCGTGGAGTG GGAGAGCAAT GGGCAGCCGG AGAACAACTA CAAGACCACG CCTCCCGTGC TGGACTCCGA CGGCTCCTTC TTCCTCTATA GCAAGCTCAC CGTGGACAAG AGCAGGTGGC AGCAGGGGAA CGTCTTCTCA TGCTCCGTGA TGCATGAGGC TCTGCACAAC CACTACACGC AGAAGAGCCT CTCCCTGTCC CCGGGT(AAA) |
| 86 | Human IgG1 constant region (effector function mutations underlined) (K): Can be prepared with or without terminal lysine | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKKVEPKSCDKTHTCPPCPAPEAAGAPSVFLFPPKPKDTL MISRTPEVTCVVVDVSHEDPEVKFNWYVDGVEVHNAKTKPREE QYNSTYRVVSVLTVLHQDWLNGKEYKCKVSNKALPAPIEKTISK AKGQPREPQVYTLPPSREEMTKNQVSLTCLVKGFYPSDIAVEWE SNGQPENNYKTTPPVLDSDGSFFLYSKLTVDKSRWQQGNVFSCS VMHEALHNHYTQKSLSLSPG(K) |
| 87 | H29 predicted non-germline T cell epitope in Ab138 | FTDFYMNWV |
| 88 | H32 predicted non-germline T cell epitope in Ab138 | FYMNWVRQA |
| 89 | H47 predicted non-germline T cell epitope in Ab138 | WVAFIRNKA |
| 90 | H50 predicted non-germline T cell epitope in Ab138 | FIRNKANGY |
| 91 | L45 predicted non-germline T cell epitope in Ab138 | KLLIYGANR |
| 92 | L46 predicted non-germline T cell epitope in Ab138 | LLIYGANRL |
| 93 | L48 predicted non-germline T cell epitope in Ab138 | IYGANRLKD |

TABLE 15-continued

| SEQ | Description | Sequence |
|---|---|---|
| | Sequence list | |
| 94 | L86 predicted non-germline T cell epitope in Ab138 | YYCQQSYKY |
| 95 | Human B2M-CD1a ECD-His6 The His6 tag (SEQ ID NO: 102) is in italic | IQRTPKIQVY SRHPAENGKS NFLNCYVSGF HPSDIEVDLL KNGERIEKVE HSDLSFSKDW SFYLLYYTEF TPTEKDEYAC RVNHVTLSQP KIVKWDRDMG GGGSGGGGSG GGGSGGGGSD GLKEPLSFHV TWIASFYNHS WKQNLVSGWL SDLQTHTWDS NSSTIVFLCP WSRGNFSNEE WKELETLFRI RTIRSFEGIR RYAHELQFEY PFEIQVTGGC ELHSGKVSGS FLQLAYQGSD FVSFQNNSWL PYPVAGNMAK HFCKVLNQNQ HENDITHNLL SDTCPRFILG LLDAGKAHLQ RQVKPEAWLS HGPSPGPGHL QLVCHVSGFY PKPVWVMWMR GEQEQQGTQR GDILPSADGT WYLRATLEVA AGEAADLSCR VKHSSLEGQD IVLY*HHHHHH* |
| 96 | CDR_H1 Consensus | GFT/DFT/EDH/FYMH/T/N |
| 97 | CDR_H2 Consensus | F/HIR/SN/G/DK/S/AAG/NGYTTESNPA/SVKG |
| 98 | CDR_H3 Consensus | ETTG/R/TIPTGWFAY |
| 99 | CDR_L1 Consensus | LASEDIS/YN/FDLA |
| 100 | CDR_L2 Consensus | GG/AD/N/SR/TL/PK/QD/E |
| 101 | CDR_L3 Consensus | QQSE/YK/SYPYT |
| 102 | His6 tag | HHHHHH |

The various features and embodiments of the present invention, referred to in individual sections above apply, as appropriate, to other sections, mutatis mutandis. Consequently, features specified in one section may be combined with features specified in other sections, as appropriate. All references cited herein, including patents, patent applications, papers, textbooks, and cited sequence Accession numbers, and the references cited therein, are hereby incorporated by reference in their entirety. In the event that one or more of the incorporated literature and similar materials differs from or contradicts this application, including but not limited to defined terms, term usage, described techniques, or the like, this application controls.

SEQUENCE LISTING

```
Sequence total quantity: 102
SEQ ID NO: 1            moltype = AA  length = 327
FEATURE                 Location/Qualifiers
source                  1..327
                        mol_type = protein
                        organism = Homo sapiens
SEQUENCE: 1
MLFLLLPLLA VLPGDGNADG LKEPLSFHVT WIASFYNHSW KQNLVSGWLS DLQTHTWDSN  60
SSTIVFLCPW SRGNFSNEEW KELETLFRIR TIRSFEGIRR YAHELQFEYP FEIQVTGGCE  120
LHSGKVSGSF LQLAYQGSDF VSFQNNSWLP YPVAGNMAKH FCKVLNQNQH ENDITHNLLS  180
DTCPRFILGL LDAGKAHLQR QVKPEAWLSH GPSPGPGHLQ LVCHVSGFYP KPVWVMWMRG  240
EQEQQGTQRG DILPSADGTW YLRATLEVAA GEAADLSCRV KHSSLEGQDI VLYWEHHSSV  300
GFIILAVIVP LLLLIGLALW FRKRCFC                                     327

SEQ ID NO: 2            moltype = AA  length = 428
FEATURE                 Location/Qualifiers
REGION                  1..428
                        note = Description of Artificial Sequence: Synthetic
                         polypeptide
source                  1..428
                        mol_type = protein
                        organism = synthetic construct
SEQUENCE: 2
IQRTPKIQVY SRHPAENGKS NFLNCYVSGF HPSDIEVDLL KNGERIEKVE HSDLSFSKDW  60
SFYLLYYTEF TPTEKDEYAC RVNHVTLSQP KIVKWDRDMG GGGSGGGGSG GGGSGGGGSD  120
GLKEPLSFHV TWIASFYNHS WKQNLVSGWL SDLQTHTWDS NSSTIVFLCP WSRGNFSNEE  180
WKELETLFRI RTIRSFEGIR RYAHELQFEY PFEIQVTGGC ELHSGKVSGS FLQLAYQGSD  240
FVSFQNNSWL PYPVAGNMAK HFCKVLNQNQ HENDITHNLL SDTCPRFILG LLDAGKAHLQ  300
RQVKPEAWLS HGPSPGPGHL QLVCHVSGFY PKPVWVMWMR GEQEQQGTQR GDILPSADGT  360
WYLRATLEVA AGEAADLSCR VKHSSLEGQD IVLYWEHHSS VGGGGLNDIF EAQKIEWHEG  420
```

```
SGHHHHHH                                                            428

SEQ ID NO: 3            moltype = AA  length = 428
FEATURE                 Location/Qualifiers
REGION                  1..428
                        note = Description of Artificial Sequence: Synthetic
                         polypeptide
source                  1..428
                        mol_type = protein
                        organism = synthetic construct
SEQUENCE: 3
IQRTPKIQVY SRHPPENGKP NFLNCYVSGF HPSDIEVDLL KNGEKMGKVE HSDLSFSKDW  60
SFYLLYYTEF TPNEKDEYAC RVNHVTLSGP RTVKWDRDMG GGGSGGGGSG GGGSGGGGSD  120
GLKEPVSFHV IRIASFSNHS WKRNLISGYL GDLQTHTSDR NCSTIIFLWP WSRGNFSNEE  180
WKELEMLFHI RCVRFLEGMH RYSRELQFEY PFEIQWTGGC ELHSGKFSGS FYRLAYQGSD  240
FMSFQNNSWL PSPVAGNMAK RLCKVLNQNQ HQNDIIHSLL SDTCPRLILG LLDAGKAHLQ  300
RQVKPEAWLS RGLSPGPGRL QLVCHVSGFY PKPVWVMWMR GEQEQQGTQR GDILPNADGT  360
WYLRATQEVA AGEAADLSCR VKHSSLEGQD IILYWEHHSS MGGGGLNDIF EAQKIEWHEG  420
SGHHHHHH                                                            428

SEQ ID NO: 4            moltype = AA  length = 411
FEATURE                 Location/Qualifiers
REGION                  1..411
                        note = Description of Artificial Sequence: Synthetic
                         polypeptide
source                  1..411
                        mol_type = protein
                        organism = synthetic construct
SEQUENCE: 4
IQRTPKIQVY SRHPAENGKS NFLNCYVSGF HPSDIEVDLL KNGERIEKVE HSDLSFSKDW  60
SFYLLYYTEF TPTEKDEYAC RVNHVTLSQP KIVKWDRDMG GGGSGGGGSG GGGSGGGGSS  120
EHAFQGPTSF HVIQTSSFTN STWAQTQGSG WLDDLQIHGW DSDSGTAIFL KPWSKGNFSD  180
KEVAELEEIF RVYIFGFARE VQDFAGDFQM KYPFEIQGIA GCELHSGGAI VSFLRGALGG  240
LDFLSVKNAS CVPSPEGGSR AQKFCALIIQ YQGIMETVRI LLYETCPRYL LGVLNAGKAD  300
LQRQVKPEAW LSSGPSPGPG RLQLVCHVSG FYPKPVWVMW MRGEQEQQGT QLGDILPNAN  360
WTWYLRATLD VADGEAAGLS CRVKHSSLEG QDIILYWRNP TSIGSHHHHH H            411

SEQ ID NO: 5            moltype = AA  length = 410
FEATURE                 Location/Qualifiers
REGION                  1..410
                        note = Description of Artificial Sequence: Synthetic
                         polypeptide
source                  1..410
                        mol_type = protein
                        organism = synthetic construct
SEQUENCE: 5
IQRTPKIQVY SRHPAENGKS NFLNCYVSGF HPSDIEVDLL KNGERIEKVE HSDLSFSKDW  60
SFYLLYYTEF TPTEKDEYAC RVNHVTLSQP KIVKWDRDMG GGGSGGGGSG GGGSGGGGSN  120
ADASQEHVSF HVIQIFSFVN QSWARGQGSG WLDELQTHGW DSESGTIIFL HNWSKGNFSN  180
EELSDLELLF RFYLFGLTRE IQDHASQDYS KYPFEVQVKA GCELHSGKSP EGFFQVAFNG  240
LDLLSFQNTT WVPSPGCGSL AQSVCHLLNH QYEGVTETVY NLIRSTCPRF LLGLLDAGKM  300
YVHRQVRPEA WLSSRPSLGS GQLLLVCHAS GFYPKPVWVT WMRNEQEQLG TKHGDILPNA  360
DGTWYLQVIL EVASEEPAGL SCRVRHSSLG GQDIILYWGH HFSMHHHHHH              410

SEQ ID NO: 6            moltype = AA  length = 407
FEATURE                 Location/Qualifiers
REGION                  1..407
                        note = Description of Artificial Sequence: Synthetic
                         polypeptide
source                  1..407
                        mol_type = protein
                        organism = synthetic construct
SEQUENCE: 6
IQRTPKIQVY SRHPAENGKS NFLNCYVSGF HPSDIEVDLL KNGERIEKVE HSDLSFSKDW  60
SFYLLYYTEF TPTEKDEYAC RVNHVTLSQP KIVKWDRDMG GGGSGGGGSG GGGSGGGGSE  120
VPQRLFPLRC LQISSFANSS WTRTDGLAWL GELQTHSWSN DSDTVRSLKP WSQGTFSDQQ  180
WETLQHIFRV YRSSFTRDVK EFAKMLRLSY PLELQVSAGC EVHPGNASNN FFHVAFQGKD  240
ILSFQGTSWE PTQEAPLWVN LAIQVLNQDK WTRETVQWLL NGTCPQFVSG LLESGKSELK  300
KQVKPKAWLS RGPSPGPGRL LLVCHVSGFY PKPVWVKWMR GEQEQQGTQP GDILPNADET  360
WYLRATLDVV AGEAAGLSCR VKHSSLEGQD IVLYWGGSYT SHHHHHH                 407

SEQ ID NO: 7            moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
```

```
SEQUENCE: 7
DIQMTQSPSS LSASVGDRVT ITCLASEDIS NDLAWYQQKP GKAPKLLIYG ANRLKDGVPS  60
RFSGSGSGTD YTLTISSLQP EDFATYYCQQ SYKYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 8           moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 8
LASEDISNDL A                                                       11

SEQ ID NO: 9           moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 9
GANRLKD                                                            7

SEQ ID NO: 10          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 10
QQSYKYPYT                                                          9

SEQ ID NO: 11          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 11
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 12          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 12
DIQMTQSPSS LSASVGDRVT ITCLASEDIS NDLAWYQQKP GKAPKLLIYG ANRLKDGVPS  60
RFSGSGSGTD YTLTISSLQP EDFATYYCQQ SYKYPYTFGQ GTKLEIK                107

SEQ ID NO: 13          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 13
FGQGTKLEIK                                                         10

SEQ ID NO: 14          moltype = AA  length = 453
FEATURE                Location/Qualifiers
REGION                 1..453
                       note = Description of Artificial Sequence: Synthetic
                        polypeptide
VAR_SEQ                453
                       note = May or may not be present
source                 1..453
                       mol_type = protein
```

```
                       organism = synthetic construct
SEQUENCE: 14
EVQLVESGGG LVQPGGSLRL SCAASGFTFT DFYMNWVRQA PGKGLEWVAF IRNKANGYTT  60
ESNPSVKGRF TISRDNAKNS LYLQMNSLRA EDTAVYYCAR ETTGIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 15          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 15
GFTFTDFYMN                                                        10

SEQ ID NO: 16          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 16
FIRNKANGYT TESNPSVKG                                              19

SEQ ID NO: 17          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 17
ETTGIPTGWF AY                                                     12

SEQ ID NO: 18          moltype = AA  length = 98
FEATURE                Location/Qualifiers
REGION                 1..98
                       note = Description of Artificial Sequence: Synthetic
                        polypeptide
source                 1..98
                       mol_type = protein
                       organism = synthetic construct
SEQUENCE: 18
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKV                         98

SEQ ID NO: 19          moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 19
EPKSCDKTHT CPPCP                                                  15

SEQ ID NO: 20          moltype = AA  length = 110
FEATURE                Location/Qualifiers
REGION                 1..110
                       note = Description of Artificial Sequence: Synthetic
                        polypeptide
source                 1..110
                       mol_type = protein
                       organism = synthetic construct
SEQUENCE: 20
APEAAGAPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK             110

SEQ ID NO: 21          moltype = AA  length = 106
FEATURE                Location/Qualifiers
REGION                 1..106
                       note = Description of Artificial Sequence: Synthetic
```

```
                         polypeptide
source                  1..106
                        mol_type = protein
                        organism = synthetic construct
SEQUENCE: 21
GQPREPQVYT LPPSREEMTK NQVSLTCLVK GFYPSDIAVE WESNGQPENN YKTTPPVLDS  60
DGSFFLYSKL TVDKSRWQQG NVFSCSVMHE ALHNHYTQKS LSLSPG                106

SEQ ID NO: 22           moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 22
EVQLVESGGG LVQPGGSLRL SCAASGFTFT DFYMNWVRQA PGKGLEWVAF IRNKANGYTT  60
ESNPSVKGRF TISRDNAKNS LYLQMNSLRA EDTAVYYCAR ETTGIPTGWF AYWGQGTLVT  120
VSS                                                               123

SEQ ID NO: 23           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 23
WGQGTLVTVS S                                                      11

SEQ ID NO: 24           moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 24
DIQMTQSPSS LSASVGDRVT ITCLASEDIY FDLAWYQQKP GKAPKLLIYG GDRLKEGVPS  60
RFSGSGSGTD YTLTISSLQP EDFATYYCQQ SYSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 25           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 25
LASEDIYFDL A                                                      11

SEQ ID NO: 26           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 26
GGDRLKE                                                           7

SEQ ID NO: 27           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 27
QQSYSYPYT                                                         9

SEQ ID NO: 28           moltype = AA  length = 107
FEATURE                 Location/Qualifiers
REGION                  1..107
                        note = Description of Artificial Sequence: Synthetic
```

```
                         polypeptide
source                   1..107
                         mol_type = protein
                         organism = synthetic construct
SEQUENCE: 28
DIQMTQSPSS LSASVGDRVT ITCLASEDIY FDLAWYQQKP GKAPKLLIYG GDRLKEGVPS  60
RFSGSGSGTD YTLTISSLQP EDFATYYCQQ SYSYPYTFGQ GTKLEIK                107

SEQ ID NO: 29            moltype = AA  length = 453
FEATURE                  Location/Qualifiers
REGION                   1..453
                         note = Description of Artificial Sequence: Synthetic
                          polypeptide
VAR_SEQ                  453
                         note = May or may not be present
source                   1..453
                         mol_type = protein
                         organism = synthetic construct
SEQUENCE: 29
EVQLVESGGG LVQPGGSLRL SCAASGFTFT DHYMTWVRQA PGKGLEWVAF IRNKANGYTT  60
ESNPAVKGRF TISRDNAKNS LYLQMNSLRA EDTAVYYCAR ETTGIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 30            moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 30
GFTFTDHYMT                                                         10

SEQ ID NO: 31            moltype = AA  length = 19
FEATURE                  Location/Qualifiers
REGION                   1..19
                         note = Description of Artificial Sequence: Synthetic peptide
source                   1..19
                         mol_type = protein
                         organism = synthetic construct
SEQUENCE: 31
FIRNKANGYT TESNPAVKG                                               19

SEQ ID NO: 32            moltype = AA  length = 123
FEATURE                  Location/Qualifiers
REGION                   1..123
                         note = Description of Artificial Sequence: Synthetic
                          polypeptide
source                   1..123
                         mol_type = protein
                         organism = synthetic construct
SEQUENCE: 32
EVQLVESGGG LVQPGGSLRL SCAASGFTFT DHYMTWVRQA PGKGLEWVAF IRNKANGYTT  60
ESNPAVKGRF TISRDNAKNS LYLQMNSLRA EDTAVYYCAR ETTGIPTGWF AYWGQGTLVT  120
VSS                                                                123

SEQ ID NO: 33            moltype = AA  length = 214
FEATURE                  Location/Qualifiers
REGION                   1..214
                         note = Description of Artificial Sequence: Synthetic
                          polypeptide
source                   1..214
                         mol_type = protein
                         organism = synthetic construct
SEQUENCE: 33
DIQMTQSPSS LSASVGDRVT ITCLASEDIY FDLAWYQQKP GKAPKLLIYG GDRLKEGVPS  60
RFSGSGSGTD YTLTISSLQP EDFATYYCQQ SESYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 34            moltype = AA  length = 9
FEATURE                  Location/Qualifiers
REGION                   1..9
                         note = Description of Artificial Sequence: Synthetic peptide
```

```
source                  1..9
                        mol_type = protein
                        organism = synthetic construct
SEQUENCE: 34
QQSESYPYT                                                     9

SEQ ID NO: 35           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 35
DIQMTQSPSS LSASVGDRVT ITCLASEDIY FDLAWYQQKP GKAPKLLIYG GDRLKEGVPS  60
RFSGSGSGTD YTLTISSLQP EDFATYYCQQ SESYPYTFGQ GTKLEIK               107

SEQ ID NO: 36           moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 36
DIQMTQSPSS LSASVGDRVT ITCLASEDIY FDLAWYQQKP GKAPKLLIYG GDRLKDGVPS  60
RFSGSGSGTD YTLTISSLQP EDFATYYCQQ SESYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                           214

SEQ ID NO: 37           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 37
GGDRLKD                                                       7

SEQ ID NO: 38           moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 38
DIQMTQSPSS LSASVGDRVT ITCLASEDIY FDLAWYQQKP GKAPKLLIYG GDRLKDGVPS  60
RFSGSGSGTD YTLTISSLQP EDFATYYCQQ SESYPYTFGQ GTKLEIK               107

SEQ ID NO: 39           moltype = AA  length = 453
FEATURE                 Location/Qualifiers
REGION                  1..453
                        note = Description of Artificial Sequence: Synthetic
                         polypeptide
VAR_SEQ                 453
                        note = May or may not be present
source                  1..453
                        mol_type = protein
                        organism = synthetic construct
SEQUENCE: 39
EVQLVESGGG LVQPGGSLRL SCAASGFTFT DHYMHWVRQA PGKGLEWVAF IRNKAGGYTT  60
ESNPAVKGRF TISRDNAKNS LYLQMNSLRA EDTAVYYCAR ETTGIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                            453

SEQ ID NO: 40           moltype = AA  length = 10
FEATURE                 Location/Qualifiers
REGION                  1..10
                        note = Description of Artificial Sequence: Synthetic peptide
source                  1..10
```

```
                       mol_type = protein
                       organism = synthetic construct
SEQUENCE: 40
GFTFTDHYMH                                                        10

SEQ ID NO: 41          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 41
FIRNKAGGYT TESNPAVKG                                              19

SEQ ID NO: 42          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 42
EVQLVESGGG LVQPGGSLRL SCAASGFTFT DHYMHWVRQA PGKGLEWVAF IRNKAGGYTT  60
ESNPAVKGRF TISRDNAKNS LYLQMNSLRA EDTAVYYCAR ETTGIPTGWF AYWGQGTLVT  120
VSS                                                               123

SEQ ID NO: 43          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 43
DIQMTQSPSS LSASVGDRVT ITCLASEDIY FDLAWYQQKP GKAPKLLIYG ASTPKDGVPS  60
RFSGSGSGTD YTLTISSLQP EDFATYYCQQ SEKYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 44          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 44
GASTPKD                                                           7

SEQ ID NO: 45          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 45
QQSEKYPYT                                                         9

SEQ ID NO: 46          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 46
DIQMTQSPSS LSASVGDRVT ITCLASEDIY FDLAWYQQKP GKAPKLLIYG ASTPKDGVPS  60
RFSGSGSGTD YTLTISSLQP EDFATYYCQQ SEKYPYTFGQ GTKLEIK               107

SEQ ID NO: 47          moltype = AA  length = 453
FEATURE                Location/Qualifiers
REGION                 1..453
                       note = Description of Artificial Sequence: Synthetic
                        polypeptide
```

```
VAR_SEQ                453
                       note = May or may not be present
source                 1..453
                       mol_type = protein
                       organism = synthetic construct
SEQUENCE: 47
EVQLVESGGG LVQPGGSLRL SCAASGFTFT DHYMHWVRQA PGKGLEWVAF IRNSAGGYTT  60
ESNPAVKGRF TISRDNAKNS LYLQMNSLRA EDTAVYYCAR ETTRIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 48          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 48
FIRNSAGGYT TESNPAVKG                                               19

SEQ ID NO: 49          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 49
ETTRIPTGWF AY                                                      12

SEQ ID NO: 50          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 50
EVQLVESGGG LVQPGGSLRL SCAASGFTFT DHYMHWVRQA PGKGLEWVAF IRNSAGGYTT  60
ESNPAVKGRF TISRDNAKNS LYLQMNSLRA EDTAVYYCAR ETTRIPTGWF AYWGQGTLVT  120
VSS                                                                123

SEQ ID NO: 51          moltype = AA  length = 453
FEATURE                Location/Qualifiers
REGION                 1..453
                       note = Description of Artificial Sequence: Synthetic
                        polypeptide
VAR_SEQ                453
                       note = May or may not be present
source                 1..453
                       mol_type = protein
                       organism = synthetic construct
SEQUENCE: 51
EVQLVESGGG LVQPGGSLRL SCAASGFTFT DHYMHWVRQA PGKGLEWVAF IRNKAGGYTT  60
ESNPAVKGRF TISRDNAKNS LYLQMNSLRA EDTAVYYCAR ETTTIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 52          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 52
ETTTIPTGWF AY                                                      12

SEQ ID NO: 53          moltype = AA  length = 123
```

```
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 53
EVQLVESGGG LVQPGGSLRL SCAASGFTFT DHYMHWVRQA PGKGLEWVAF IRNKAGGYTT  60
ESNPAVKGRF TISRDNAKNS LYLQMNSLRA EDTAVYYCAR ETTTIPTGWF AYWGQGTLVT  120
VSS                                                                123

SEQ ID NO: 54          moltype = AA  length = 453
FEATURE                Location/Qualifiers
REGION                 1..453
                       note = Description of Artificial Sequence: Synthetic
                        polypeptide
VAR_SEQ                453
                       note = May or may not be present
source                 1..453
                       mol_type = protein
                       organism = synthetic construct
SEQUENCE: 54
EVQLVESGGG LVQPGGSLRL SCAASGFTFT DHYMTWVRQA PGKGLEWVAF IRNKAGGYTT  60
ESNPAVKGRF TISRDNAKNS LYLQMNSLRA EDTAVYYCAR ETTGIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 55          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 55
EVQLVESGGG LVQPGGSLRL SCAASGFTFT DHYMTWVRQA PGKGLEWVAF IRNKAGGYTT  60
ESNPAVKGRF TISRDNAKNS LYLQMNSLRA EDTAVYYCAR ETTGIPTGWF AYWGQGTLVT  120
VSS                                                                123

SEQ ID NO: 56          moltype = AA  length = 453
FEATURE                Location/Qualifiers
REGION                 1..453
                       note = Description of Artificial Sequence: Synthetic
                        polypeptide
VAR_SEQ                453
                       note = May or may not be present
source                 1..453
                       mol_type = protein
                       organism = synthetic construct
SEQUENCE: 56
EVQLVESGGG LVQPGGSLRL SCAASGFTFT DHYMTWVRQA PGKGLEWVAF IRNSAGGYTT  60
ESNPAVKGRF TISRDNAKNS LYLQMNSLRA EDTAVYYCAR ETTRIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 57          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 57
EVQLVESGGG LVQPGGSLRL SCAASGFTFT DHYMTWVRQA PGKGLEWVAF IRNSAGGYTT  60
ESNPAVKGRF TISRDNAKNS LYLQMNSLRA EDTAVYYCAR ETTRIPTGWF AYWGQGTLVT  120
VSS                                                                123

SEQ ID NO: 58          moltype = AA  length = 453
```

```
FEATURE                 Location/Qualifiers
REGION                  1..453
                        note = Description of Artificial Sequence: Synthetic
                         polypeptide
VAR_SEQ                 453
                        note = May or may not be present
source                  1..453
                        mol_type = protein
                        organism = synthetic construct
SEQUENCE: 58
EVQLVESGGG LVQPGGSLRL SCAASGFTFT DHYMHWVRQA PGKGLEWVGH ISGSAGGYTT  60
ESNPAVKGRF TISRDNAKNS LYLQMNSLRA EDTAVYYCAR ETTRIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 59           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 59
HISGSAGGYT TESNPAVKG                                              19

SEQ ID NO: 60           moltype = AA  length = 123
FEATURE                 Location/Qualifiers
REGION                  1..123
                        note = Description of Artificial Sequence: Synthetic
                         polypeptide
source                  1..123
                        mol_type = protein
                        organism = synthetic construct
SEQUENCE: 60
EVQLVESGGG LVQPGGSLRL SCAASGFTFT DHYMHWVRQA PGKGLEWVGH ISGSAGGYTT  60
ESNPAVKGRF TISRDNAKNS LYLQMNSLRA EDTAVYYCAR ETTRIPTGWF AYWGQGTLVT  120
VSS                                                               123

SEQ ID NO: 61           moltype = AA  length = 453
FEATURE                 Location/Qualifiers
REGION                  1..453
                        note = Description of Artificial Sequence: Synthetic
                         polypeptide
VAR_SEQ                 453
                        note = May or may not be present
source                  1..453
                        mol_type = protein
                        organism = synthetic construct
SEQUENCE: 61
EVQLVESGGG LVQPGGSLRL SCAASGFTFE DHYMHWVRQA PGKGLEWVAH TRDKAGGYTT  60
ESNPAVKGRF TISRDNAKNS LYLQMNSLRA EDTAVYYCAR ETTRIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 62           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 62
GFTFEDHYMH                                                        10

SEQ ID NO: 63           moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
```

```
SEQUENCE: 63
HTRDKAGGYT TESNPAVKG                                        19

SEQ ID NO: 64          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 64
EVQLVESGGG LVQPGGSLRL SCAASGFTFE DHYMHWVRQA PGKGLEWVAH TRDKAGGYTT  60
ESNPAVKGRF TISRDNAKNS LYLQMNSLRA EDTAVYYCAR ETTRIPTGWF AYWGQGTLVT  120
VSS                                                         123

SEQ ID NO: 65          moltype = AA  length = 453
FEATURE                Location/Qualifiers
REGION                 1..453
                       note = Description of Artificial Sequence: Synthetic
                        polypeptide
VAR_SEQ                453
                       note = May or may not be present
source                 1..453
                       mol_type = protein
                       organism = synthetic construct
SEQUENCE: 65
EVQLVESGGG LVQPGGSLRL SCAASGFDFT DHYMHWVRQA PGKGLEWVAH TRDKAGGYTT  60
ESNPAVKGRF TISRDNAKNS LYLQMNSLRA EDTAVYYCAR ETTRIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                        453

SEQ ID NO: 66          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 66
GFDFTDHYMH                                                  10

SEQ ID NO: 67          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 67
EVQLVESGGG LVQPGGSLRL SCAASGFDFT DHYMHWVRQA PGKGLEWVAH TRDKAGGYTT  60
ESNPAVKGRF TISRDNAKNS LYLQMNSLRA EDTAVYYCAR ETTRIPTGWF AYWGQGTLVT  120
VSS                                                         123

SEQ ID NO: 68          moltype = AA  length = 453
FEATURE                Location/Qualifiers
REGION                 1..453
                       note = Description of Artificial Sequence: Synthetic
                        polypeptide
VAR_SEQ                453
                       note = May or may not be present
source                 1..453
                       mol_type = protein
                       organism = synthetic construct
SEQUENCE: 68
EVQLVESGGG LVQPGGSLRL SCAASGFTFE DHYMHWVRQA PGKGLEWVGH ISGSAGGYTT  60
ESNPAVKGRF TISRDNAKNS LYLQMNSLRA EDTAVYYCAR ETTRIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                        453
```

```
SEQ ID NO: 69          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 69
EVQLVESGGG LVQPGGSLRL SCAASGFTFE DHYMHWVRQA PGKGLEWVGH ISGSAGGYTT  60
ESNPAVKGRF TISRDNAKNS LYLQMNSLRA EDTAVYYCAR ETTRIPTGWF AYWGQGTLVT  120
VSS                                                                123

SEQ ID NO: 70          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 70
DIQMTQSPSS LSASVGDRVT ITCLASEDIY FDLAWYQQKP GKAPKLLIYG GDRLQEGVPS  60
RFSGSGSGTD YTLTISSLQP EDFATYYCQQ SYSYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 71          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 71
GGDRLQE                                                            7

SEQ ID NO: 72          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 72
DIQMTQSPSS LSASVGDRVT ITCLASEDIY FDLAWYQQKP GKAPKLLIYG GDRLQEGVPS  60
RFSGSGSGTD YTLTISSLQP EDFATYYCQQ SYSYPYTFGQ GTKLEIK                107

SEQ ID NO: 73          moltype = AA  length = 453
FEATURE                Location/Qualifiers
REGION                 1..453
                       note = Description of Artificial Sequence: Synthetic
                        polypeptide
VAR_SEQ                453
                       note = May or may not be present
source                 1..453
                       mol_type = protein
                       organism = synthetic construct
SEQUENCE: 73
EVQLVESGGG LVQPGGSLRL SCAASGFTFT DHYMHWVRQA PGKGLEWVAH TRDKAGGYTT  60
ESNPAVKGRF TISRDNAKNS LYLQMNSLRA EDTAVYYCAR ETTRIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 74          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 74
EVQLVESGGG LVQPGGSLRL SCAASGFTFT DHYMHWVRQA PGKGLEWVAH TRDKAGGYTT  60
```

```
ESNPAVKGRF TISRDNAKNS LYLQMNSLRA EDTAVYYCAR ETTRIPTGWF AYWGQGTLVT  120
VSS                                                                123

SEQ ID NO: 75          moltype = AA  length = 453
FEATURE                Location/Qualifiers
REGION                 1..453
                       note = Description of Artificial Sequence: Synthetic
                        polypeptide
VAR_SEQ                453
                       note = May or may not be present
source                 1..453
                       mol_type = protein
                       organism = synthetic construct
SEQUENCE: 75
EVQLVESGGG LVQPGGSLRL SCAASGFTFT DHYMHWVRQA PGKGLEWVGH IRNAAGGYTT  60
ESNPAVKGRF TISRDNAKNS LYLQMNSLRA EDTAVYYCAR ETTRIPTGWF AYWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 76          moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 76
HIRNAAGGYT TESNPAVKG                                               19

SEQ ID NO: 77          moltype = AA  length = 123
FEATURE                Location/Qualifiers
REGION                 1..123
                       note = Description of Artificial Sequence: Synthetic
                        polypeptide
source                 1..123
                       mol_type = protein
                       organism = synthetic construct
SEQUENCE: 77
EVQLVESGGG LVQPGGSLRL SCAASGFTFT DHYMHWVRQA PGKGLEWVGH IRNAAGGYTT  60
ESNPAVKGRF TISRDNAKNS LYLQMNSLRA EDTAVYYCAR ETTRIPTGWF AYWGQGTLVT  120
VSS                                                                123

SEQ ID NO: 78          moltype = AA  length = 214
FEATURE                Location/Qualifiers
REGION                 1..214
                       note = Description of Artificial Sequence: Synthetic
                        polypeptide
source                 1..214
                       mol_type = protein
                       organism = synthetic construct
SEQUENCE: 78
DIQMTQSPSS LSASVGDRVT ITCLASEDIY FDLAWYQQKP GKAPKLLIYG GDRLQEGVPS  60
RFSGSGSGTD YTLTISSLQP EDFATYYCQQ SESYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 79          moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 79
DIQMTQSPSS LSASVGDRVT ITCLASEDIY FDLAWYQQKP GKAPKLLIYG GDRLQEGVPS  60
RFSGSGSGTD YTLTISSLQP EDFATYYCQQ SESYPYTFGQ GTKLEIK                107

SEQ ID NO: 80          moltype = DNA  length = 369
FEATURE                Location/Qualifiers
misc_feature           1..369
                       note = Description of Artificial Sequence: Synthetic
                        polynucleotide
source                 1..369
                       mol_type = other DNA
```

```
                         organism = synthetic construct
SEQUENCE: 80
gaggtgcagc tggtggagtc tgggggaggc ttggtccagc ctgggggtc cctgagactc  60
tcctgtgcag cctctggatt caccttcact gatcactaca tgacctgggt ccgccaggct  120
ccagggaagg ggctggagtg ggtggccttt attagaaaca aagctggtgg ttacacaaca  180
gagtccaatc cggctgtgaa ggggcgattc accatctcca gagacaacgc caagaactca  240
ctgtatctgc aaatgaacag cctgagagcc gaggacacgg ctgtgtatta ctgtgcgaga  300
gaaactacgg gtatacctac aggttggttt gcttactggg gccagggaac cctggtcacc  360
gtctcctca                                                         369

SEQ ID NO: 81            moltype = DNA  length = 321
FEATURE                  Location/Qualifiers
misc_feature             1..321
                         note = Description of Artificial Sequence: Synthetic
                          polynucleotide
source                   1..321
                         mol_type = other DNA
                         organism = synthetic construct
SEQUENCE: 81
gacatccaga tgacccagtc tccatcctcc ctgtctgcat ctgtaggaga cagagtcacc  60
atcacttgcc tagcaagtga ggacatttac tttgatttag cgtggtatca gcagaaacca  120
gggaaagccc ctaagctcct gatctatggt ggggacaggt tgaaagaggg ggtcccatca  180
aggttcagtg gcagtggatc tgggacagat tatactctca ccatcagcag tctgcaacct  240
gaagattttg caacttacta ctgtcaacag agttacagtt atccgtacac gtttggccag  300
gggaccaagc tggagatcaa a                                           321

SEQ ID NO: 82            moltype = DNA  length = 1359
FEATURE                  Location/Qualifiers
misc_feature             1..1359
                         note = Description of Artificial Sequence: Synthetic
                          polynucleotide
misc_feature             1357..1359
                         note = This region may or may not be present
source                   1..1359
                         mol_type = other DNA
                         organism = synthetic construct
SEQUENCE: 82
gaggtgcagc tggtggagtc tgggggaggc ttggtccagc ctgggggtc cctgagactc  60
tcctgtgcag cctctggatt caccttcact gatcactaca tgacctgggt ccgccaggct  120
ccagggaagg ggctggagtg ggtggccttt attagaaaca aagctggtgg ttacacaaca  180
gagtccaatc cggctgtgaa ggggcgattc accatctcca gagacaacgc caagaactca  240
ctgtatctgc aaatgaacag cctgagagcc gaggacacgg ctgtgtatta ctgtgcgaga  300
gaaactacgg gtatacctac aggttggttt gcttactggg gccagggaac cctggtcacc  360
gtctcctcag cgtcgaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaagcc  720
gctggggcac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtcc ccgggtaaa                        1359

SEQ ID NO: 83            moltype = DNA  length = 642
FEATURE                  Location/Qualifiers
misc_feature             1..642
                         note = Description of Artificial Sequence: Synthetic
                          polynucleotide
source                   1..642
                         mol_type = other DNA
                         organism = synthetic construct
SEQUENCE: 83
gacatccaga tgacccagtc tccatcctcc ctgtctgcat ctgtaggaga cagagtcacc  60
atcacttgcc tagcaagtga ggacatttac tttgatttag cgtggtatca gcagaaacca  120
gggaaagccc ctaagctcct gatctatggt ggggacaggt tgaaagaggg ggtcccatca  180
aggttcagtg gcagtggatc tgggacagat tatactctca ccatcagcag tctgcaacct  240
gaagattttg caacttacta ctgtcaacag agttacagtt atccgtacac gtttggccag  300
gggaccaagc tggagatcaa acgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
```

```
ctgagcaaag cagactacga gaaacacaaa gtctacgcct gcgaagtcac ccatcagggc  600
ctgagctcgc ccgtcacaaa gagcttcaac aggggagagt gt                    642

SEQ ID NO: 84          moltype = DNA  length = 369
FEATURE                Location/Qualifiers
misc_feature           1..369
                       note = Description of Artificial Sequence: Synthetic
                        polynucleotide
source                 1..369
                       mol_type = other DNA
                       organism = synthetic construct
SEQUENCE: 84
gaggtgcagc tggtggagtc tgggggaggc ttggtccagc ctgggggtc cctgagactc  60
tcctgtgcag cctctggatt caccttcact gatcactaca tgcactgggt ccgccaggct  120
ccagggaagg ggctggagtg ggtggcccac actagagata aagctggtgg ttacacaaca  180
gagtccaatc cggctgtgaa ggggcgattc accatctcca gagacaacgc caagaactca  240
ctgtatctgc aaatgaacag cctgagagcc gaggacacgg ctgtgtatta ctgtgcgaga  300
gaaactacga gaatacctac aggttggttt gcttactggg gccagggaac cctggtcacc  360
gtctcctca                                                          369

SEQ ID NO: 85          moltype = DNA  length = 1359
FEATURE                Location/Qualifiers
misc_feature           1..1359
                       note = Description of Artificial Sequence: Synthetic
                        polynucleotide
misc_feature           1357..1359
                       note = This region may or may not be present
source                 1..1359
                       mol_type = other DNA
                       organism = synthetic construct
SEQUENCE: 85
gaggtgcagc tggtggagtc tgggggaggc ttggtccagc ctgggggtc cctgagactc  60
tcctgtgcag cctctggatt caccttcact gatcactaca tgcactgggt ccgccaggct  120
ccagggaagg ggctggagtg ggtggcccac actagagata aagctggtgg ttacacaaca  180
gagtccaatc cggctgtgaa ggggcgattc accatctcca gagacaacgc caagaactca  240
ctgtatctgc aaatgaacag cctgagagcc gaggacacgg ctgtgtatta ctgtgcgaga  300
gaaactacga gaatacctac aggttggttt gcttactggg gccagggaac cctggtcacc  360
gtctcctcag cgtcgaccaa gggcccatcg gtcttccccc tggcaccctc ctccaagagc  420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca acaccaaggt ggacaagaaa  660
gttgagccca aatcttgtga caaaactcac acatgcccac cgtgcccagc acctgaagcc  720
gctggggcac cgtcagtctt cctcttcccc ccaaaaccca aggacaccct catgatctcc  780
cggacccctg aggtcacatg cgtggtggtg gacgtgagcc acgaagaccc tgaggtcaag  840
ttcaactggt acgtggacgg cgtggaggtg cataatgcca agacaaagcc gcgggaggag  900
cagtacaaca gcacgtaccg tgtggtcagc gtcctcaccg tcctgcacca ggactggctg  960
aatggcaagg agtacaagtg caaggtctcc aacaaagccc tcccagcccc catcgagaaa  1020
accatctcca aagccaaagg gcagccccga gaaccacagg tgtacaccct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctata gcaagctcac cgtggacaag  1260
agcaggtggc agcaggggaa cgtcttctca tgctccgtga tgcatgaggc tctgcacaac  1320
cactacacgc agaagagcct ctccctgtcc ccgggtaaa                        1359

SEQ ID NO: 86          moltype = AA  length = 330
FEATURE                Location/Qualifiers
REGION                 1..330
                       note = Description of Artificial Sequence: Synthetic
                        polypeptide
VAR_SEQ                330
                       note = May or may not be present
source                 1..330
                       mol_type = protein
                       organism = synthetic construct
SEQUENCE: 86
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 87          moltype = AA  length = 9
FEATURE                Location/Qualifiers
REGION                 1..9
                       note = Description of Artificial Sequence: Synthetic peptide
source                 1..9
                       mol_type = protein
```

```
                         organism = synthetic construct
SEQUENCE: 87
FTDFYMNWV                                                                  9

SEQ ID NO: 88            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 88
FYMNWVRQA                                                                  9

SEQ ID NO: 89            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 89
WVAFIRNKA                                                                  9

SEQ ID NO: 90            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 90
FIRNKANGY                                                                  9

SEQ ID NO: 91            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 91
KLLIYGANR                                                                  9

SEQ ID NO: 92            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 92
LLIYGANRL                                                                  9

SEQ ID NO: 93            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 93
IYGANRLKD                                                                  9

SEQ ID NO: 94            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 94
YYCQQSYKY                                                                  9

SEQ ID NO: 95            moltype = AA  length = 400
FEATURE                  Location/Qualifiers
REGION                   1..400
                         note = Description of Artificial Sequence: Synthetic
                          polypeptide
```

```
source                  1..400
                        mol_type = protein
                        organism = synthetic construct
SEQUENCE: 95
IQRTPKIQVY SRHPAENGKS NFLNCYVSGF HPSDIEVDLL KNGERIEKVE HSDLSFSKDW  60
SFYLLYYTEF TPTEKDEYAC RVNHVTLSQP KIVKWDRDMG GGGSGGGGSG GGGSGGGGSD  120
GLKEPLSFHV TWIASFYNHS WKQNLVSGWL SDLQTHTWDS NSSTIVFLCP WSRGNFSNEE  180
WKELETLFRI RTIRSFEGIR RYAHELQFEY PFEIQVTGGC ELHSGKVSGS FLQLAYQGSD  240
FVSFQNNSWL PYPVAGNMAK HFCKVLNQNQ HENDITHNLL SDTCPRFILG LLDAGKAHLQ  300
RQVKPEAWLS HGPSPGPGHL QLVCHVSGFY PKPVWVMWMR GEQEQQGTQR GDILPSADGT  360
WYLRATLEVA AGEAADLSCR VKHSSLEGQD IVLYHHHHHH                        400

SEQ ID NO: 96           moltype = AA  length = 10
FEATURE                 Location/Qualifiers
REGION                  1..10
                        note = Description of Artificial Sequence: Synthetic peptide
VAR_SEQ                 3
                        note = T or D
VAR_SEQ                 5
                        note = T or E
VAR_SEQ                 7
                        note = H or F
VAR_SEQ                 10
                        note = H, T or N
source                  1..10
                        mol_type = protein
                        organism = synthetic construct
SEQUENCE: 96
GFXFXDXYMX                                                         10

SEQ ID NO: 97           moltype = AA  length = 19
FEATURE                 Location/Qualifiers
REGION                  1..19
                        note = Description of Artificial Sequence: Synthetic peptide
VAR_SEQ                 1
                        note = F or H
VAR_SEQ                 3
                        note = R or S
VAR_SEQ                 4
                        note = N, G or D
VAR_SEQ                 5
                        note = K, S or A
VAR_SEQ                 7
                        note = G or N
VAR_SEQ                 16
                        note = A or S
source                  1..19
                        mol_type = protein
                        organism = synthetic construct
SEQUENCE: 97
XIXXXAXGYT TESNPXVKG                                               19

SEQ ID NO: 98           moltype = AA  length = 12
FEATURE                 Location/Qualifiers
REGION                  1..12
                        note = Description of Artificial Sequence: Synthetic peptide
VAR_SEQ                 4
                        note = G, R or T
source                  1..12
                        mol_type = protein
                        organism = synthetic construct
SEQUENCE: 98
ETTXIPTGWF AY                                                      12

SEQ ID NO: 99           moltype = AA  length = 11
FEATURE                 Location/Qualifiers
REGION                  1..11
                        note = Description of Artificial Sequence: Synthetic peptide
VAR_SEQ                 7
                        note = S or Y
VAR_SEQ                 8
                        note = N or F
source                  1..11
                        mol_type = protein
                        organism = synthetic construct
SEQUENCE: 99
LASEDIXXDL A                                                       11

SEQ ID NO: 100          moltype =   length =
```

-continued

```
SEQUENCE: 100
000

SEQ ID NO: 101          moltype = AA  length = 9
FEATURE                 Location/Qualifiers
REGION                  1..9
                        note = Description of Artificial Sequence: Synthetic peptide
VAR_SEQ                 4
                        note = E or Y
VAR_SEQ                 5
                        note = K or S
source                  1..9
                        mol_type = protein
                        organism = synthetic construct
SEQUENCE: 101
QQSXXYPYT                                                        9

SEQ ID NO: 102          moltype = AA  length = 6
FEATURE                 Location/Qualifiers
REGION                  1..6
                        note = Description of Artificial Sequence: Synthetic 6xHis
                         tag
source                  1..6
                        mol_type = protein
                        organism = synthetic construct
SEQUENCE: 102
HHHHHH                                                           6
```

The invention claimed is:

1. A method of inhibiting Cluster of Differentiation 1a (CD1a)-dependent T cell activation in a subject in need thereof, the method comprising:

administering to the subject a therapeutically effective amount of an antibody, or antigen binding fragment thereof, that specifically binds to human CD 1a, wherein the antibody comprises:

a CDR-H1 comprising the amino acid sequence of SEQ ID NO: 30, a CDR-H2 comprising the amino acid sequence of SEQ ID NO: 41, a CDR-H3 comprising the amino acid sequence of SEQ ID NO: 17, a CDR-L1 comprising the amino acid sequence of SEQ ID NO: 25, a CDR-L2 comprising the amino acid sequence of SEQ ID NO: 26, and a CDR-L3 comprising the amino acid sequence of SEQ ID NO: 27, thereby inhibiting CD1a-dependent T cell activation.

2. The method of claim 1, wherein the antibody, or antigen-binding fragment thereof, comprises at least one of the following:

(i) a heavy chain variable region (VH) framework sequence obtained from a human germline VH sequence selected from the group consisting of IGHV1-2*02, IGHV1-3*01, IGHV1-46*01, IGHV1-69*01, IGHV1-69*02, IGHV1-8*01, IGHV3-7*01, IGHV3-13*01, IGHV3-23*01, IGHV3-23*04, IGHV3-30*01, IGHV3-30*18, IGHV5-10-1*01, IGHV5-10-1*04, and IGHV5-51*01;

(ii) a light chain variable region (VL) framework sequence obtained from a human germline VL sequence selected from the group consisting of IGKV1-12*01, IGKV1-13*02, IGKV1-33*01, IGKV1-39*01, IGKV1-5*01, IGKV3-11*01, IGKV3-15*01, IGKV3-20*01, IGKV3D-20*02, and IGKV4-1*01;

(iii) a heavy chain constant domain comprising an IgA, IgD, IgE, IgM, or IgG; and/or (iv) a human Vκ or Vλ light chain constant domain.

3. The method of claim 1, wherein the antibody, or antigen-binding fragment thereof, comprises:

(i) a VH comprising the amino acid sequence of SEQ ID NO: 55 and a VL comprising the amino acid sequence of SEQ ID NO: 28;

(ii) a HC comprising, or consisting of, the amino acid sequence of SEQ ID NO: 54 and a LC comprising, or consisting of, the amino acid sequence of SEQ ID NO: 24; or (iii) the amino acid sequence encoded by the insert in the plasmid deposited at the ATCC and having ATCC Accession No. PTA-126810 and comprising the amino acid sequence encoded by the insert in the plasmid deposited at the ATCC and having ATCC Accession No. PTA-126811.

4. The method of claim 1, wherein the antibody, or antigen binding fragment thereof, comprises a VL comprising the sequence of SEQ ID NO:28 and a VH comprising the sequence of SEQ ID NO: 55.

5. The method of claim 1, wherein the antibody, or antigen binding fragment thereof, comprises a light chain comprising the amino acid sequence of SEQ ID NO: 24 and a heavy chain comprising the amino acid sequence of SEQ ID NO: 54.

6. The method of claim 1, wherein the antibody, or antigen binding fragment thereof, binds an epitope on CD 1a, wherein the epitope comprises Glu82 and/or His170, according to the numbering of SEQ ID NO: 1, and where the epitope:

(i) optionally further comprises Ile92 and/or Arg93, according to the numbering of SEQ ID NO: 1, and (ii) optionally comprises at least one of the following amino acid residues: Glu78, Lys81, Thr85, Ile89, Arg93, Asp173, and Asn177, according to the numbering of SEQ ID NO: 1; and (iii) optionally comprises at least one of the following residues: Leu86, Asn168, Ile174, His176, Asp181, and Arg185, according to the numbering of SEQ ID NO: 1; and (iv) optionally comprises at least one of the following residues: Glu79, Leu83, Glu84, Arg88, Ile92, Gln169, Leu178, Ser180, and Thr182 according to the numbering of SEQ ID NO: 1; and (v) optionally does not comprise Asn146 and/or Asn168 according to the numbering of SEQ ID NO: 1.

7. The method of claim 1, wherein the binding inhibits CD1a from binding a T cell receptor.

8. The method of claim 1, wherein the binding inhibits CD69 expression.

9. The method of claim 1, wherein the binding inhibits IL-2 production.

10. The method of claim 1, wherein the binding inhibits serum IgE levels.

11. The method of claim 1, wherein the binding inhibits antigen-specific IgE antibodies.

12. The method of claim 1, wherein the binding inhibits expression of a gene selected from the group consisting of: Thymic Stromal Lymphopoietin (TSLP), filaggrin (FLG), interleukin-33 (IL-33), C—C motif chemokine ligand 26 (CCL-26), IL-23p40, C—X—C chemokine ligand 1 (CXCL-1), and CCL-20.

13. The method of claim 1, wherein the antibody, or antigen binding fragment thereof, is comprised in a pharmaceutical composition with a pharmaceutically acceptable carrier or excipient.

14. The method of claim 1, wherein the therapeutically effective amount of the antibody, or antigen binding fragment thereof, is sufficient to inhibit CD1a-dependent T cell activation in the subject in need thereof.

15. The method of claim 1, wherein the subject in need thereof suffers from an inflammatory bowel disease.

16. The method of claim 1, wherein the subject in need thereof suffers from an inflammatory skin disease.

17. The method of claim 1, wherein the subject in need thereof suffers from atopic dermatitis.

18. The method of claim 1, wherein the subject in need thereof suffers from an allergy.

19. The method of claim 1, wherein the subject in need thereof suffers from: inflammatory bowel disease, allergies, allergic rhinitis, allergic conjunctivitis, vernal keratoconjunctivitis, a seasonal allergy, pet allergy, asthma, food allergy, peanut allergy, atopic dermatitis, contact dermatitis, chronic rhinosinusitis with nasal polyps (CRSwNP), allergic rhinitis, bronchitis, chronic obstructive pulmonary disease (COPD), viral exacerbations of respiratory disease, viral infection in children and adults, respiratory syncytial virus RSV, rhinovirus, influenza, urticarias, eosinophilic esophagitis, chronic fibrosis, liver fibrosis, non-alcoholic steatohepatitis (NASH), chronic kidney disease, idiopathic pulmonary fibrosis (IPF), scleroderma, systemic sclerosis, acute kidney injury, sepsis, pancreatitis, type 1 diabetes, graft-versus-host disease (GVHD), tissue transplant, Alzheimer's, rheumatoid arthritis, irritable bowel syndrome (IBS), Crohn's disease, ulcerative colitis, multiple sclerosis, psoriasis, celiac disease, or Raynaud's disease.

* * * * *